US010238644B2

(12) United States Patent
Nordsiek et al.

(10) Patent No.: US 10,238,644 B2
(45) **Date of Patent: *Mar. 26, 2019**

(54) 2×2×2 WEEK DOSING REGIMEN FOR TREATING ACTING KERATOSIS WITH PHARMACEUTICAL COMPOSITIONS FORMULATED WITH 3.75% IMIQUIMOD

(71) Applicant: Medicis Pharmaceutical Corporation, Bridgewater, NJ (US)

(72) Inventors: Michael T. Nordsiek, Wayne, PA (US); Sharon F. Levy, Philadelphia, PA (US); James Hurn-Joung Lee, Devon, PA (US); James H. Kulp, West Chester, PA (US); Kodumudi S. Balaji, Lansdale, PA (US); Tze-Chiang Meng, Lino Lakes, MN (US); Jason J. Wu, Wayne, PA (US); Valyn S. Bahm, Phoenixville, PA (US); Robert Babilon, Boyertown, PA (US)

(73) Assignee: Medicis Pharmaceutical Corporation, Bridgewater, NJ (US)

(*) Notice: Subject to any disclaimer, the term of this patent is extended or adjusted under 35 U.S.C. 154(b) by 159 days.

This patent is subject to a terminal disclaimer.

(21) Appl. No.: 15/187,751

(22) Filed: Jun. 20, 2016

(65) Prior Publication Data

US 2016/0303111 A1 Oct. 20, 2016

Related U.S. Application Data

(60) Division of application No. 13/568,003, filed on Aug. 6, 2012, now Pat. No. 9,370,509, which is a continuation of application No. 13/181,499, filed on Jul. 12, 2011, now Pat. No. 8,236,816, which is a continuation of application No. 12/636,613, filed on Dec. 11, 2009, now abandoned.

(60) Provisional application No. 61/205,145, filed on Jan. 15, 2009, provisional application No. 61/144,731, filed on Jan. 14, 2009, provisional application No. 61/139,536, filed on Dec. 19, 2008.

(51) Int. Cl.

| | |
|---|---|
| ***A61K 9/00*** | (2006.01) |
| ***A61K 9/06*** | (2006.01) |
| ***A61K 9/70*** | (2006.01) |
| ***A61K 31/47*** | (2006.01) |
| ***A61K 47/10*** | (2017.01) |
| ***A61K 47/12*** | (2006.01) |
| ***A61K 47/14*** | (2017.01) |
| ***A61K 31/437*** | (2006.01) |
| ***A61K 31/4745*** | (2006.01) |

(52) U.S. Cl.

CPC ........ *A61K 31/4745* (2013.01); *A61K 9/0014* (2013.01); *A61K 9/06* (2013.01); *A61K 9/7061* (2013.01); *A61K 31/437* (2013.01); *A61K 31/47* (2013.01); *A61K 47/10* (2013.01); *A61K 47/12* (2013.01); *A61K 47/14* (2013.01)

(58) Field of Classification Search

CPC .. A61K 31/437; A61K 31/47; A61K 31/4745; A61K 47/10; A61K 47/12; A61K 47/14; A61K 9/0014; A61K 9/06; A61K 9/7061

See application file for complete search history.

(56) References Cited

U.S. PATENT DOCUMENTS

| | | | |
|---|---|---|---|
| 4,411,893 | A | 10/1983 | Johnson et al. |
| 4,689,338 | A | 8/1987 | Gerster |
| 4,722,941 | A | 2/1988 | Eckert et al. |
| 4,746,515 | A | 5/1988 | Cheng et al. |
| 4,751,087 | A | 6/1988 | Wick |
| 5,238,944 | A | 8/1993 | Wick et al. |
| 6,245,776 | B1 | 6/2001 | Skwierczynski et al. |
| 6,335,030 | B1 | 1/2002 | Hoeck et al. |
| 6,693,113 | B2 | 2/2004 | Lindstrom |

(Continued)

FOREIGN PATENT DOCUMENTS

| | | |
|---|---|---|
| CN | 1583175 A | 2/2005 |
| EP | 1889609 A2 | 2/2008 |

(Continued)

OTHER PUBLICATIONS

Salasche et al. 2002, J. Am. Acad. Dermatol., vol. 47(4), pp. 571-577.*
Edwards et al. 1986, Arch Dermatol, vol. 122, pp. 779-782.*
Aldara Package Insert, obtained Sep. 3, 2002 online at http://www.accessdata.fda.gov/drugsaUdadocs/label/2002/20723s11 s121bl.pdf.
Aldara Product, Admitted Prior Art (see e.g., '816 patent, col. 2, In. 61—col. 7, In. 19; see also 2005 revised Aldara labeling (http://www.accessdata.fda.gov/drugsatfdadocs/appletter/2005/020723s018ltr.pdf and http://www.accessdata.fda.gov/drugsatfda docs/label/2005/020723s018lbl.pdf)).
Alomar, A. et al., "Vehicle-controlled, randomized, double-blind study to assess safety and efficacy of imiquimod 5% cream applied once daily 3 days per week in one or two courses of treatment of actinic keratoses on the head," Br. J. Dermatol., 157(1):133-41, 2007.

(Continued)

*Primary Examiner* — Kara R McMillian
(74) *Attorney, Agent, or Firm* — Kilpatrick Townsend & Stockton LLP

(57) ABSTRACT

Pharmaceutical formulations and methods for the topical or transdermal delivery of 1-isobutyl-1H-imidazo[4,5-c]-quinolin-4-amine or 1-(2-methylpropyl)-1H-imidazo[4,5-c]quinolin-4-amine, i.e., imiquimod, to treat actinic keratosis with short durations of therapy, than currently prescribed for the commercially available Aldara® 5% imiquimod cream, as now approved by the U.S. Food & Drug Administration ("FDA"), are disclosed and described. More specifically, lower dosage strength imiquimod formulations to deliver an efficacious dose of imiquimod for treating actinic keratosis with an acceptable safety profile and dosing regimens that are short and more convenient for patient use than the dosing regimen currently approved by the U.S. Food & Drug Administration ("FDA") for Aldara® 5% imiquimod cream to treat actinic keratosis are also disclosed and described.

20 Claims, 111 Drawing Sheets

(56) References Cited

U.S. PATENT DOCUMENTS

| | | | | |
|---|---|---|---|---|
| 6,706,728 | B2 | 3/2004 | Hedenstrom et al. | |
| 6,894,060 | B2 | 5/2005 | Slade | |
| 7,038,051 | B2 | 5/2006 | Gerster et al. | |
| 7,507,703 | B2 | 3/2009 | Woodward | |
| 7,696,159 | B2 | 4/2010 | Owens et al. | |
| 7,893,083 | B2 | 2/2011 | Mandrea | |
| 7,902,211 | B2 * | 3/2011 | Statham | A61K 9/0014 514/290 |
| 7,902,214 | B2 * | 3/2011 | Statham | A61K 9/0014 514/290 |
| 7,906,526 | B2 * | 3/2011 | Statham | A61K 9/0014 514/290 |
| 7,928,116 | B2 * | 4/2011 | Statham | A61K 9/0014 514/290 |
| 7,928,117 | B2 * | 4/2011 | Statham | A61K 9/0014 514/290 |
| 8,222,270 | B2 * | 7/2012 | Nordsiek | A61K 9/0014 514/290 |
| 8,236,816 | B2 * | 8/2012 | Nordsiek | A61K 9/0014 514/290 |
| 8,299,109 | B2 * | 10/2012 | Nordsiek | A61K 9/0014 514/290 |
| 9,370,509 | B2 * | 6/2016 | Nordsiek | A61K 9/0014 |
| 9,492,682 | B2 * | 11/2016 | Gold | A61N 5/062 |
| 2002/0147210 | A1 | 10/2002 | Smith | |
| 2003/0007939 | A1 | 1/2003 | Murad | |
| 2003/0072814 | A1 | 4/2003 | Maibach et al. | |
| 2003/0199538 | A1 | 10/2003 | Skwierczynski et al. | |
| 2004/0087614 | A1 | 5/2004 | Baumann et al. | |
| 2004/0180919 | A1 * | 9/2004 | Miller | A61K 8/4946 514/291 |
| 2004/0181130 | A1 | 9/2004 | Miller et al. | |
| 2005/0232869 | A1 | 10/2005 | Tamarkin et al. | |
| 2006/0105028 | A1 | 5/2006 | Zhang et al. | |
| 2006/0216333 | A1 | 9/2006 | Miller et al. | |
| 2007/0049518 | A1 | 3/2007 | Chandler et al. | |
| 2007/0081962 | A1 | 4/2007 | Munshi | |
| 2007/0123558 | A1 | 5/2007 | Statham et al. | |
| 2007/0134273 | A1 | 6/2007 | Romagne et al. | |
| 2007/0166384 | A1 | 7/2007 | Zarraga | |
| 2007/0196452 | A1 | 8/2007 | Zhang et al. | |
| 2007/0264317 | A1 * | 11/2007 | Yosha | A61F 13/0203 424/448 |
| 2008/0015271 | A1 | 1/2008 | Abram et al. | |
| 2008/0125375 | A1 | 5/2008 | Yang et al. | |
| 2008/0125485 | A1 | 5/2008 | Cuevas Sanchez et al. | |
| 2008/0161328 | A1 | 7/2008 | Muller et al. | |
| 2008/0193487 | A1 | 8/2008 | Schild et al. | |
| 2008/0214615 | A1 | 9/2008 | Muller et al. | |
| 2008/0280943 | A1 | 11/2008 | Slade et al. | |
| 2009/0041680 | A1 | 2/2009 | Tamarkin et al. | |
| 2009/0093514 | A1 | 4/2009 | Statham et al. | |
| 2009/0130029 | A1 | 5/2009 | Tamarkin et al. | |
| 2009/0163532 | A1 | 6/2009 | Perman et al. | |
| 2009/0182004 | A1 | 7/2009 | Winckle et al. | |
| 2009/0202443 | A1 | 8/2009 | Miller et al. | |
| 2009/0232755 | A1 | 9/2009 | Bauman | |
| 2009/0246156 | A1 | 10/2009 | Kunin | |
| 2009/0281047 | A1 | 11/2009 | Brown | |
| 2009/0304812 | A1 | 12/2009 | Staniforth et al. | |
| 2010/0021394 | A1 | 1/2010 | Yu | |
| 2010/0092401 | A1 | 4/2010 | Vallejo et al. | |
| 2010/0096287 | A1 | 4/2010 | Stoesz et al. | |
| 2010/0129439 | A1 | 5/2010 | Alexis et al. | |
| 2010/0150869 | A1 | 6/2010 | Sredni et al. | |
| 2010/0160368 | A1 | 6/2010 | Gregory | |
| 2010/0267678 | A1 | 10/2010 | Zhang et al. | |
| 2011/0021555 | A1 | 1/2011 | Nordsiek et al. | |
| 2011/0038900 | A1 | 2/2011 | Chakrapani et al. | |
| 2011/0135604 | A1 | 6/2011 | Casarez et al. | |
| 2011/0207766 | A1 | 8/2011 | Nordsiek et al. | |
| 2011/0257216 | A1 | 10/2011 | Nordsiek et al. | |
| 2011/0257217 | A1 | 10/2011 | Nordsiek et al. | |
| 2011/0257218 | A1 | 10/2011 | Nordsiek et al. | |
| 2011/0263633 | A1 | 10/2011 | Nordsiek et al. | |
| 2011/0263634 | A1 | 10/2011 | Nordsiek et al. | |
| 2011/0263635 | A1 | 10/2011 | Nordsiek et al. | |
| 2011/0263636 | A1 | 10/2011 | Nordsiek et al. | |
| 2011/0263637 | A1 | 10/2011 | Nordsiek et al. | |

FOREIGN PATENT DOCUMENTS

| | | | |
|---|---|---|---|
| IN | 1581/MUM/2005 | | 8/2007 |
| WO | WO 02/102377 | A1 | 12/2002 |
| WO | WO 2007/007208 | A2 | 1/2007 |
| WO | WO 2008/010963 | A2 | 1/2008 |
| WO | WO 2008/016475 | A2 | 2/2008 |
| WO | WO 2008/098232 | A1 | 8/2008 |
| WO | WO 2008/118765 | A1 | 10/2008 |
| WO | WO 2008/140713 | A1 | 11/2008 |
| WO | WO 2009/019473 | A1 | 2/2009 |
| WO | WO 2009/095226 | A2 | 8/2009 |
| WO | WO 2009/155070 | A2 | 12/2009 |
| WO | WO 2009/158687 | A1 | 12/2009 |
| WO | WO 2010/050889 | A1 | 5/2010 |
| WO | WO 2010/088924 | A1 | 8/2010 |

OTHER PUBLICATIONS

Baptista, J. et al., "Topical photodynamic therapy and imiquimod cream in the treatment of actinic keratoses," Skin Cancer 2006: 21 :49-53, 2006.

Barthelette S et al., *Common Dermatologic Presentations: The Red Face*, JCOM vol. 11 (1) 36-50 (2004).

Ben M'Barek, L. et al., "5% topical imiquimod tolerance in transplant recipients," Dermatol., 215(2):130-3, 2007.

Berman, B. "Imiquimod: a new immune response modifier for the treatment of external genital warts and other diseases in dermatology," Int. J. Dermatol., 41(Suppl S1):7-11, 2002.

Berman, B. et al., "Determination of the area of skin capable of being covered by the application of 250 mg of 5% imiquimod cream," Dermatologic surgery: Official Publication for American Society for Dermatologic Surgery, 30(5):784-786, 2004.

Berman, B. et al., "Novel dermatologic uses of the immune response modifier imiquimod 5% cream," Skin Therapy Lett., 7(9):1-6, 2002.

Berman, B. et al., "Pharmacotherapy of actinic keratosis," Expert Opin. Pharmacother., 10(18):3015-31, 2009.

Bianchi, L. et al., "Actinic keratosis treated with an immune response modifier: a case report of six patients," Clin. Exp. Dermatol., 28(Suppl 1):39-41, 2003.

Burns, C., "Imiquimod for the treatment of skin cancer," Dermatol. Clin., 23(1):151-64, 2005.

Chen, J. et al., "Short-course therapy with imiquimod 5% cream for solar keratoses: A randomized controlled trial," Australasian J. Dermatol., 44:250-255, 2003.

Chollet, J. et al., "Development of a topically active imiquimod formulation," Pharm. Devel. Tech., 4(1):35-43, 1999.

CL2183-2009 Andromaco Opposition—Chilean counterpart.

CL2183-2009 Asilfa Opposition—Chilean counterpart.

CL2183-2009 Recalcine Opposition—Chilean counterpart.

Correa, Carlos, "Pautas para el examen de patentes farmacéuticas: Una perspectiva desde la Salud Pública," Universito of Buenos Aires, ICTSD, WHO, UNCTAD, Mar. 2008, 66 pages [Guidelines for the examination of pharmaceutical patents: Developing a public health perspective].

Del Rosso, J., "Imiquimod 5% Cream in the Treatment of Cutaneous Epithelial Malignancy: Optical Use and Duration of Therapy," Cosmetic Dermatology, vol. 18, No. 9, Sep. 2005.

Del Rosso, J. et al., "Safety and efficacy of multiple 16-week courses of topical imiquimod for the treatment of large areas of skin involved with actinic keratoses," J. Clin. Aesth. Dermatol., 2(4):20-8, 2009.

Del Rosso, J., "New and emerging topical approaches for actinic keratoses," Cutis., 72(4):273-6, 279, 2003.

Del Rosso, J., "The use of topical imiquimod for the treatment of actinic keratosis: a status report," Cutis, 76(4):241-8, 2005.

(56) References Cited

OTHER PUBLICATIONS

Dixon, A., "Treating actinic keratoses with imiquimod," Australian Family Physician, vol. 36, No. 5, May 2007, pp. 341-342.
Edwards et al., "Self-administered topical 5% imiquimod cream for external anogenital warts," Arch. Dermatol., 134:25-30, 1998.
Edwards et al., "Effect of Intralesional alpha-2 interferon on actinic keratosis," Arch Dermatol, 1986, vol. 122, pp. 779-782.
Eklind, J., et al., "Imiquimod to Treat Different Cancers of the Epidermis," American Society for Dermatologic Surgery, Inc., 2003;29:890-896.
Ezughah, F. et al., "Confirmation of histological clearance of superficial basal cell carcinoma with multiple serial sectioning and Mohs' micrographic surgery following treatment with imiquimod 5% cream," J. Derm. Treat., 19:111-117, 2008.
Final Office Action dated Jan. 19, 2011 in U.S. Appl. No. 12/028,771.
Garland, S., "Imiquimod," Curr. Opin. Infect. Dis., 16(2):85-9, 2003.
Gebauer, K. et al., "Effect of dosing frequency on the safety and efficacy of imiquimod 5% cream for treatment of actinic keratosis on the forearms and hands: a phase II, randomized placebo-controlled trial," Br. J. Dermatol., 161(4):897-903, 2009.
Greenberg, H.L. et al., "Severe Reaction to 5% Irniquirnod Cream with Excellent Clinical and Cosmetic Outcomes," Journal of Drugs in Dermatology, 2007:6(4):452-458.
Gupta, A. et al., "Imiquimod: a review," J. Cutan. Med. Surg., 6(6):554-60, 2002.
Gupta, A. et al., "Viral and nonviral uses of imiquimod: a review," J. Cutaneous Med. Surg., 8(5):338-52, 2004.
Gupta, A. et al., "Evaluation of the effectiveness of imiquimod and 5-fluorouracil for the treatment of actinic keratosis: Critical review and meta-analysis of efficacy studies," J. Cutan. Med. Surg., 9(5):209-14, 2005.
Hadley, G. et al., "Imiquimod for actinic keratosis: systematic review and meta-analysis," J. Invest. Dermatol., 126(6):1251-5, 2006.
Hanke, CW et al., "Imiquimod 2.5% and 3.75% for the treatment of actinic keratosis: Results of two placebo-controlled studies of daily application to the face and balding scalp for two 3-week cycles," Journal of the American Academy of Dermatology, V.V. Mosby, St. Louis, MO., vo. 62, No. 4, Apr. 1, 2010, pp. 573-581.
Hanson et al., "Observation and Qualification of Ultraviolet-induced Reactive Oxygen Species in Ex Vivo Human Skin," Photochemistry and Photobiology / vol. 76 (No. 1 ), 2002; pp. 57-63.
Harrison, L. et al., "Pharmacokinetics and safety of imiquimod 5% cream in the treatment of actinic kertoses of the face, scalp, or hands and arms," Arch. Dermatol. Res., 296:6-11, 2004.
Harrison, L. et al., "A pharmaceutical comparison of different commercially available imiquimod 5% cream poducts," J. Dermatol. Treat., 20(3):160-164, 2009.
He, Q., "Preparation of imiquimod cream and its clinical application in the treatment of condyloma acuminatum," Herald of Medicine, Yiyao Daobao, 23(10):758-760, 2004. (English abstract).
International Search Report and Written Opinion dated Jun. 27, 2008 in PCT/US0853522.
Jorizzo, Joseph L. "Current and Novel Treatment Options for Actinic Keratosis," DOI: 1 0.1007/s10227-004-0804-2 J Cutan Med Surg 2005; 13-21.
Korman, N. et al., "Dosing with 5% imiquimod cream 3 times per week for the treatment of actinic keratosis: results of two phase 3, randomized, double-blind, parallel-group, vehicle-controlled trials," Arch. Dermatol. Res., 141(4):467-73, 2005.
Kose, O. et al., "Comparison of the efficacy and tolerability of 3% diclofenac sodium gel and 5% imiquimod cream in the treatment of actinic keratosis," J. Dermatol. Treat., 19(3):159-63, 2008.
Krawtchenko, N., "A randomised study of topical 5% imiquimod vs. topical5-fluorouracil vs. cryosurgery in immunocompetent patients with actinic keratoses: a comparison of clinical and histological outcomes including 1-year follow-up," Br. J. Dermatol., 157(Suppl. 2):34-40, 2007.
Larko, O., "The current options in the management of actinic keratosis," G ital Dermatol Venereol 2009; 144:445-52.
Lebwohl, M. et al., "Imiquimod 5% cream for the treatment of actinic keratosis: results from two phase III, randomized, double-blind, parallel group, vehicle-controlled trials," J. Am. Acad. Dermatol., 50(5):714-21, 2004.
Lee, PK et al., "Imiquimod 5% cream for the treatment of actinic keratoses," Skin Therapy Lett. vol. 10(2). pp. 1-6, Mar. 2005.
Li, et al., "Imiquimod as an antiangiogenic agent" J. Drugs Dermatol., vol. 4, No. 6, pp. 708-17 (2005).
Majewski, S. et al., "Imiquimod is a strong inhibitor of tumor cell-induced angiogenesis," Int. J. Dermatol., 44(1):14-19, 2005.
Miller, R. et al., "Review article imiquimod applied topically: a novel immune response modifier and new class of drug," Int. J. of Immunopharm., 21(1):1-14, 1999.
Monograph of Aldara Product (Feb. 3, 2004).
Muzio, G. et al., "Treatment of non-genital warts with topical imiquimod 5% Cream," Eur. J. Derm., 12:347-349, 2002.
Office Action issued in Peruvian Patent Application No. 1323, dated Jul. 15, 2013, 46 pages.
Office Action dated May 4, 2010 in U.S. Appl. No. 12/028,771.
Ooi, T. et al., "Imiquimod-induced regression of actinic keratosis is associated with infiltration by T lymphocytes and dendritic cells: a randomized controlled trial," Br. J. Dermatol., 154(1):72-8, 2006.
Oster-Schmidt, C. et al., "Solar keratosis: From precancerous lesion to pre-invasive squamous cell carcinoma—Therapeutic approach with a bioinductive method," .JDDG; 2003; 1:790-796.
Panama—Report on State of Art—foreign counterpart application No. 88551.
Papadavid, E. et al., "Imiquimod: an immune response modifier in the treatment of precancerous skin lesions and skin cancer," Expert Opin. Pharmacother., 8(11):1743-55, 2007.
Partial translation of Panama Report—foreign counterpart application No. 88551.
Perras, C., "Imiquimod 5% cream for actinic keratosis," Issues Emerg. Health Technol., 61:1-4, 2004.
Persaud, A. et al., "Clinical effect of imiquimod 5% cream in the treatment of actinic keratosis," J. Am. Acad. Dermatol., 47(4):553-6, 2002.
Persaud, A. et al., "Imiquimod cream in the treatment of actinic keratoses," J. Am. Acad. Dermatol., 47(4 Suppl): S236-9, 2002.
Peters-Kennedy, J. et al., "Apparent clinical resolution of pinnal actinic keratoses and squamous cell carcinoma in a cat using topical imiquimod 5% cream," J Feline Med. Surg., 10(6):593-9, 2008.
Price, N., The Treatment of Actinic Keratoses with a Combination of 5-Fluormouracil and Imiquimod Creams, Journal of Drugs in Dermatology, 2007; 6(8):778-781.
Quirk, C. et al., "Two-year interim results from a 5-year study evaluating clinical recurrence of superficial basal cell carcinoma after treatment with imiquimod 5% cream daily for 6 weeks," Aus. J. Derm., 47:258-265, 2006.
Ray, C.M. et al., "Successful treatment of malignant melanoma in situ with topical 5% imiquimod cream," International Journal of Dermatology 2005; 44: 428-434.
Redacted Third-Party Correspondence dated Aug. 7, 2012, 34 pages.
Rivers, J. et al., "Open-label study to assess the safety and efficacy of imiquimod 5% cream applied once daily three times per week in cycles for treatment of actinic keratoses on the head," J. Cutaneous Med. Surgery, 12(3):97-101, 2008.
Salasche, S. et al., "Cycle therapy of actinic keratoses of the face and scalp with 5% topical imiquimod cream: An open-label trial," J. Am. Acad. Dermatol., 47(4):571-7, 2002.
Sachse, M. et al., "Efficiency of topical irniquirnod 5% cream in the management of chronic radiation dermatitis with multiple neoplasias," Eur J Dennatol ;?006; 16 (1 ): 56-58.
Shaffelburg, M., "Treatment of actinic keratoses with sequential use of photodynamic therapy; and imiquimod 5% cream," J. Drugs Dermatol., 8(1):35-39, 2009.
Silapunt, Sirunya et al., "Topical and Light-based Treatments for Actinic Keratoses," Seminars in Cutaneous Medicine and Surgery, vol. 22, No. 3 Sep. 2003; 162-170.

(56) References Cited

OTHER PUBLICATIONS

Skinner, R., "Role of topical therapies in the management of cutaneous disease," J. Cutan. Med. Surg., 8(Suppl 3):22-31, 2004.
Smith, K. et al., Topical 5% imiquimod for the therapy of actinic cheilitis, JAm Acad Dermatol, 2002; 4 7(4): 497-501.
Smith, K. et al., "Does Imiquimod Histologically Rejuvenate Ultraviolet Radiation-Damaged Skin?," Derrnatol. Surg., 33:1419-1429, 2007.
Somani, N. et al., "Imiquimod 5% Cream for the Treatment of Actinic Keratoses," Skin Therapy Letter, vol. 10, No. 2, Mar. 2005, 1-10.
Sotiriou, E. et al., "Intraindividual, right-left comparison of topical 5-aminolevulinic acid photodynamic therapy vs. 5% imiquimod cream for actinic keratoses on the upper extremities," J. Eur. Acad. Dermatol. Venereol., 23(9):1061-5, 2009.
Stockfleth, E. et al., "A randomized, double-blind, vehicle-controlled study to assess 5% imiquimod cream for the treatment of multiple actinic keratoses," Arch. Dermatol., 138(11):1498-502, 2002.
Stockfleth, E. et al., "Multicentre, open-label study using imiquimod 5% cream in one or two 4-week courses of treatment for multiple actinic keratoses on the head," Br. J. Dermatol., 157(Suppl 2):41-6, 2007.
Stockfleth, E. et al., "Treatment of multiple, multiform actinic keratoses on the head with imiquimod 5% cream," Eur. J. Dermatol., 19(4):355-9, 2009.
Stockfleth, E. et al., "Successful treatment of actinic keratosis with imiquimod cream 5%: a report of six cases," Br. J. Dermatol., 144(5):1050-3, 2001.
Stockfleth, E., "Topical management of actinic keratosis and field cancerisation," G. Ital. Dermatol. Venereol., 144(4):459-62, 2009.
Swanson, N. et al., "Optimizing imiquimod for actinic keratoses on face or scalp: imiquimod 2.5% and 3.75% daily for two 2-week or 3-week cycles," The 12th World Congress on Cancers of the Skin, Presentation Date: May 4, 2009.
Swanson, N. et al., "Imiquimod 2.5% and 3.75% for the treatment of actinic keratosis: Results of two placebo-controlled studies of daily application to the face and balding scalp for two 2-week cycles," Journal of the American Academy of Dermatology, V.V. Mosby, St. Louis, Mo., vol. 62, No. 4, Apr. 1, 2010, pp. 582-590.
Syed et al., "Treatment of genital herpes in males with imiquimod 1% cream a randomised, double-blind, placebo-controlled study," Clin. Drug Invest., 16:187-191, 1998.
Syed, T. et al., "Management of female genital warts with an analog of imiquimod 2% in cream: a randomized, double-blind, placebo-controlled study," J. Dermatol., 25:429-33, 1998.
Syed, T. et al., "Treatment of external genital warts in men with imiquimod 2% in cream. A placebo-controlled, double-blind study," J. Infection, 41:148-151, 2000.
Szeimies, R. et al., "Imiquimod 5% cream for the treatment of actinic keratosis: results from a phase III, randomized, double-blind, vehicle-controlled, clinical trial with histology," J. Am. Acad. Dermatol., 51(4):547-55, 2004.
Tan, J. et al., "Efficacy of imiquimod as an adjunct to cryotherapy for actinic keratoses," J. Cutan. Med. Surg., 11(6):195-201, 2007.
Tanghetti, E. et al., "Comparison of 5% 5-fluorouracil cream and 5% imiquimod cream in the management of actinic keratoses on the face and scalp," J. Drugs Dermatol., 6(2):144-7, 2007.
Torres, A. et al., "Immune-mediated changes in actinic keratosis following topical treatment with imiquimod 5% cream," J. Transl. Med., 5(7):1-18, 2007.
Travis, L. et al., "Successful treatment of vulvar intraepitheilial neoplasia with topical imiquimod 5% cream in a lung transplanted patient," Acta Derm. Venereol., 82:475-6, 2002.
Tyring, S. et al., "A randomized, controlled, molecular study of condylomata acuminata clearance during treatment with imiquimod," J. Infect. Dis., 1998, 178(2):551-5.
Tyring, S., "Imiquimod applied topically: A novel immune response modifier," Skin Therapy Lett., 6(6)1-4, 2001.
Ulrich, C. et al., "Topical immunomodulation under systemic immunosuppression: results of a multicentre, randomized, placebo-controlled safety and efficacy study of imiquimod 5% cream for the treatment of actinic keratoses in kidney, heart, and liver transplant patients," Br. J. Dermatol., 157(Suppl 2):25-31, 2007.
Vidal, D., "Topical imiquimod: mechanism of action and clinical applications," Mini Rev. Med. Chem., 6(5):499-503, 2006.
Wagstaff, A. et al., "Topical imiquimod: a review of its use in the management of anogenital warts, actinic keratoses, basal cell carcinoma and other skin lesions," Drugs, 67(15):2187-210, 2007.
Walker, J. et al., "Is imiquimod effective and safe for actinic keratosis?," J. Fam. Pract., 52(3):84-5, 2003.
Wu, J. et al., "Treatment of Bowen's disease and basal cell carcinoma of the nose with imiquimod 5% cream," Australasian J. Dermatol., 44(2):123-125, 2003.
Wygledowska-Kania, M. et al., "Efficacy of precancerous lesions (precancerous Keratosis) treatment with 5% imiquimod cream," Clinical Dermatology, 2007; 9(4): 219-222.
Zeichner, J. et al., "Placebo-controlled, double-blind, randomized pilot study of imiquimod 5% cream applied once per week for 6 months for the treatment of actinic keratoses," J. Am. Acad. Dermatol., 60(1):59-62, 2009.

* cited by examiner

FIG. 1A

Summary of Primary and Secondary Efficacy Endpoints
2-Week Treatment Cycle Regimen
ITT Population

| | GW01-0702 | | | GW01-0704 | | |
|---|---|---|---|---|---|---|
| | 3.75% (N=81) | 2.5% (N=81) | Placebo (N=80) | 3.75% (N=79) | 2.5% (N=79) | Placebo (N=79) |
| Complete Clearance at End of Study | 21/81 (25.9) | 19/81 (23.5) | 2/80 (2.5) | 36/79 (45.6) | 30/79 (38.0) | 8/79 (10.1) |
| 95% confidence interval | 16.8, 36.9 | 14.8, 34.2 | 0.3, 8.7 | 34.3, 57.2 | 27.3, 49.6 | 4.5, 19.0 |
| P value vs Placebo | <.001** | <.001** | -- | <.001** | <.001** | -- |
| P value vs 2.5% Imiquimod Cream | 0.777 | -- | -- | 0.358 | -- | -- |
| Partial Clearance at End of Study | 37/81 (45.7) | 34/81 (42.0) | 15/80 (18.8) | 58/79 (73.4) | 43/79 (54.4) | 21/79 (26.6) |
| 95% confidence interval | 34.6, 57.1 | 31.1, 53.5 | 10.9, 29.0 | 62.3, 82.7 | 42.8, 65.7 | 17.3, 37.7 |
| P value vs Placebo | <.001** | <.001** | -- | <.001** | <.001** | -- |
| P value vs 2.5% Imiquimod Cream | 0.693 | -- | -- | 0.014** | -- | -- |
| Percent Change in Number of AK Lesions From Baseline to End of Study | | | | | | |
| N | 81 | 81 | 80 | 79 | 79 | 79 |
| Mean (Standard Deviation) | -59.7 (44.4) | -52.8 (42.4) | -22.7 (55.3) | -77.9 (40.5) | -65.9 (40.0) | -32.5 (48.5) |
| Median | -72.7 | -60.0 | -21.1 | -90.9 | -76.5 | -30.0 |
| Minimum, Maximum | -100.0 to 100.0 | -100.0 to 75.0 | -100.0 to 300.0 | -100.0 to 188.9 | -100.0 to 90.0 | -100.0 to 91.7 |
| P value vs Placebo | <.001** | <.001** | | <.001** | <.001** | |
| P value vs 2.5% Imiquimod Cream | 0.336 | | | 0.060 | | |

Rate of Complete Clearance vs Study Week
ITT Population

Rate of Complete Clearance vs Study Week
ITT Population

Efficacy Measures:
Mean% Change from Baseline Count by Study

FIG. 10A

Summary of Primary and Secondary Efficacy Endpoints
Subpopulations - Sex
Combined 2-Week Treatment Cycle Studies (GW01-0702 and GW01-0704, ITT Population)

| | Male | | | | Female | | |
|---|---|---|---|---|---|---|---|
| | 3.75% (N=132) | 2.5% (N=127) | Placebo (N=130) | | 3.75% (N=28) | 2.5% (N=33) | Placebo (N=29) |
| Complete Clearance at End of Study, n (%) | 46/132 (34.8) | 29/127 (22.8) | 6/130 (4.6) | | 11/28 (39.3) | 20/33 (60.6) | 4/29 (13.8) |
| 95% confidence interval | 26.8, 43.6 | 15.9, 31.1 | 1.7, 9.8 | | 21.5, 59.4 | 42.1, 77.1 | 3.9, 31.7 |
| P value (dose) | - | - | - | <.001 | - | - | - |
| P value (subpopulation) | - | - | - | 0.002 | - | - | - |
| P value (interaction) | - | - | - | 0.044 | - | - | - |
| Partial Clearance at End of Study, n (%) | 79/132 (59.8) | 55/127 (43.3) | 26/130 (20.0) | | 16/28 (57.1) | 22/33 (66.7) | 10/29 (34.5) |
| 95% confidence interval | 51.0, 68.3 | 34.5, 52.4 | 13.5, 27.9 | | 37.2, 75.5 | 48.2, 82.0 | 17.9, 54.3 |
| P value (dose) | - | - | - | <.001 | - | - | - |
| P value (subpopulation) | - | - | - | 0.031 | - | - | - |
| P value (interaction) | - | - | - | 0.164 | - | - | - |
| Percent Change in Number of AK Lesions from Baseline to End of Study | | | | | | | |
| N | 132 | 127 | 130 | | 28 | 33 | 29 |
| Median | -80.9 | -66.7 | -22.2 | | -88.2 | -100.0 | -50.0 |
| Mean (SD) | -69.1 (42.6) | -54.2 (42.5) | -24.8 (52.7) | | -66.9 (47.5) | -78.7 (31.3) | -39.7 (48.2) |
| P value (dose) | - | - | - | <.001 | - | - | - |
| P value (subpopulation) | - | - | - | 0.021 | - | - | - |
| P value (interaction) | - | - | - | 0.118 | - | - | - |

FIG. 10B

Summary of Primary Efficacy Variable,
Rate of Complete Clearance at Week 17 (End of Study)
Subgroup Analysis
n/N(%)

| | Imiquimod Cream | | | |
|---|---|---|---|---|
| | 2.5% (N=82) | 3.75 (N=80) | Placebo (N=78) | Combined (N=240) |
| Sex | | | | |
| Male | 15/62 (24.2) | 21/63 (33.3) | 4/63 (6.3) | 40/188 (21.3) |
| Female | 4/20 (20.0) | 5/17 (29.4) | 0/15 (0.0) | 9/52 (17.3) |
| Age | | | | |
| < 65 | 6/37 (16.2) | 19/44 (43.2) | 3/44 (6.8) | 28/125 (22.4) |
| >=65 | 13/45 (28.9) | 7/36 (19.4) | 1/34 (2.9) | 21/115 (18.3) |
| Skin Type | | | | |
| Type I or II | 12/43 (27.9) | 12/42 (28.6) | 2/39 (5.1) | 26/124 (21.0) |
| Type III, IV, or V | 7/39 (17.9) | 14/38 (36.8) | 2/39 (5.1) | 23/116 (19.8) |
| Baseline Lesion Count | | | | |
| <=10 | 15/48 (31.3) | 18/40 (45.0) | 3/40 (7.5) | 36/128 (28.1) |
| >10 | 4/34 (11.8) | 8/40 (20.0) | 1/38 (2.6) | 13/112 (11.6) |
| Treatment Area | | | | |
| Face | 16/63 (25.4) | 20/54 (37.0) | 1/60 (1.7) | 37/177 (20.9) |
| Scalp | 3/19 (15.8) | 6/26 (23.1) | 3/18 (16.7) | 12/63 (19.0) |

FIG. 10C

Summary of Primary Efficacy Variable,
Rate of Complete Clearance at Week 17 (End of Study)
Subgroup Analysis
n/N(%)

| | Imiquimod Cream | | | |
|---|---|---|---|---|
| | 2.5% (N=82) | 3.75 (N=82) | Placebo (N=86) | Combined (N=250) |
| Sex | | | | |
| Male | 16/66 (24.2) | 20/60 (33.3) | 5/72 (6.9) | 41/198 (20.7) |
| Female | 6/16 (37.5) | 9/22 (40.9) | 0/14 (0.0) | 15/52 (28.8) |
| Age | | | | |
| < 65 | 9/38 (23.7) | 19/50 (38.0) | 2/42 (4.8) | 30/130 (23.1) |
| >=65 | 13/44 (29.5) | 10/32 (31.3) | 3/44 (6.8) | 26/120 (21.7) |
| Skin Type | | | | |
| Type I or II | 12/40 (30.0) | 22/58 (37.9) | 5/51 (9.8) | 39/149 (26.2) |
| Type III, IV, or V | 10/42 (23.8) | 7/24 (29.2) | 0/35 (0.0) | 17/101 (16.8) |
| Baseline Lesion Count | | | | |
| <=10 | 17/50 (34.0) | 19/51 (37.3) | 4/59 (6.8) | 40/160 (25.0) |
| >10 | 5/32 (15.6) | 10/31 (32.3) | 1/27 (3.7) | 16/90 (17.8) |
| Treatment Area | | | | |
| Face | 14/52 (26.9) | 22/61 (36.1) | 3/62 (4.8) | 39/175 (22.3) |
| Scalp | 8/30 (26.7) | 7/21 (33.3) | 2/24 (8.3) | 17/75 (22.7) |

FIG. 13A

Summary of Percent Change from Baseline in Number of AK Lesions
By Visit
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Week 1 | | | | | | |
| N | 160 | 160 | 159 | 162 | 164 | 164 |
| Mean (Standard Deviation) | 56.1 (86.2) | 44.2 (72.2) | 4.5 (29.2) | 47.5 (103.1) | 22.8 (54.2) | 4.4 (24.4) |
| Median | 19.1 | 14.3 | 0.0 | 0.0 | 0.0 | 0.0 |
| Minimum, Maximum | -66.7 to 533.3 | -40.0 to 400.0 | -80.0 to 133.3 | -33.3 to 771.4 | -66.7 to 290.0 | -55.6 to 183.3 |
| P value vs Placebo | <.001** | <.001** | - | <.001** | <.001** | - |
| P value vs 2.5% Imiquimod Cream | 0.235 | - | - | 0.006** | - | - |
| Week 2 | | | | | | |
| N | 160 | 160 | 159 | 162 | 164 | 164 |
| Mean (Standard Deviation) | 109.0 (141.3) | 76.7 (102.3) | 6.4 (42.9) | 113.0 (185.8) | 55.4 (98.1) | 6.0 (30.8) |
| Median | 66.7 | 40.0 | 0.0 | 26.4 | 15.2 | 0.0 |
| Minimum, Maximum | -66.7 to 950.0 | -60.0 to 511.1 | -72.7 to 190.9 | -33.3 to 1042.9 | -57.1 to 537.5 | -83.3 to 150.0 |
| P value vs Placebo | <.001** | <.001** | - | <.001** | <.001** | - |
| P value vs 2.5% Imiquimod Cream | 0.025** | - | - | 0.006** | - | - |

FIG. 13B

Summary of Percent Change from Baseline in Number of AK Lesions
By Visit
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Week 3 | | | | | | |
| N | - | - | - | 162 | 164 | 164 |
| Mean (Standard Deviation) | - | - | - | 123.8 (195.6) | 70.2 (116.4) | 3.2 (38.5) |
| Median | - | - | - | 43.7 | 21.1 | 0.0 |
| Minimum, Maximum | - | - | - | -100.0 to 1042.9 | -100.0 to 537.5 | -100.0 to 233.3 |
| P value vs Placebo | - | - | - | <.001** | <.001** | - |
| P value vs 2.5% Imiquimod Cream | - | - | - | 0.006** | - | - |
| Week 4 | | | | | | |
| N | 160 | 160 | 159 | - | - | - |
| Mean (Standard Deviation) | -3.4 (61.2) | -2.4 (55.2) | -7.4 (39.6) | - | - | - |
| Median | -13.4 | -5.6 | 0.0 | - | - | - |
| Minimum, Maximum | -100.0 to 250.0 | -100.0 to 162.5 | -100.0 to 142.9 | - | - | - |
| P value vs Placebo | 0.478 | 0.333 | - | - | - | - |
| P value vs 2.5% Imiquimod Cream | 0.806 | - | - | - | - | - |

FIG. 13C

Summary of Percent Change from Baseline in Number of AK Lesions
By Visit
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Week 5 | | | | | | |
| N | 160 | 160 | 159 | - | - | - |
| Mean (Standard Deviation) | 14.0 (77.5) | 1.3 (59.4) | -3.9 (50.7) | - | - | - |
| Median | 0.0 | 0.0 | -5.0 | - | - | - |
| Minimum, Maximum | -100.0 to 412.5 | -100.0 to 287.5 | -100.0 to 260.0 | - | - | - |
| P value vs Placebo | 0.015** | 0.413 | - | - | - | - |
| P value vs 2.5% Imiquimod Cream | 0.102 | - | - | - | - | - |
| Week 6 | | | | | | |
| N | 160 | 160 | 159 | 162 | 164 | 164 |
| Mean (Standard Deviation) | 66.8 (148.2) | 34.3 (104.1) | -10.3 (46.6) | -21.1 (102.9) | -29.4 (53.3) | -10.5 (36.4) |
| Median | 29.0 | 0.0 | -7.1 | -40.0 | -33.3 | -8.3 |
| Minimum, Maximum | -100.0 to 933.3 | -100.0 to 583.3 | -100.0 to 228.6 | -100.0 to 900.0 | -100.0 to 187.5 | -100.0 to 137.5 |
| P value vs Placebo | <.001** | <.001** | - | <.001** | <.001** | - |
| P value vs 2.5% Imiquimod Cream | 0.024** | - | - | 0.006** | - | - |

FIG. 13D

Summary of Percent Change from Baseline in Number of AK Lesions
By Visit
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Week 7 | | | | | | |
| N | - | - | - | 162 | 164 | 164 |
| Mean (Standard Deviation) | - | - | - | -5.1 (122.9) | -25.5 (54.7) | -5.9 (40.9) |
| Median | - | - | - | -33.3 | -29.3 | 0.0 |
| Minimum, Maximum | - | - | - | -100.0 to 900.0 | -100.0 to 180.0 | -100.0 to 160.0 |
| P value vs Placebo' | - | - | - | <.001** | <.001** | - |
| P value vs 2.5% Imiquimod Cream | - | - | - | 0.006** | - | - |
| Week 8 | | | | | | |
| N | - | - | - | 162 | 164 | 164 |
| Mean (Standard Deviation) | - | - | - | 23.6 (151.2) | -6.9 (85.3) | -7.5 (44.9) |
| Median | - | - | - | -20.0 | -20.5 | 0.0 |
| Minimum, Maximum | - | - | - | -100.0 to 742.9 | -100.0 to 600.0 | -100.0 to 165 |
| P value vs Placebo | - | - | - | <.001** | <.001** | - |
| P value vs 2.5% Imiquimod Cream | - | - | - | 0.006** | - | - |

FIG. 13E

Summary of Percent Change from Baseline in Number of AK Lesions
By Visit
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Week 9 | | | | | | |
| N | - | - | - | 162 | 164 | 164 |
| Mean (Standard Deviation) | - | - | - | 48.1 (180.6) | 13.7 (144.3) | -12.8 (42.8) |
| Median | - | - | - | -14.3 | -17.9 | -7.4 |
| Minimum, Maximum | - | - | - | -100.0 to 957.1 | -100.0 to 1442.9 | -100.0 to 180.0 |
| P value vs Placebo | - | - | - | <.001** | <.001** | - |
| P value vs 2.5% Imiquimod Cream | - | - | - | 0.006** | - | - |
| Week 10 | | | | | | |
| N | 160 | 160 | 159 | - | - | - |
| Mean (Standard Deviation) | -58.2 (47.7) | -52.3 (42.3 | -25.7 (44.8) | - | - | - |
| Median | -72.7 | -40.0 | -25.0 | - | - | - |
| Minimum, Maximum | -100.0 to 188.9 | -100.0 to 120.0 | -100.0 to 220.0 | - | - | - |
| P value vs Placebo | <.001** | <.001** | - | - | - | - |
| P value vs 2.5% Imiquimod Cream | 0.216 | - | - | - | - | - |

FIG. 13F

Summary of Percent Change from Baseline in Number of AK Lesions
By Visit
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Week 13 | | | | | | |
| N | - | - | - | 162 | 164 | 164 |
| Mean (Standard Deviation) | - | - | - | -58.0 (44.9) | -54.9 (46.7) | -17.7 (46.0) |
| Median | - | - | - | -66.7 | -66.7 | -14.3 |
| Minimum, Maximum | - | - | - | -100.0 to 160 | -100.0 to 192.9 | -100.0 to 180.0 |
| P value vs Placebo | - | - | - | <.001** | <.001** | - |
| P value vs 2.5% Imiquimod Cream | - | - | - | 0.006** | - | - |
| Week 14 | | | | | | |
| N | 160 | 160 | 159 | - | - | - |
| Mean (Standard Deviation) | -66.7 (43.4) | -59.2 (41.6) | -27.6 (52.1) | - | - | - |
| Median | -81.8 | -71.8 | -25.0 | - | - | - |
| Minimum, Maximum | -100.0 to 188.9 | -100.0 to 90.0 | -100.0 to 300.0 | - | - | - |
| P value vs Placebo | <.001** | <.001** | - | - | - | - |
| P value vs 2.5% Imiquimod Cream | 0.048** | - | - | - | - | - |

FIG. 13G

Summary of Percent Change from Baseline in Number of AK Lesions
By Visit
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Week 17 | | | | | | |
| N | - | - | - | 162 | 164 | 164 |
| Mean (Standard Deviation) | - | - | - | -64.3 (43.0) | -57.0 (45.4) | -24.5 (47.0) |
| Median | - | - | - | -80.0 | -66.7 | -23.6 |
| Minimum, Maximum | - | - | - | -100.0 to 160 | -100.0 to 183.3 | -100.0 to 200.0 |
| P value vs Placebo | - | - | - | <.001** | <.001** | - |
| P value vs 2.5% Imiquimod Cream | - | - | - | 0.006** | - | - |

FIG. 14A

Summary of Treatment-emergent Adverse Events
n(%) of Subjects in Descending Order of Incidence in the 3.75% 2-Week Treatment Cycle Group
Adverse Events Considered Treatment-Related by the Investigator
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Any Treatment-Related AE | 31 (19.4%) | 19 (11.9%) | 4 (2.5%) | 60 (37.0%) | 44 (26.8%) | 4 (2.4%) |
| Application site pruritus | 7 (4.4) | 6 (3.8) | 1 (0.6) | 14 (8.6) | 12 (7.3) | 1 (0.6) |
| Application site irritation | 5 (3.1) | 4 (2.5) | 0 | 9 (5.6) | 6 (3.7) | 1 (0.6) |
| Application site pain | 5 (3.1) | 2 (1.3) | 0 | 15 (9.3) | 11 (6.7) | 0 |
| Fatigue | 4 (2.5) | 0 | 0 | 7 (4.3) | 5 (3.0) | 0 |
| Headache | 4 (2.5) | 1 (0.6) | 2 (1.3) | 4 (2.5) | 4 (2.4) | 0 |
| Dizziness | 3 (1.9) | 0 | 0 | 0 | 0 | 0 |
| Lymphadenopathy | 3 (1.9) | 3 (1.9) | 0 | 5 (3.1) | 4 (2.4) | 0 |
| Nausea | 3 (1.9) | 1 (0.6) | 0 | 2 (1.2) | 1 (0.6) | 0 |
| Application site swelling | 2 (1.3) | 0 | 0 | 1 (0.6) | 3 (1.8) | 0 |
| Arthralgia | 2 (1.3) | 0 | 0 | 0 | 1 (0.6) | 0 |
| Pain | 2 (1.3) | 0 | 0 | 0 | 0 | 0 |
| Pyrexia | 2 (1.3) | 0 | 0 | 5 (3.1) | 0 | 0 |
| Anorexia | 1 (0.6) | 0 | 0 | 0 | 0 | 0 |
| Application site paraesthesia | 1 (0.6) | 0 | 1 (0.6) | 0 | 0 | 0 |
| Application site scar | 1 (0.6) | 0 | 0 | 0 | 0 | 0 |
| Chills | 1 (0.6) | 0 | 0 | 2 (1.2) | 1 (0.6) | 0 |

FIG. 14B

Summary of Treatment-emergent Adverse Events
n(%) of Subjects in Descending Order of Incidence in the 3.75% 2-Week Treatment Cycle Group
Adverse Events Considered Treatment-Related by the Investigator
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Decreased appetite | 1 (0.6) | 0 | 0 | 0 | 0 | 0 |
| Dermatitis | 1 (0.6) | 0 | 0 | 0 | 0 | 0 |
| Diarrhoea | 1 (0.6) | 0 | 0 | 0 | 0 | 0 |
| Herpes simplex | 1 (0.6) | 0 | 0 | 2 (1.2) | 2 (1.2) | 0 |
| Inflammation | 1 (0.6) | 0 | 0 | 0 | 0 | 0 |
| Influenza like illness | 1 (0.6) | 4 (2.5) | 0 | 12 (7.4) | 6 (3.7) | 0 |
| Lethargy | 1 (0.6) | 1 (0.6) | 0 | 2 (1.2) | 0 | 0 |
| Musculoskeletal stiffness | 1 (0.6) | 1 (0.6) | 0 | 0 | 0 | 0 |
| Pruritus | 1 (0.6) | 0 | 0 | 1 (0.6) | 0 | 0 |
| Rash papular | 1 (0.6) | 0 | 0 | 0 | 0 | 0 |
| Sunburn | 1 (0.6) | 0 | 0 | 0 | 0 | 0 |
| Upper respiratory tract infection | 1 (0.6) | 0 | 1 (0.6) | 0 | 0 | 0 |
| Aphthous stomatitis | 0 | 1 (0.6) | 0 | 0 | 1 (0.6) | 0 |
| Application site dryness | 0 | 1 (0.6) | 0 | 0 | 0 | 0 |
| Application site infection | 0 | 1 (0.6) | 0 | 0 | 1 (0.6) | 0 |
| Cheilitis | 0 | 3 (1.9) | 0 | 3 (1.9) | 1 (0.6) | 1 (0.6) |
| Myalgia | 0 | 1 (0.6) | 0 | 3 (1.9) | 0 | 0 |
| Oral herpes | 0 | 1 (0.6) | 0 | 1 (0.6) | 2 (1.2) | 0 |

FIG. 14C

Summary of Treatment-emergent Adverse Events
n(%) of Subjects in Descending Order of Incidence in the 3.75% 2-Week Treatment Cycle Group
Adverse Events Considered Treatment-Related by the Investigator
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Abdominal discomfort | 0 | 0 | 0 | 0 | 1 (0.6) | 0 |
| Abnormal sensation in eye | 0 | 0 | 0 | 0 | 0 | 1 (0.6) |
| Anxiety | 0 | 0 | 0 | 0 | 1 (0.6) | 0 |
| Anxiety disorder | 0 | 0 | 0 | 0 | 1 (0.6) | 0 |
| Application site bleeding | 0 | 0 | 0 | 5 (3.1) | 2 (1.2) | 0 |
| Application site burn | 0 | 0 | 0 | 0 | 1 (0.6) | 0 |
| Application site dermatitis | 0 | 0 | 0 | 1 (0.6) | 0 | 0 |
| Application site discolouration | 0 | 0 | 0 | 1 (0.6) | 0 | 0 |
| Application site discomfort | 0 | 0 | 0 | 2 (1.2) | 0 | 0 |
| Application site erythema | 0 | 0 | 0 | 2 (1.2) | 0 | 0 |
| Application site exfoliation | 0 | 0 | 0 | 0 | 1 (0.6) | 0 |
| Application site hypersensitivity | 0 | 0 | 0 | 1 (0.6) | 2 (1.2) | 0 |
| Application site photosensitivity reaction | 0 | 0 | 0 | 0 | 1 (0.6) | 0 |
| Application site reaction | 0 | 0 | 0 | 1 (0.6) | 1 (0.6) | 0 |
| Application site scab | 0 | 0 | 0 | 1 (0.6) | 0 | 0 |
| Application site vesicles | 0 | 0 | 0 | 1 (0.6) | 0 | 0 |
| Blood glucose increased | 0 | 0 | 0 | 1 (0.6) | 1 (0.6) | 0 |
| Burning sensation | 0 | 0 | 0 | 0 | 1 (0.6) | 0 |

FIG. 14D

Summary of Treatment-emergent Adverse Events
n(%) of Subjects in Descending Order of Incidence in the 3.75% 2-Week Treatment Cycle Group
Adverse Events Considered Treatment-Related by the Investigator
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Disturbance in attention | 0 | 0 | 0 | 0 | 1 (0.6) | 0 |
| Dysgeusia | 0 | 0 | 0 | 0 | 1 (0.6) | 0 |
| Dysphonia | 0 | 0 | 0 | 2 (1.2) | 0 | 0 |
| Eye irritation | 0 | 0 | 0 | 1 (0.6) | 0 | 1 (0.6) |
| Flushing | 0 | 0 | 0 | 0 | 1 (0.6) | 0 |
| Gastroenteritis | 0 | 0 | 0 | 1 (0.6) | 0 | 0 |
| Herpes zoster | 0 | 0 | 0 | 2 (1.2) | 0 | 0 |
| Hypersensitivity | 0 | 0 | 0 | 0 | 1 (0.6) | 0 |
| Impetigo | 0 | 0 | 0 | 0 | 2 (1.2) | 0 |
| Influenza | 0 | 0 | 0 | 1 (0.6) | 1 (0.6) | 0 |
| Lip edema | 0 | 0 | 0 | 0 | 1 (0.6) | 0 |
| Lip pain | 0 | 0 | 0 | 0 | 1 (0.6) | 0 |
| Lip swelling | 0 | 0 | 0 | 0 | 1 (0.6) | 0 |
| Muscle spasms | 0 | 0 | 0 | 1 (0.6) | 0 | 0 |
| Musculoskeletal pain | 0 | 0 | 0 | 1 (0.6) | 0 | 0 |
| Pain of skin | 0 | 0 | 0 | 1 (0.6) | 0 | 0 |
| Pancytopenia | 0 | 0 | 0 | 1 (0.6) | 0 | 0 |
| Periorbital edema | 0 | 0 | 0 | 1 (0.6) | 2 (1.2) | 0 |

FIG. 14E

Summary of Treatment-emergent Adverse Events
n(%) of Subjects in Descending Order of Incidence in the 3.75% 2-Week
Treatment Cycle Group
Adverse Events Considered Treatment-Related by the Investigator
Combined Studies, ITT Population

|  | 2-Week Treatment Cycle Regimen | | | 3-Week Treatment Cycle Regimen | | |
|---|---|---|---|---|---|---|
|  | 3.75% (N=160) | 2.5% (N=160) | Placebo (N=159) | 3.75% (N=162) | 2.5% (N=164) | Placebo (N=164) |
| Rash erythematous | 0 | 0 | 0 | 0 | 1 (0.6) | 0 |
| Skin irritation | 0 | 0 | 0 | 1 (0.6) | 0 | 0 |
| Skin tightness | 0 | 0 | 0 | 1 (0.6) | 0 | 0 |
| Sleep disorder | 0 | 0 | 0 | 0 | 1 (0.6) | 0 |
| Tenderness | 0 | 0 | 0 | 0 | 1 (0.6) | 0 |
| Viral skin infection | 0 | 0 | 0 | 1 (0.6) | 0 | 0 |
| Vision blurred | 0 | 0 | 0 | 1 (0.6) | 0 | 0 |

FIG. 16A

Summary of Local Skin Reactions (LSR)
Most Severe Reaction Grade During Study
Overall
Combined Studies, ITT Population

| | 2-Week Treatment Cycle Regimen | | | 3-Week Treatment Cycle Regimen | | |
|---|---|---|---|---|---|---|
| | 3.75% (N-160) | 2.5% (N-160) | Placebo (N-159) | 3.75% (N-162) | 2.5% (N-164) | Placebo (N-164) |
| Erythema | | | | | | |
| N | 159 | 160 | 159 | 161 | 163 | 162 |
| 0 = None | 5 (3.1) | 6 (3.8) | 35 (22.0) | 3 (1.9) | 3 (1.8) | 13 (8.0) |
| 1 = Faint to mild redness | 22 (13.8) | 41 (25.6) | 92 (57.9) | 19 (11.8) | 26 (16.0) | 106 (65.4) |
| 2 = Moderate redness | 92 (57.9) | 90 (56.3) | 32 (20.1) | 67 (41.6) | 88 (54.0) | 43 (26.5) |
| 3 = Intense redness | 40 (25.2 ) | 23 (14.4) | 0 (0.0) | 72 (44.7) | 46 (28.2) | 0 (0.0) |
| >0 (any reaction) | 154 (96.3%) | 154 (96.3%) | 124 (78.0%) | 158 (97.5%) | 160 (97.6%) | 149 (90.9%) |
| Mean Score (SD) | 2.05 (0.72) | 1.81 (0.72) | 0.98 (0.65) | 2.29 (0.75) | 2.09 (0.71) | 1.19 (0.56) |
| Edema | | | | | | |
| N | 159 | 160 | 159 | 161 | 163 | 162 |
| 0 = None | 39 (24.5) | 59 (36.9) | 128 (80.5) | 37 (23.0) | 43 (26.4) | 126 (77.8) |
| 1 = Mild visible or barely palpable Swelling/induration | 64 (40.3) | 56 (35.0) | 29 (18.2) | 53 (32.9) | 60 (36.8) | 33 (20.4) |
| 2 = Easily palpable swelling/induration | 47 (29.6) | 39 (24.4) | 2 (1.3) | 50 (31.1) | 48 (29.4) | 3 (1.9) |
| 3 = Gross swelling/induration | 9 (5.7) | 6 (3.8) | 0 (0.0) | 21 (13.0) | 12 (7.4) | 0 (0.0) |
| >0 (any reaction) | 120 (75.0%) | 101 (63.1%) | 31 (19.5%) | 124 (76.5%) | 120 (73.2%) | 36 (22.0%) |
| Mean Score (SD) | 1.16 (0.86) | 0.95 (0.87) | 0.21 (0.44) | 1.34 (0.98) | 1.18 (0.91) | 0.24 (0.47) |

FIG. 16B

Summary of Local Skin Reactions (LSR)
Most Severe Reaction Grade During Study
Overall
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Weeping/Exudate | | | | | | |
| N | 159 | 160 | 159 | 161 | 163 | 162 |
| 0 = None | 78 (49.1) | 97 (60.6) | 153 (96.2) | 51 (31.7) | 72 (44.2) | 148 (91.4) |
| 1 = Minimal exudate | 54 (34.0) | 46 (28.8) | 6 (3.8) | 60 (37.3) | 44 (27.0) | 14 (8.6) |
| 2 = Moderate exudate | 18 (11.3) | 15 (9.4) | 0 (0.0) | 34 (21.1) | 35 (21.5) | 0 (0.0) |
| 3 = Heavy exudate | 9 (5.7) | 2 (1.3) | 0 (0.0) | 16 (9.9) | 12 (7.4) | 0 (0.0) |
| >0 (any reaction) | 81 (50.6%) | 63 (39.4%) | 6 (3.8%) | 110 (67.9%) | 91 (55.5%) | 14 (8.5%) |
| Mean Score (SD) | 0.74 (0.87) | 0.51 (0.72) | 0.04 (0.19) | 10.9 (0.96) | 0.92 (0.97) | 0.09 (0.28) |
| Flaking/Scaling/Dryness | | | | | | |
| N | 159 | 160 | 159 | 161 | 163 | 162 |
| 0 = None | 12 (7.5) | 19 (11.9) | 36 (22.6) | 4 (2.5) | 8 (4.9) | 18 (11.1) |
| 1 = Mild dryness/flaking | 72 (45.3) | 78 (48.8) | 89 (56.0) | 60 (37.3) | 66 (40.5) | 107 (66.0) |
| 2 = Moderate dryness/flaking | 62 (39.0) | 56 (35.0) | 32 (20.1) | 76 (47.2) | 71 (43.6) | 37 (22.8) |
| 3 = Severe dryness/flaking | 13 (8.2) | 7 (4.4) | 2 (1.3) | 21 (13.0) | 18 (11.0) | 0 (0.0) |
| >0 (any reaction) | 147 (91.9%) | 141 (88.1%) | 123 (77.4%) | 157 (96.9%) | 155 (94.5%) | 144 (87.8%) |
| Mean Score (SD) | 1.48 (0.75) | 1.32 (0.74) | 1.00 (0.69) | 1.71 (0.72) | 1.61 (0.75) | 1.12 (0.57) |

FIG. 16C

Summary of Local Skin Reactions (LSR)
Most Severe Reaction Grade During Study
Overall
Combined Studies, ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Scabbing/Crusting | | | | | | |
| N | 159 | 160 | 159 | 161 | 163 | 162 |
| 0 = None | 10 (6.3) | 25 (15.6) | 87 (54.7) | 8 (5.0) | 12 (7.4) | 96 (59.3) |
| 1 = Crusting | 46 (28.9) | 54 (33.8) | 67 (42.1) | 35 (21.7) | 49 (30.1) | 58 (35.8) |
| 2 = Serous scab | 81 (50.9) | 66 (41.3) | 5 (3.1) | 62 (38.5 | 65 (39.9) | 8 (4.9) |
| 3 = Eschar | 22 (13.8) | 15 (9.4) | 0 (0.0) | 56 (34.8) | 37 (22.7) | 0 (0.0) |
| >0 (any reaction) | 149 (93.1%) | 135 (84.4%) | 72 (45.3%) | 153 (94.4%) | 151 (92.1%) | 66 (40.2%) |
| Mean Score (SD) | 1.72 (0.78) | 1.44 (0.87) | 0.48 (0.56) | 2.03 (0.88) | 1.78 (0.88) | 0.46 (0.59) |
| Erosion/Ulceration | | | | | | |
| N | 159 | 160 | 159 | 161 | 163 | 162 |
| 0 = None | 60 (37.7) | 76 (47.5) | 145 (91.2) | 33 (20.5) | 44 (27.0) | 149 (92.0) |
| 1 = Erosion | 82 (51.6) | 69 (43.1) | 14 (8.8) | 79 (49.1) | 80 (49.1) | 13 (8.0) |
| 2 = Ulceration | 17 (10.7) | 15 (9.4) | 0 (0.0) | 49 (30.4) | 39 (23.9) | 0 (0.0) |
| >0 (any reaction) | 99 (61.9%) | 84 (52.5%) | 14 (8.8%) | 128 (79.0%) | 119 (72.6%) | 13 (7.9%) |
| Mean Score (SD) | 0.73 (0.64) | 0.62 (0.65) | 0.09 (0.28) | 1.10 (0.71) | 0.97 (0.72) | 0.08 (0.27) |

FIG. 17A

Summary of Local Skin Reactions (LSR)
Area Under the Curve of Sum of LSR Scores (Days)
Combined Studies, ITT Population

| | 2-Week Treatment Cycle Regimen | | | | 3-Week Treatment Cycle Regimen | | |
|---|---|---|---|---|---|---|---|
| | 3.75% (N=160) | 2.5% (N=160) | Placebo (N=159) | | 3.75% (N=162) | 2.5% (N=164) | Placebo (N=164) |
| $AUC_{Tot}$ | | | | | | | |
| N | 148 | 158 | 153 | | 152 | 155 | 160 |
| Mean (Standard Deviation) | 272.0(123.0) | 242.5 (126.2) | 139.8 (104.1) | | 413.5 (187.7) | 372.0 (180.6) | 188.6 (136.7) |
| Minimum, Maximum | 0.0 to 709.4 | 0.0 to 593.6 | 0.0 to 376.5 | | 0.0 to 1176 | 14.0 to 911.5 | 0.0 to 847.0 |
| P value (dose) | | | | <.001 | | | |
| P value (regimen) | | | | <.001 | | | |
| P value (analysis center) | | | | <.001 | | | |

LSR Mean Score vs Study Week
Erythema
ITT Population

FIG. 23

Summary of Safety Parameters
Combined Studies - ITT Population

| | 2-Week Treatment Cycle Regimen | | | 3-Week Treatment Cycle Regimen | | |
|---|---|---|---|---|---|---|
| | 3.75% | 2.5% | Placebo | 3.75% | 2.5% | Placebo |
| Total in Population | 160 | 160 | 159 | 162 | 164 | 164 |
| Requiring Rest Period | 17 (10.5) | 11 (6.9) | 0 (0.0) | 44 (27.2) | 28 (17.1) | 0 (0.0) |
| Discontinuing the Study Prematurely for Any Reason | 11 (6.9) | 6 (3.8) | 9 (5.7) | 10 (6.2) | 7 (4.3) | 10 (6.1) |
| Discontinuing the Study Prematurely for Safety Reasons | 2 (1.3) | 1 (0.6) | 3 (1.9) | 4 (2.5) | 2 (1.2) | 1 (0.6) |
| Any Adverse Event | 77 (48.1) | 70 (43.8) | 53 (33.3) | 97 (59.9) | 82 (50.0) | 53 (32.3) |
| Any Treatment-Related Event | 31 (19.4) | 19 (11.9) | 4 (2.5) | 60 (37.0) | 44 (26.8) | 4 (2.4) |
| Any Application Site Reaction | 17 (10.6) | 10 (6.3) | 2 (1.3) | 39 (24.1) | 28 (17.1) | 5 (3.0) |
| Any Serious Adverse Event | 5 (3.1) | 5 (3.1) | 2 (1.3) | 7 (4.3) | 4 (2.4) | 2 (1.2) |
| Any Severe Adverse Event | 6 (3.8) | 8 (5.0) | 2 (1.3) | 9 (5.6) | 6 (3.7) | 0 (0.0) |
| Any Severe LSR | 54 (33.8) | 33 (20.6) | 2 (1.3) | 89 (54.9) | 68 (41.5) | 0 (0.0) |

Improvement in Photodamage from Baseline

| Study | 2.5% Imiq | 3.75% Imiq | Pbo |
|---|---|---|---|
| 1 | 1.45 | 1.85 | 0.80 |
| 2 | 1.63 | 2.03 | 0.66 |

3 = Significant improvement

2 = Much improved

1 = Slightly improved

0 = No change from Baseline

-1 = Slightly worse

-2 = Much worse

-3 = Significantly worse

Summary of Primary and Secondary Efficacy Endpoints
Combined Studies, Analysis Within Regimen
ITT Population

| | 2-Week Treatment Cycle Regimen | | | 3-Week Treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Complete Clearance at End of Study | 57/160 (35.6) | 49/160 (30.60) | 10/159 (6.3) | 55/162 (34.0) | 41/164 (25.0) | 9/164 (5.5) |
| 95% confidence interval | 28.2, 43.6 | 23.6, 38.4 | 3.1, 11.3 | 26.7, 41.6 | 18.6, 32.3 | 2.5, 10.2 |
| P value vs Placebo | <.001** | <.001** | - | <.001** | <.001** | - |
| P value vs 2.5% Imiquimod Cream | 0.379 | - | - | 0.082 | - | - |
| | | | | | | |
| Partial Clearance at End of Study | 95/160 (59.4) | 77/160 (48.1) | 36/159 (22.6) | 87/162 (53.7) | 70/164 (42.7) | 21/164 (12.8) |
| 95% confidence interval | 51.3, 67.1 | 40.2, 56.2 | 16.4, 29.9 | 45.7, 61.6 | 35.0, 50.6 | 8.1, 18.9 |
| P value vs Placebo | <.001** | <.001** | - | <.001** | <.001** | - |
| P value vs 2.5% Imiquimod Cream | 0.047** | - | - | 0.034** | - | - |
| | | | | | | |
| Percent Change in Number of AK Lesions from Baseline to End Study | | | | | | |
| N | 160 | 160 | 159 | 162 | 164 | 164 |
| Mean (Standard Deviation) | -68.7 (43.4) | -59.2 (41.6) | -27.6 (52.1) | -64.3 (43.0) | -57.0 (45.4) | -24.5 (47.0) |
| Median | -81.8 | -71.8 | -25.0 | -80.0 | -66.7 | -23.6 |
| Minimum, Maximum | -100.0 to 188.9 | -100.0 to 90.0 | -100.0 to 300.0 | -100.0 to 160.0 | -100.0 to 183.3 | -100.0 to 200.0 |
| P value vs Placebo | <.001** | <.001** | - | <.001** | <.001** | - |
| P value vs 2.5% Imiquimod Cream | 0.048** | - | - | 0.133 | - | - |

FIG. 28

Safety Comparison:
Incidence of Adverse Events
Selected Common (%)

| | 2 Weeks | | | 3 Weeks | | | Aldara |
|---|---|---|---|---|---|---|---|
| | Pbo | 2.5% | 3.75% | Pbo | 2.5% | 3.75% | |
| Application site reaction | 1 | 6 | 11 | 3 | 17 | 24 | 33 |
| Headache | 3 | 2 | 6 | <1 | 4 | 5 | 5 |
| Flu-like illness | 0 | 4 | 1 | 0 | 4 | 8 | NS |
| Nasopharyngitis | 5 | 4 | 3 | <1 | 3 | 1 | NS |
| Upper Resp Tract Infxn | 4 | 3 | 3 | <1 | 2 | 3 | 15 |
| Fatigue | 0 | 1 | 4 | <1 | 3 | 5 | 1 |
| Sinusitis | 1 | 2 | 0 | 3 | 2 | 5 | 7 |
| Lymphadenopathy | 0 | 3 | 2 | 0 | 2 | 4 | NS |
| Carcinoma Squamous | <1 | 1 | <1 | 1 | 1 | 0 | 4 |

FIG. 28A

Number (%) of Subjects in the Phase 3 Studies with Treatment-emergent Adverse Events with Incidence >1% in the 3.75% Imiquimob 2-Week Treatment Cycle Group (ITT Population)

| | 2-Week Treatment Cycle Regimen | | | 3-Week Treatment Cycle Regimen | | |
|---|---|---|---|---|---|---|
| | Imiquimod Cream | | | Imiquimod Cream | | |
| | 3.75% (N=160) | 2.5% (N=160) | Placebo (N=159) | 3.75% (N=162) | 2.5% (N=164) | Placebo (N=164) |
| Subjects with any AE, n (%) | 77 (48.1%) | 70 (43.8%) | 53 (33.3%) | 97 (59.9%) | 82 (50.0%) | 53 (32.3%) |
| Headache | 10 (6.3) | 3 (1.9) | 5 (3.1) | 8 (4.9) | 6 (3.7) | 1 (0.6) |
| Application site pruritus | 7 (4.4) | 6 (3.8) | 1 (0.6) | 15 (9.3) | 12 (7.3) | 1 (0.6) |
| Fatigue | 7 (4.4) | 2 (1.3) | 0 | 8 (4.9) | 5 (3.0) | 1 (0.6) |
| Nausea | 6 (3.8) | 1 (0.6) | 2 (1.3) | 2 (1.2) | 2 (1.2) | 0 |
| Application site irritation | 5 (3.1) | 4 (2.5) | 0 | 9 (5.6) | 6 (3.7) | 1 (0.6) |
| Application site pain | 5 (3.1) | 2 (1.3) | 0 | 15 (9.3) | 11 (6.7) | 0 |
| Pyrexia | 5 (3.1) | 0 | 0 | 6 (3.7) | 1 (0.6) | 0 |
| Anorexia | 4 (2.5) | 0 | 0 | 0 | 0 | 0 |
| Dizziness | 4 (2.5) | 1 (0.6) | 0 | 1 (0.6) | 0 | 1 (0.6) |
| Herpes simplex | 4 (2.5) | 0 | 1 (0.6) | 2 (1.2) | 2 (1.2) | 0 |
| Nasopharyngitis | 4 (2.5) | 4 (2.5) | 8 (5.0) | 2 (1.2) | 3 (1.8) | 1 (0.6) |
| Pain | 4 (2.5) | 1 (0.6) | 0 | 0 | 0 | 0 |
| Upper Respiratory tract infection | 4 (2.5) | 4 (2.5) | 6 (3.8) | 4 (2.5) | 4 (2.4) | 1 (0.6) |
| Urinary tract infection | 4 (2.5) | 0 | 4 (2.5) | 2 (1.2) | 4 (2.4) | 1 (0.6) |
| Back pain | 3 (1.9) | 1 (0.6) | 3 (1.9) | 1 (0.6) | 2 (1.2) | 3 (1.8) |
| Chest pain | 3 (1.9) | 0 | 0 | 1 (0.6) | 1 (0.6) | 1 (0.6) |
| Diarrhoea | 3 (1.9) | 2 (1.3) | 0 | 3 (1.9) | 1 (0.6) | 2 (1.2) |
| lymphadenopathy | 3 (1.9) | 4 (2.5) | 0 | 7 (4.3) | 4 (2.4) | 0 |
| Application site swelling | 2 (1.3) | 0 | 0 | 1 (0.6) | 3 (1.8) | 0 |

FIG. 28B

Number (%) of Subjects in the Phase 3 Studies with Treatment-emergent Adverse Events with Incidence >1% in the 3.75% Imiquimod 2-Week Treatment Cycle Group (ITT Population)

| | 2-Week Treatment Cycle Regimen | | | 3-Week Treatment Cycle Regimen | | |
|---|---|---|---|---|---|---|
| | Imiquimod Cream | | | Imiquimod Cream | | |
| | 3.75% (N=160) | 2.5% (N=160) | Placebo (N=159) | 3.75% (N=162) | 2.5% (N=164) | Placebo (N=164) |
| Arthralgia | 2 (1.3) | 4 (2.5) | 0 | 2 (1.2) | 3 (1.8) | 2 (1.2) |
| Blood glucose increased | 2 (1.3) | 0 | 0 | 2 (1.2) | 3 (1.8) | 0 |
| Dermatitis | 2 (1.3) | 0 | 0 | 2 (1.2) | 0 | 0 |
| Food poisoning | 2 (1.3) | 0 | 0 | 0 | 0 | 0 |
| Insomnia | 2 (1.3) | 0 | 0 | 1 (0.6) | 0 | 0 |
| Seborrhoeic keratosis | 2 (1.3) | 0 | 0 | 0 | 0 | 0 |
| Squamous cell carcinoma | 2 (1.3) | 0 | 1 (0.6) | 0 | 2 (1.2) | 2 (1.2) |
| Vomiting | 2 (1.3) | 0 | 1 (0.6) | 0 | 0 | 0 |

V=Vehicle
L2=2.5%, 2 weeks
H2=3.75%, 2 weeks
L3=2.5%, 3 weeks
H3=3.75%, 3 weeks

FIG. 32A

Summary of Primary an Secondary Efficacy Endpoints
Subpopulation - Age
Combined 2-Week Treatment Cycle Studies (GW01-0702 and GW01-0704)
(ITT Population)

| | <65 | | | >=65 | |
|---|---|---|---|---|---|
| | 3.75% (N=82) | 2.5% (N=88) | | 3.75% (N=78) | 2.5% (N=72) |
| Complete Clearance at End of Study, n (%) | 28/82 (34.1) | 20/88 (22.7) | | 29/78 (37.2) | 29/72 (40.3) |
| 95% confidence interval | 24.0, 45.4 | 14.5, 32.9 | | 26.5, 48.9 | 28.9, 52.5 |
| P value (dose) | - | - | 0.364 | - | - |
| P value (subpopulation) | - | - | 0.045 | - | - |
| P value (interaction) | - | - | 0.146 | - | - |
| | | | | | |
| Partial Clearance at End of Study, n (%) | 47/82 (57.3) | 37/88 (42.0) | | 48/78 (61.5) | 40/72 (55.6) |
| 95% confidence interval | 45.9, 68.2 | 31.6, 53.0 | | 49.8, 72.3 | 43.4, 67.3 |
| P value (dose) | - | - | 0.057 | - | - |
| P value (subpopulation) | - | - | 0.113 | - | - |
| P value (interaction) | - | - | 0.417 | - | - |
| | | | | | |
| Percent Change in Number of AK Lesions from Baseline to End of Study | | | | | |
| N | 82 | 88 | | 78 | 72 |
| Median | -80.0 | -66.7 | | -86.6 | -79.5 |
| Mean (SD) | -68.6 (38.4) | -54.6 (41.3) | | -68.7 (48.3) | -65.0 (41.6) |
| P value (dose) | - | - | 0.062 | - | - |
| P value (subpopulation) | - | - | 0.270 | - | - |
| P value (interaction) | - | - | 0.281 | - | - |

FIG. 33A

Summary of Primary and Secondary Efficacy Endpoints
Subpopulation - Fitzpatrick Skin Type
Combined 2-Week Treatment Cycle Studies (GW01-0702 and GW01-0704)
(ITT Population)

| | I or II | | | III, IV, V, or VI | |
|---|---|---|---|---|---|
| | 3.75% (N=96) | 2.5% (N=91) | | 3.75% (N=64) | 2.5% (N=69) |
| Complete Clearance at End of Study, n (%) | 39/96 (40.6) | 24/91 (26.4) | | 18/64 (28.1) | 25/96 (36.2) |
| 95% confidence interval | 30.7, 51.1 | 17.7, 36.7 | | 17.6, 40.8 | 25.0, 48.7 |
| P value (dose) | - | - | 0.576 | - | - |
| P value (subpopulation) | - | - | 0.842 | - | - |
| P value (interaction) | - | - | 0.036 | - | - |
| | | | | | |
| Partial Clearance at End of Study, n (%) | 62/96 (64.6) | 41/91 (45.1) | | 33/64 (51.6) | 36/69 (52.2) |
| 95% confidence interval | 54.2, 74.1 | 34.6, 55.8 | | 38.7, 64.2 | 39.8, 64.4 |
| P value (dose) | - | - | 0.091 | - | - |
| P value (subpopulation) | - | - | 0.582 | - | - |
| P value (interaction) | - | - | 0.072 | - | - |
| | | | | | |
| Percent Change in Number of AK Lesions from Baseline to End of Study | | | | | |
| N | 96 | 91 | | 64 | 69 |
| Median | -87.5 | -66.7 | | -75.7 | -75.0 |
| Mean (SD) | -74.3 ((36.2) | -54.3 (44.1) | | -60.2 (51.5) | -65.8 (37.3) |
| P value (dose) | - | - | 0.132 | - | - |
| P value (subpopulation) | - | - | 0.783 | - | - |
| P value (interaction) | - | - | 0.008 | - | - |

FIG. 34A

Summary of Primary and Secondary Efficacy Endpoints
Subpopulations - Baseline Lesion Count
Combined 2-Week Treatment Cycle Studies (GW01-0702 and GW01-0704), ITT Population
Active Treatment Only

| | Baseline AK Count <=10 | | | Baseline AK Count >10 | |
|---|---|---|---|---|---|
| | 3.75% (N=82) | 2.5% (N=86) | | 3.75% (N=78) | 2.5% (N=74) |
| Complete Clearance at End of Study, n (%) | 33/82 (40.2) | 36/86 (41.9) | | 24/78 (30.8) | 13/74 (17.6) |
| 95% confidence interval | 29.6, 51.7 | 31.3, 53.0 | | 20.8, 42.2 | 9.7, 28.2 |
| P value (dose) | - | - | 0.181 | - | - |
| P value (subpopulation) | - | - | <.001 | - | - |
| P value (interaction) | - | - | 0.108 | - | - |
| | | | | | |
| Partial Clearance at End of Study, n (%) | 46/82 (56.1) | 47/86 (54.7) | | 49/78 (62.8) | 30/74 (40.5) |
| 95% confidence interval | 44.7, 67.0 | 43.5, 65.4 | | 51.1, 73.5 | 29.3, 52.6 |
| P value (dose) | - | - | 0.033 | - | - |
| P value (subpopulation) | - | - | 0.524 | - | - |
| P value (interaction) | - | - | 0.061 | - | - |
| | | | | | |
| Percent Change in Number of AK Lesions from Baseline to End of Study | | | | | |
| N | 82 | 86 | | 78 | 74 |
| Median | -78.9 | -80.0 | | -82.6 | -64.1 |
| Mean (SD) | -65.5 (42.5) | -64.3 (42.6) | | -72.0 (44.3) | -53.4 (39.9) |
| P value (dose) | - | - | 0.038 | - | - |
| P value (subpopulation) | - | - | 0.641 | - | - |
| P value (interaction) | - | - | 0.069 | - | - |

FIG. 35A

Summary of Primary and Secondary Efficacy Endpoints
Subpopulations - Location of Treatment Area
Combined 2-Week Treatment Cycle Studies (GW01-0702 and GW01-0704), ITT Population
Active Treatment Only

| | Face | | | Balding Scalp | |
|---|---|---|---|---|---|
| | 3.75% (N=121) | 2.5% (N=117) | | 3.75% (N=39) | 2.5% (N=43) |
| Complete Clearance at End of Study, n (%) | 45/121 (37.2) | 41/117 (35.0) | | 12/39 (30.8) | 8/43 (18.6) |
| 95% confidence interval | 28.6, 46.4 | 26.5, 44.4 | | 17.0, 47.6 | 8.4, 33.4 |
| P value (dose) | - | - | 0.195 | - | - |
| P value (subpopulation) | - | - | 0.046 | - | - |
| P value (interaction) | - | - | 0.329 | - | - |
| Partial Clearance at End of Study, n (%) | 71/121 (58.7) | 60/117 (51.3) | | 24/39 (61.5) | 17/43 (39.5) |
| 95% confidence interval | 49.4, 67.6 | 41.9, 60.6 | | 44.6, 76.6 | 25.0, 55.6 |
| P value (dose) | - | - | 0.021 | - | - |
| P value (subpopulation) | - | - | 0.496 | - | - |
| P value (interaction) | - | - | 0.253 | - | - |
| Percent Change in Number of AK Lesions from Baseline to End of Study | | | | | |
| N | 121 | 117 | | 39 | 43 |
| Median | -81.8 | -75.0 | | -80.0 | -45.5 |
| Mean (SD) | -69.6 (43.8) | -64.4 (39.9) | | -65.8 (42.5) | -45.3 (43.4) |
| P value (dose) | - | - | 0.018 | - | - |
| P value (subpopulation) | - | - | 0.035 | - | - |
| P value (interaction) | - | - | 0.158 | - | - |

FIG. 35B

Summary of Primary and Secondary Efficacy Endpoints
Subpopulations - Location of Treatment Area
Combined 2-Week Treatment Cycle Studies (GW01-0702 and GW01-0704), ITT Population

| | Face | | | | Balding Scalp | | |
|---|---|---|---|---|---|---|---|
| | 3.75% (N=121) | 2.5% (N=117) | Placebo (N=119) | | 3.75% (N=39) | 2.5% (N=43) | Placebo (N=40) |
| Complete Clearance at End of Study, n (%) | 45/121 (37.2) | 41/117 (35.0) | 8/119 (6.7) | | 12/39 (30.8) | 8/43 (18.6) | 2/40 (5.0) |
| 95% confidence interval | 28.6, 46.4 | 26.5, 44.4 | 2.9, 12.8 | | 17.0, 47.6 | 8.4, 33.4 | 0.6, 16.9 |
| P value (dose) | - | - | - | <.001 | - | - | - |
| P value (subpopulation) | - | - | - | 0.126 | - | - | - |
| P value (interaction) | - | - | - | 0.598 | - | - | - |
| Partial Clearance at End of Study, n (%) | 71/121 (58.7) | 60/117 (51.3) | 27/119 (22.7) | | 24/39 (61.5) | 17/43 (39.5) | 9/40 (22.5) |
| 95% confidence interval | 49.4, 67.6 | 41.9, 60.6 | 15.5, 31.3 | | 44.6, 76.6 | 25.0, 55.6 | 10.8, 38.5 |
| P value (dose) | - | - | - | <.001 | - | - | - |
| P value (subpopulation) | - | - | - | 0.589 | - | - | - |
| P value (interaction) | - | - | - | 0.489 | - | - | - |
| Percent Change in Number of AK Lesions from Baseline to End of Study | | | | | | | |
| N | 121 | 117 | 119 | | 39 | 43 | 40 |
| Median | -81.8 | -75.0 | -20.0 | | -80.0 | -45.5 | -35.1 |
| Mean (SD) | -69.6 (43.8) | -64.4 (39.9) | -24.5 (54.9) | | -65.8 (42.5) | -45.3 (43.4) | -36.6 (41.9) |
| P value (dose) | - | - | - | <.001 | - | - | - |
| P value (subpopulation) | - | - | - | 0.452 | - | - | - |
| P value (interaction) | - | - | - | 0.029 | - | - | - |

FIG. 36

Percent Complete Clearance

| Study | 2.5% Imiq | 3.75% Imiq | Pbo | Aldara |
|---|---|---|---|---|
| 1 | 23.5* | 25.9* | 2.5 | 46 |
| 2 | 38.1* | 45.6* | 10.1 | 44 |
| Pooled | 31* | 36* | 6 | 45 |

* Statistically significant from placebo

FIG. 36A

% Complete Clearance by Study

| Study | 3.75% Imiq | 2.5% Imiq | Pbo |
|---|---|---|---|
| 1 (2wk) | 25.9* | 23.5* | 2.5 |
| 2 (2wk) | 45.6* | 38.0* | 10.1 |
| Pooled 2wk | 35.6* | 30.6* | 6.3 |
| 3 (3wk) | 32.5* | 23.2* | 5.1 |
| 4 (3wk) | 35.4* | 26.8* | 5.8 |
| Pooled 3wk | 34.0* | 25.0* | 5.5 |

FIG. 37

Percent Partial Clearance

| Study | 2.5% Imiq | 3.75% Imiq | Pbo | Aldara |
|---|---|---|---|---|
| 1 | 42.0* | 45.7* | 18.8 | 60 |
| 2 | 54.4* | 73.4* | 26.6 | 58 |
| Pooled | 48* | 59* | 23 | 59 |

FIG. 37A

% Partial Clearance by Study

| Study | 3.75% Imiq | 2.5% Imiq | Pbo |
|---|---|---|---|
| 1 (2wk) | 45.7* | 42.0* | 18.8 |
| 2 (2wk) | 73.4* | 54.4* | 26.6 |
| Pooled 2wk | 59.4* | 48.1* | 22.6 |
| 3 (3wk) | 56.3* | 46.3* | 11.5 |
| 4 (3wk) | 51.2* | 39.0* | 14.0 |
| Pooled 3wk | 53.7* | 42.7* | 12.8 |

* Statistically significant from placebo

FIG. 38

AK Median % Reduction

| Study | 2.5% Imiq | 3.75% Imiq | Pbo | Aldara |
|---|---|---|---|---|
| 1 | -60.0* | -72.7* | -21.1 | - |
| 2 | -76.5* | -90.9* | -30.0 | - |
| Pooled | -71.8* | 82* | -26 | -83 |

FIG. 38A

AK Median % Reduction by Study

| Study | 3.75% Imiq | 2.5% Imiq | Pbo |
|---|---|---|---|
| 1 (2wk) | 72.7* | 60.0* | 21.1 |
| 2 (2wk) | 90.9* | 76.5* | 30.0 |
| Pooled 2wk | 81.8* | 71.8* | 25 |
| 3 (3wk) | 82.3* | 66.7* | 23.6 |
| 4 (3wk) | 78.9* | 66.7* | 22.5 |
| Pooled 3wk | 80.0* | 66.7* | 23.6 |

FIG. 39

Rest Periods

| | 2.5% Imiq | 3.75% Imiq | Pbo | Aldara |
|---|---|---|---|---|
| % Subjects Who Took at Least One Rest Period | 6.9% | 10.6% | 0% | 16% |

FIG. 39A

Selected Safety Parameters
Combined 2wk or 3wk Studies

| | Combined 2 Week Studies | | | Combined 3 Week Studies | | |
|---|---|---|---|---|---|---|
| | 3.75% IMIQ (N=160) | 2.5% IMIQ (N=160) | Placebo (N=159) | 3.75% IMIQ (N=162) | 2.5% IMIQ (N=164) | Placebo (N=164) |
| Discontinued study due to safety reasons | 1.3% | 0.6% | 1.9% | 2.5% | 1.2% | 0.6% |
| Tx-related AEs | 19.4% | 11.9% | 2.5% | 37.0% | 26.8% | 2.4% |
| Rest periods | 10.6% | 6.9% | 0% | 27.2% | 17.1% | 0% |

FIG. 40

Local Skin Reactions (LSRs)
% of Subjects with Severe LSRs

| LSR Term | 2.5% Imiq | 3.75% Imiq | Pbo | Aldara |
|---|---|---|---|---|
| Erythema | 14.4 | 25.2 | 0 | 18 |
| Flaking/Scaling/Dryness | 4.4 | 8.2 | 1.3 | 7 |
| Scabbing/Crusting | 9.4 | 13.8 | 0 | 8 |
| Edema | 3.8 | 5.7 | 0 | 0 |
| Weeping/Exudate | 1.3 | 5.7 | 0 | 0 |

FIG. 41

Safety Comparison:
Incidence of Adverse Events
Selected Common (%)

| | 2.5% Imiq | 3.75% Imiq | Pbo | Aldara |
|---|---|---|---|---|
| Application site reaction | 6 | 11 | 1 | 33 |
| Headache | 2 | 6 | 3 | 5 |
| Flu-like illness | 4 | 1 | 0 | NS |
| Nasopharyngitis | 4 | 3 | 5 | NS |
| Upper Resp Tract Infxn | 3 | 3 | 4 | 15 |
| Fatigue | 1 | 4 | 0 | 1 |
| Sinusitis | 2 | 0 | 1 | 7 |
| Lymphadenopathy | 3 | 2 | 0 | NS |
| Carcinoma Squamous | 1 | <1 | <1 | 4 |

FIG. 41A

Incidence of Most Common (>1%) Treatment-Related Adverse Events

| MedDRA Term | Combined 2 Week Studies 3.75% | Combined 2 Week Studies Placebo | Combined 3 Week Studies 3.75% | Combined 3 Week Studies Placebo |
|---|---|---|---|---|
| App. site pruritus | 7 (4.4%) | 1 (0.6%) | 14 (8.6%) | 1 (0.6%) |
| App. site pain | 5 (3.1%) | 0% | 15 (9.3%) | 0% |
| App. site irritation | 5 (3.1%) | 0% | 9 (5.6%) | 1 (0.6%) |
| Fatigue | 4 (2.5%) | 0% | 7 (4.3%) | 0% |
| Headache | 4 (2.5%) | 2 (1.3%) | 4 (2.5%) | 0% |
| Dizziness | 3 (1.9%) | 0% | 0% | 0% |
| Lymphadenopathy | 3 (1.9%) | 0% | 5 (3.1%) | 0% |
| Nausea | 3 (1.9%) | 0% | 2 (1.2%) | 0% |
| Pyrexia | 2 (1.3%) | 0% | 5 (3.1%) | 0% |
| App. site swelling | 2 (1.3%) | 0% | 1 (0.6%) | 0% |
| Arthralgia | 2 (1.3%) | 0% | 0% | 0% |
| Pain | 2 (1.3%) | 0% | 0% | 0% |

FIG. 43

2.5% IMIQ

- 39 yr old white male

| Visit | AK Counts | Erythema |
|---|---|---|
| Baseline | 11 | 0 |
| Week 02 | IND | 2 |
| Week 06 | IND | 1 |
| Week 10 | 0 | 1 |
| Week 14 | 0 | 0 |

- Cycle 1 = No rest periods or missed doses
- Cycle 2 = No rest periods or missed doses
- Average packets used = 1.25 per dose
- Adverse Events - Lymphadenopathy (related)

FIG. 44

2.5% IMIQ

- 74 yr old white male with Fitzpatrick skin type III

| Visit | AK Counts | Erythema |
|---|---|---|
| Baseline | 8 | 0 |
| Week 02 | 19 | 2 |
| Week 04 | 12 | 1 |
| Week 06 | 33 | 3 |
| Week 10 | 1 | 0 |
| Week 14 | 2 | 0 |

- Cycle 1 = No rest periods or missed doses
- Cycle 2 = No rest periods or missed doses
- Average packets used = 2 per dose
- No Adverse Events were reported

FIG. 45

3.75% IMIQ

- 66 yr old white female with Fitzpatrick skin type III

| Visit | AK Counts | Erythema |
|---|---|---|
| Baseline | 9 | 0 |
| Week 02 | IND | 2 |
| Week 06 | IND | 1 |
| Week 14 | 0 | 1 |

- Cycle 1 = Rest periods on days 11, 12, 13 and 14
- Cycle 2 = Missed dose on day 29
- Average packets used = 1.26 per dose
- Adverse Event - dizziness, facial stinging, sunburn (mild, related)

FIG. 46

3.75% IMIQ

- 73 yr old white male with Fitzpatrick skin type III

| Visit | AK Counts | Erythema |
|---|---|---|
| Baseline | 9 | 0 |
| Week 02 | 22 | 3 |
| Week 04 | 3 | 0 |
| Week 06 | 5 | 2 |
| Week 10 | 2 | 0 |
| Week 14 | 2 | 0 |

- Cycle 1 = No rest periods or missed doses
- Cycle 2 = No rest periods or missed doses
- Average packets used = 1.18 per dose
- No related Adverse Events

FIG. 47

2.5% IMIQ

- 70 yr old white male
- Treatment Area: Face

| Visit | AK Counts | Erythema |
|---|---|---|
| Baseline | 10 | 1 |
| Week 3 | IND | 3 |
| Week 9 | 13 | 3 |
| Week 17 | 5 | 1 |

- Cycle 1 = 21 days with no rest periods or missed doses
- Cycle 2 = 21 days with no rest periods or missed doses
- Average packets used = 2.0 / day
- No Adverse Events were recorded

FIG. 48

2.5% IMIQ

- 65 yr old white female
- Treatment Area: Face

| Visit | AK Counts | Erythema |
|---|---|---|
| Baseline | 7 | 1 |
| Week 3 | 1 | 1 |
| Week 9 | 0 | 0 |
| Week 17 | 0 | 0 |

- Cycle 1 = 21 days with no rest periods or missed doses
- Cycle 2 = 21 days with no rest periods or missed doses
- Average packets used = 1.69 / day
- All Adverse Events were recorded as "not related"

FIG. 49

3.75% IMIQ

- 79 yr old white male
- Treatment Area: Face

| Visit | AK Counts | Erythema |
|---|---|---|
| Baseline | 14 | 1 |
| Week 3 | 16 | 3 |
| Week 9 | 6 | 2 |
| Week 17 | 0 | 0 |

- Cycle 1 = 21 days with no rest periods or missed doses
- Cycle 2 = 21 days with no rest periods or missed doses
- Average packets used = 1.14 / day
- No Adverse Events reported

FIG. 50

3.75% IMIQ

- 78 yr old white male
- Treatment Area: Scalp

| Visit | AK Counts | Erythema |
|---|---|---|
| Baseline | 8 | 1 |
| Week 3 | IND | 3 |
| Week 9 | 2 | 1 |
| Week 17 | 0 | 0 |

- Cycle 1 = 21 days with no rest periods or missed doses
- Cycle 2 = 21 days with no rest periods or missed doses
- Average packets used = 2.0 / day
- All Adverse Events were recorded as “not related”

FIG. 51

Summary of Primary and Secondary Efficacy Endpoint
Combined Studies, Analysis Within regimen
ITT Population

| | 2-Week treatment Cycle Regimen | | | 3-Week treatment Cycle Regimen | | |
|---|---|---|---|---|---|---|
| | 3.75% (N=160) | 2.5% (N=160) | Placebo (N=159) | 3.75% (N=162) | 2.5% (N=164) | Placebo (N=164) |
| Complete Clearance at End of Study | 57/160 (35.6) | 49/160 (30.6) | 10/159 (6.3) | 55/162 (34.0) | 41/164 (25.0) | 9/164 (5.5) |
| 95% confidence interval | 28.2, 43.6 | 23.6, 38.4 | 3.1, 11.3 | 26.7, 41.8 | 18.6, 32.3 | 25, 10.2 |
| P value vs Placebo | <.001** | <.001** | - | <.001** | <.001** | - |
| P value vs 2.5% Imiquimod Cream | 0.379 | - | - | 0.082 | - | - |
| Partial Clearance at End of Study | 59/160 (59.4) | 77/160 (48.1) | 36/159 (22.6) | 87/162 (53.7) | 70/164 (42.7) | 21/164 (12.8) |
| 95% confidence interval | 51.3, 67.1 | 40.2, 56.2 | 16.4, 29.9 | 45.7, 61.6 | 35.0, 50.6 | 8.1, 18.9 |
| P value vs Placebo | <.001** | <.001** | - | <.001** | <.001** | - |
| P value vs 2.5% Imiquimod Cream | 0.047** | - | - | 0.034** | - | - |
| Percent Change in Number of AK Lesions from Baseline to End of Study | | | | | | |
| N | 160 | 160 | 159 | 162 | 164 | 164 |
| Mean (Standard Deviation) | -68.7 (43.4) | -59.2 (41.6) | -27.6 (52.1) | -64.3 (43.0) | -57.0 (45.4) | -24.5 (47.0) |
| Median | -81.8 | -71.8 | -25.0 | -80.0 | -66.7 | -23.6 |
| Minimum, Maximum | -100.0 to 188.9 | -100.0 to 90.0 | -100.0 to 300.0 | -100.0 to 160.0 | -100.0 to 183.3 | -100.0 to 200.0 |
| P value vs Placebo | <.001** | <.001** | - | - | <.001** | - |
| P value vs 2.5% Imiquimod Cream | 0.048** | - | - | - | - | - |

FIG. 52

Summary of Primary and Secondary Efficacy Endpoint
Combined Studies, Analysis Across Regimens
ITT Population

| | 2-Week treatment Cycle Regimen | | | | | 3-Week treatment Cycle Regimen | | |
|---|---|---|---|---|---|---|---|---|
| | 3.75% (N=160) | 2.5% (N=160) | Placebo (N=159) | (1) | (2) | 3.75% (N=162) | 2.5% (N=164) | Placebo (N=164) |
| Complete Clearance at End of Study, n (%) | 57/160 (35.6) | 49/160 (30.6) | 10/159 (6.3) | | | 55/162 (34.0) | 41/164 (25.0) | 9/164 (5.5) |
| 95% confidence interval | 28.2, 43.6 | 23.6, 38.4 | 3.1, 11.3 | | | 28.7, 41.8 | 18.6, 32.3 | 25, 10.2 |
| P value (dose) | - | - | - | | | - | - | - |
| P value (regimen) | - | - | - | | | - | - | - |
| P value (analysis site) | | | | | | | | |
| Partial Clearance at End of Study, n (%) | 59/160 (59.4) | 77/160 (48.1) | 36/159 (22.6) | | | 87/162 (53.7) | 70/164 (42.7) | 21/164 (12.8) |
| 95% confidence interval | 51.3, 67.1 | 40.2, 56.2 | 16.4, 29.9 | | | 45.7, 61.6 | 35.0, 50.6 | 8.1, 18.9 |
| P value (dose) | - | - | - | <.001 | <.001 | - | - | - |
| P value (regimen) | - | - | - | -0.233 | 0.164 | - | - | - |
| P value (analysis site) | | | | <.001 | <.001 | | | |
| Percent Change in Number of AK Lesions from Baseline to End of Study | | | | | | | | |
| N | 160 | 160 | 159 | | | 162 | 164 | 164 |
| Median | -81.8 | -71.8 | -25.0 | | | -80.0 | -66.7 | -23.6 |
| Mean (SD) | -68.7 (43.4) | -59.2 (41.6) | -27.6 (52.1) | | | -64.3 (43.0) | -57.0 (45.4) | -24.5 (47.0) |
| P value (dose) | - | - | - | <.001 | | - | - | - |
| P value (regimen) | - | - | - | -0.635 | | - | - | - |
| P value (analysis site) | - | - | - | <.001 | | - | - | - |

FIG. 53

Summary of Investigator's Global Integrated Photodamage Score (IGIP)
Combined Studies
ITT Population

| | 2-Week Treatment Cycle | | | 3-Week Treatment Cycle | | | | | |
|---|---|---|---|---|---|---|---|---|---|
| | Regimen | | | Regimen | | | Combined | | |
| | 3.75% (N=160) | 2.5% (N=160) | Placebo (N=159) | 3.75% (N=162) | 2.5% (N=164) | Placebo (N=164) | 3.75% (N=322) | 2.5% (N=324) | Placebo (N=323) |
| IGIP Score | | | | | | | | | |
| N | 151 | 153 | 151 | 148 | 151 | 145 | 299 | 304 | 296 |
| 3 = Significantly improved from baseline | 64 (42.4) | 43 (28.1) | 14 (9.3) | 68 (45.9) | 54 (35.8) | 14 (9.7) | 132 (44.1) | 97 (31.9) | 28 (9.5) |
| 2 = Much improved from baseline | 39 (25.8) | 38 (24.8) | 28 (18.5) | 37 (25.0) | 40 (26.5) | 20 (13.8) | 76 (25.4) | 78 (25.7) | 48 (16.2) |
| 1= Slightly improved from baseline | 28 (18.5) | 35 (22.9) | 24 (15.9) | 23 (15.5) | 34 (22.5) | 34 (23.4) | 51 (17.1) | 69 (22.7) | 58 (19.6) |
| 0 = No change from baseline | 17 (11.3) | 34 (22.2) | 73 (48.3) | 18 (12.2) | 20 (13.2) | 68 (46.9) | 35 (11.7) | 54 (17.8) | 141 (47.6) |
| -1 = Slightly worse from baseline | 2 (1.3) | 2 (1.3) | 12 (7.9) | 2 (1.4) | 2 (1.3) | 7 (4.8) | 4 (1.3) | 4 (1.3) | 19 (6.4) |
| -2 = Much worse from baseline | 0 (0.0) | 0 (0.0) | 0 (0.0) | 0 (0.0) | 1 (0.7) | 2 (1.4) | 0 (0.0) | 1 (0.3) | 2 (0.7) |
| -3 = Significantly worse from baseline | 1 (0.7) | 1 (0.7) | 0 (0.0) | 0 (0.0) | 0 (0.0) | 0 (0.0) | 1 (0.3) | 1 (0.3) | 0 (0.0) |
| Mean (Standard Deviation) | 1.94 (1.16) | 1.54 (1.21) | 0.73 (1.14) | 2.02 (1.11) | 1.80 (1.14) | 0.72 (1.11) | 1.98 (1.13) | 1.67 (1.18) | 0.73 (1.12) |

FIG. 54

Summary of Serum Pharmacokinetic Parameters at Day 21
for Imiquimod, PK Population

| SUBJECT/ STATISTICS | Cmax (ng/mL) | Crain (ng/mL) | Tmax (hr) | AUC (0-24) (hr*ng/mL) | L2 (1/hr) | T4 (hr) | RAUC | RCmax | Lzeff (hr-1) | Te off (hr) |
|---|---|---|---|---|---|---|---|---|---|---|
| 001-601 | 0.140 | 0.071 | 9.000 | 2.558 | 0.220 | 31.496 | - | - | - | - |
| 001-602 | 0.401 | 0.199 | 9.000 | 7.022 | 0.0216 | 32.107 | 5.514 | 4.506 | 0.0083 | 83.119 |
| 001-603 | 0.290 | 0.143 | 4.000 | 4.733 | 0.0220 | 31.489 | 1.987 | 2.148 | 0.0292 | 23.766 |
| 001-605 | 0.415 | 0.224 | 9.000 | 7.219 | 0.0082 | 84.059 | 3.829 | 2.943 | 0.0126 | 54.956 |
| 001-606 | 0.425 | 0.201 | 4.000 | 7.019 | 0.0713 | 9.724 | 2.083 | 1.889 | 0.0273 | 25.422 |
| 001-607 | 0.274 | 0.155 | 9.000 | 4.628 | 0.0355 | 19.512 | 1.285 | 0.996 | 0.0627 | 11.053 |
| 001-609 | 0.353 | 0.189 | 16.000 | 7.127 | 0.0329 | 21.061 | 2.440 | 1.642 | 0.0220 | 31.539 |
| 001-610 | 0.389 | 0.303 | 9.050 | 7.679 | 0.0271 | 25.557 | 3.328 | 2.720 | 0.0149 | 46.533 |
| 001-611 | 0.059 | 0.065 | 4.000 | 1.139 | - | - | 1.152 | 0.523 | 0.0843 | 8.219 |
| 001-612 | 0.541 | 0.390 | 4.000 | 10.118 | 0.0352 | 19.668 | 6.912 | 4.963 | 0.0065 | 106.432 |
| 001-613 | 0.588 | 0.325 | 9.000 | 11.800 | 0.0226 | 30.670 | 7.097 | 5.069 | 0.0063 | 109.511 |
| 001-614 | 0.245 | 0.162 | 4.000 | 4.873 | 0.0182 | 38.024 | 4.359 | 2.882 | 0.0109 | 63.830 |
| 001-615 | 0.440 | 0.292 | 4.000 | 8.581 | 0.0298 | 23.232 | 3.505 | 2.353 | 0.0140 | 49.508 |
| 001-616 | 0.128 | 0.067 | 9.000 | 2.358 | 0.0381 | 18.198 | 1.641 | 1.196 | 0.0392 | 17.696 |
| 001-617 | 0.221 | 0.145 | 4.000 | 3.869 | 0.0358 | 19.367 | 6.026 | 3.203 | 0.0076 | 91.652 |
| 001-618 | 0.079 | 0.061 | 6.000 | 1.613 | - | - | - | - | - | - |
| 001-620 | 0.486 | 0.388 | 12.000 | 9.220 | 0.0200 | 34.735 | 5.937 | 5.116 | 0.0065 | 106.847 |
| N | 17 | 17 | 17 | 17 | 15 | 15 | 15 | 15 | 15 | 15 |
| MEAN | 0.323 | 0.199 | 7.356 | 5.974 | 0.0294 | 29.260 | 3.873 | 2.810 | 0.0235 | 55.339 |
| SD | 0.159 | 0.109 | 3.500 | 3.088 | 0.0142 | 16.979 | 2.153 | 1.514 | 0.0229 | 36.380 |
| CV% | 49.244 | 54.552 | 47.587 | 51.690 | 48.4908 | 58.028 | 55.598 | 53.889 | 97.4555 | 65.741 |
| GEOMETRIC MEAN | 0.274 | 0.169 | 6.623 | 5.029 | 0.0266 | 26.106 | 3.277 | 2.370 | 0.0164 | 42.143 |
| MIN | 0.069 | 0.061 | 4.000 | 1.139 | 0.0082 | 9.724 | 1.152 | 0.523 | 0.0063 | 8.219 |
| MEDIAN | 0.353 | 0.189 | 9.000 | 7.019 | 0.0271 | 25.557 | 3.505 | 2.720 | 0.0140 | 49.508 |
| MAX | 0.588 | 0.390 | 16.000 | 11.800 | 0.0713 | 84.059 | 7.097 | 5.116 | 0.0843 | 109.511 |

2×2×2 WEEK DOSING REGIMEN FOR TREATING ACTING KERATOSIS WITH PHARMACEUTICAL COMPOSITIONS FORMULATED WITH 3.75% IMIQUIMOD

CROSS-REFERENCE TO RELATED APPLICATIONS

This application is a divisional of U.S. application Ser. No. 13/568,003, filed Aug. 6, 2012, now U.S. Pat. No. 9,370,509, which is continuation of U.S. application Ser. No. 13/181,499 filed Jul. 12, 2011, now U.S. Pat. No. 8,236,816, which is a continuation of U.S. application Ser. No. 12/636,613 filed Dec. 11, 2009, which application claims the benefit of U.S. Provisional Application Ser. No. 61/205,145 filed Jan. 15, 2009, U.S. Provisional Application Ser. No. 61/144,731 filed Jan. 14, 2009, U.S. Provisional Application Ser. No. 61/139,536 filed Dec. 19, 2008, the teachings of which are hereby incorporated by reference in their entireties for all purposes.

FIELD OF THE INVENTION

The present invention relates to pharmaceutical formulations and methods for the topical or transdermal delivery of 1-isobutyl-1H-imidazo[4,5-c]-quinolin-4-amine, also known as (aka) 1-(2-methylpropyl)-1H-imidazo[4,5-c]quinolin-4-amine, aka imiquimod, to treat actinic keratosis with shorter durations of therapy, than currently prescribed for the commercially available ALDARA 5% imiquimod cream, as now approved by the U.S. Food & Drug Administration ("FDA"). More specifically, the present invention is directed to lower dosage strength imiquimod formulations to deliver an efficacious dose for treating actinic keratosis with an acceptable safety profile, but with a dosing regimen that is shorter and more convenient for patient use than the dosing regimen currently approved by the FDA for ALDARA 5% imiquimod cream.

BACKGROUND

Actinic keratosis (AKs) is a precancerous (premalignant) skin disorder caused by or associated with chronic exposure to radiant energy, such as sunlight. Actinic keratosis lesions are small, red, rough spots or lesions occurring on sun exposed areas of the skin. Actinic keratosis lesions possess many of the same cellular changes observed in a skin cancer called squamous cell carcinoma (SCC). Research shows that a mutated version of the p53 gene is found in sun-damaged cells in the body and is present in more than about 90% of people who have AKs and squamous cell carcinomas. Although most actinic keratosis lesions do not actually become cancerous, some lesions can become malignant.

It is believed that actinic keratosis develops in skin cells called "keratinocytes", which are the cells that constitute about 90% of the epidermis, the outermost layer of skin. Chronic sun exposure, over time, generates mutations in these cells and causes the cells to change in size, shape, the way they are organized, and the way they behave. In addition, the cellular damage can even extend to the dermis, the layer of skin beneath the epidermis.

Actinic keratosis lesions generally measure in size between about 2 to about 6 millimeters in diameter, AK lesions can range in color from skin-toned to reddish and often have a white scale on top. On occasion, AK lesions will form into the shape of animal horns. When this occurs, the AKs are known as "cutaneous horns."

People who are at higher risk for developing actinic keratosis tend to be fair-skinned and spend significant time outdoors, e.g., at work or at play, over the course of many years. AK lesions usually develop on those areas of the body that have been constantly exposed to the sun for years. Additionally, the skin often becomes wrinkled, mottled, and discolored from chronic sun exposure. Common locations for actinic keratosis include the face, ears, lips, balding scalp, back of the neck, upper chest, the tops of the hands and forearms. When AK lesions develop on the lips, the condition is known as actinic cheilitis. Actinic cheilitis can be characterized by a diffuse scaling on the lower lip that cracks and dries. In some cases, the lips will have a whitish discoloration on the thickened lip.

Actinic keratosis is generally more common after age 40, because actinic keratosis take years to develop. However, even younger adults may develop actinic keratosis when living in geographic areas that are exposed to high-intensity sunlight year round, such as Florida and Southern California.

Actinic keratosis has become a significant health care issue in the United States of America. It is estimated that over 20 million Americans suffer from actinic keratosis, and that that number continues to grow. In fact, actinic keratosis is so common today that treatment for actinic keratosis ranks as one of the most frequent reasons people consult a dermatologist.

The compound characterized as 1-isobutyl-1H-imidazo[4,5-c]-quinolin-4-amine or 1-(2-methylpropyl)-1H-imidazo[4,5-c]quinolin-4-amine, and known as imiquimod, is disclosed in U.S. Pat. No. 4,689,338 and described therein as an antiviral agent and as an interferon inducer, which is incorporated herein by reference in its entirety. A variety of formulations for topical administration of imiquimod are also described therein. This U.S. Pat. No. 4,689,338 is incorporated herein by reference in its entirety.

U.S. Pat. No. 4,751,087 discloses the use of a combination of ethyl oleate and glyceryl monolaurate as a skin penetration enhancer for nitroglycerin, with all three components being contained in the adhesive layer of a transdermal patch, wherein this U.S. patent is incorporated herein by reference in its entirety.

U.S. Pat. No. 4,411,893 discloses the use of N,N-dimethyldodecylamine-N-oxide as a skin penetration enhancer in aqueous systems, wherein this U.S. patent is incorporated herein by reference in its entirety.

U.S. Pat. No. 4,722,941 discloses readily absorbable pharmaceutical compositions that comprise a pharmacologically active agent distributed in a vehicle comprising an absorption-enhancing amount of at least one fatty acid containing 6 to 12 carbon atoms and optionally a fatty acid monoglyceride. Such compositions are said to be particularly useful for increasing the absorption of pharmacologically active bases, wherein this U.S. patent is incorporated herein by reference in its entirety.

U.S. Pat. No. 4,746,515 discloses a method of using glyceryl monolaurate to enhance the transdermal flux of a transdermally deliverable drug through intact skin, wherein this U.S. patent is incorporated herein by reference in its entirety.

U.S. Pat. Nos. 5,238,944, 7,038,051, 6,693,113, 6,894,060 U.S. Patent Publication No. 2007/0123558, U.S. Patent Publication No. 2004/087614, U.S. Patent Publication No. 2002/147210, and WO2008US53522 disclose topical formulations and/or topical and transdermal delivery systems containing 1-isobutyl-1H-imidazo[4,5-c]-quinolin-4-amine or 1-(2-methylpropyl)-1H-imidazo[4,5-c]quinolin-4-amine, wherein each are incorporated herein by reference in their entireties.

Currently, the FDA has approved a 5% imiquimod cream, commercially available under the brand name Aldara®, to treat certain dermal and mucosal associated conditions, such as (1) the topical treatment of clinically typical, nonhyperkeratotic actinic keratosis (AK) on the face or scalp in immunocompetent adults, (2) topical treatment of biopsy-confirmed, primary superficial basal cell carcinoma (sBCC) in immunocompetent adults, and (3) the topical treatment of external genital and perianal warts/condyloma acuminate in patients 12 years or older.

Aldara® is the brand name for an FDA-approved 5% imiquimod cream, which is an immune response modifier. Each gram of the Aldara® 5% imiquimod cream contains 50 mg of imiquimod in an off-white oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben. The Aldara® 5% imiquimod cream is packaged in single-use packets or sachets, each containing 250 mg of cream, equivalent to 12.5 mg of imiquimod.

Chemically, imiquimod, as indicated above, is known as 1-(2-methylpropyl)-1H-imidazo[4,5-c]quinolin-4-amine or 1-isobutyl-1H-imidazo[4,5-c]-quinolin-4-amine. Imiquimod has a molecular formula of $C_{14}H_{16}N_4$ and a molecular weight of 240.3. The chemical structural formula for imiquimod is as follows:

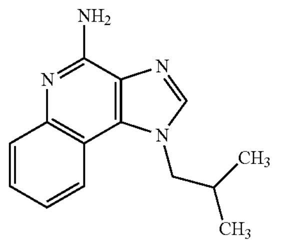 [SMILES: CC(C)Cn1cnc2c(N)nc3ccccc3c21]

Notwithstanding FDA approval, Aldara® 5% imiquimod cream treatment is not without limitation, including an unsimplified and lengthy dosing regimen. Generally speaking, the treatment regimen for actinic keratosis using FDA-approved Aldara® 5% imiquimod cream consists of applying the Aldara® 5% imiquimod cream two times per week for a full 16 weeks to a defined/limited treatment area on the face or scalp (but not both concurrently). The surface treatment area for Aldara® 5% imiquimod cream is limited to approximately 25 $cm^2$ (e.g., a 5 cm×5 cm area, which may be of any shape; the treatment area does not have to be square) and is defined as one contiguous area. The number of AK lesions treated with Aldara® 5% imiquimod cream per treatment area is generally between about 4 and about 8. Because the treatment area is quite small, less than one single-use Aldara® packet or sachet (250 mg of total cream, of which 12.5 mg is imiquimod) is generally used per application. Inconsistencies in both compliance and therapeutic results frequently occur with the treatment of actinic keratosis with FDA-approved Aldara® 5% imiquimod cream due to the lengthy treatment period, i.e., 16 weeks, the complicated dosing regimen, i.e., twice weekly, and the high incidence of application site reactions.

Subsequent to FDA-approval of Aldara® 5% imiquimod cream to treat actinic keratosis, a pilot study was conducted that was an open-label trial that included 25 patients who had between 5 and 20 discrete AKs within a cosmetic unit of the forehead, scalp, or cheek. During this pilot study, treatment consisted of once-daily application of 5% imiquimod cream, three times a week for four weeks to the entire cosmetic unit, followed by a rest period of four weeks. The cycle was repeated if any AKs remained after a complete eight-week cycle. A maximum of three cycles was permitted (24 weeks). Thirty-three sites (i.e., cosmetic units) in 25 subjects were evaluated. According to the authors, compliance was excellent with a very tolerable safety profile. Complete clearing of all AKs was noted in 82% (27/33) of anatomic sites in 25 study subjects. Almost half the sites (15/33) were clear at the end of the first cycle. A "therapeutic interval" was noted during the rest period wherein clinical inflammation subsided but AKs continued to clear. An added effect, according to the authors, was the uncovering and clinical appearance and subsequent eradication of incipient (subclinical) AKs in the treatment area. As a result, the authors concluded that there was excellent compliance with the cycle therapy regimen utilized in this study and that the identification of a therapeutic interval may prove to be beneficial in formulating individualized dosing regimens. The authors warned, however, that the findings of the study must be evaluated cautiously. The authors also cautioned that, because this study was an open-label trial in a small number of study subjects, safety, efficacy and duration of efficacy needs to be corroborated by controlled, randomized trials with larger study populations. See Salasche S. J., Levine N., and Morrison L.: Cycle therapy of actinic keratoses of the face and scalp with 5% topical imiquimod cream: An open-label trial. *J Am Acad Dermatol.* 47(4): 571-7 (October 2002).

Also subsequent to FDA-approval of Aldara® 5% imiquimod cream to treat actinic keratosis, a dual-center, randomized, double-blind, vehicle-controlled study was conducted to evaluate the safety and efficacy of short courses of therapy with Aldara® 5% imiquimod cream in clearing ≥75% of baseline solar keratoses ("SK") within a field of treatment. Subjects with 5-15 baseline SK within one treatment area (scalp, forehead and temples, or both cheeks) were randomized to apply imiquimod or vehicle cream to the entire treatment area three times a week for 3 weeks. Subjects were assessed 4 weeks after completing the first course for clearance of lesions. Subjects with <75% clearance were commenced on a second 3-week course of study cream. Subjects with ≥75% clearance were followed up until study completion without further therapy. All subjects were evaluated at the study endpoint of 14 weeks after initiating therapy for assessment of the primary outcome (≥75% clearance of baseline solar keratoses). According to the authors, twenty-one out of 29 (72%) imiquimod-treated subjects cleared ≥75% of baseline lesions compared with 3/10 (30%) subjects using the vehicle cream (Fisher's exact test, P=0.027) and the imiquimod was well tolerated. Also according to the authors, the results of this study suggest that 5% imiquimod administered three times per week may offer a therapeutic alternative to patients with SK on the face, and scalp, and that one or two short courses may be an alternative to the continuous longer Aldara® 5% imiquimod cream therapy approved by the FDA. The authors did caution, however, that, because the study had a relatively short follow-up endpoint, additional studies may be needed to evaluate if the therapeutic outcome can be sustained. See Chen K. et al.: Links Short-course therapy with imiquimod 5% cream for solar keratoses: a randomized controlled trial. *Australasian J Dermatol.* 44(4):250-5 (November 2005).

In addition, a multi-center, vehicle-controlled, double-blind study to assess the safety and efficacy of imiquimod 5% cream applied once daily 3 days per week in one or two courses of treatment of actinic keratoses on the head was conducted and reported in 2007. According to the authors, a total of 259 patients diagnosed with AK were enrolled in twenty study centers in Europe and applied imiquimod for 4 weeks, entered a 4-week rest period and if they did not have complete clearance, the patients then entered a second course of treatment. The area of treatment was confined to about 25 $cm^2$. As reported by the authors, patients in the imiquimod group had an overall complete clearance rate of 55.0% (71/129) vs. a rate of 2.3% (3/130) for the vehicle group and that there was a high rate of agreement between the clinical assessment and histological findings with respect to AK lesion clearance. The authors further reported that, at both 8-week post-treatment visits, the negative predictive value of the investigator assessment was 92.2% for clinical assessments vs. histological results. The authors concluded that a 4-week course of treatment with three times weekly dosing of imiquimod 5% cream, with a repeated course of treatment for those patients who fail to clear after the first course of treatment, is a safe and effective treatment for AK, and the overall complete clearance rate (complete clearance after either course 1 or course 2) is comparable to the 16-week Aldara® 5% imiquimod cream treatment regimen, while decreasing drug exposure to the patient and decreasing the overall treatment time. See Alomar, A., J. Bichel, et al.: Vehicle-controlled, randomized, double-blind study to assess safety and efficacy of imiquimod 5% cream applied once daily 3 days per week in one or two courses of treatment of actinic keratoses on the head. *British Journal of Dermatology.* 157(1): 133-41 (2007).

Another vehicle-controlled, double-blind, randomized study of imiquimod 5% cream applied 3 days per week in one or two courses of treatment for actinic keratoses on the head was conducted and also reported in 2007. According to the authors, patients with actinic keratosis lesions on the head applied imiquimod or vehicle cream 3×/wk for 4 weeks (course 1), patients with remaining lesions received another course of treatment, and complete and partial clearance rates were evaluated after course 1, after course 2 (overall), and 1 year later. The authors concluded that imiquimod 3×/wk in one or two courses of treatment appears to be effective for the treatment of actinic keratoses on the head, providing long-term clinical benefits and that some recurrences do occur, so long-term follow-up is recommended. See Jorizzo, J., S. Dinehart, et al.: Vehicle-controlled, double-blind, randomized study of imiquimod 5% cream applied 3 days per week in one or two courses of treatment for actinic keratoses on the head. *Journal of the American Academy of Dermatology.* 57(2): 265-8 (2007).

Another multicenter, open-label study using imiquimod 5% cream in one or two 4-week courses of treatment for multiple actinic keratoses on the head was conducted and also reported in 2007. According to the authors, this was an open-label, phase IIIb study involving 180 dermatology clinics and practices in Germany, and patients were eligible if they had clinically typical, visible AK lesions located anywhere on the head, excluding the upper and lower eyelids, nostrils, lip vermilion, and inside the ears. The authors reported that patients applied imiquimod study cream to the treatment area once daily 3×/week for 4 weeks (course 1) followed by a 4-week post treatment period and that patients with AK lesions remaining in the treatment area underwent a second 4-week treatment course. Apparently, the treatment area was not restricted and patients were allowed to use one or two sachets per application. The size of the treatment areas and number of sachets applied were not reported. The median number of AK lesions at baseline was 7. The authors further reported that 829 patients entered the study and that, overall, the complete clearance rate was 68.9% (571/829), the partial clearance rate (percentage of patients with ≥75% reduction in the number of baseline AK lesions) was 80.2%. The authors acknowledged that local skin reactions (LSRs) and application site reactions (ASRs) were the most commonly reported adverse events, and that four patients discontinued from the study due to LSRs or ASRs. The authors concluded that a shorter treatment regimen of imiquimod 5% cream, i.e., once daily 3×/week for 4 weeks for 1 or two courses, can produce complete clearance rates similar to those seen with 16 weeks of Aldara® 5% imiquimod cream treatment and has the advantage of lower drug exposure, resulting in a better benefit-risk profile for the patient. See Stockfleth, E., W. Sterry, et al.: Multicentre, open-label study using imiquimod 5% cream in one or two 4-week courses of treatment for multiple actinic keratoses on the head. *British Journal of Dermatology.* 157 Suppl 2: 41-6 (2007).

Another randomized study of topical 5% imiquimod vs. topical 5-fluorouracil vs. cryosurgery in immunocompetent patients with actinic keratoses, including a comparison of clinical and histological outcomes including 1-year follow-up, was conducted. According to the authors, this study compared the initial and 12-month clinical clearance, histological clearance, and cosmetic outcomes of topically applied 5% imiquimod (IMIQ) cream, 5% 5-fluorouracil (5-FU) ointment and cryosurgery for the treatment of AK of patients who were randomized to one of the following three treatment groups: one or two courses of cryosurgery (20-40 seconds per lesion), topical 5-FU (twice daily for 4 weeks), or one or two courses of topical imiquimod (three times per week for 4 weeks each). In this study, the treatment area was confined to one anatomic area of 50 $cm^2$ or less. The authors reported that: (1) sixty-eight percent (17/25) of patients treated with cryosurgery, 96% (23/24) of patients treated with 5-FU, and 85% (22/26) of patients treated with IMIQ achieved initial clinical clearance, P=0.03; (2) the histological clearance rate for cryosurgery was 32% (8/25), 67% (16/24) for 5-FU, and 73% (19/26) in the imiquimod group, P=0.03; (3) the 12-month follow-up showed a high rate of recurrent and new lesions in the 5-FU and cryosurgery arms; (4) the sustained clearance rate of initially cleared individual lesions was 28% (7/25) for cryosurgery, 54% (13/24) for 5-FU and 73% (19/26) for imiquimod ($p<0.01$); (5) sustained clearance of the total treatment field was 4% (1/25), 33% (8/24), and 73% (19/26) of patients after cryosurgery, 5-FU, and imiquimod, respectively ($P<0.01$); and (6) the patients in the imiquimod group were judged to have the best cosmetic outcomes (P=0.0001). The authors concluded that imiquimod treatment of AK resulted in superior sustained clearance and cosmetic outcomes compared with cryosurgery and 5-FU and that imiquimod should be considered as a first line therapy for sustained treatment of AK. See Krawtchenko, N., J. Roewert-Huber, et al.: A randomized study of topical 5% imiquimod vs. topical 5-fluorouracil vs. cryosurgery in immunocompetent patients with actinic keratoses: a comparison of clinical and histological outcomes including 1-year follow-up. British Journal of Dermatology. 157 Suppl 2: 34-40 (2007).

Also subsequent to FDA-approval of Aldara® 5% imiquimod cream to treat actinic keratosis, an open-label study to assess the safety and efficacy of imiquimod 5% cream applied once daily three times per week in cycles for treatment of actinic keratoses on the head was conducted. During this open-label study, imiquimod 5% cream was administered three times per week for four weeks followed by four weeks of rest (cycle 1) to AK lesions on the head. If AK lesions remained visible at the end of cycle 1, a second treatment cycle was instituted. According to the authors, 50% (30 of 60) of the subjects who experienced complete clearance of AK lesions, and 75% (30 of 40) of the subjects who experienced partial clearance of AK lesions after imiquimod treatment at the end of cycle 2. The authors further reported that 77% of the subjects, who achieved complete clearance, had no visible AK lesions 12 weeks post-treatment and that the imiquimod was well tolerated. The authors concluded that 5% Imiquimod cycle therapy, when administered three time per week for four weeks followed by four weeks of rest (cycle 1) combined with a second treatment cycle repeat, may be a safe and effective alternative to continuous imiquimod therapy for the treatment of AK lesions. The authors cautioned, however, that while cycle therapy does not affect the short-term AK recurrence rate, long-term follow-up is required. The authors also cautioned that further randomized, vehicle-controlled trials are needed. See Rivers J. K. et al.: Open-label study to assess the safety and efficacy of imiquimod 5% cream applied once daily three times per week in cycles for treatment of actinic keratoses on the head. *J Cutan Med Surg.* 12(3):97-101 (May-June 2008).

In view of the above, there is a need for improved actinic keratosis topical treatment that overcomes the current limitations associated with the current FDA-approved topical treatment regimen for actinic keratosis, i.e., 16 weeks, twice per week, with FDA-approved Aldara® 5% imiquimod cream.

SUMMARY OF THE INVENTION

The present invention overcomes the above-mentioned limitations associated with the treatment of actinic keratosis with FDA-approved Aldara® 5% imiquimod cream through the discovery of novel and improved imiquimod treatment regimens of short duration, lower dosage strength imiquimod pharmaceutical formulations, and simplified dosing regimens to treat actinic keratosis.

Generally speaking, the present invention provides for new and improved substantially less-irritating lower dosage strength imiquimod pharmaceutical formulations, which are suitable for daily application in connection with substantially condensed treatment regimens and substantially expanded treatment areas, for topical and/or transdermal administration of an effective amount of imiquimod to treat subjects who are diagnosed with clinically typical, nonhyperkeratotic actinic keratosis (AK), preferably on the face or balding scalp of immunocompetent patients. In addition, the present invention provides for new and improved actinic keratosis treatments, wherein: (1) treatment periods of the present invention are substantially shorter in duration, i.e., up to six weeks and preferably up to four weeks, than the current FDA-approved 16-week treatment regimen for actinic keratosis treatment; (2) dosing regimens of the present invention are substantially simpler, i.e., one application daily each day for up to six weeks and preferably up to four weeks, than the current dosing regimen, i.e., once-a-day but only twice per week for 16 weeks, for the current FDA-approved Aldara® 5% imiquimod cream for actinic keratosis treatment; (3) treatment areas of the present invention are substantially larger, i.e., up to about 250 $cm^2$, than the current FDA-approved treatment area, i.e., up to about 25 $cm^2$, for Aldara® 5% imiquimod cream for actinic keratosis treatment; (4) number of AK lesions being treated in accordance with the present invention are substantially greater in number, i.e., between about 5 and about 20 or more AK lesions per treatment area, than the number of AK lesions, i.e., between about 4 and about 8 AK lesions per treatment area, generally being treated with the current FDA-approved Aldara® 5% imiquimod cream for actinic keratosis treatment; (5) less-irritating imiquimod pharmaceutical formulations of the present invention are formulated with a lower dosage strength, i.e., between about 1% and about 4.25% imiquimod, than the current FDA-approved Aldara® 5% imiquimod cream for actinic keratosis treatment; and (6) lower subject incidence of application site reactions is experienced in accordance with the present invention, as compared with higher subject incidence of application site reactions experienced with the current FDA-approved Aldara® 5% imiquimod cream and treatment regimen for actinic keratosis treatment.

In other words, the present invention provides for new and improved actinic keratosis treatments that cover larger treatment areas, have short durations of therapies, use lower imiquimod dosage strengths, have simplified daily dosing regimens, and have a lower incidence of application site reactions, as compared to treatment of actinic keratosis with Aldara® 5% imiquimod cream, as currently approved by the FDA.

The present invention thus provides numerous surprising advantages over current FDA-approved Aldara® 5% imiquimod cream therapy for actinic keratosis treatment. For example, the present invention provides for (1) an expanded imiquimod treatment area estimated to be approximately 200-250 $cm^2$, e.g., the full face or entire balding scalp, (2) a shortened treatment regimen, i.e., up to about 6 weeks and preferably up to about 4 weeks, (3) a simplified dosing regimen, i.e., once daily on each day of the treatment period, (4) low systemic imiquimod blood levels even though the treatment area is vastly expanded and the dosing frequency is increased, (5) treatment of an increased number of clinical lesions per treatment period, e.g., about 5 to about 20 AK lesions or more, and (6) a lower subject incidence of application site reactions, even though there is an increase in imiquimod surface area penetration due to the expanded treatment area and increased applied amounts in accordance with the present invention, during the topical treatment regimen of actinic keratosis, than currently associated with FDA-approved Aldara® 5% imiquimod cream therapy.

Thus, the present invention overcomes certain of the limitations associated with the treatment of actinic keratosis with FDA-approved Aldara® 5% imiquimod cream and addresses current medical needs for (1) a larger treatment area (full face or balding scalp: >25 $cm^2$ vs. up to 25 $cm^2$ for Aldara® 5% imiquimod cream), (2) a shorter treatment period, e.g., two 2-week or two 3-week treatment cycles with an interim 2-week or 3-week no-treatment period sandwiched between them, respectively, vs. the full 16-week treatment regimen for Aldara® 5% imiquimod cream), (3) a more intuitive dosing regimen (daily dosing vs. twice weekly dosing for Aldara® 5% imiquimod cream) and (4) less or a lower incidence of application site reactions.

The less-irritating lower dosage strength imiquimod pharmaceutical formulations of the present invention may comprise:

a) a lower dosage strength of 1-isobutyl-1H-imidazo[4,5-c]-quinolin-4-amine or 1-(2-methylpropyl)-1H-imidazo[4, 5-c]quinolin-4-amine (imiquimod) for delivering an effective amount of imiquimod; and b) a pharmaceutically acceptable vehicle for imiquimod, which vehicle comprises a fatty acid, such as isostearic acid, palmitic acid, stearic acid, linoleic acid, unrefined oleic acid, refined oleic acid, such as Super Refined® oleic acid NF (e.g., a highly purified oleic acid, i.e., an oleic acid which has low polar impurities, such as peroxides, a low peroxide value and is marketed by CRODA; see e.g., www.crodausa.com) and a combination thereof, in a total amount of about 3 percent to about 45 percent by weight based on the total weight of the formulation.

The lower dosage strength imiquimod formulations of the present invention, especially those wherein the vehicle comprises an isostearic acid as the fatty acid, are uniquely designed to have physical and chemical stability, solubility, emollient properties and dose proportionate delivery similar to or better than Aldara® 5% imiquimod cream. More specifically, the lower dosage strength imiquimod formulations of the present invention, especially those wherein the vehicle comprises an isostearic acid as the fatty acid, are believed to generally have similar or improved skin emolliency at the application site and dose proportionate release rates as to both the release rates of the imiquimod and the total amount of imiquimod released, relative to the Aldara® 5% imiquimod cream. In other words, the lower dosage strength imiquimod formulations of the present invention are concentration influenced and have similar release rates to the Aldara® 5% imiquimod cream. Additionally, the greater the amount of imiquimod in the formulation, the faster and the greater the total amount of imiquimod is released, evidencing that the amount in and the rate of release from the formulations are imiquimod concentration dependent. Thus, while the lower dose strength imiquimod formulations of the present invention deliver different cumulative amounts to the stratum corneum and epidermis, i.e., local skin delivery, than the Aldara® 5% imiquimod cream, such lower dosage strength imiquimod formulations are believed to have a proportional and linear relationship that is similar with the Aldara® 5% imiquimod cream as to both the rate of imiquimod release and the total amount of imiquimod released and delivered locally to the skin over time, so that the imiquimod concentrations in the formulations of the present invention, the imiquimod release rates and the amount of imiquimod unabsorbed and delivered to the stratum corneum and epidermis, which has been released from the formulations, are generally proportional and linear to the Aldara® 5% imiquimod cream.

In addition, the lower dosage strength imiquimod formulations of the present invention, especially those wherein the vehicle comprises an isostearic acid as the fatty acid, are uniquely designed to be stable and fall within the range of the specifications for the commercially available Aldara® 5% imiquimod cream, such as to viscosity, pH, and stability, including microscopic and macroscopic stability. More specifically, the imiquimod present in the lower dosage strength imiquimod formulations of the present invention, especially those wherein the vehicle comprises an isostearic acid as the fatty acid, (monograph range: 90 to 110%) and benzyl alcohol (monograph range: 50 to 105%) remain within limits at both about 25° C. and about 40° C. over about a one month period and within limits at both about 25° C. and about 40° C. over about a six month period. Furthermore, the lower dosage strength imiquimod formulations of the present invention, especially those wherein the vehicle comprises an isostearic acid as the fatty acid, remain stabile for about six months at about 25° C. and about 40° C., and also remain stable with respect to macroscopic and microscopic appearance, viscosity (monograph range: 2,000 to 35000 cPs) and pH (monograph range 4.0 to 5.5). In addition, the lower dosage strength imiquimod formulations of the present invention are uniquely designed to meet the requirements specified in both United States Pharmacopeia ("USP") and the European Pharmacopeia ("EP") as to preservative efficacy and remain free of degradation products when stored at about 25° C./60% RH, about 30° C./65% RH and about 40° C./75% RH over about one, about two, about three and about six months and analyzed at about 318 nm wavelength.

The present invention also contemplates lower dosage strength imiquimod formulations, that have unique pharmacokinetic profiles when used, for example, in connection with the short durations of therapy to treat actinic keratosis in accordance with the present invention. By way of example, a 3.75% imiquimod lower dosage strength formulation of the present invention, when approximately 500 mg of such a formulation (about 18.75 mg imiquimod) or less is applied daily for 21 days to a treatment area of about 200 $cm^2$ on the face or balding scalp, achieves steady state by about week 2, e.g., between about day 8 and day 14, and provides an in-vivo serum profile selected from the following (See FIG. 54):

(a) a Day 21 $T_{max}$ of from about 4 hours to about 16 hours and preferably a mean $T_{max}$ of about 7.4 hours with a standard deviation ("SD") of about 3.5, a median $T_{max}$ of about 9 hours and a geometric mean $T_{max}$ of about 6.6 hours and a coefficient of variation ("CV") of about 48%;

(b) a Day 21 $C_{max}$ of from about 0.07 to about 0.6 ng/ml and preferably a mean $C_{max}$ of about 0.3 ng/ml with a standard deviation of about 0.16, a median $C_{max}$ of about 0.35 and a geometric mean $C_{max}$ of about 0.27 ng/ml and a coefficient of variation of about 49%;

(c) a Day 21 $T_{1/2}$ of from about 9.7 to about 84 hours and preferably a mean $T_{1/2}$ of about 29.3 hours with a standard deviation of about 17, a median $T_{1/2}$ of about 25.6 hours and a geometric mean $T_{1/2}$ of about 26 hours and a coefficient of variation of about 58%;

(d) a Day 21 $AUC_{0-24}$ of from about 1.1 to about 12 ng·hr/ml and preferably a mean $AUC_{0-24}$ of about 6 ng·hr/ml with a standard deviation of about 3, a median $AUC_{0-24}$ of about 7 ng·hr/ml and a geometric mean $AUC_{0-24}$ of about 5 ng·hr/ml and a coefficient of variation of about 52%;

(e) a Day 21 λz of from about 0.008 $hr^{-1}$ to about 0.07 $hr^{-1}$ and preferably a mean λz of about 0.03 $hr^{-1}$ with a standard deviation of about 0.01, a median λz of about 25.6 $hr^{-1}$ and a geometric mean λz of about 0.03 $hr^{-1}$ and a coefficient of variation of about 49%;

(f) a Day 21 $C_{min}$ of from about 0.06 to about 0.4 and preferably a mean $C_{min}$ of about 0.20 with an SD of about 0.11, a median $C_{min}$ of about 0.19 and a geometric mean $C_{min}$ of about 0.17 and a coefficient of variation of about 55%;

(g) at Day 14/7 (a ratio of the trough concentration at Day 14 over the trough concentration at Day 7), a trough concentration geometric mean ratio of about 1.09 with a 90% confidence interval ("CI") within a range of between about 0.8 and about 1.5;

(h) at Day 21/14 (a ratio of the trough concentration at Day 21 over the trough concentration at Day 14), a trough concentration geometric mean ratio of about 1.33 with a 90% confidence interval ("CI") within a range of between about 0.9 and about 1.9;

(i) at Day 22/21 (a ratio of the trough concentration at Day 22 over the trough concentration at Day 21) a trough concentration geometric mean ratio of about 0.93 with a 90% confidence interval ("CI") within a range of between about 0.6 and about 1.3;

(j) a mean peak imiquimod serum concentration of about 0.323 ng/ml at Day 21;

(k) a Day 21 RAUC of from about 1 to about 7 and preferably a mean RAUC of about 4 with a standard deviation of about 2, a median RAUC of about 3.5 and a geometric mean RAUC of about 3.3 and a coefficient of variation of about 56%;

(l) a Day 21 $RC_{max}$ of from about 0.5 to about 5 and preferably a mean $RC_{max}$ of about 3 with a standard deviation of about 1.5, a median $RC_{max}$ of about 2.7 and a geometric mean $RC_{max}$ of about 2.4 and a coefficient of variation of about 54%;

(m) a Day 21 $L\lambda z_{eff}$ of from about 0.006 $hr^{-1}$ to about 0.08 $hr^{-1}$ and preferably a mean $L\lambda z_{eff}$ of about 0.02 $hr^{-1}$ with a standard deviation of about 0.02, a median $L\lambda z_{eff}$ of about 0.01 $hr^{-1}$ and a geometric mean $L\lambda z_{eff}$ of about 0.16 $hr^{-1}$ and a coefficient of variation of about 97%; and (n) a Day 21 $T^{1/2}{}_{eff}$ of from about 8 hr to about 110 hr and preferably a mean $T^{1/2}{}_{eff}$ of about 55 hr with a standard deviation of about 36, a median $T^{1/2}{}_{eff}$ of about 50 hr and a geometric mean $T^{1/2}{}_{eff}$ of about 42 $hr^{-1}$ and a coefficient of variation of about 66%.

In accordance with the present invention, a mean peak serum concentration is achieved with a 3.75% lower dosage strength imiquimod formulation of Examples 23-28. More specifically, a mean peak serum concentration of about 0.323 ng/ml is achieved with a 3.75% lower dosage strength imiquimod formulation of Examples 23-28 after about 18.75 mg of imiquimod is applied to a treatment area of about 200 $cm^2$ on the face or balding scalp each day for 21 days.

In addition, the present invention contemplates lower dosage strength formulations that are pharmaceutically equivalent, therapeutically equivalent, bioequivalent and/or interchangeable, regardless of the method selected to demonstrate equivalents or bioequivalence, such as dermatopharmacokinetic and pharmacokinetic methodologies, microdialysis, in vitro and in vivo methods and/or clinical endpoints. Thus, the present invention contemplates lower dosage strength imiquimod formulations that are bioequivalent, pharmaceutically equivalent and/or therapeutic equivalent, especially, 2.5% and 3.75% lower dosage strength imiquimod formulations that are bioequivalent, pharmaceutically equivalent and/or therapeutically equivalent, when used daily in accordance with the short durations of therapy of the present invention to treat actinic keratosis, e.g., used on treatment areas, namely, full face or balding scalp, that are between greater than about 25 $cm^2$ and about 250 $cm^2$ on a daily basis for up to about six weeks, including the 3×3×3 weeks 2-cycle treatment regimen, and preferably up to about 4 weeks, including the 2×2×2 weeks 2-cycle treatment regimen.

Thus, the present invention contemplates: (a) pharmaceutically equivalent lower dosage strength imiquimod formulations which contain the same amount of imiquimod in the same dosage form; (b) bioequivalent lower dosage strength imiquimod formulations which are chemically equivalent and which, when administered to the same individuals in the same dosage regimens, result in comparable bioavailabilities; (c) therapeutic equivalent lower dosage strength imiquimod formulations which, when administered to the same individuals in the same dosage regimens, provide essentially the same efficacy and/or toxicity; and (d) interchangeable lower dosage strength imiquimod formulations of the present invention which are pharmaceutically equivalent, bioequivalent and therapeutically equivalent.

By the term "lower dosage strength(s)", as used herein, it refers to a pharmaceutical formulation containing imiquimod in an amount of between about 1.0 percent and about 4.25 percent by weight based on the total weight of the formulation and preferably a pharmaceutical formulation containing imiquimod in an amount of about 2.5% or about 3.75%.

By the term "short duration(s)" of therapy, as used herein, it refers to the daily topical application of an effective amount of imiquimod to a defined treatment area diagnosed with AK lesions for a total on-treatment period of up to about 6 weeks, depending upon which lower dosage strength imiquimod formulation of the present invention is selected for daily application, and more preferably a total on-treatment period of up to about 4 weeks, wherein an optional defined intervening rest period (no treatment) of up to about 3 weeks, and more preferably a rest period (no treatment) of up to about 2 weeks, may be taken at some point during the treatment period, to treat actinic keratosis. Thereby, the "short durations of therapy" may include, by way of example, a total duration of 9 weeks (3 weeks on, 3 weeks off, 3 weeks on), and more preferably 6 weeks (2 weeks on, 2 weeks off, 2 weeks on) from beginning of dosing to the end of dosing, inclusive of the rest period. Nevertheless, it should be understood by those versed in this art that the 2-cycle treatment regimens with a rest period sandwiched in between are preferred. In addition, the "short durations" of therapy may also include an 8 week examination period (no further treatment) following the treatment period.

The term "short duration(s)" of therapy of the present invention also refers to a two-cycle treatment regimen that involves either a 4-week or 6-week treatment regimen, wherein each treatment cycle consists of two or three weeks of once-daily applications of an effective amount of imiquimod, for each day of the cycle, separated by a 2-week or 3-week no-treatment period, respectively, such as follows:

(a) applying an effective amount of imiquimod to a treatment area affected with actinic keratosis once per day for fourteen (14) consecutive days or 2 weeks (cycle 1—treatment on), followed by no application for fourteen (14) days or 2 weeks (treatment off), followed by again applying an effective amount of imiquimod to the affected area once per day for fourteen (14) days or 2 weeks (cycle 2—treatment on) for a total of twenty-eight (28) doses or 4 weeks of application therapy to effectively treat actinic keratosis; or (b) applying an effective amount of imiquimod to a treatment area affected with actinic keratosis once per day for twenty-one (21) consecutive days or 3 weeks (cycle 1—treatment on), followed by no application for twenty-one (21) days or 3 weeks (treatment off), followed by again applying an effective amount of imiquimod once per day to the affected area for twenty-one (21) days or 3 weeks (cycle 2—treatment on) for a total of forty-two (42) doses or 6 weeks of application therapy to effectively treat actinic keratosis.

As indicated above, when the short durations of therapy are used in combination with the lower dosage strength imiquimod formulations of the present invention, it is surprisingly found that (1) simplified daily dosing regimens can be used, (2) the treatment area can be expanded, e.g., to treat greater than about 25 $cm^2$, e.g., areas as large as approximately 200 $cm^2$-250 $cm^2$ or more (e.g., full face or balding scalp) may now be treated, and (3) the number of AK lesions to be treated is higher, e.g., to between about 5 and about 20

AK lesions or more per treatment area. Also quite surprisingly, it is found that the expanded treatment area and increased number of AK lesions can be effectively treated with lower dosage strength imiquimod formulations without inducing significant local skin reactions or irritation in the treatment area or treatment limiting adverse events which could result in premature therapy termination or significant voluntary rest periods of several days that are generally associated with higher concentrations of imiquimod therapy. It is also surprisingly found that as much as between about 250 mg and 500 mg or more of a low dosage strength imiquimod formulation may be used per application in accordance with the present invention, especially when the short durations of therapy are used in combination with the low dosage strength imiquimod formulations of the present invention.

In comparison, the Aldara® 5% imiquimod cream approved by the FDA for actinic keratosis concerns a treatment area defined as one contiguous area of approximately 25 $cm^2$ on the face (e.g., forehead or one cheek) or the scalp, treating no more than about 4 to about 8 AK lesions per treatment area, a dosing schedule of only twice per week for a full 16 weeks to the defined treatment area on the face or scalp (but not both concurrently) and the application of no more than 250 mg of Aldara® 5% imiquimod cream formulation to the treatment area per application.

Also quite surprisingly, local skin reaction sum scores and mean local skin reaction erythema scores that are generated during the short durations of therapy with lower dosage strength imiquimod formulations in accordance with the present invention create unique bimodal or camelback patterns which parallel the 2-cycle imiquimod treatments of the present invention, wherein (1) the highest local skin reaction sum score and the mean local skin reaction erythema score generally and characteristically occur or peak during or at the end of the first cycle of treatment, (2) the local skin reaction sum score and the mean local skin reaction erythema score return to normal or baseline or about normal or baseline at the end of the no treatment period between cycles, (3) the local skin reaction sum score and the mean local skin reaction erythema score are again experienced by the subject during or at the end of the second cycle of treatment at generally but not necessarily a reduced score, as compared to the local skin reaction sum score and the mean local skin reaction erythema score during the first cycle of treatment, and (4) the local skin reaction sum score and the mean local skin reaction erythema score generally return to normal or base line shortly after the second cycle of treatment. See, e.g., FIGS. 18, 18A-B, 20, 20A-B and 43-50 and Example 28. When the bimodal or camelback pattern of local skin reaction sum score and mean local skin reaction erythema score are plotted as 2-dimensional graphs, wherein the local skin reaction sum score and the mean local skin reaction erythema score are measured on the vertical axis and the subject visits during the imiquimod 2-cycle therapy are measured on the horizontal axis, the unique bimodal or camelback patterns are observed. See, e.g., FIGS. 18, 18A-B, 20, and 20A-B. Given this unexpected result that the local skin reaction sum score and the mean local skin reaction erythema score are generally decreasing overall during the course of therapy and return to about normal or baseline at the end of the two-week no treatment period between the two treatment cycles and again return to normal or baseline at about the end of the second cycle of treatment, imiquimod therapy compliance should be significantly improved and the therapeutic results, e.g., complete clearance or partial clearance or reduction of AK lesions, more consistently achieved.

Also quite surprisingly, the efficacy achieved by the lower dosage strength imiquimod formulations when used in either of the short durations of therapy, e.g., two-week or three-week 2-cycle treatment regimens, of the present invention for treatment of actinic keratosis as to total clearance, partial clearance and a reduction in the number of AK lesions is statistically significant over placebo. See, e.g., FIG. 51. It is also surprising that the efficacy achieved for treatment of actinic keratosis as to complete clearance or partial clearance of AK lesions is basically statistically equivalent between the lower dosage strength imiquimod formulations two-week or three-week 2-cycle treatment regimens of the present invention when the same lower dosage strength imiquimod formulations are used in accordance with either 2-cycle treatment regimen and compared with one another between the two 2-cycle treatment regimens. See, e.g., FIG. 51. Even more surprising, however, the efficacy achieved by a lower dosage strength 3.75% imiquimod formulation when used in either a two-week or three-week 2-cycle treatment regimen of the present invention for treatment of actinic keratosis as for partial clearance of AK lesions is statistically significant over a lower dosage strength 2.5% imiquimod formulation when used in either a two-week or three-week 2-cycle treatment regimen. See, e.g., FIG. 51. Nevertheless, it should be noted that the efficacies that are achieved for complete clearance and partial clearance for either lower dosage strength imiquimod formulation, i.e., 2.5% or 3.75%, when they are used in either a two-week or three-week 2-cycle treatment regimen in accordance with the present invention are at about a 95% confidence level and a P value of less than about 0.001 versus placebo. See FIG. 51. It should also be noted that the efficacy P value that is achieved for partial clearance for a 3.75% lower dosage strength imiquimod formulation versus a 2.5% lower dosage strength imiquimod formulation that is utilized in accordance with a two-week or three-week 2-cycle treatment regimen of the present invention is about 0.047 or about 0.034, respectively. See, e.g., FIG. 51.

It is also quite surprising that the efficacy achieved by a lower dosage strength 3.75% imiquimod formulation when used in a two-week 2-cycle treatment regimen of the present invention for treatment of actinic keratosis as to a reduction in the number of AK lesions is statistically significant over a lower dosage strength 2.5% imiquimod formulation when used in a two-week 2-cycle treatment regimen, but no difference or essentially equivalent when both lower dosage strength imiquimod formulations are used in a three-week 2-cycle treatment regimen, in accordance with the present invention. See, e.g., FIG. 51. It should be noted that the efficacy P value that is achieved for a percent reduction in the number of AK lesions for a 3.75% lower dosage strength imiquimod formulation versus a 2.5% lower dosage strength imiquimod formulation that is utilized in accordance with a two-week or three-week 2-cycle treatment regimen of the present invention is about 0.048 or about 0.133, respectively. However, the 0.133 P value is not statistically significant. See, e.g., FIG. 51.

It is also quite surprisingly found that it is believed that no statistical significance in efficacy is achieved between a three-week 2-cycle treatment regimen versus a two-week 2-cycle treatment regimen regardless of the lower dosage strength imiquimod formulation used to treat actinic keratosis. See, e.g., FIG. 52. In other words, there is believed to be no additional efficacy benefit with the longer 3 week 2-cycle treatment regimen than the two week 2-cycle treatment regimen of the present invention to treat actinic keratosis, irrespective of which lower dosage strength imiquimod formulation is used in either of the 2-cycle treatment regimens in accordance with the present invention. See, e.g., FIGS. 52, 1-13G, 25-27, 36-38A and 42. It should be noted that the P values that are achieved for (a) complete clearance, (b) partial clearance and (c) a reduction in the number of lesions, for the two-week 2-cycle treatment regimens and the three-week 2-cycle treatment regimens of the present invention are (a) about 0.462 General Linear Model ("GLM") and about 0.499 (LA), (b) about 0.233 (GLM) and about 0.164 (LA), and (c) about 0.635 (GLM), respectively. See, e.g., FIG. 52.

While it is believed that there is no greater efficacy achieved between the two 2-cycle treatment regimens of the present invention, it is found that there is generally a greater incidence of side effects, e.g., local skin reactions, and rest periods associated with the three-week 2-cycle treatment period as compared with the two-week 2-cycle treatment period when the same lower dosage strength imiquimod formulation is used in each of the 2-cycle treatment regimens in accordance with the present invention. Even though there is an increase in incidence of side effects and rest periods associated with the three week 2-cycle treatment regimen, it is believed that an acceptable safety profile is still maintained when using either the two-week or three-week 2-cycle treatment regimens in accordance with the present invention. See, e.g., FIGS. 14A-23, 28, 28A-B and 39-42. Nonetheless, it is quite surprisingly found that there is a lower subject incidence of application site reactions associated with either of the 2-cycle treatment periods of the present invention than associated with use of the Aldara® 5% imiquimod cream to treat actinic keratosis in accordance with the FDA-approved treatment regimen, even though the Aldara® 5% imiquimod cream is applied only twice weekly to a treatment area of approximately 25 $cm^2$ for 16 weeks. See, e.g., FIGS. 28, 28A-B, 41 and 41A. Thus, it should be understood by those versed in this art that, while both 2-cycle treatment regimens of the present invention provide efficacious dosing regimens with acceptable safety profiles, that are short and more convenient for patient use than the dosing regimen currently approved by the FDA for Aldara® 5% imiquimod cream, to treat actinic keratosis, the 2 week 2-cycle treatment regimen of the present invention is preferred. It should also be understood that the short durations of therapy and lower dosage strength imiquimod formulations of the present invention are believed to be optimized to treat actinic keratosis. By "optimized", it is meant herein that the short durations of therapy and lower dosage strength imiquimod formulations of the present invention are designed to achieve efficacy, stability and release rates profiles that are at least essentially equivalent to and linear with Aldara® 5% imiquimod cream, respectively, but with an improved acceptable safety profile.

By the term "acceptable safety profile", it is meant herein to mean that treatment of actinic keratosis with a short duration of therapy and a lower dosage strength imiquimod formulation in accordance with the present invention, including the 2-cycle treatment regimens, does not cause treatment limiting side effects or rest periods in an appreciable number of subjects undergoing actinic keratosis therapy to a level that causes premature termination of treatment. The term "acceptable safety profile" also refers to treatment of actinic keratosis with a short duration of therapy and a lower dosage strength imiquimod formulation of the present invention with a lower subject incidence of application site reactions as compared with treatment of actinic keratosis with Aldara® 5% imiquimod cream.

Also quite surprisingly, it is found that, when a lower dosage strength imiquimod formulation, i.e., about 2.5%, is used in a 2-cycle, 2×2×2 weeks, treatment regimen in accordance with the present invention, to treat actinic keratosis diagnosed in females, a clearance rate, inclusive of complete clearance and partial clearance, of about 60% is achieved. See FIG. 31. Equally surprising, it is found that when a low dosage strength imiquimod formulation, i.e., about 3.75%, is used in either a 2-cycle, 2×2×2 week or a 2-cycle, 3×3×3 weeks, treatment regimen in accordance with the present invention, to treat actinic keratosis diagnosed in male or female subjects or in subjects with Type I, II or III skin, about 10 lesions or less at baseline, or with lesions on the face or scalp, equivalent or comparable clearance rates, inclusive of complete clearance and partial clearance, are achieved. See, e.g., FIGS. 31, 33, 33A, 34, 34A, 35 and 35A-B. Also surprising, it is found that when a low dosage strength imiquimod formulation, i.e., about 3.75%, is used in either a 2-cycle, 2×2×2 week or a 2-cycle, 3×3×3 week, treatment regimen in accordance with the present invention, to treat actinic keratosis diagnosed in subjects who are 65 years of age or older or in subjects who have greater than 10 lesions at baseline, the 2-cycle, 2×2×2 week treatment regimen is more effective. See, e.g., FIGS. 32, 32A, 34 and 34A.

It is also surprisingly found that, when a lower dosage strength imiquimod formulation is used in connection with a short duration of therapy, e.g., either a two-week or three-week 2-cycle treatment regimen, of the present invention for treatment of actinic keratosis, the Investigators Global Integrated Photodamage ("IGIP") score is significantly or much improved as compared with baseline. See, e.g., FIGS. 24 and 53. For example, and as shown in FIG. 53, when the 3.75% imiquimod studies are combined, approximately 44% (132 of 299) of the subjects under going treatment show significant improvement, approximately 25% (76 of 299) of the subjects under going treatment show much improvement and approximately 17% (51 of 299) of the subjects under going treatment show slight improvement in the IGIP score from baseline, whereas when the 2.5% imiquimod studies are combined, approximately 32% (97 of 304) of the subjects under going treatment show significant improvement, approximately 26% (78 of 304) of the subjects under going treatment show much improvement and approximately 23% (69 of 304) of the subjects under going treatment show slight improvement in the IGIP score from baseline.

The salient elements of a pharmaceutical formulation according to the present invention are (a) imiquimod and (b) a fatty acid, e.g., isostearic, palmitic, stearic, linoleic, unrefined oleic acid or refined oleic acid, such as Super Refined® oleic acid NF (e.g., a highly purified oleic acid, i.e., an oleic acid which has low polar impurities, such as peroxides, a low peroxide value and is marketed by CRODA; see e.g., www.crodausa.com) and mixtures thereof. A pharmaceutical formulation of the invention can be in any form known to the art, such as a cream, an ointment, a foam, a gel, a lotion or a pressure-sensitive adhesive composition, each form containing the necessary elements in particular amounts and further containing various additional elements.

A cream of the invention contains an effective amount of imiquimod, such as between about greater than 1 percent and about 4.25 percent by weight of imiquimod, based on the total weight of the cream; about 5 percent to about 30 percent by weight of fatty acid, based on the total weight of the cream; and optional ingredients such as emollients, emulsifiers, thickeners, and/or preservatives.

An ointment of the invention contains an ointment base in addition to imiquimod and fatty acid. An ointment of the invention contains an effective amount of imiquimod, such as between about greater than 1 percent and about 4.25 percent by weight of imiquimod; about 3 percent to about 45 percent, more preferably about 3 percent to about 30 percent by weight fatty acid; and about 40 percent to about 95 percent by weight ointment base, all weights being based on the total weight of the ointment. Optionally, an ointment of the invention can also contain emulsifiers, emollients and thickeners.

A pressure-sensitive adhesive composition of the invention contains imiquimod, fatty acid, and an adhesive. The adhesives utilized in a pressure sensitive adhesive composition of the invention are preferably substantially chemically inert to imiquimod. A pressure sensitive adhesive composition of the invention preferably contains an effective amount of imiquimod, such as between about greater than 1 percent and about 4.25 percent by weight of imiquimod; about 10 percent to about 40 percent by weight, more preferably of about 15 percent to about 30 percent by weight, and most preferably about 20 percent to about 30 percent by weight of fatty acid; all weights being based on the total weight of the pressure sensitive adhesive composition.

Optionally, pressure sensitive adhesive compositions of the invention can also contain one or more skin penetration enhancers. The total amount of skin penetration enhancer(s) present in a pressure sensitive adhesive composition of the invention is preferably about 3 percent to about 25 percent by weight, and more preferably about 3 percent to about 10 percent by weight based on the total weight of the pressure sensitive adhesive composition.

A pressure-sensitive adhesive coated sheet material of the invention can be made from a pressure-sensitive adhesive composition of the invention in the form of an article such as a tape, a patch, a sheet, or a dressing.

A lower dosage strength formulation of the present invention may be used to topically and/or transdermally administer an effective amount of imiquimod to effectively treat actinic keratosis with short durations of therapy and with an acceptable safety profile. Thus, lower dosage strength formulations according to the present invention can be applied to any suitable location, for example, topically to dermal, lip and/or mucosal surfaces. In the case of dermal application, for example, depending on the concentration, formulation composition, and dermal surface, the therapeutic effect of imiquimod may extend only to the superficial layers of the dermal surface or to tissues below the dermal surface.

It should be understood that while lower dosage strength formulations of the present invention containing, by weight based on the total weight of the formulation, between about 1% and about 4.25% imiquimod are contemplated, preferably between about 1.5%, 1.75%, 2.0%, 2.25%, 2.5%, 2.75%, 3.0%, 3.25%, 3.5%, 3.75%, 4.0% and 4.25%, and even more preferably between about 2.0%, 2.25%, 2.5%, 2.75%, 3.0%, 3.25%, 3.5%, 3.75% and 4.0%, and still even more preferably between about 2.5%, 2.75%, 3.0%, 3.25%, 3.5% and 3.75% are contemplated. Lower dosage strength formulations of the present invention that contain about 2.5% imiquimod or about 3.75% imiquimod by weight based on the total weight of the formulation are most preferred. It should also be understood that lower dosage strength imiquimod formulations of the present invention, which have dose proportionate release rates as to both the release rates of the imiquimod and the total amount of imiquimod released, relative to the Aldara® 5% imiquimod cream, are also preferred.

Thus, it should be understood by those versed in this art that an amount of imiquimod present in a formulation of the present invention will be an effective amount when a formulation of the present invention is applied daily in accordance with a short duration of therapy as described herein to a targeted area diagnosed with actinic keratosis and permitted following each individual application to remain in contact with the targeted area for a sufficient time to allow an effective amount of imiquimod to clear such a disease or lesions of the disease, to partially clear the number of lesions of such a disease, to reduce the number of lesions, to prevent the recurrence of such a disease without inducing treatment limiting local skin reactions or adverse events, including unscheduled rest periods caused by such treatment limiting local skin reactions or adverse events, in an appreciable number of people undergoing treatment. For example, when treating actinic keratosis in accordance with the present invention, an effective amount will achieve a partial clearance in AK lesions as a targeted endpoint, e.g., at least about 40% and preferably at least about 50% and more preferably at least about 60% and still more preferably at least about 70% and most preferably at least about a 75% reduction in the number of AK lesions in the treatment area compared with baseline, or at least about 60% and preferably at least about 70% and even more preferably at least about 80% and most preferably at least about 90% median reduction in the number of AK lesions in the treatment area compared with baseline as a secondary endpoint, or at least about 25% complete clearance and preferably at least about 30% complete clearance and even more preferably at least about 35% complete clearance and most preferably at least about 45% complete clearance of the AK lesions as a primary endpoint. See, e.g., FIGS. 36, 36A, 37, 37A, 38, 38A, 51 and 52. By "complete clearance", as used herein, the term means the absence of clinically visible or palpable AK lesions in the treatment area.

Results from use of the lower dosage strength imiquimod formulations in accordance with the short durations of therapy of the present invention demonstrate that lower dosage strength imiquimod formulations dosed once daily for two week or three week 2 cycle treatment periods are effective and well-tolerated treatments for actinic keratosis on the face or balding scalp. The condensed dosing regimens of the present invention allows for short treatment periods, minimizing exposure to imiquimod and further supporting an improved benefit-risk profile, as compared with FDA-approved Aldara® 5% imiquimod cream 16 week, twice-weekly therapy.

Benefits of treatment with the lower dosage strength imiquimod formulations in accordance with the short durations of therapy of the present invention include complete clearance or partial clearance (≥66%, preferably ≥75%, even more preferably ≥88% and even more preferably ≥95%) of AK lesions for a majority of the subjects that are treated. See Example 24 and FIGS. 51 and 52. More particularly, complete or partial clearances of AK lesions are achieved as follows: (1) ≥35% (57 of 160 subjects) complete clearance is achieved for a 2-week 2 cycle treatment using a 3.75% lower dosage strength imiquimod formulation of the present invention; (2) ≥30% (49 of 160 subjects) complete clearance is achieved for a 2-week 2 cycle treatment using a 2.5% lower dosage strength imiquimod formulation of the present invention; (3) ≥34% (55 of 162 subjects) complete clearance is achieved for a 3-week 2 cycle treatment using a 3.75% lower dosage strength imiquimod formulation of the present invention; and (4) ≥25% (41 of 164 subjects) complete clearance is achieved for a 2-week 2 cycle treatment using a 2.5% lower dosage strength imiquimod formulation of the present invention; whereas (5) ≥59% (95 of 160 subjects) partial clearance is achieved for a 2-week 2 cycle treatment using a 3.75% lower dosage strength imiquimod formulation of the present invention; (6) ≥48% (77 of 160 subjects) partial clearance is achieved for a 2-week 2 cycle treatment using a 2.5% lower dosage strength imiquimod formulation of the present invention; (7) ≥53% (87 of 162 subjects) partial clearance is achieved for a 3-week 2 cycle treatment using a 3.75% lower dosage strength imiquimod formulation of the present invention; and (8) ≥42% (70 of 164 subjects) partial clearance is achieved for a 2-week 2 cycle treatment using a 2.5% lower dosage strength imiquimod formulation of the present invention. Although subjects who are treated with the lower dosage strength imiquimod formulations in accordance with the short durations of therapy of the present invention may experience local skin reactions (LSRs), see, e.g., FIGS. 16A-20, 20A-B and 29 and 40, the treatment is well tolerated and there is a marked lower subject incidence of application site reactions, e.g., see FIGS. 14A-E, 28, 28A-B, 41 and 41A, as compared with the longer FDA-approved Aldara® 5% imiquimod cream treatment regimen, i.e., 16 weeks, twice weekly, for AK therapy.

This same larger "treatment area" of the present invention may be defined as an area of greater than 25 $cm^2$ (e.g., a treatment area greater than a 5 cm×5 cm area in any shape) and up to between about 200 $cm^2$ and 250 $cm^2$ or more on the face (e.g. forehead or one cheek) or on the balding scalp, including the full face or entire balding scalp. The number of AK lesions to be treated in the treatment area may range from about 5 to about 20 or more. It should be also appreciated by those versed in this art that the present invention also affords the added benefit of the uncovering and clinical appearance and subsequent complete or partial eradication of incipient (subclinical) AK lesions in the treatment area. It is presently believed that, because the treatment area exceeds 25 $cm^2$, the lower dose strength imiquimod formulations and the short durations of therapy, when practiced in accordance with the present invention, will increase subject tolerance and compliance, improve the therapeutic results, e.g., complete clearance or partial clearance or reduction of AK lesions, lower subject incidence of application site reactions (see, e.g., FIGS. 28, 28A-B, 41 and 41A), and reduce voluntary rest periods (see, e.g., FIGS. 39 and 39A) during therapy, as compared to Aldara® 5% imiquimod cream if applied to the same larger treatment area in accordance with the present invention. Moreover, it is believed that, because the expanded treatment area is so much larger than the smaller treatment area, i.e., less than or equal to approximately 25 $cm^2$, currently treated with Aldara® 5% imiquimod cream, the expanded treatment area of the present invention will be much more weighted to non-lesional/normal skin than previously experienced with the smaller treatment area treated with Aldara® 5% imiquimod cream. Preferably, the concentration of imiquimod applied is between about 1 percent to about 4.25 percent by weight based on the total weight of a formulation of the present invention. Also, to treat actinic keratosis in accordance with the present invention, an effective amount of imiquimod should be applied once per day for at least up to about 6 weeks, e.g., once per day for a full 2 or 3 weeks (14 or 21 days) to a diagnosed or defined treatment area on, for example, the face or balding scalp (cycle 1), then stopped or discontinued for 2 or 3 weeks (14 or 21 days), a scheduled rest period, followed by application again once per day for a full 2 or 3 weeks (14 or 21 days) to the defined treatment area (cycle 2) to achieve a secondary and more preferably a primary endpoint, e.g., to achieve at least about a 75% reduction in AK lesions as a targeted secondary endpoint and more preferably complete clearance of the AK lesions as a primary endpoint. Also when treating actinic keratosis in accordance with the two-week or three week 2-cycle treatment periods of the present invention, an effective amount of imiquimod applied to the treatment area will not only achieve a secondary or primary endpoint, but will also induce a lower subject incidence of application site skin reactions and a fewer number of voluntary rest periods taken by the subjects under going treatment, e.g., no more than about 11% and more preferably no more than about 7% of the subjects will take one or more rest periods during the short two-week 2-cycle treatment period or no more than about 17% and more preferably no more than about 27% of subjects will take one or more rest periods during the short three-week 2-cycle treatment period. See, e.g., FIGS. 21, 39 and 39A.

While the present invention has identified what it believes to be preferred concentrations of imiquimod formulations, numbers of applications per week and durations of therapy, it should be understood by those versed in this art that any effective concentration of imiquimod in a formulation that delivers an effective amount of imiquimod and any numbers of application per week during a short duration of therapy, as described herein, that can effectively treat actinic keratosis, without causing treatment limiting local skin reactions or related adverse events, including too many rest periods, is contemplated by the present invention.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The foregoing and other objects, advantages and features of the present invention, and the manner in which the same are accomplished, will become more readily apparent upon consideration of the following detailed description of the invention taken in conjunction with the accompanying figure and examples, which illustrate an embodiment, wherein:

FIG. 1A is a summary of primary and secondary efficacy endpoints for a two-week treatment cycle regimen concerning ITT population for studies GW01-0702 and GW01-0704. Complete clearance is defined as the absence of clinically visible or palpable AK lesions in the treatment area. Partial clearance is defined as at least a 75% reduction in the number of AK lesions in the treatment area compared with Baseline. P values are from Cochran-Mantel-Haenszel test, stratified by analysis site, taking 2 treatment groups at a time. The P values marked with  are statistically significant using Hochberg's modified Bonferroni procedure. LOCF=Last observation that is carried forward. Confidence intervals are calculated using exact binomial statistics. As used in this FIG. 1**A, "2.5%" refers to a 2.5% imiquimod lower dosage strength formulation of Examples 23-28 and "3.75%" refers to a 3.75% imiquimod lower dosage strength formulation of Examples 23-28;

FIG. 10A shows a summary of primary and secondary efficacy endpoints for male and female subpopulations for combined two-week treatment cycle studies GW01-0702 and GW01-0704 for an ITT population using either a 2.5% or a 3.75% lower dosage strength imiquimod formulation of Examples 23-28. The P values for clearance rates are from a generalized linear module (GENMOD), assuming a multinomial distribution (DIST=MULT) and a cumulative logit link function (LINK=CLOGIT), including effects of dose, subpopulation, and interaction. The P values for percent change in AK lesion count are from the analysis of variance (GLM) including effects of dose, subpopulation, and interaction;

FIG. 10B shows a summary of primary efficacy variable, rate of complete clearance at week 17 (end of study) subgroup analysis n/N (%) for study GW01-0703 using either a 2.5% or a 3.75% lower dosage strength imiquimod formulation of Examples 23-28;

FIG. 10C shows a summary of primary efficacy variable, rate of complete clearance at week 17 (end of study) subgroup analysis n/N (%) for study GW01-0705 using either a 2.5% or a 3.75% lower dosage strength imiquimod formulation of Examples 23-28;

FIGS. 13A-G show a summary of percent change from baseline in number of AK lesions by visit for combined studies for an ITT population using either a 2.5% or a 3.75% lower dosage strength imiquimod formulation of Examples 23-28. The P values are from the Cochran-Mantel-Haenszel test, that is stratified by analysis site, taking two treatment groups at a time. The P values marked with ** are statistically significant using Hochberg's modified Bonferroni procedure;

FIGS. 14A-E show a summary of treatment-emergent adverse events n (%) of subjects in descending order of incidence in a 3.75% or 2.5% two-week or three-week treatment cycle group where the adverse events are considered treatment related by the investigator for combined studies for an ITT population using either a 2.5% or a 3.75% lower dosage strength imiquimod formulation of Examples 23-28. The counts reflect number of subjects in each treatment group reporting one or more adverse events that map to the MedDRA system organ class. A subject may be counted only once in each row of the table. Treatment-related includes Probably Related and Related. A treatment-emergent AE is an AE with onset date on or after day 1 of treatment;

FIGS. 16A-C show a summary of local skin reactions (LSR) for most severe reaction grade during study overall for combined studies for an ITT population using a 2.5% or a 3.75% lower dosage strength imiquimod formulation in 2 week or 3 week two-cycle therapies in accordance with the present invention. Because a subject in the two-week 3.75% treatment group, a subject in the three-week 2.5% treatment, a subject in the 3.75% treatment group and two subjects in the three-week placebo group do not have post-baseline visits, they are excluded from the analysis;

FIG. 17A shows a summary of local skin reactions (LSR) area under the curve of sum of LSR scores (days) for combined studies for an ITT population using either a 2.5% or a 3.75% lower dosage strength imiquimod formulation of Examples 23-28. The P values are from the analysis of variance (GLM) including effects of dose, regimen, and analysis center within regimen. The time period for the AUC extends to eight weeks after the end of treatment for both the two-week treatment cycle regimen (week 14) and the three-week treatment cycle regimen (week 17). Only subjects who receive treatment in both treatment cycles are included in this analysis;

FIG. 23 shows a summary of select safety parameters associated with applications of the 2.5% and 3.75% imiquimod cream formulations of Example 23 that are used in 2×2×2 week, 2-cycle regimens and used in 3×3×3 week 2-cycle regimens. The results demonstrate the overall acceptable safety profile of both the 2.5% and 3.75% imiquimod formulations of Example 23 according to either of the 2 or 3 week cycle regimens. Of note, the safety results suggest a preferable safety profile when either the 2.5% or the 3.75% imiquimod formulation is used in a 2×2×2 week, 2-cycle regimen versus a 3×3×3 week, 2-cycle regimen.

FIG. 24 shows improvement in the Investigator Global integrated photodamage score from baseline for a two week 2-cycle treatment period (2×2×2 weeks). In this FIG. 24, Study 1 refers to the GW01-0702 study and Study 2 refers to the GW01-0704 study herein through-out. As used in this FIG. 24, "Pbo" refers to placebo and "Imiq" refers to imiquimod;

FIG. 25A shows a summary of primary and secondary efficacy endpoints for combined studies, analysis within regimen for an ITT population using a 3.75% lower dosage strength imiquimod formulation of Examples 23-28. Complete clearance is defined as the absence of clinically visible or palpable AK lesions in the treatment area. Partial clearance is defined as at least a 75% reduction in the number of AK lesions in the treatment area compared with Baseline. P values are from Cochran-Mantel-Haenszel test, stratified by analysis site, within regimen, taking 2 treatment groups at a time. The P values marked with ** are statistically significant using Hochberg's modified Bonferroni procedure. LOCF=Last observation that is carried forward. Confidence intervals are calculated using exact binomial statistics;

FIG. 28 shows safety comparison of incidence of adverse events for studies GW01-0703, GW01-0702, GW01-0704 and GW01-0705, as compared with Aldara® 5% imiquimod cream. As used in this FIG. 28, "2 weeks" refers to a two week, 2-cycle therapy, "3 weeks" refers to a three week, 2-cycle therapy, "Pbo" refers to placebo, "2.5%" refers to a 2.5% imiquimod lower dosage strength formulation of Examples 23-28 and "3.75%" refers to a 3.75% imiquimod lower dosage strength formulation of Examples 23-28;

FIGS. 28A-B show a number (%) of subjects in phase 3 studies with treatment-emergent adverse events with incidence greater than 1% in the 3.75% imiquimod two-week treatment cycle group for an ITT population. Counts reflect number of subjects in each treatment group reporting one or more adverse events that map to the MedDRA system organ class. A subject may be counted once only in each row of the table. A treatment-emergent AE is an AE with onset date on or after day 1 of treatment. As used in these FIGS. 28A-B, "2.5%" refers to a 2.5% imiquimod lower dosage strength formulation of Examples 23-28 and "3.75%" refers to a 3.75% imiquimod lower dosage strength formulation of Examples 23-28;

FIG. 32A shows a summary of primary and secondary efficacy endpoints for age subpopulations over and under 65 for combined two-week treatment cycle studies (GW01-0702 and GW01-0704) for an ITT population for active treatment only using a 3.75% lower dosage strength imiquimod formulation of Examples 23-28. The P values for clearance rates are from a generalized linear module (GENMOD), assuming a multinomial distribution (DIST=MULT) and a cumulative logit link function (LINK=CLOGIT), including effects of dose, subpopulation, and interaction. The P values for percent change in AK lesion count are from the analysis of variance (GLM) including effects of dose, subpopulation, and interaction. As used in this FIG. 32A, "2.5%" refers to a 2.5% imiquimod lower dosage strength formulation of Examples 23-28, "3.75%" refers to a 3.75% imiquimod lower dosage strength formulation of Examples 23-28, "<65" refers to an age population that is less than 65 years old and ">=65" refers to an age population that is 65 years old or older;

FIG. 33A shows a summary of primary and secondary efficacy endpoints for Fitzpatrick skin type subpopulations for combined two-week treatment cycle studies (GW01-0702 and GW01-0704) for an ITT population for active treatment only using a 3.75% lower dosage strength imiquimod formulation of Examples 23-28. The P values for clearance rates are from a generalized linear module (GENMOD), assuming a multinomial distribution (DIST=MULT) and a cumulative logit link function (LINK=CLOGIT), including effects of dose, subpopulation, and interaction. The P values for percent change in AK lesion count are from the analysis of variance (GLM) including effects of dose, subpopulation, and interaction. As used in this FIG. 33A, "2.5%" refers to a 2.5% imiquimod lower dosage strength formulation of Examples 23-28, "3.75%" refers to a 3.75% imiquimod lower dosage strength formulation of Examples 23-28, and "I", "II", "III", "IV" "V" or "VI" refer to Fitzpatrick skin type;

FIG. 34A shows a summary of primary and secondary efficacy endpoints for baseline lesion count subpopulations for combined two-week treatment cycle studies (GW01-0702 and GW01-0704) for an ITT population for active treatment only using a 3.75% lower dosage strength imiquimod formulation of Examples 23-28. The P values for clearance rates are from a generalized linear module (GENMOD), assuming a multinomial distribution (DIST=MULT) and a cumulative logit link function (LINK=CLOGIT), including effects of dose, subpopulation, and interaction. The P values for percent change in AK lesion count are from the analysis of variance (GLM) including effects of dose, subpopulation, and interaction. As used in this FIG. 34A, "2.5%" refers to a 2.5% imiquimod lower dosage strength formulation of Examples 23-28 and "3.75%" refers to a 3.75% imiquimod lower dosage strength formulation of Examples 23-28;

FIG. 35A shows a summary of primary and secondary efficacy endpoints for location of treatment area (face or balding scalp) subpopulations for combined two-week treatment cycle studies (GW01-0702 and GW01-0704) for an ITT population for active treatment only using a 3.75% lower dosage strength imiquimod formulation of Examples 23-28. The P values for clearance rates are from a generalized linear module (GENMOD), assuming a multinomial distribution (DIST=MULT) and a cumulative logit link function (LINK=CLOGIT), including effects of dose, subpopulation, and interaction. The P values for percent change in AK lesion count are from the analysis of variance (GLM) including effects of dose, subpopulation, and interaction. As used in this FIG. 35A, "2.5%" refers to a 2.5% imiquimod lower dosage strength formulation of Examples 23-28, "3.75%" refers to a 3.75% imiquimod lower dosage strength formulation of Examples 23-28, and "Face" and "Balding Scalp" refer to the treatment area;

FIG. 35B shows a summary of primary and secondary efficacy endpoints for location of treatment area (face or balding scalp) subpopulations for combined two-week treatment cycle studies (GW01-0702 and GW01-0704) for an ITT population using a 3.75% lower dosage strength imiquimod formulation of Examples 23-28. The P values for clearance rates are from a generalized linear module (GENMOD), assuming a multinomial distribution (DIST=MULT) and a cumulative logit link function (LINK=CLOGIT), including effects of dose, subpopulation, and interaction. The P values for percent change in AK lesion count are from the analysis of variance (GLM) including effects of dose, subpopulation, and interaction. As used in this FIG. 35B, "2.5%" refers to a 2.5% imiquimod lower dosage strength formulation of Examples 23-28, "3.75%" refers to a 3.75% imiquimod lower dosage strength formulation of Examples 23-28, and "Face" and "Balding Scalp" refer to the treatment area;

FIG. 36 shows percent complete clearance compared with Aldara® 5% imiquimod cream. In this FIG. 36 and throughout the specification, study 1 refers to GW01-0702 study and study 2 refers to GW01-0704 study. As used in this FIG. 36, "Pbo" refers to placebo, "Imiq" refers to imiquimod, and "Aldara" refers to Aldara® 5% imiquimod cream. See also FIG. 1;

FIG. 36A shows percent complete clearance compared with placebo. In this FIG. 36 and throughout the specification, study 1 refers to GW01-0702 study, study 2 refers to GW01-0704 study, study 3 refers to GW01-0703 study and study 4 refers to GW01-0705 study. As used in this FIG. 36A, "Pbo" refers to placebo and "Imiq" refers to imiquimod;

FIG. 37 shows percent partial clearance compared with Aldara® 5% imiquimod cream. In this FIG. 37 and throughout the specification, study 1 refers to GW01-0702 study and study 2 refers to GW01-0704 study. As used in this FIG. 37, "Pbo" refers to placebo, "2.5% Imiq" refers to a 2.5% imiquimod lower dosage strength formulation of Examples 23-28, "3.75% Imiq" refers to a 3.75% imiquimod lower dosage strength formulation of Examples 23-28, and "Aldara" refers to Aldara® 5% imiquimod cream. See also FIG. 4A;

FIG. 37A shows a partial clearance compared with placebo. In this FIG. 37A and throughout the specification, study 1 refers to GW01-0702 study, study 2 refers to GW01-0704 study, study 3 refers to GW01-0703 study and study 4 refers to GW01-0705 study. As used in this FIG. 37A, "Pbo" refers to placebo, "2.5% Imiq" refers to a 2.5% imiquimod lower dosage strength formulation of Examples 23-28, and "3.75% Imiq" refers to a 3.75% imiquimod lower dosage strength formulation of Examples 23-28;

FIG. 38 shows AK median % reduction compared with Aldara® 5% imiquimod cream. In this FIG. 38 and throughout the specification, study 1 refers to GW01-0702 study and study 2 refers to GW01-0704 study. As used in this FIG. 38, "Pbo" refers to placebo, "2.5% Imiq" refers to a 2.5% imiquimod lower dosage strength formulation of Examples 23-28, "3.75% Imiq" refers to a 3.75% imiquimod lower dosage strength formulation of Examples 23-28, and "Aldara" refers to Aldara® 5% imiquimod cream;

FIG. 38A shows AK median % reduction compared with placebo. In this FIG. 38A and throughout the specification, study 1 refers to GW01-0702 study, study 2 refers to GW01-0704 study, study 3 refers to GW01-0703 study and study 4 refers to GW01-0705 study. As used in this FIG. 38A, "Pbo" refers to placebo, "2.5% Imiq" refers to a 2.5% imiquimod lower dosage strength formulation of Examples 23-28, "3.75% Imiq" refers to a 3.75% imiquimod lower dosage strength formulation of Examples 23-28, and "Aldara" refers to Aldara® 5% imiquimod cream;

FIG. 39 shows rest periods for the 2-cycle, 2×2×2 (2 week) treatment regimen, as compared with Aldara® 5% imiquimod cream. As used in this FIG. 39, "Pbo" refers to placebo, "2.5% Imiq" refers to a 2.5% imiquimod lower dosage strength formulation of Examples 23-28, "3.75% Imiq" refers to a 3.75% imiquimod lower dosage strength formulation of Examples 23-28, and "Aldara" refers to Aldara® 5% imiquimod cream;

FIG. 39A shows selected safety parameters for combined two-week, two-cycle studies (GW01-0702 and GW01-0704) or three-week, two-cycle studies (GW01-0703 and GW01-0705). As used in this FIG. 39A, "2.5% Imiq" refers to a 2.5% imiquimod lower dosage strength formulation of Examples 23-28, "3.75% Imiq" refers to a 3.75% imiquimod lower dosage strength formulation of Examples 23-28 and "Tx" refers to treatment;

FIG. 40 shows local skin reactions ("LSRs"); % of subjects with severe LSRs for the 2-cycle, 2×2×2 (2 week) treatment regimen, as compared with Aldara® 5% imiquimod cream. As used in this FIG. 40, "Pbo" refers to placebo, "2.5% Imiq" refers to a 2.5% imiquimod lower dosage strength formulation of Examples 23-28, "3.75% Imiq" refers to a 3.75% imiquimod lower dosage strength formulation of Examples 23-28, and "Aldara" refers to Aldara® 5% imiquimod cream. See also FIG. 16A-C;

FIG. 41 shows a comparison regarding the incidence of selected common adverse events for the 2-cycle, 2×2×2 (2 week) treatment regimen, as compared with Aldara® 5% imiquimod cream. As used in this FIG. 41, "Pbo" refers to placebo, "2.5% Imiq" refers to a 2.5% imiquimod lower dosage strength formulation of Examples 23-28, "3.75% Imiq" refers to a 3.75% imiquimod lower dosage strength formulation of Examples 23-28, "Aldara" refers to Aldara® 5% imiquimod cream, and "NS" refers to not specified;

FIG. 41A shows incidence of most common (greater than 1%) treatment-related adverse events for combined two-week studies (GW01-0702 and GW01-0704) or three-week studies (GW01-0703 and GW01-0705);

FIG. 43 shows a clinical case study of a 39 year old white male in which a 2.5% imiquimod (IMIQ) formulation is used in a 2 cycle, 2×2×2 weeks, to treat actinic keratosis;

FIG. 44 shows a clinical case study of a 74 year old white male in which a 2.5% imiquimod (IMIQ) formulation is used in a 2 cycle, 2×2×2 weeks, to treat actinic keratosis;

FIG. 45 shows a clinical case study of a 66 year old white female in which a 3.75% imiquimod (IMIQ) formulation is used in a 2 cycle, 2×2×2 weeks, to treat actinic keratosis;

FIG. 46 shows a clinical case study of a 73 year old white male in which a 3.75% imiquimod (IMIQ) formulation is used in a 2 cycle, 2×2×2 weeks, to treat actinic keratosis;

FIG. 47 shows a clinical case study of a 70 year old white male in which a 2.5% imiquimod (IMIQ) formulation is used in a 2 cycle, 3×3×3 weeks to treat actinic keratosis;

FIG. 48 shows a clinical case study of a 65 year old white female in which a 2.5% imiquimod (IMIQ) formulation is used in a 2 cycle, 3×3×3 weeks to treat actinic keratosis;

FIG. 49 shows a clinical case study of a 79 year old white male in which a 3.75% imiquimod (IMIQ) formulation is used in a 2 cycle, 3×3×3 weeks to treat actinic keratosis;

FIG. 50 shows a clinical case study of a 78 year old white male in which a 3.75% imiquimod (IMIQ) formulation is used in a 2 cycle, 3×3×3 weeks to treat actinic keratosis; and FIG. 51 shows a summary of primary and secondary efficacy endpoints in which (a) the results of the GW01-0702 and GW01-0704 (2×2×2) studies for each imiquimod formulation strength, i.e., about 2.5% or about 3.75% w/w, that are used in the studies are combined, respectively, (b) the results of the GW01-0703 and GW01-0705 (3×3×3) studies for each imiquimod formulation strength, i.e., about 2.5% or about 3.75% w/w, that are used in the studies are combined, respectively, and (c) the analysis is within regimen ITT populations. Complete clearance is defined as the absence of clinically visible or palpable AK lesions in the treatment area. Partial clearance is defined as at least about a 75% reduction in the number of AK lesions in the treatment area as compared with Baseline. P values are from Cochran-Mantel-Haenszel test, are stratified by analysis site, within regimen, taking 2 treatment groups at a time. The P values that are marked with  are statistically significant using Hochberg modified Bonferroni procedure. LOCF=last observation carried forward. Confidence intervals are calculated using exact binomial statistics. In this FIG. 51, "2.5%" refers to a 2.5% imiquimod lower dosage strength formulation of Examples 23-28 and "3.75%" refers to a 3.75% imiquimod lower dosage strength formulation of Examples 23-28. See also FIG. 25**A;

FIG. 52 shows a summary of primary and secondary efficacy endpoints from combined studies and an analysis across regimens for the ITT Population. Column (1) P values for all parameters are from the analysis of variance based on a General Linear Model ("GLM") including effects of dose, regimen, and analysis site within regimen. Column (2) P values are based on a logistic analysis of the effects of dose, regimen, and analysis site. In this FIG. 52, "2.5%" refers to a 2.5% imiquimod lower dosage strength formulation of Examples 23-28 and "3.75%" refers to a 3.75% imiquimod lower dosage strength formulation of Examples 23-28;

FIG. 53 shows a summary of an Investigators Global Integrated Photodamage ("IGIP") score for the (a) GW01-0702 and GW01-0704 studies, (b) GW01-0703 and GW01-0705 studies and (c) combined studies, i.e., GW01-0702, GW01-0703, GW01-0704 and GW01-0705 studies, for a two-week 2-cycle treatment period (2×2×2 weeks) and a three-week 2-cycle treatment period (3×3×3 weeks) for the Intent-To-Treat ("ITT") population. In this FIG. 53, "2.5%" refers to a 2.5% imiquimod lower dosage strength formulation of Examples 23-28 and "3.75%" refers to a 3.75% imiquimod lower dosage strength formulation of Examples 23-28;

FIG. 54 shows a summary of serum pharmacokinetic parameters at day 21 for a 3.75% imiquimod formulation of Examples 23-28, PK population. The serum analyte is imiquimod. The calculation of accumulation ratio (RAUC, RCmax) and effective half-life for accumulation (T½ and T½ eff), is restricted to subjects who take all seven doses during the week of treatment and who take at least 80% of the prescribed doses during the prior two weeks. The PK parameters are not calculated for subject 001-619 and subject 001-608. There is no concentration data for subject 001-619, and subject 001-608 did not take all required doses during the 21 days of treatment. $AUC_{0-24}$ equals AUCss and $C_{min}$ equals predose concentration (t=0). In this FIG. 51, "Imiquimod" refers to a 3.75% imiquimod lower dosage strength formulation of Examples 23-28. See also Example 25;

DETAILED DESCRIPTION OF THE INVENTION

Figure 1:
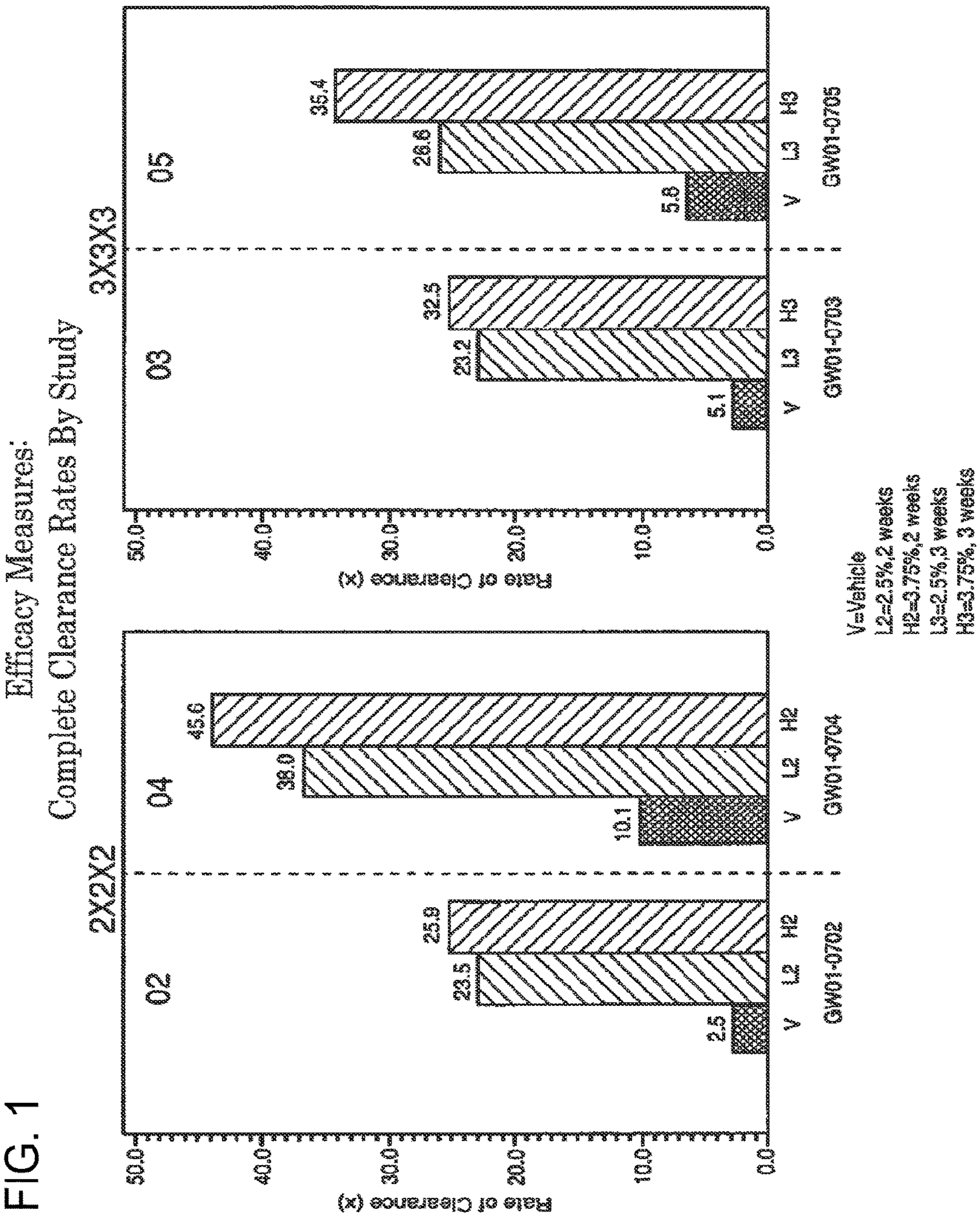
FIG. 1 shows efficacy measures of complete clearance rates by study for studies GW01-0702, GW01-0703, GW01-0704 and GW01-0705 for the 2-cycle 2×2×2 (2 weeks) treatment regimen and for the 2-cycle 3×3×3 (3 weeks) treatment regimen.
Figure 2:
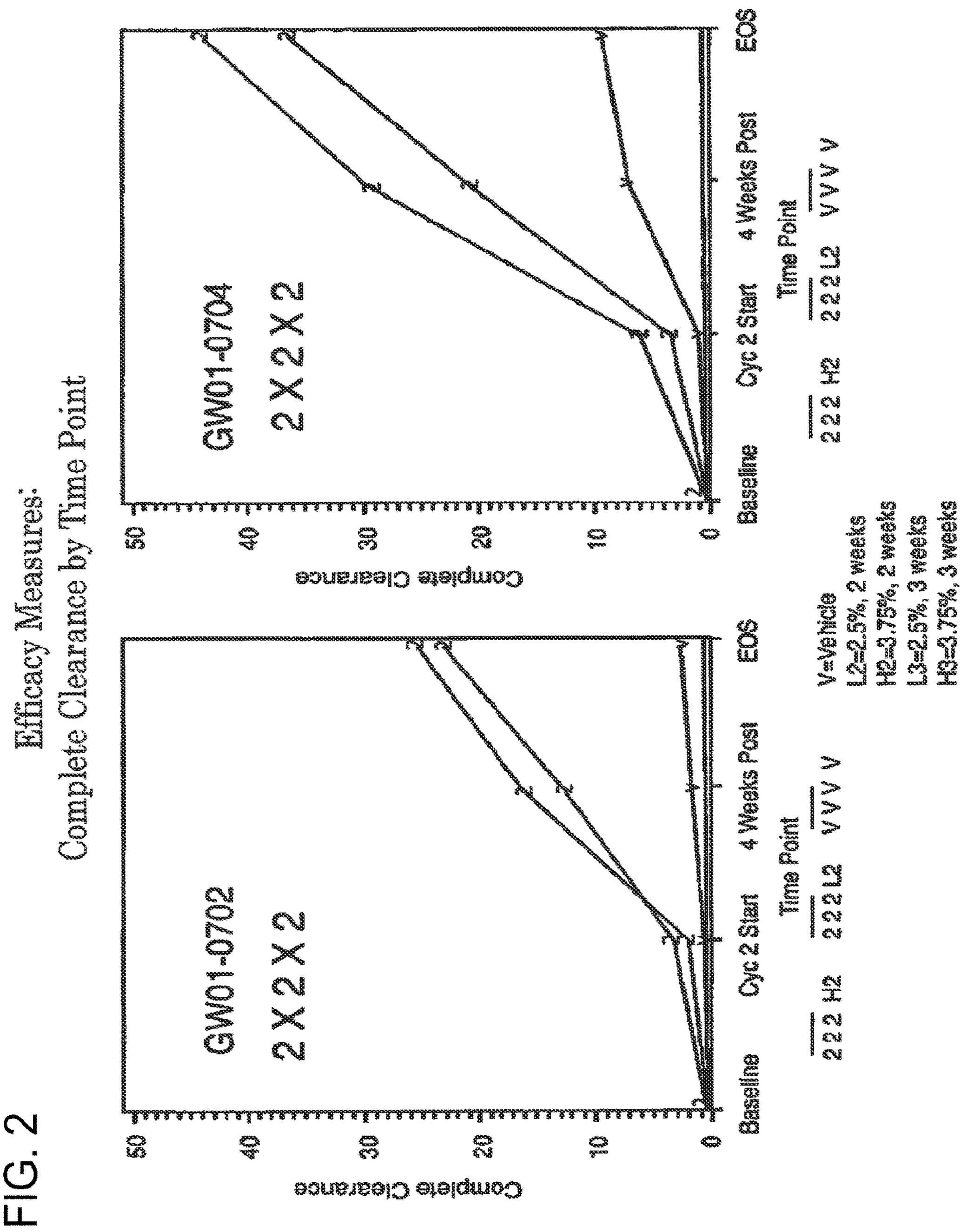
FIG. 2 shows efficacy measures of complete clearance, by time point, for studies GW01-0702 and GW01-0704 for the 2-cycle 2×2×2 (2 weeks) treatment regimen. As used in this FIG. 2, "Complete Clearance" refers to the rate of complete clearance of AK lesions, "Cyc 2 Start" refers to the start of the second cycle, "4 Weeks Post" refers to 4 weeks post treatment, and "EOS" refers to End of Study.
Figure 2A:
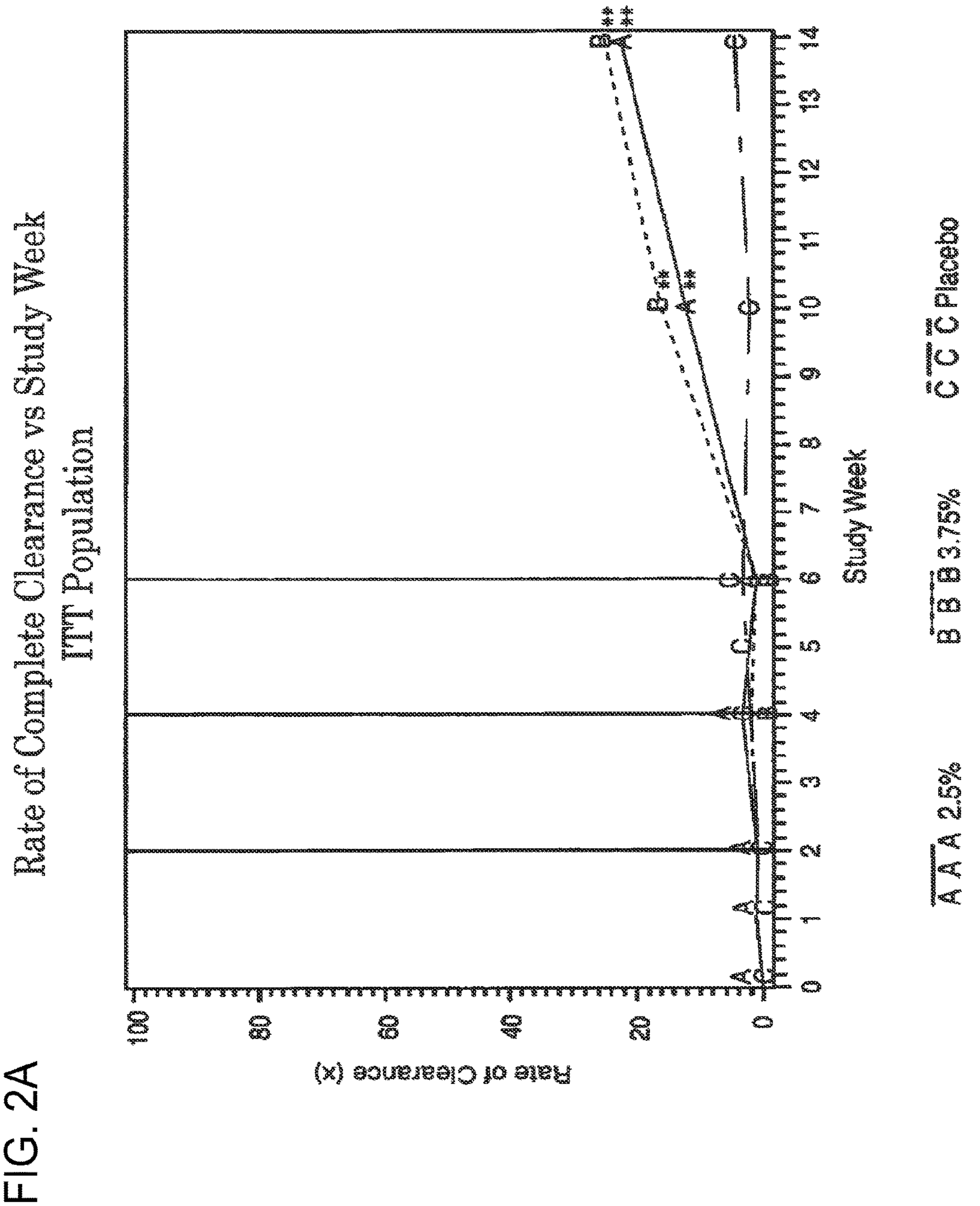
FIG. 2A shows a rate of complete clearance vs. study week an ITT population for study GW01-0702. Points that are marked with  shows statistically difference from placebo. As used in this FIG. 2**A, "Rate of Complete Clearance" refers to rate of complete AK lesion clearance, "A" refers to a 2.5% imiquimod lower dosage strength formulation of Examples 23-28, "B" refers to a 3.75% imiquimod lower dosage strength formulation of Examples 23-28, and "C" refers to placebo.
Figure 2B:
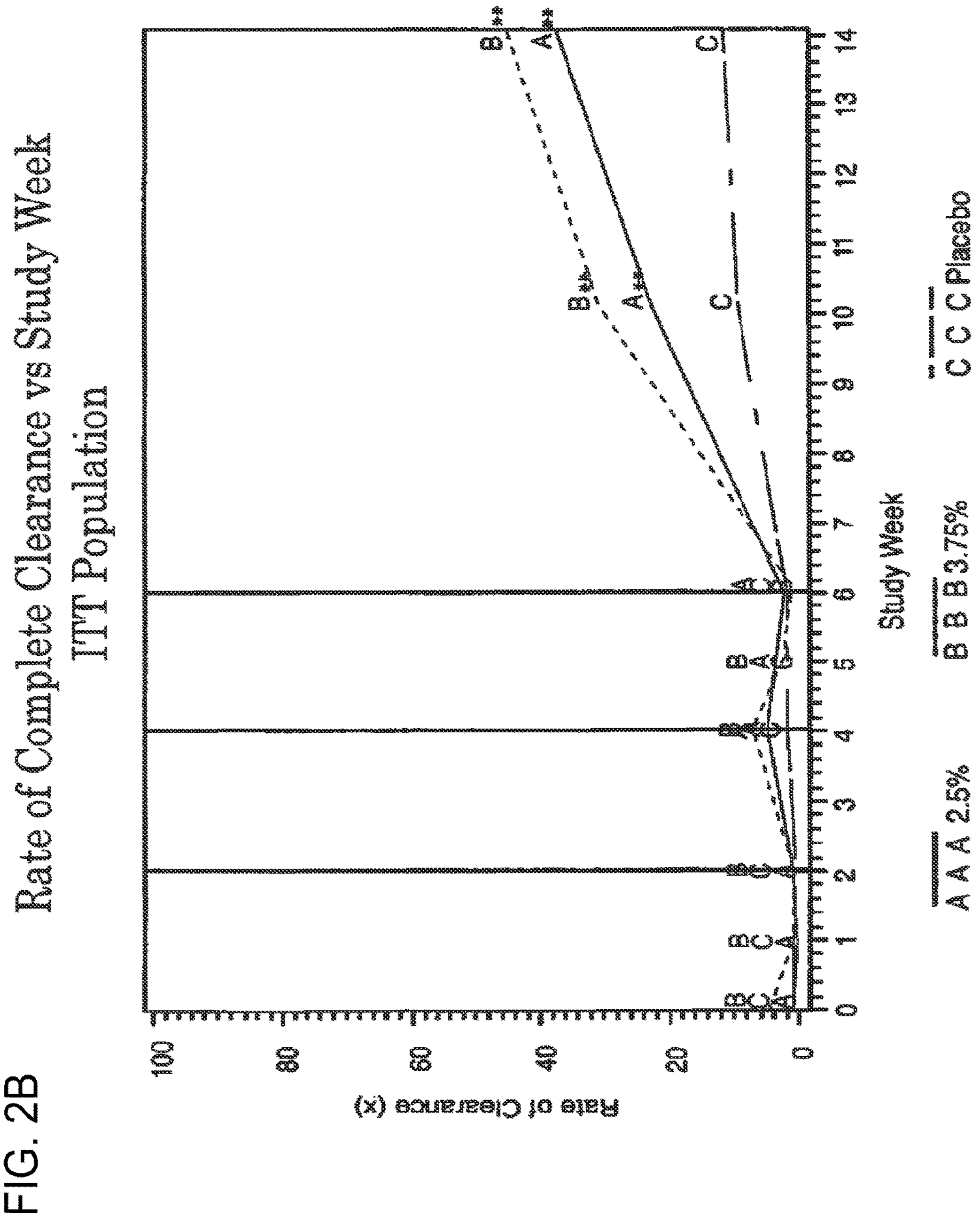
FIG. 2B shows a rate of complete clearance vs. study week of an ITT population for study GW01-0704. Points that are marked with  shows statistically difference from placebo. Points marked with ## show statistically significant difference between active treatments. As used in this FIG. 2**B, "Rate of Complete Clearance" refers to rate of complete AK lesion clearance, "A" refers to a 2.5% imiquimod lower dosage strength formulation of Examples 23-28, "B" refers to a 3.75% imiquimod lower dosage strength formulation of Examples 23-28, and "C" refers to placebo.
Figure 3:
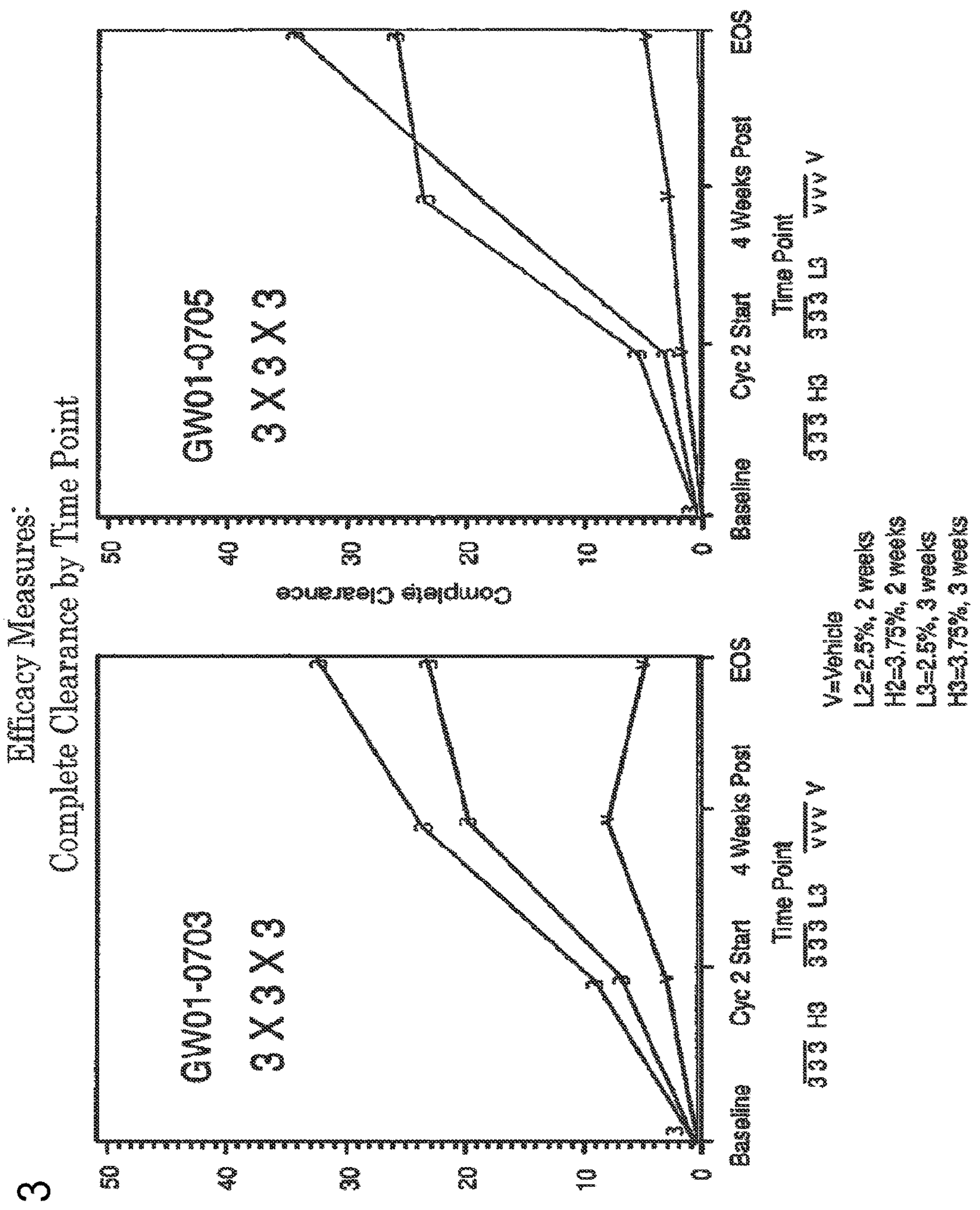
FIG. 3 shows efficacy measures of complete clearance, by time point, for studies GW01-0703 and GW01-0705 for the 2-cycle 3×3×3 (3 weeks) treatment regimen. As used in this FIG. 3, "Complete Clearance" refers to complete clearance of AK lesions, "Cyc 2 Start" refers to the start of the second cycle, "4 Weeks Post" refers to 4 weeks post treatment, and "EOS" refers to End of Study. See also FIGS. 2A and 2B.
Figure 3A:
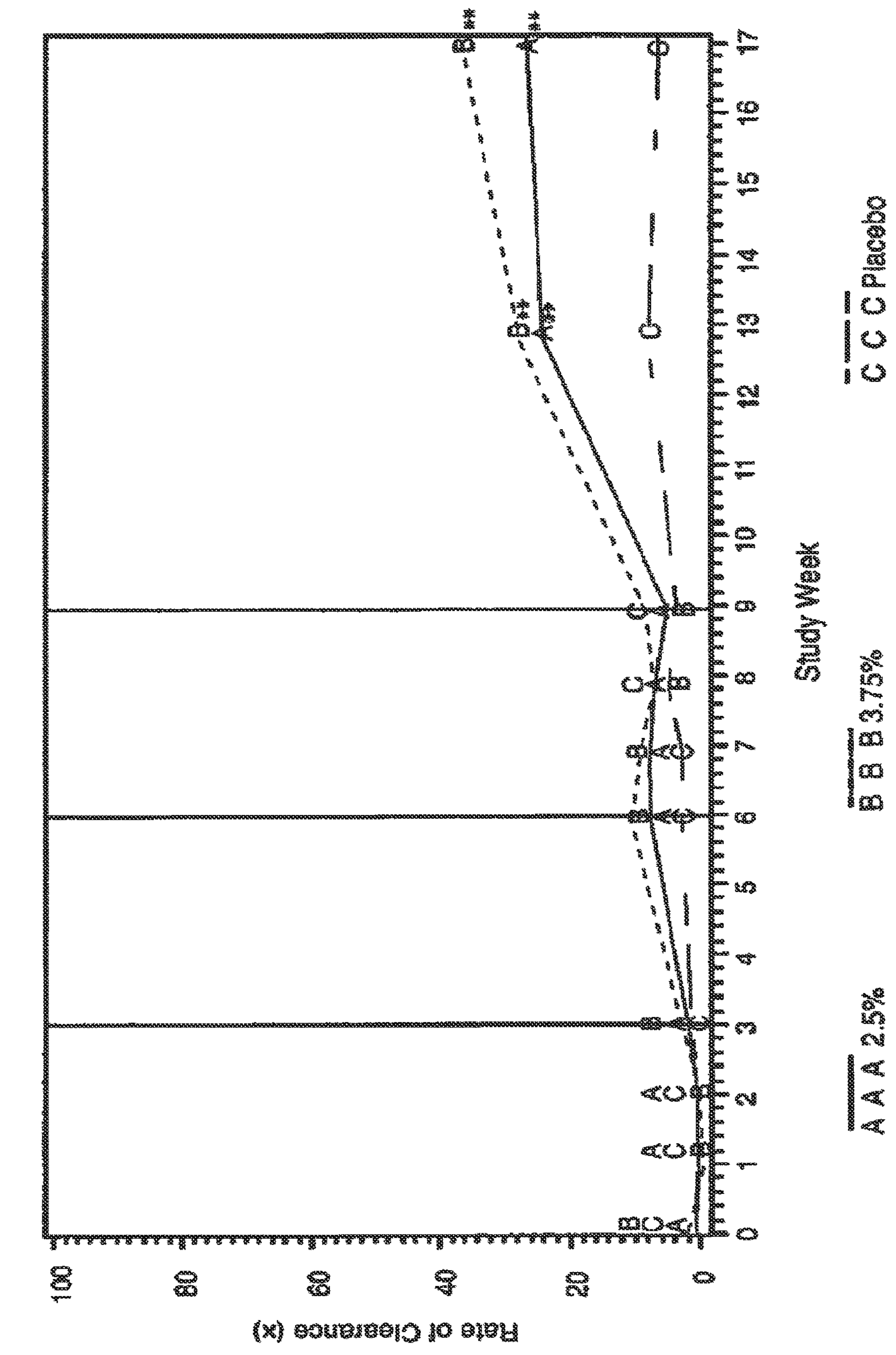
FIG. 3A shows a rate of complete clearance vs. study week of an ITT population for study GW01-0703. Points that are marked with  shows statistically difference from placebo. Points marked with ## show statistically significant difference between active treatments. As used in this FIG. 3**A, "Rate of Complete Clearance" refers to rate of complete AK lesion clearance, "A" refers to a 2.5% imiquimod lower dosage strength formulation of Examples 23-28, "B" refers to a 3.75% imiquimod lower dosage strength formulation of Examples 23-28, and "C" refers to placebo.
Figure 3B:
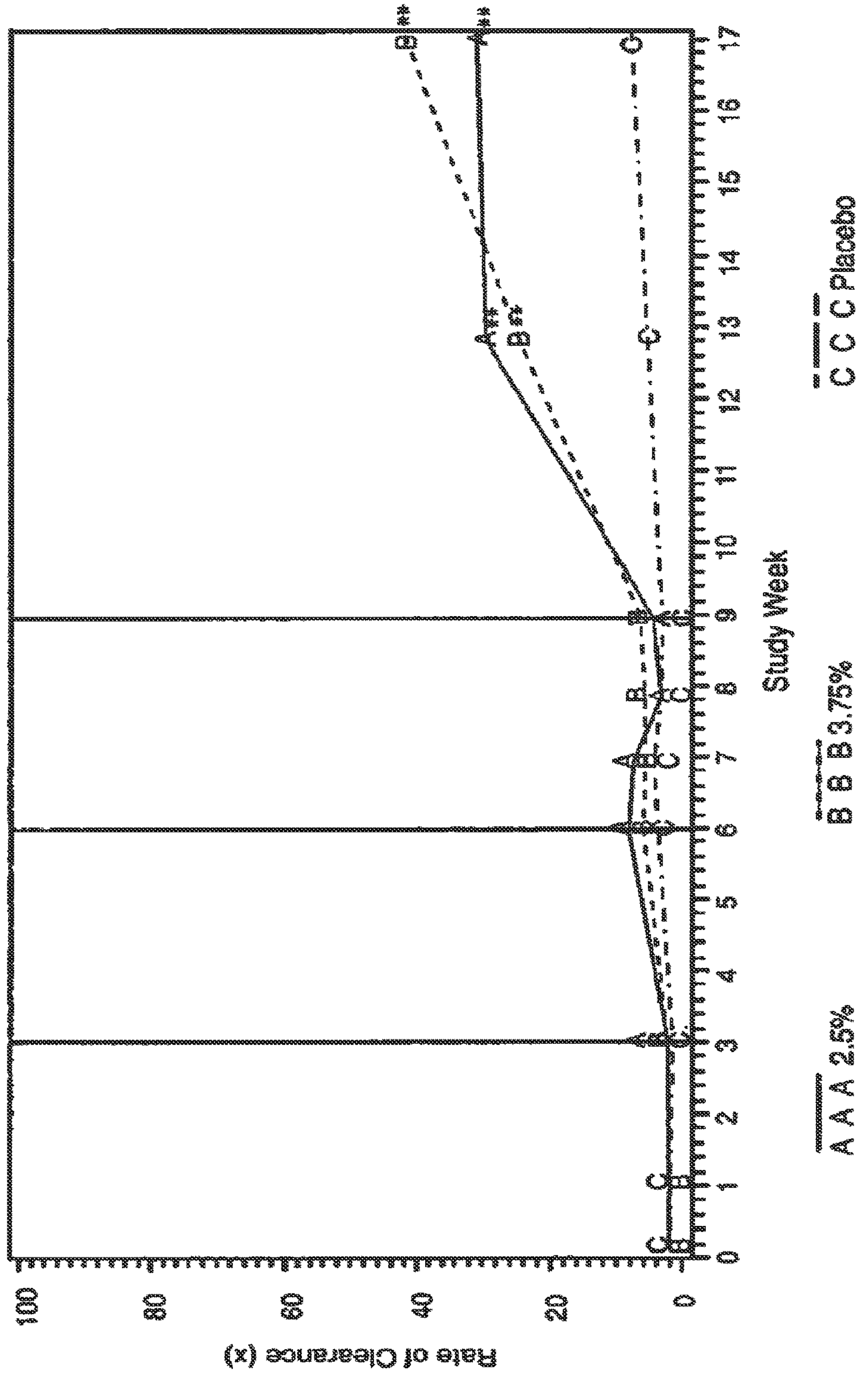
FIG. 3B shows a rate of complete clearance vs. study week of an ITT population for study GW01-0705. Points that are marked with  shows statistically difference from placebo. Points marked with ## show statistically significant difference between active treatments. As used in this FIG. 3**B, "Rate of Complete Clearance" refers to rate of complete AK lesion clearance, "A" refers to a 2.5% imiquimod lower dosage strength formulation of Examples 23-28, "B" refers to a 3.75% imiquimod lower dosage strength formulation of Examples 23-28, and "C" refers to placebo.
Figure 4A:
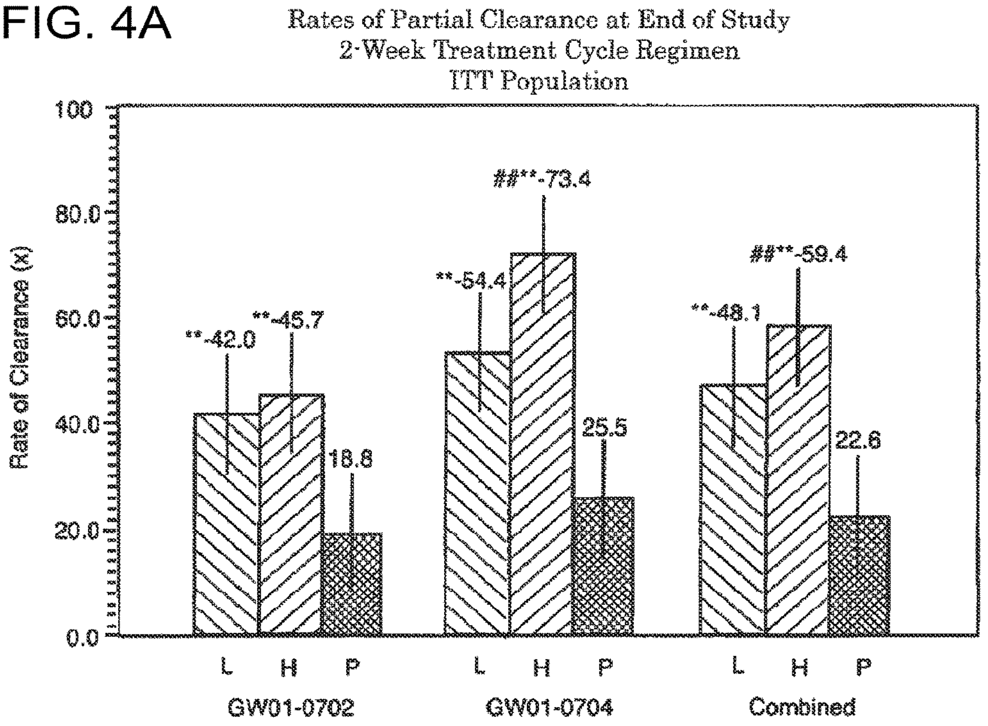
FIG. 4A shows rates of partial clearance at end of study of a two-week treatment cycle regimen of an ITT population for studies GW01-0702 and GW01-0704. In this FIG. 4A, "Rate of Partial Clearance" refers to rate of partial AK lesion clearance (defined as at least about 75% reduction in the number of AK lesions in the treatment area as compared with Baseline), "L" refers to a 2.5% imiquimod lower dosage strength formulation of Examples 23-28, "H" refers to a 3:75% imiquimod lower dosage strength formulation of Examples 23-28, P=placebo, and that the bars marked with ** show statistically significant difference from placebo, whereas the bars marked with ## show statistically significant difference from 2.5%. The vertical blue lines indicate 95% confidence limits.
Figure 4B:
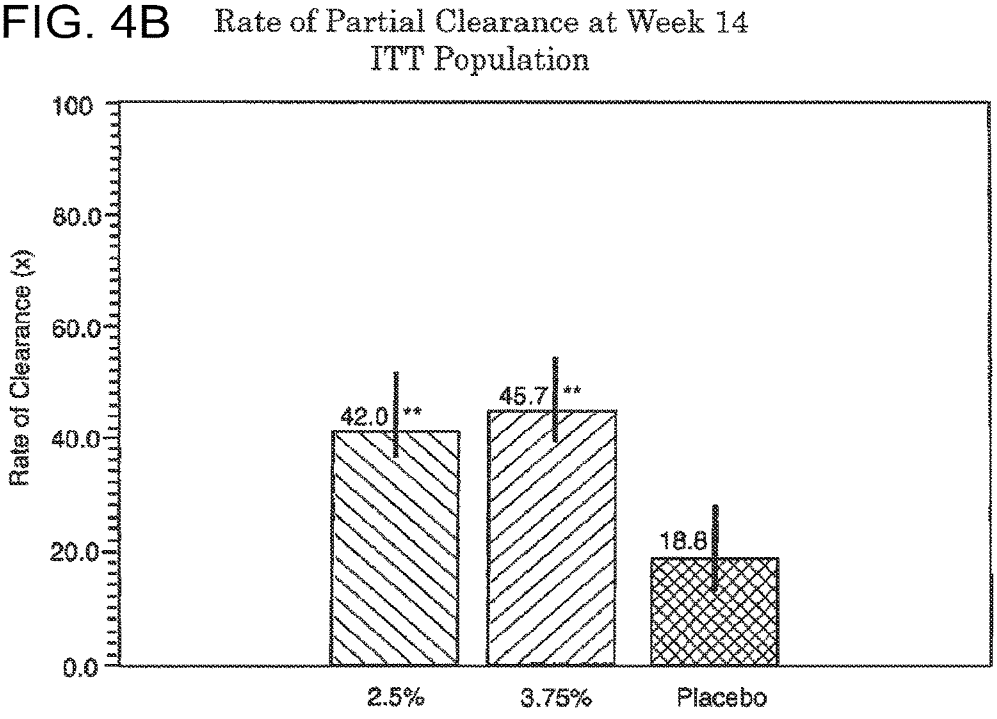
FIG. 4B shows a rate of partial clearance at week 14 for an ITT population for study GW01-0702. Partial clearance is defined as at least a 75% reduction in the number of AK lesions in the treatment area compared with baseline. The bars marked with  show statistically significant difference from placebo. Dark black vertical lines represent 95% confidence intervals on the rates. In this FIG. 4**B, "Rate of Partial Clearance" refers to rate of partial AK lesion clearance (defined as at least about 75% reduction in the number of AK lesions in the treatment area as compared with Baseline), "2.5%" refers to a 2.5% imiquimod lower dosage strength formulation of Examples 23-28, and "3.75%" refers to a 3.75% imiquimod lower dosage strength formulation of Examples 23-28.
Figure 4C:
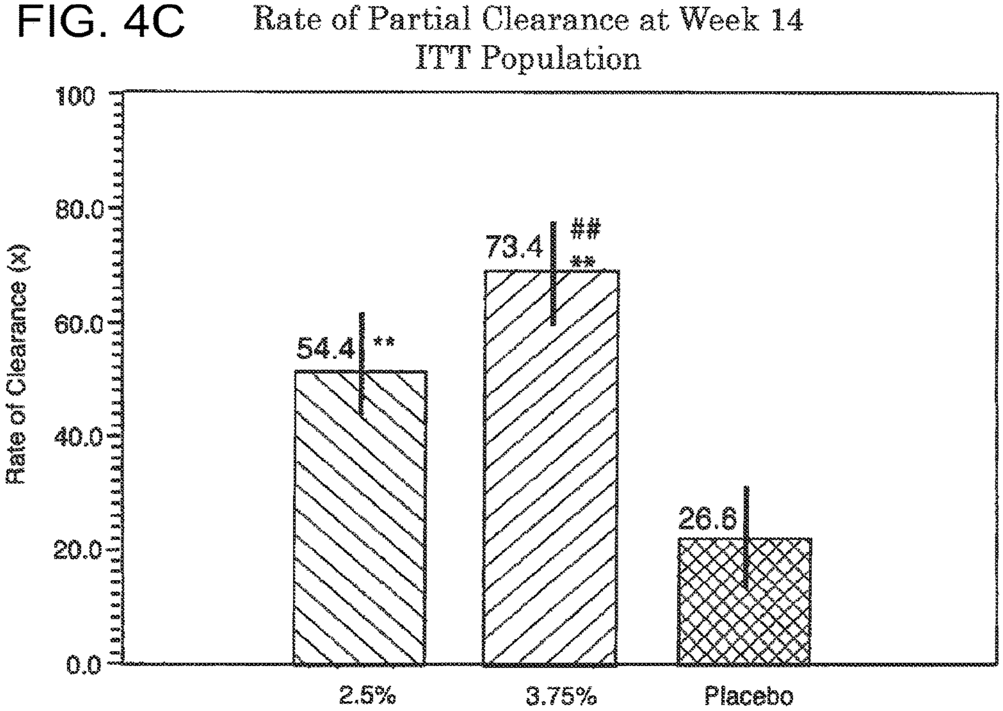
FIG. 4C shows a rate of partial clearance at week 14 for an ITT population for study GW01-0704. Partial clearance is defined as at least a 75% reduction in the number of AK lesions in the treatment area compared with baseline. The bars marked with  show statistically significant difference from placebo. The bars marked with ## show statistically difference between active treatments. Dark black vertical lines represent 95% confidence intervals on the rates. In this FIG. 4**C, "Rate of Partial Clearance" refers to rate of partial AK lesion clearance (defined as at least about 75% reduction in the number of AK lesions in the treatment area as compared with Baseline), "2.5%" refers to a 2.5% imiquimod lower dosage strength formulation of Examples 23-28, and "3.75%" refers to a 3.75% imiquimod lower dosage strength formulation of Examples 23-28.
Figure 4D:
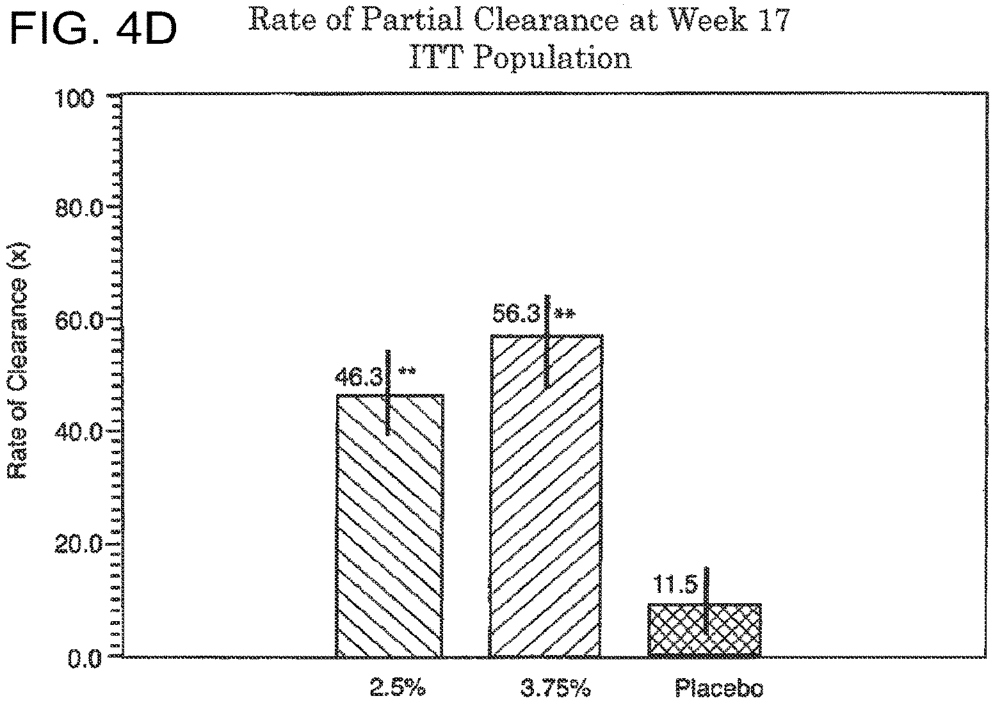
FIG. 4D shows a rate of partial clearance at week 17 for an ITT population for study GW01-0703. Partial clearance is defined as at least a 75% reduction in the number of AK lesions in the treatment area compared with baseline. The bars marked with  show statistically significant difference from placebo. Dark black vertical lines represent 95% confidence intervals on the rates. In this FIG. 4**D, "Rate of Partial Clearance" refers to rate of partial AK lesion clearance (defined as at least about 75% reduction in the number of AK lesions in the treatment area as compared with Baseline), "2.5%" refers to a 2.5% imiquimod lower dosage strength formulation of Examples 23-28, and "3.75%" refers to a 3.75% imiquimod lower dosage strength formulation of Examples 23-28.
Figure 4E:
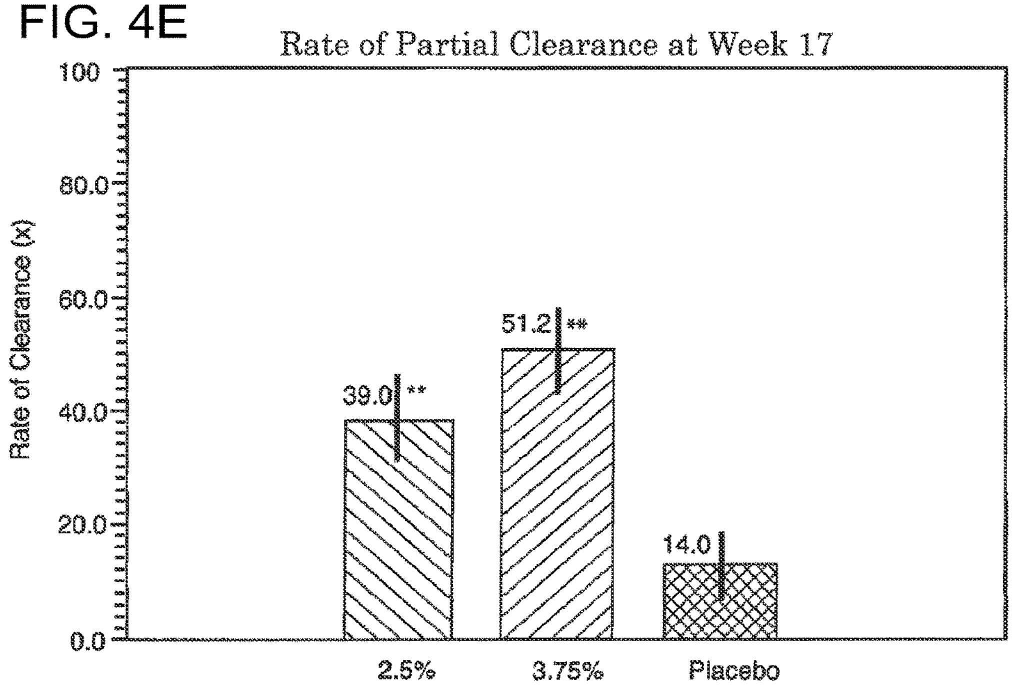
FIG. 4E shows a rate of partial clearance at week 17 for an ITT population for study GW01-0705. Partial clearance is defined as at least a 75% reduction in the number of AK lesions in the treatment area compared with baseline. The bars marked with  show statistically significant difference from placebo. Dark black vertical lines represent 95% confidence intervals on the rates. In this FIG. 4**E, "Rate of Partial Clearance" refers to rate of partial AK lesion clearance (defined as at least about 75% reduction in the number of AK lesions in the treatment area as compared with Baseline), "2.5%" refers to a 2.5% imiquimod lower dosage strength formulation of Examples 23-28, and "3.75%" refers to a 3.75% imiquimod lower dosage strength formulation of Examples 23-28.
Figure 4F:
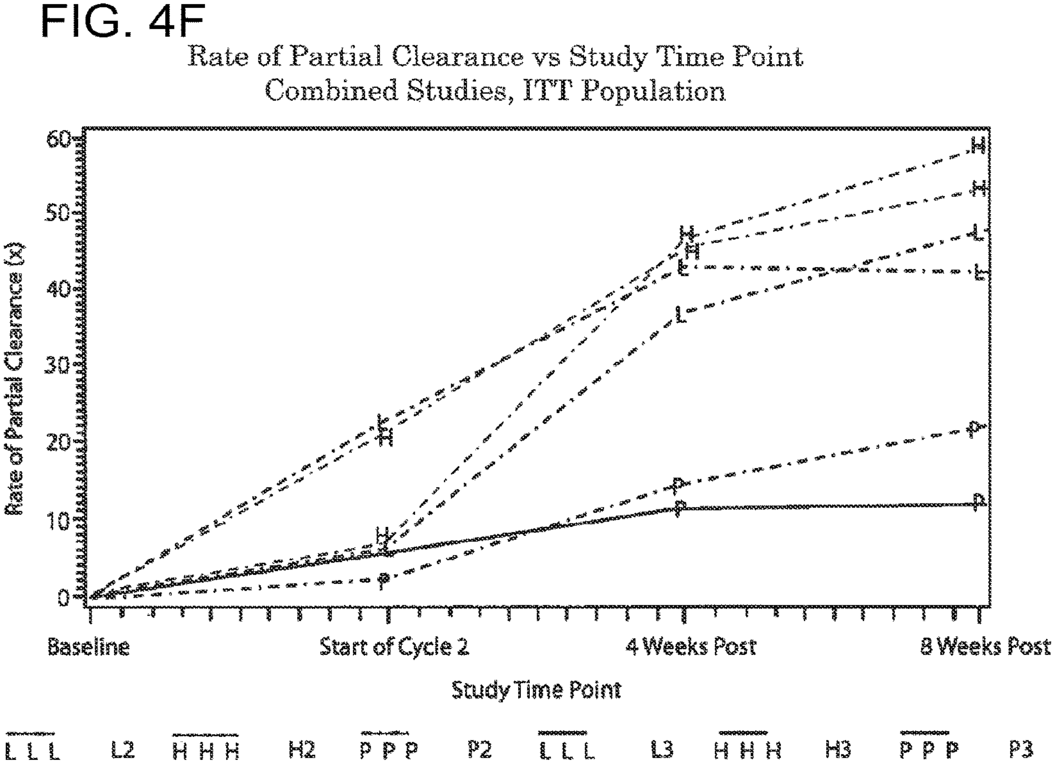
FIG. 4F shows a rate of partial clearance vs. study time point combined studies for an ITT population regarding the use of a 3.75% lower dosage strength imiquimod formulation of Examples 23-28. Note the following: L2=2.5% two-week treatment cycle regimen, L3=2.5% three-week treatment cycle regimen, H2=3.75% two-week treatment cycle regimen, H3=3.75% three-week treatment cycle regimen, P2=placebo two-week treatment cycle regimen, and P3=placebo three-week treatment cycle regimen. In this FIG. 4F, "Rate of Partial Clearance" refers to rate of partial AK lesion clearance (defined as at least about 75% reduction in the number of AK lesions in the treatment area as compared with Baseline), "Start of Cycle 2" refers to the start of the second cycle, "4 Weeks Post" refers to 4 weeks post treatment, and "8 Weeks Post" refers to 8 weeks post treatment.
Figure 5:
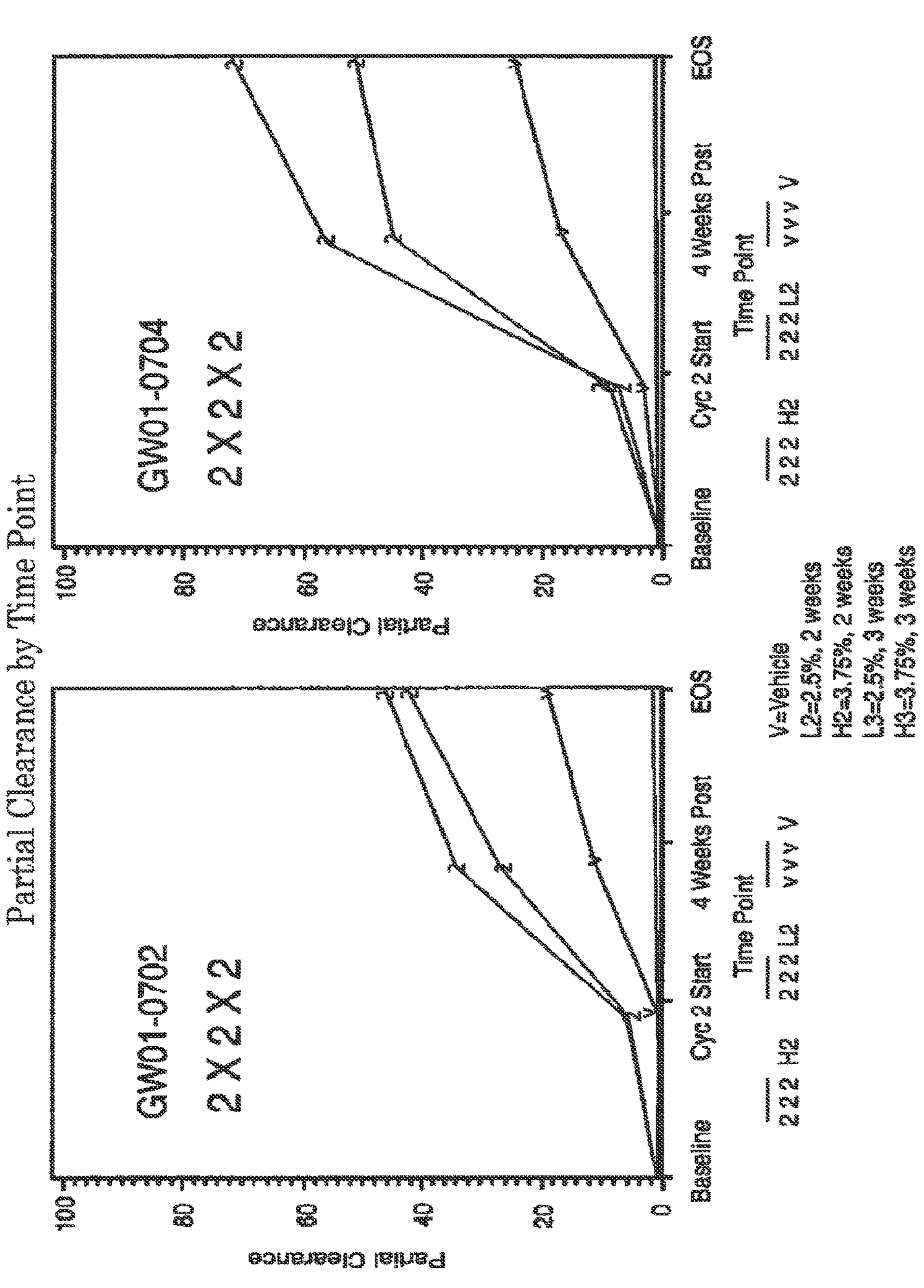
FIG. 5 shows efficacy measures of partial clearance, by time point, for studies GW01-0702 and GW01-0704. See also FIG. 37A. As used in this FIG. 5, "Partial Clearance" refers to partial clearance of AK lesions (defined as at least about 75% reduction in the number of AK lesions in the treatment area as compared with Baseline), "Cyc 2 Start" refers to the start of the second cycle, "4 Weeks Post" refers to 4 weeks post treatment, "EOS" refers to End of Study, and "2×2×2" refers to a two week, 2-cycle treatment, as through out the FIGS. and the specification.
Figure 5A:
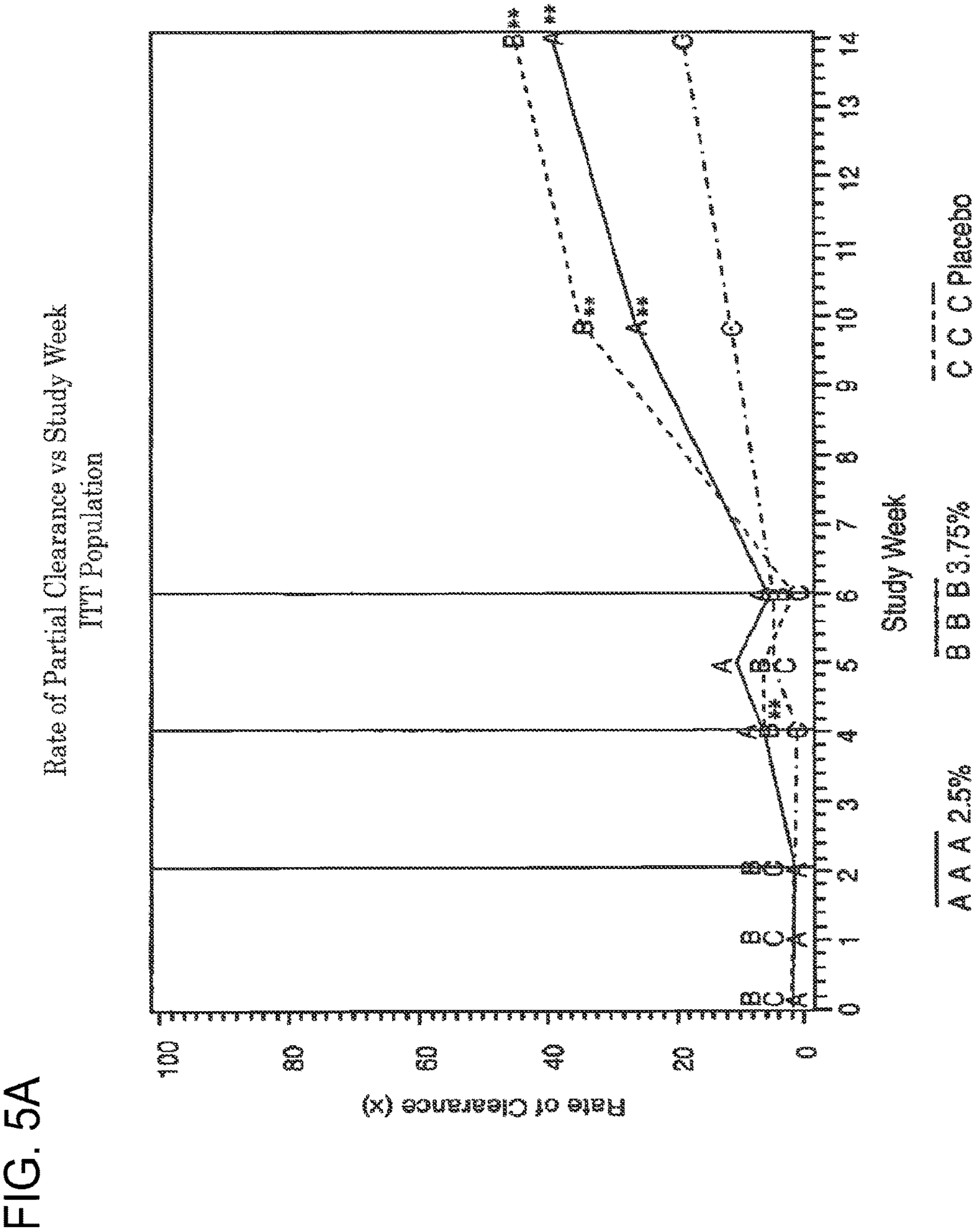
FIG. 5A shows a rate of partial clearance vs. study week for an ITT population for study GW01-0702. The points marked with  shows statistically difference from placebo. The points marked with ## shows statistically difference between active treatments. As used in this FIG. 5**A, "Rate of Partial Clearance" refers to rate of partial AK lesion clearance (defined as at least about 75% reduction in the number of AK lesions in the treatment area as compared with Baseline), "A" refers to a 2.5% imiquimod lower dosage strength formulation of Examples 23-28, "B" refers to a 3.75% imiquimod lower dosage strength formulation of Examples 23-28, and "C" refers to placebo.
Figure 5B:
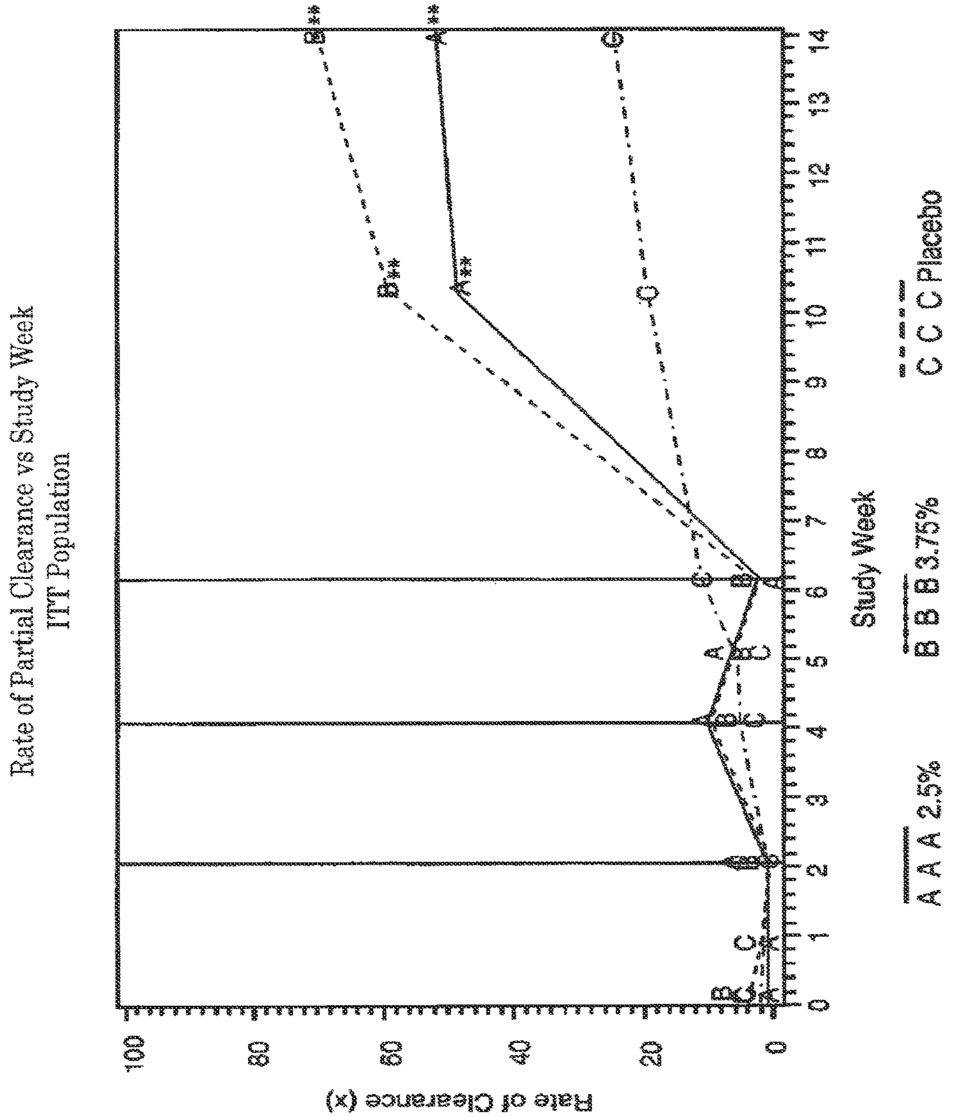
FIG. 5B shows a rate of partial clearance vs. study week for an ITT population for study GW01-0704. The points marked with  shows statistically difference from placebo. The points marked with ## shows statistically difference between active treatments. As used in this FIG. 5**B, "Rate of Partial Clearance" refers to rate of AK partial lesion clearance (defined as at least about 75% reduction in the number of AK lesions in the treatment area as compared with Baseline), "A" refers to a 2.5% imiquimod lower dosage strength formulation of Examples 23-28, "B" refers to a 3.75% imiquimod lower dosage strength formulation of Examples 23-28, and "C" refers to placebo.
Figure 6:
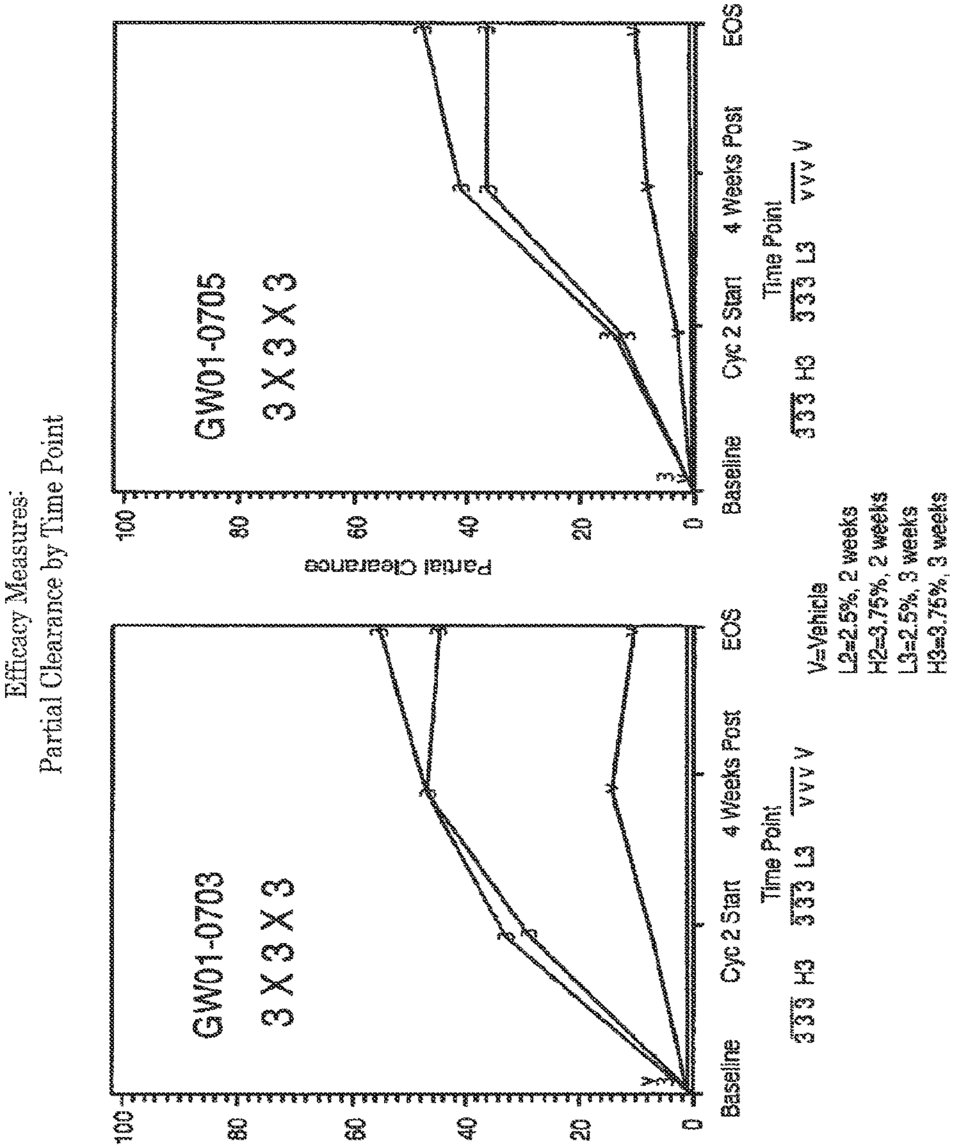
FIG. 6 shows efficacy measures of partial clearance, by time point, for studies GW01-0703 and GW01-0705. As used in this FIG. 6, Partial Clearance" refers to rate percent of partial clearance of AK lesions (defined as at least about 75% reduction in the number of AK lesions in the treatment area as compared with Baseline), "Cyc 2 Start" refers to the start of the second cycle, "4 Weeks Post" refers to 4 weeks post treatment, and "EOS" refers to End of Study. See also FIG. 37A.
Figure 6A:
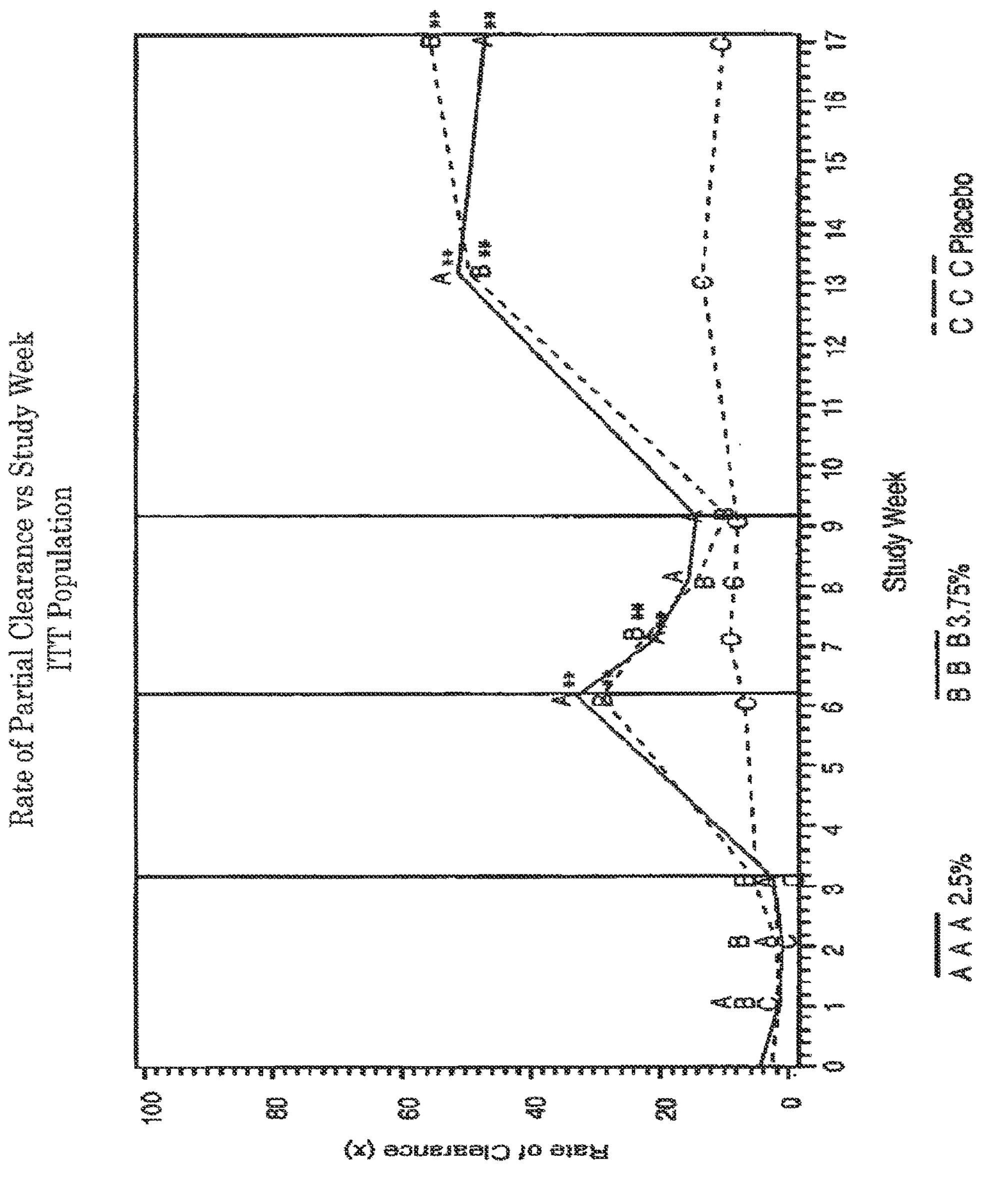
FIG. 6A shows a rate of partial clearance vs. study week for an ITT population for study GW01-0703. The points marked with  shows statistically significant difference from placebo. The points marked with ## shows statistically significant difference between active treatments. As used in this FIG. 6**A, "Rate of Partial Clearance" refers to rate of partial AK lesion clearance (defined as at least about 75% reduction in the number of AK lesions in the treatment area as compared with Baseline), "A" refers to a 2.5% imiquimod lower dosage strength formulation of Examples 23-28, "B %" refers to a 3.75% imiquimod lower dosage strength formulation of Examples 23-28, and "C" refers to placebo.
Figure 6B:
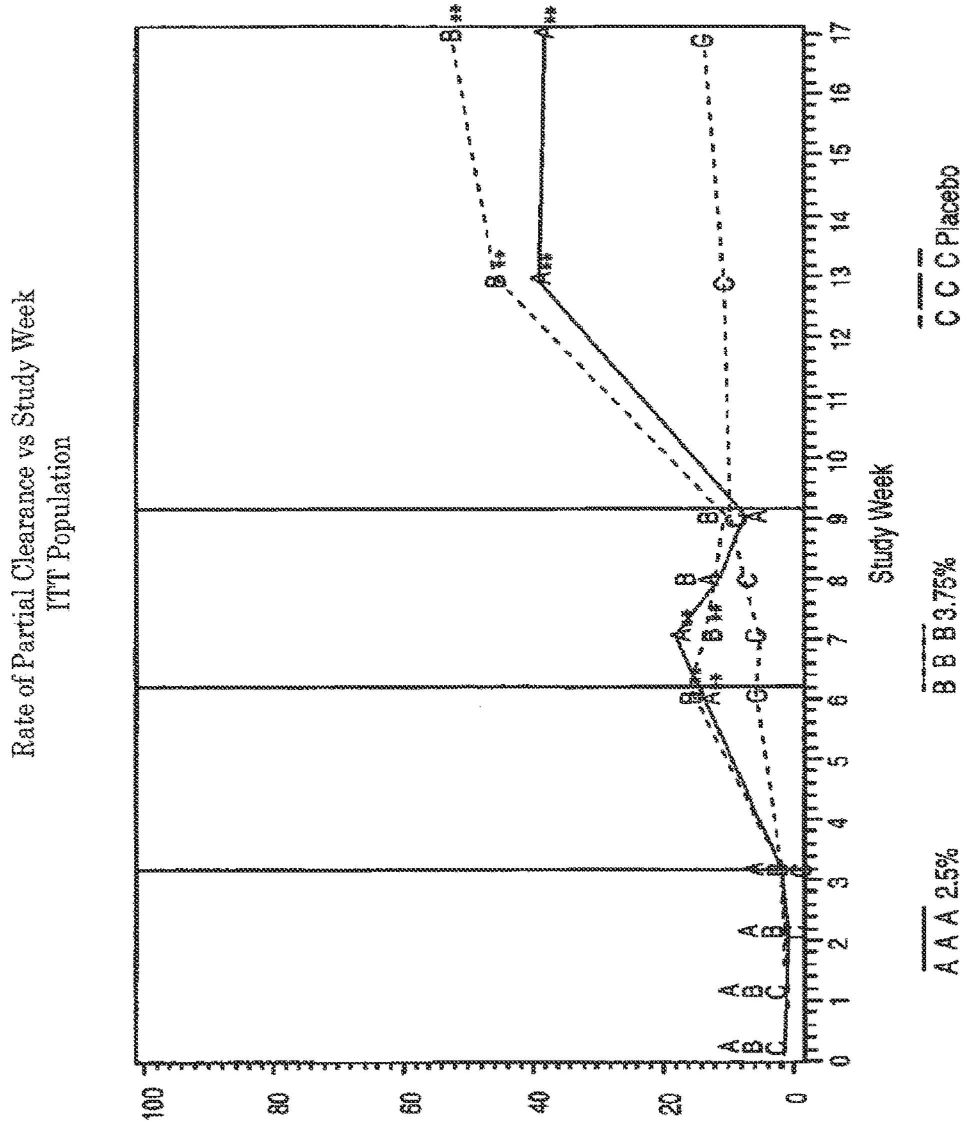
FIG. 6B shows a rate of partial clearance vs. study week for an ITT population for study GW01-0705. The points marked with  shows statistically significant difference from placebo. The points marked with ## shows statistically significant difference between active treatments. As used in this FIG. 6**B, "Rate of Partial Clearance" refers to rate of partial AK lesion clearance (defined as at least about 75% reduction in the number of AK lesions in the treatment area as compared with Baseline), "A" refers to a 2.5% imiquimod lower dosage strength formulation of Examples 23-28, "B" refers to a 3.75% imiquimod lower dosage strength formulation of Examples 23-28, and "C" refers to placebo.
Figure 7:
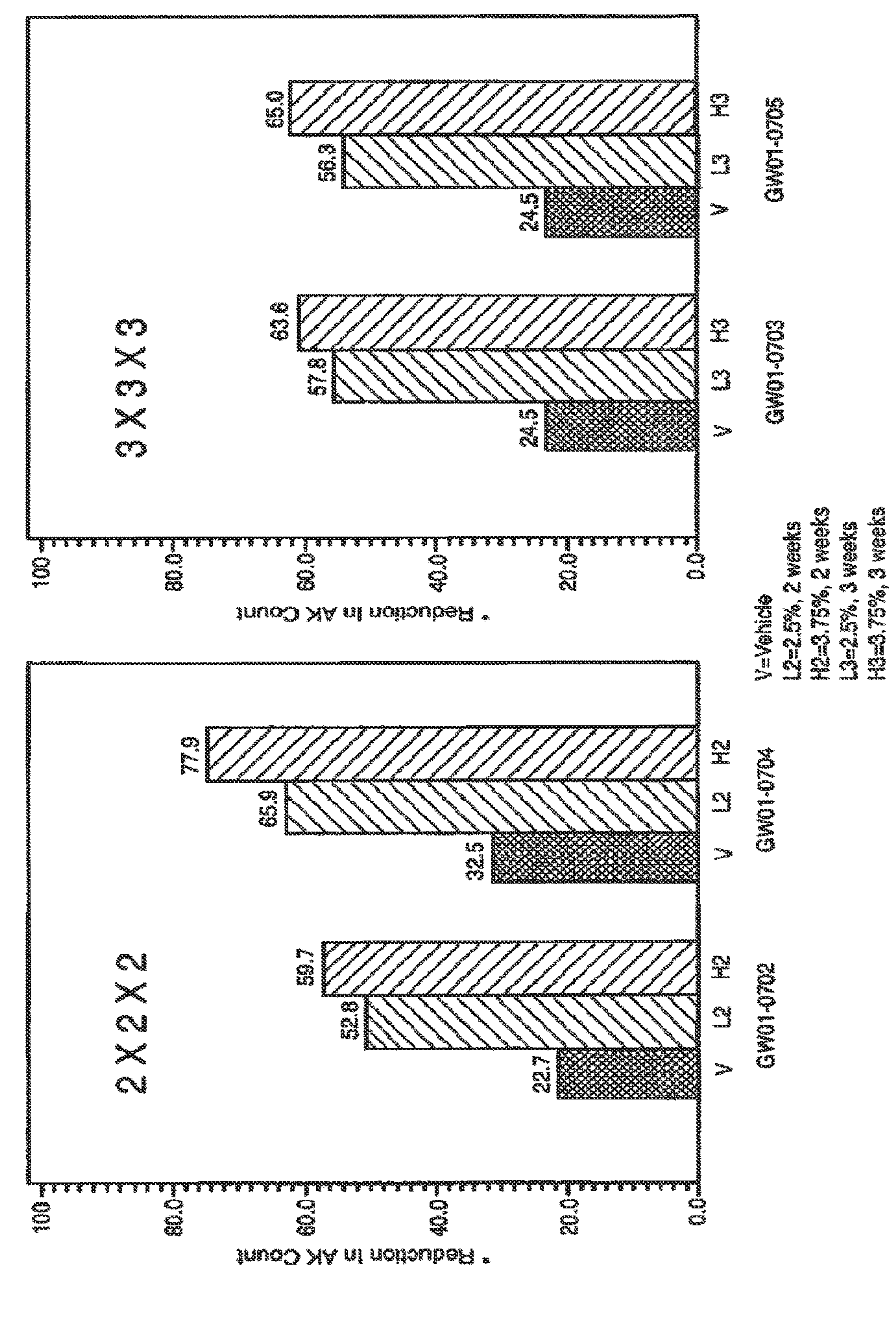
FIG. 7 shows efficacy measures of mean % change from baseline count, by study, for studies GW01-0703, GW01-0702, GW01-0704 and GW01-0705. See also FIG. 9A.
Figure 8:
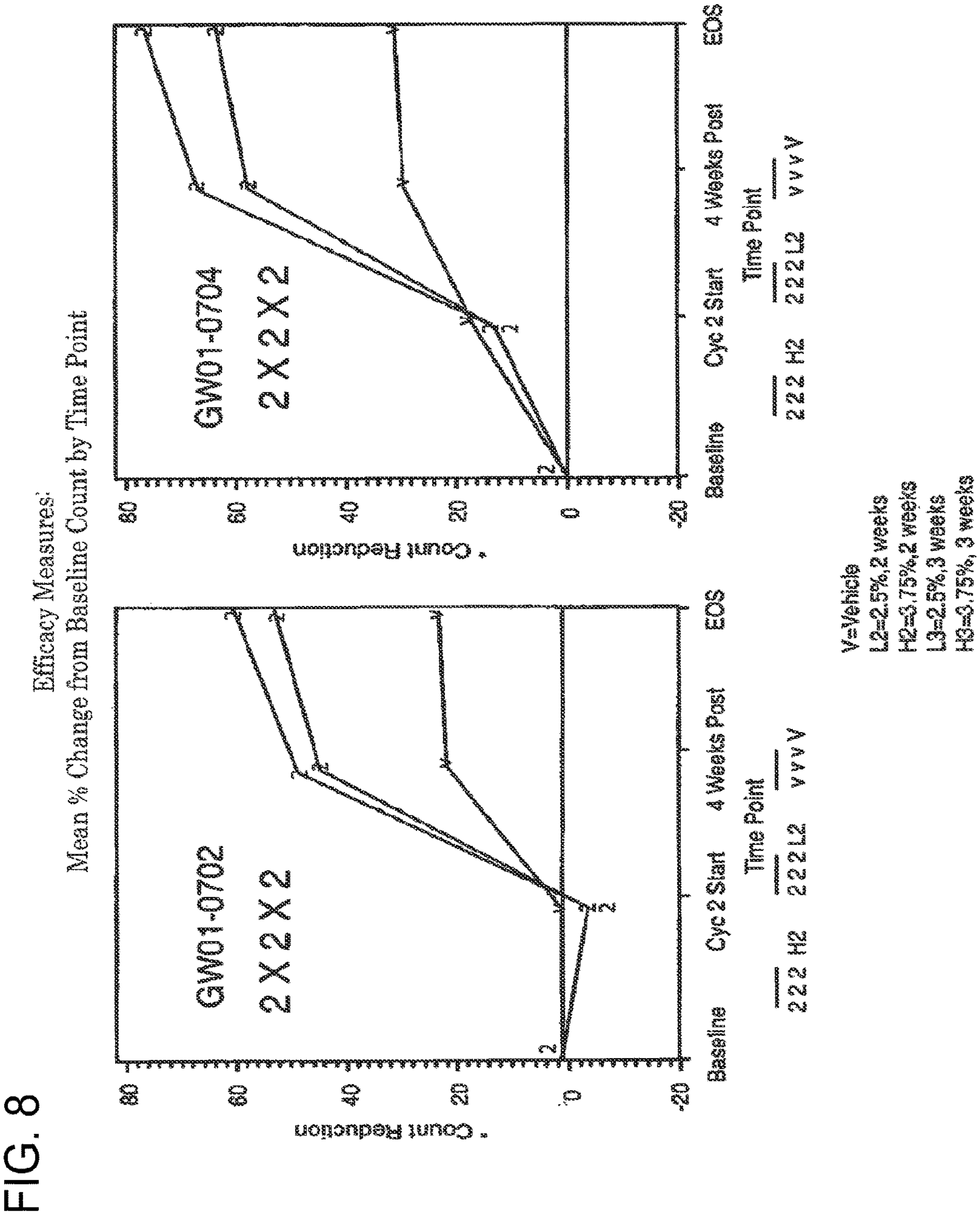
FIG. 8 shows efficacy measures of mean % change from baseline count, by time point, for studies GW01-0702 and GW01-0704. As used in this FIG. 8, "% Count Reduction" refers to the percent reduction in AK count from Baseline, "Cyc 2 Start" refers to the start of the second cycle, "4 Weeks Post" refers to 4 weeks post treatment, and "EOS" refers to End of Study. See also FIG. 9A.
Figure 8A:
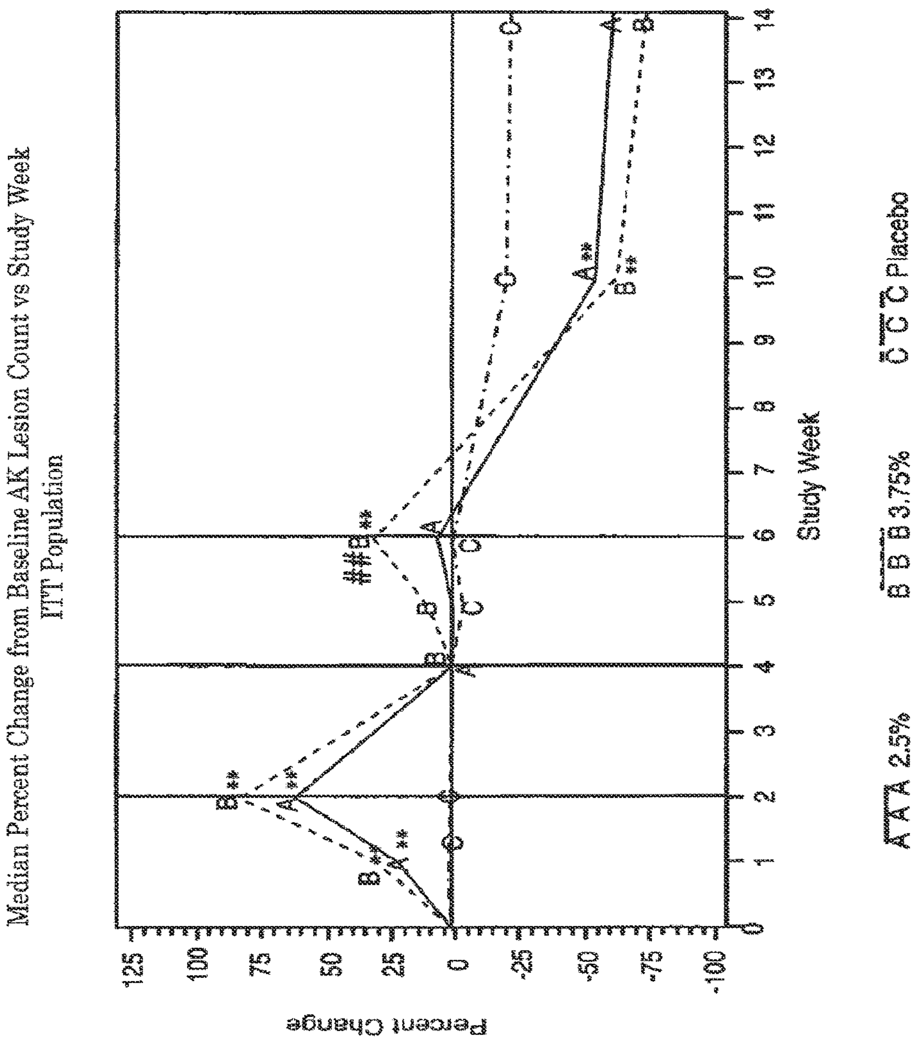
FIG. 8A shows a median percent change from baseline AK lesion count vs. study week for an ITT population for study GW01-0702. The points marked with  shows statistically significant difference from placebo. The points marked with ## shows statistically significant difference between active treatments. As used in this FIG. 8**A, "Median Percent Change" refers to median percent change in AK lesion count from Baseline, "A" refers to a 2.5% imiquimod lower dosage strength formulation of Examples 23-28, "B" refers to a 3.75% imiquimod lower dosage strength formulation of Examples 23-28, and "C" refers to placebo.
Figure 8B:
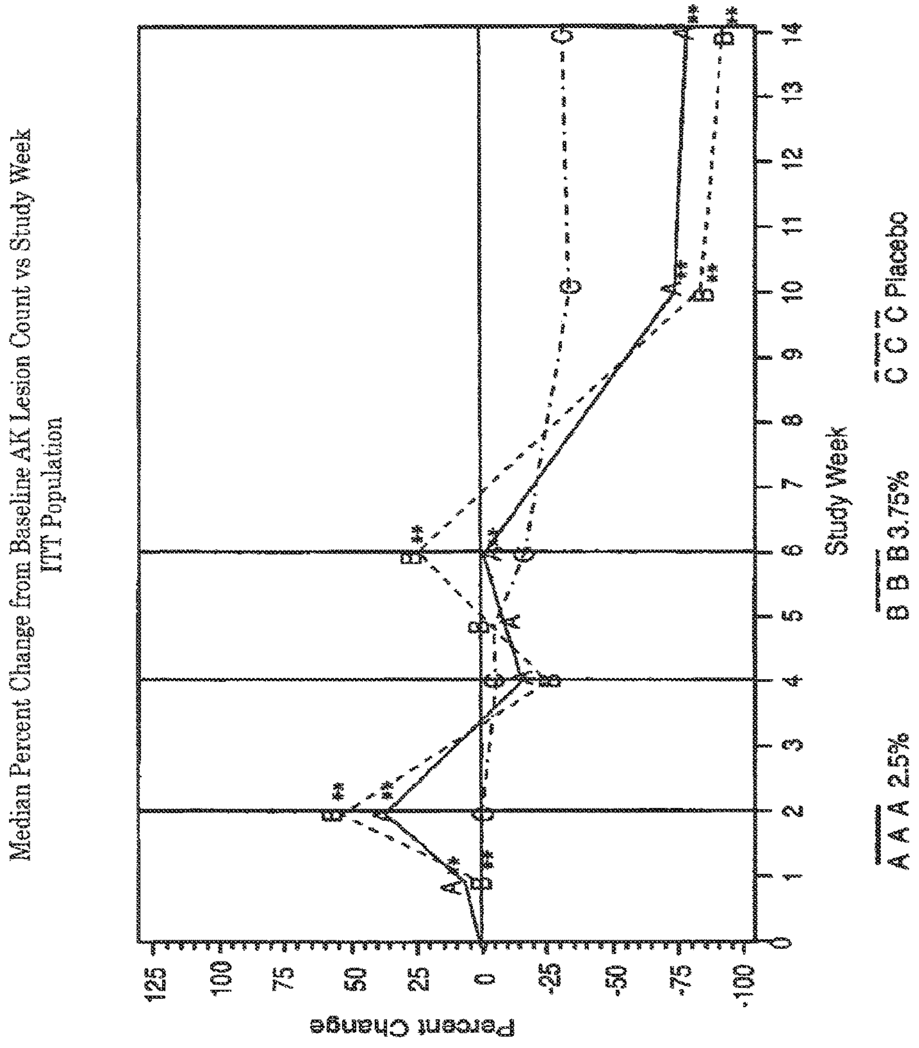
FIG. 8B shows a median percent change from baseline AK lesion count vs. study week for an ITT population for study GW01-0704. The points marked with  shows statistically significant difference from placebo. The points marked with ## shows statistically significant difference between active treatments. As used in this FIG. 8**B, "Median Percent Change" refers to median percent change in AK lesion count from Baseline, "A" refers to a 2.5% imiquimod lower dosage strength formulation of Examples 23-28, "B %" refers to a 3.75% imiquimod lower dosage strength formulation of Examples 23-28, and "C" refers to placebo.
Figure 9:
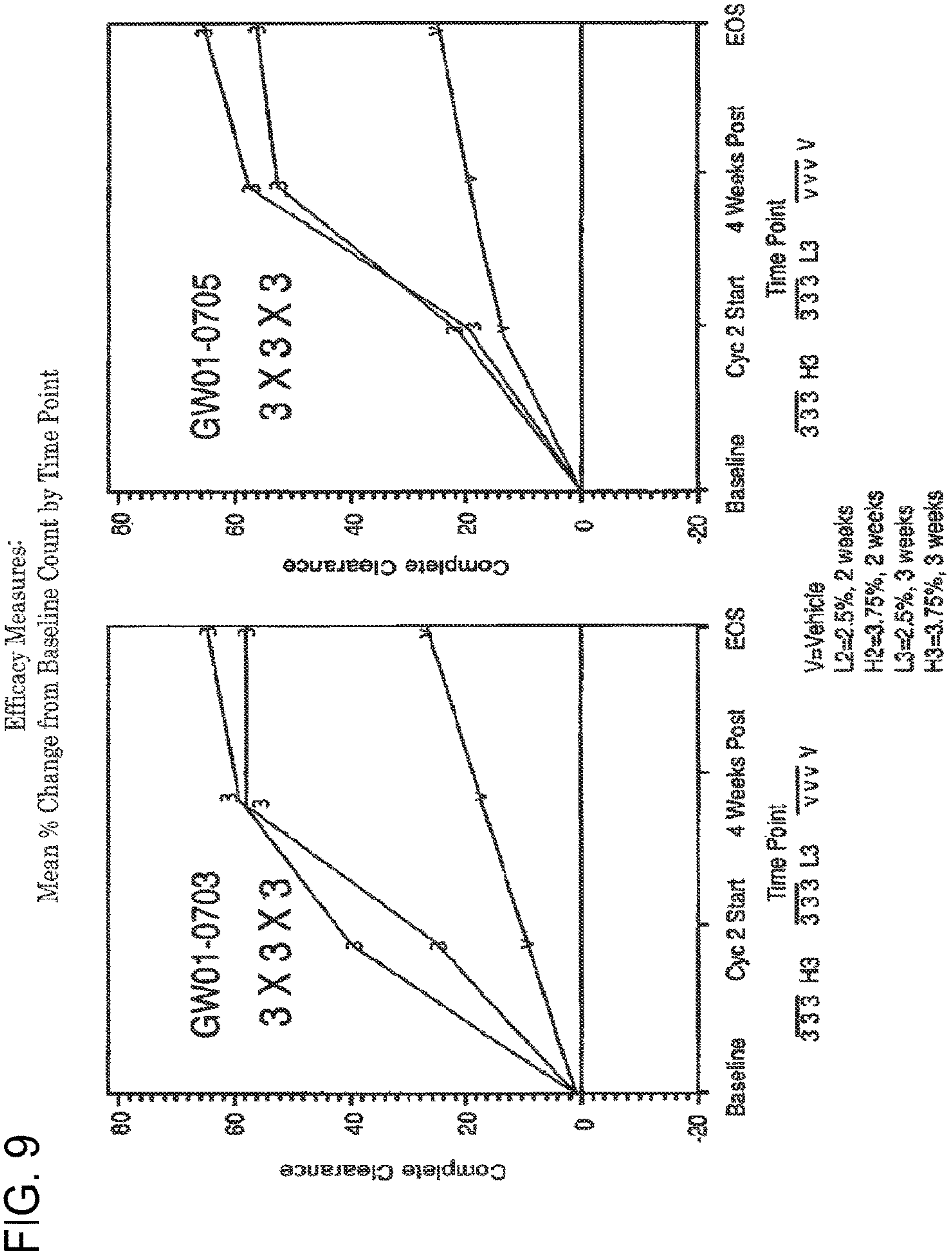
FIG. 9 shows efficacy measures of mean % change from baseline count, by time point, for studies GW01-0703 and GW01-0705. As used in this FIG. 9, "Mean % Change from Baseline Count" refers to the mean percent reduction in AK count, "Cyc 2 Start" refers to the start of the second cycle, "4 Weeks Post" refers to 4 weeks post treatment, and "EOS" refers to End of Study. See also FIGS. 8A and 8B.
Figure 9A:
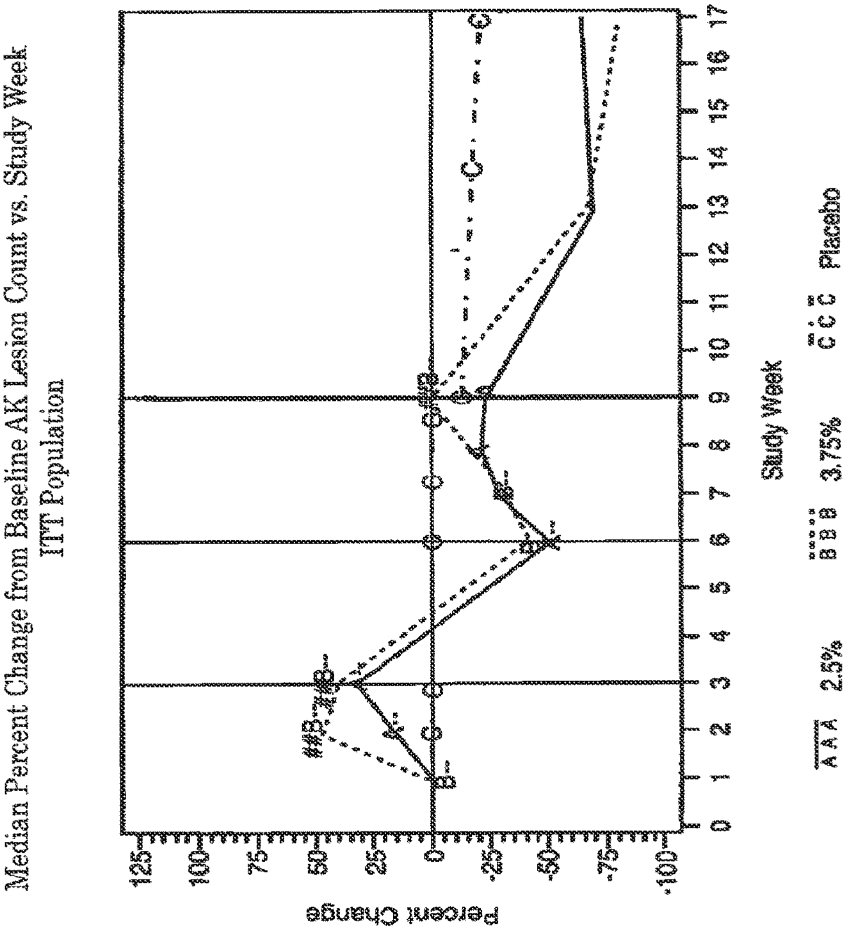
FIG. 9A shows a summary of AK lesion Count for an ITT population regarding GW01-0703. As used in this FIG. 9A, "2.5%" refers to a 2.5% imiquimod lower dosage strength formulation of Examples 23-28 and "3.75%" refers to a 3.75% imiquimod lower dosage strength formulation of Examples 23-28. The P values are from the Cochran-Mantel-Haenszel test, that is stratified by analysis site, taking two treatment groups at a time. The P values marked with ** are statistically significant using Hochberg's modified Bonferroni procedure. Lesion counts which are recorded as 'indeterminate' are excluded from analysis.
Figure 9B:
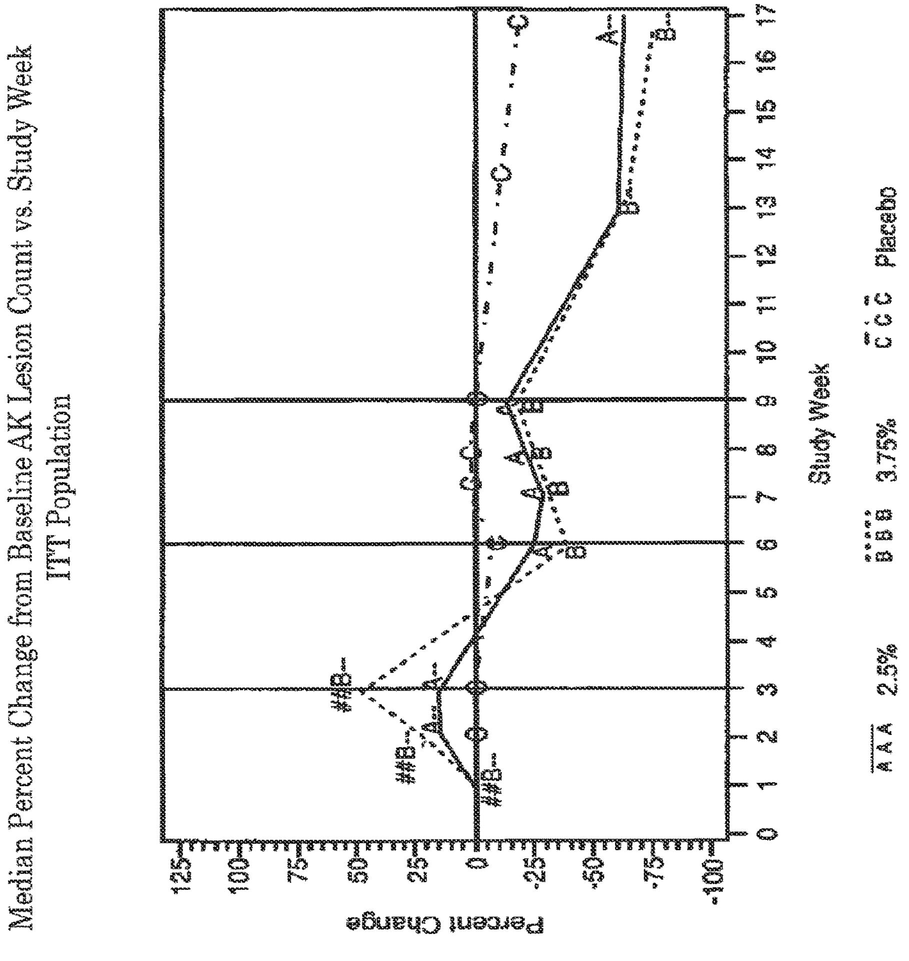
FIG. 9B shows a summary of AK lesion Count for an ITT population regarding GW01-0705. As used in this FIG. 9A, "2.5%" refers to a 2.5% imiquimod lower dosage strength formulation of Examples 23-28 and "3.75%" refers to a 3.75% imiquimod lower dosage strength formulation of Examples 23-28. The P values are from the Cochran-Mantel-Haenszel test, that is stratified by analysis site, taking two treatment groups at a time. The P values marked with ** are statistically significant using Hochberg's modified Bonferroni procedure. Lesion counts which are recorded as 'indeterminate' are excluded from analysis.
Figure 10:
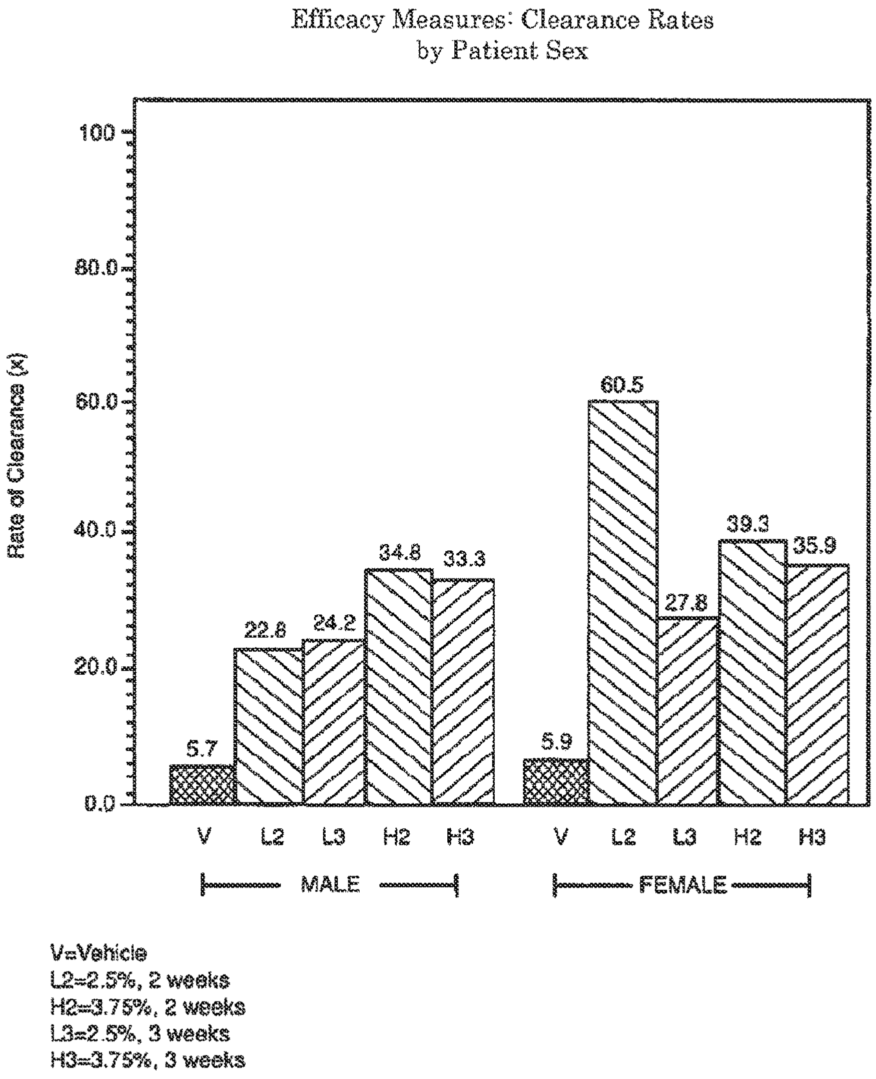
FIG. 10 shows efficacy measures of clearance rates, by subject sex, for studies GW01-0703, GW01-0702, GW01-0704 and GW01-0705. As used in this FIG. 10, "Rate of Clearance" refers to the rate of complete AK lesion clearance.
Figure 11:
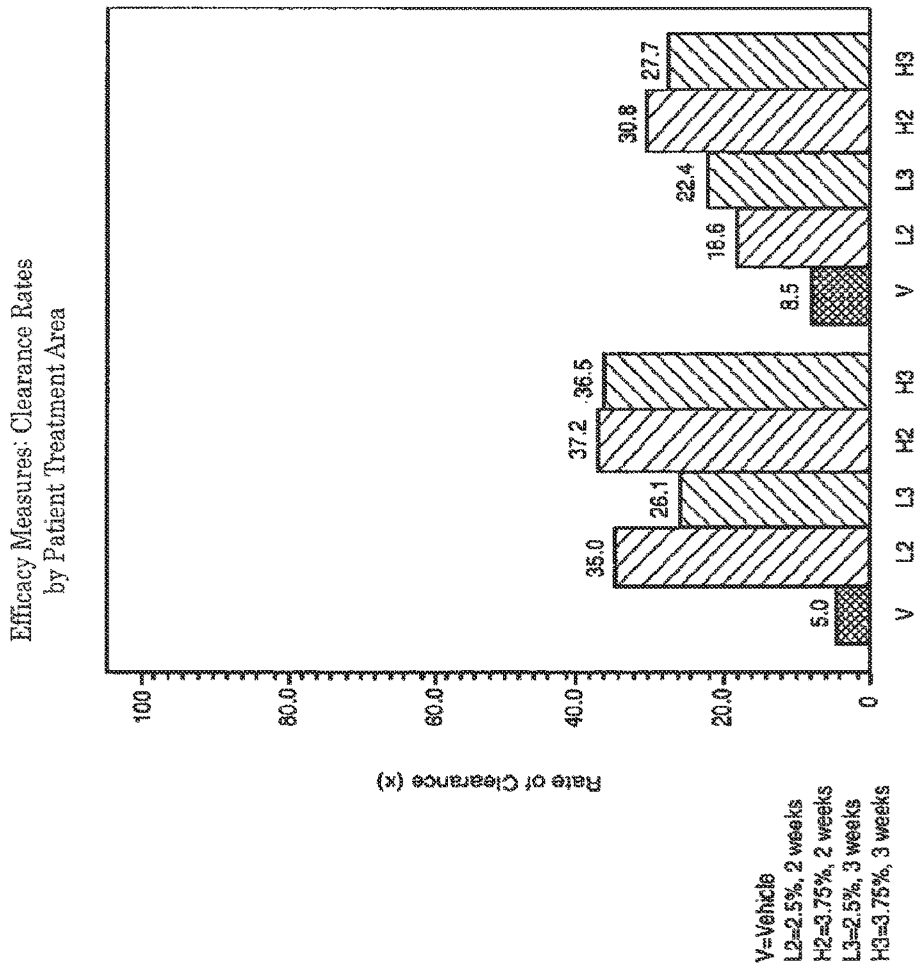
FIG. 11 shows efficacy measures of clearance rates, by subject treatment area, for studies GW01-0703, GW01-0702, GW01-0704 and GW01-0705. As used in this FIG. 11, "Rate of Clearance" refers to the rate of complete AK lesion clearance.
Figure 12:
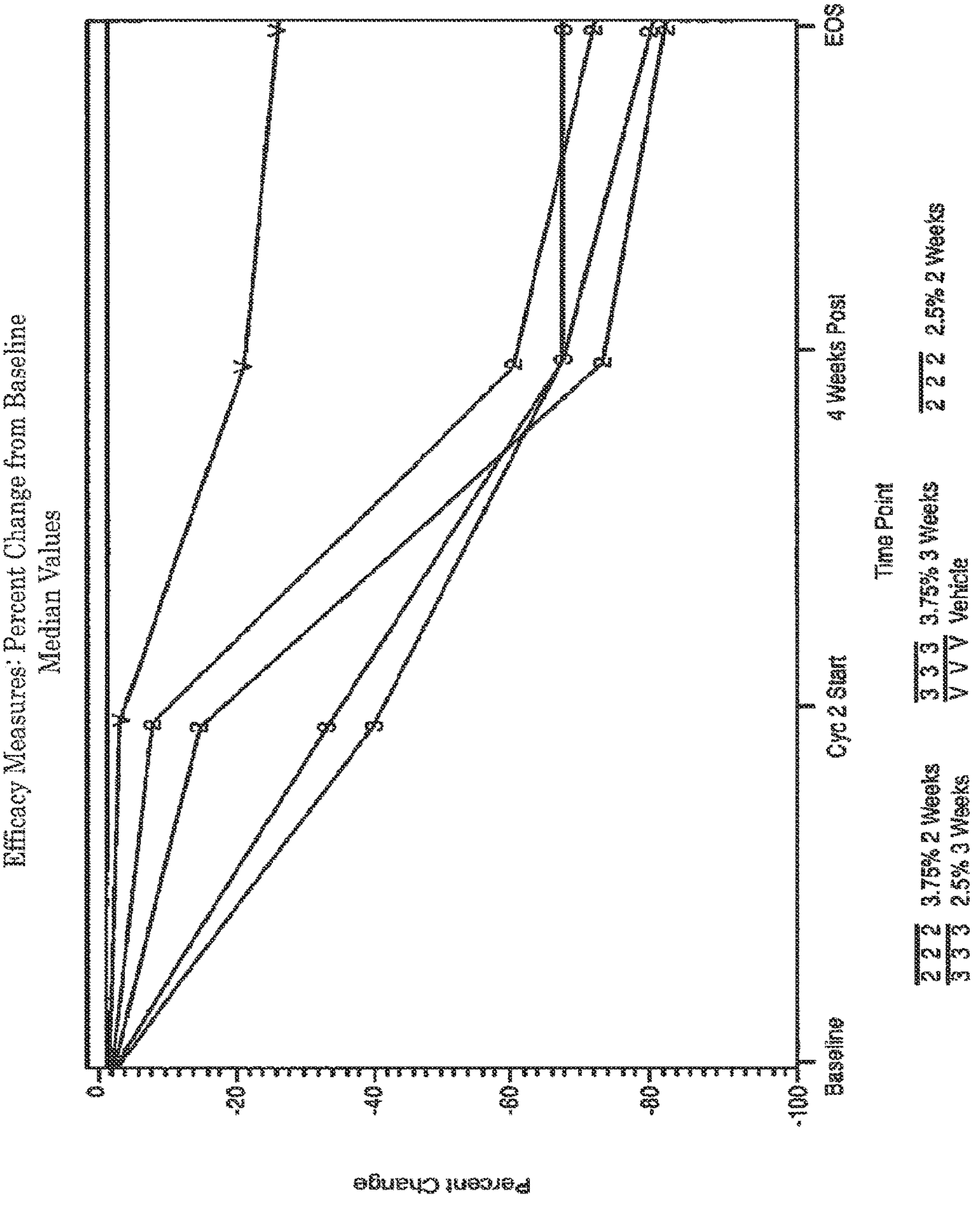
FIG. 12 shows efficacy measures of median percent change from baseline between 0 and −100 for studies GW01-0703, GW01-0702, GW01-0704 and GW01-0705. As used in this FIG. 11, "Percent Change" refers to the median percent by which there is a change in the number of AK lesions using either a 2.5% or a 3.75% lower dosage strength imiquimod formulation of Examples 23-28 in either a two, 2-cycle or a three week, 2-cycle treatment.
Figure 12A:
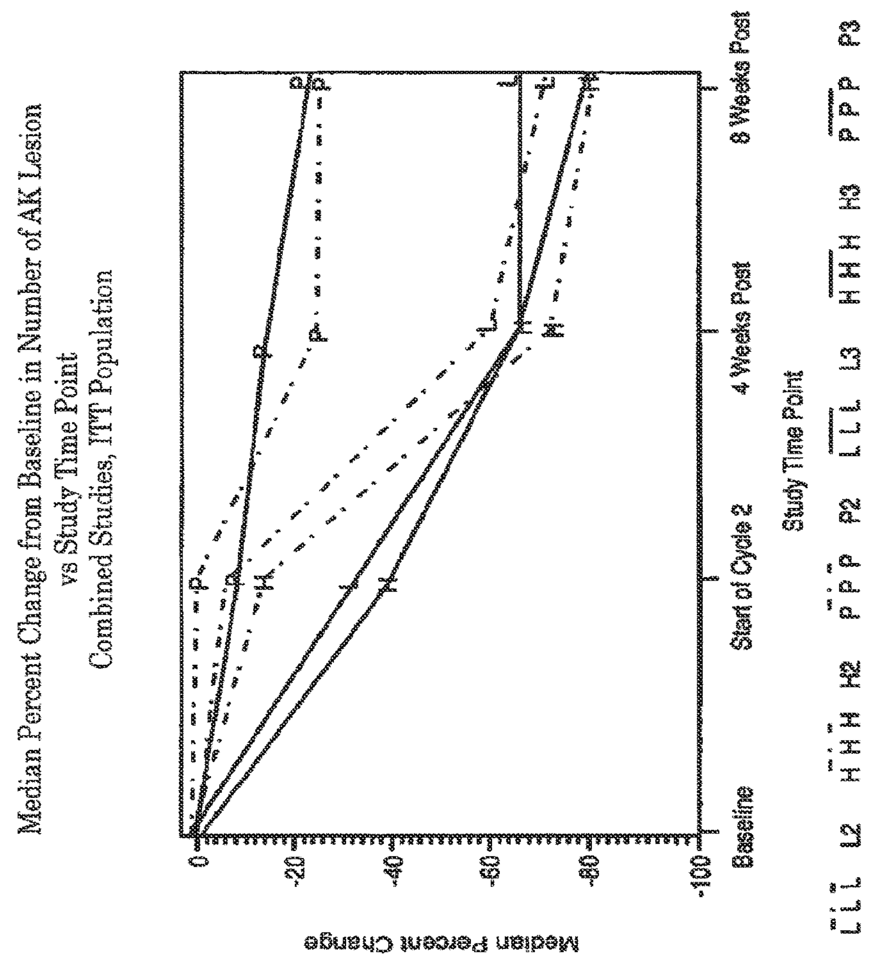
FIG. 12A shows a median percent change from baseline in number of AK lesions vs. study timepoint for combined studies for an ITT population using either a 2.5% or a 3.75% lower dosage strength imiquimod formulation of Examples 23-28. Note the following: L2=2.5% two-week treatment cycle regimen, L3=2.5% three-week treatment cycle regimen, H2=3.75% two-week treatment cycle regimen, H3=3.75% three-week treatment cycle regimen, P2=placebo two-week treatment cycle regimen, and P3=placebo three-week treatment cycle regimen. As used in this FIG. 12A, "Median Percent Change" refers to the median percent change in number of AK lesions from baseline, "Start of Cycle 2" refers to the start of the second cycle, "4 Weeks Post" refers to 4 weeks post treatment, "8 Weeks Post" refers to 8 weeks post treatment, and "P" refers to placebo.
Figure 13:
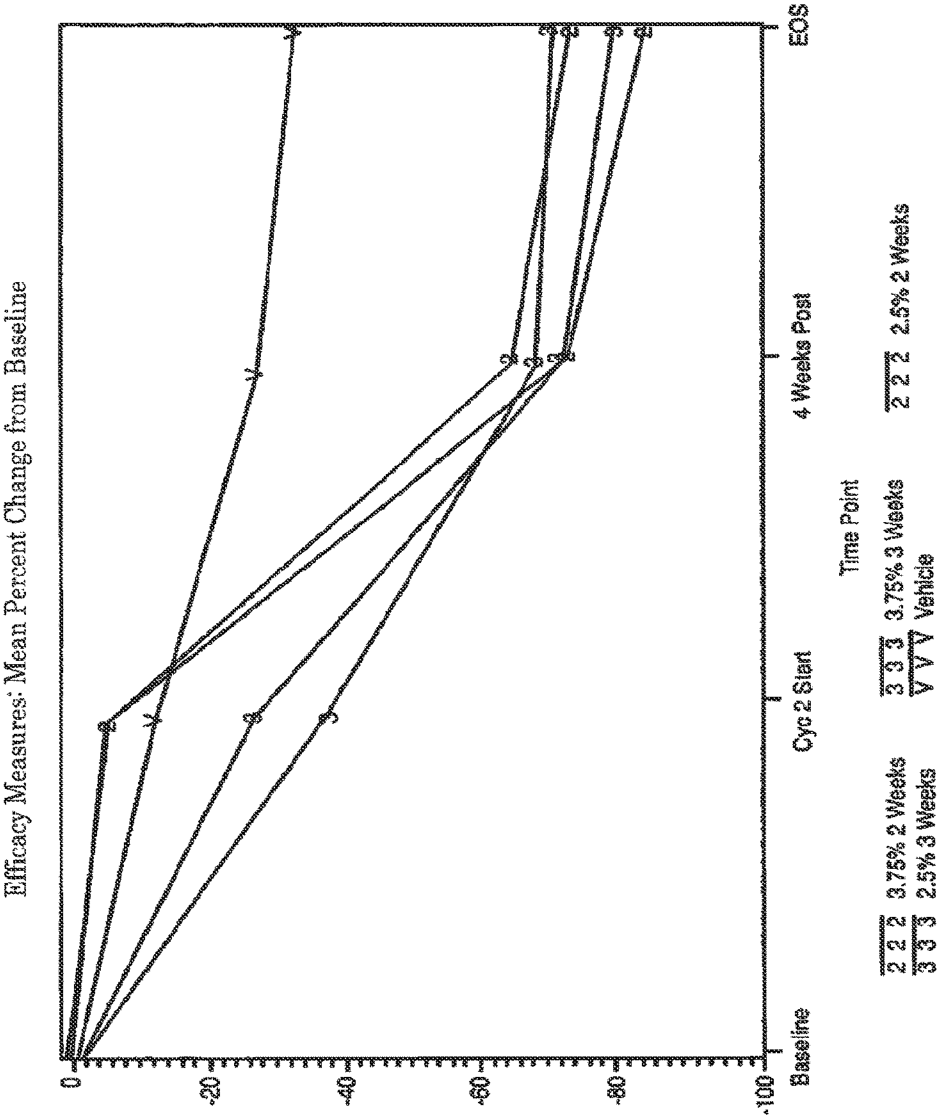
FIG. 13 shows efficacy measures of mean percent change from baseline between 0 and −80 for studies GW01-0703, GW01-0702, GW01-0704 and GW01-0705 using either a 2.5% or a 3.75% lower dosage strength imiquimod formulation of Examples 23-28. As used in this FIG. 13, "Percent Change" refers to the mean percent change in number of AK lesions from baseline, "Cyc 2 Start" refers to the start of the second cycle, "4 Weeks Post" refers to 4 weeks post treatment, and "EOS" refers to End of Study (8 weeks post treatment)
Figure 15:
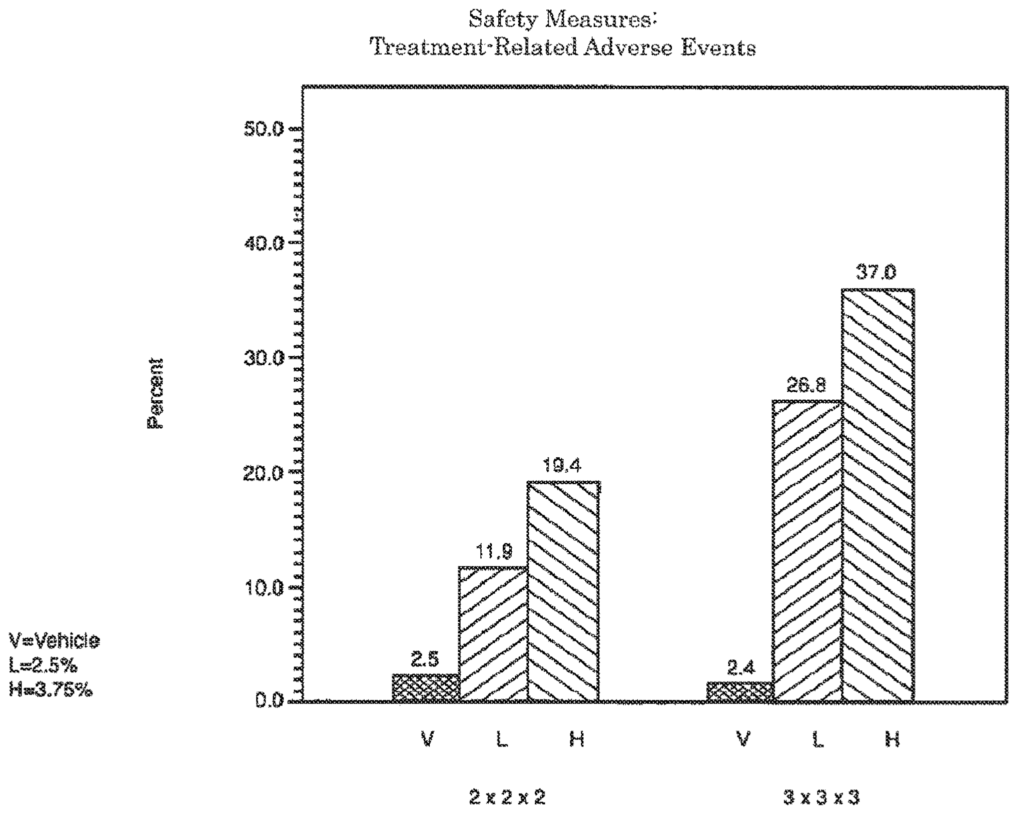
FIG. 15 shows safety measures of incidence of treatment-related adverse events for studies GW01-0703, GW01-0702, GW01-0704 and GW01-0705. As used in this FIG. 15, "H" refers to a 3.75% lower dosage strength imiquimod formulation of Examples 23-28 and "L" refers to a 2.5% lower dosage strength imiquimod formulation of Examples 23-28, and "V" refers to vehicle. See also FIGS. 14A-14E.
Figure 17:
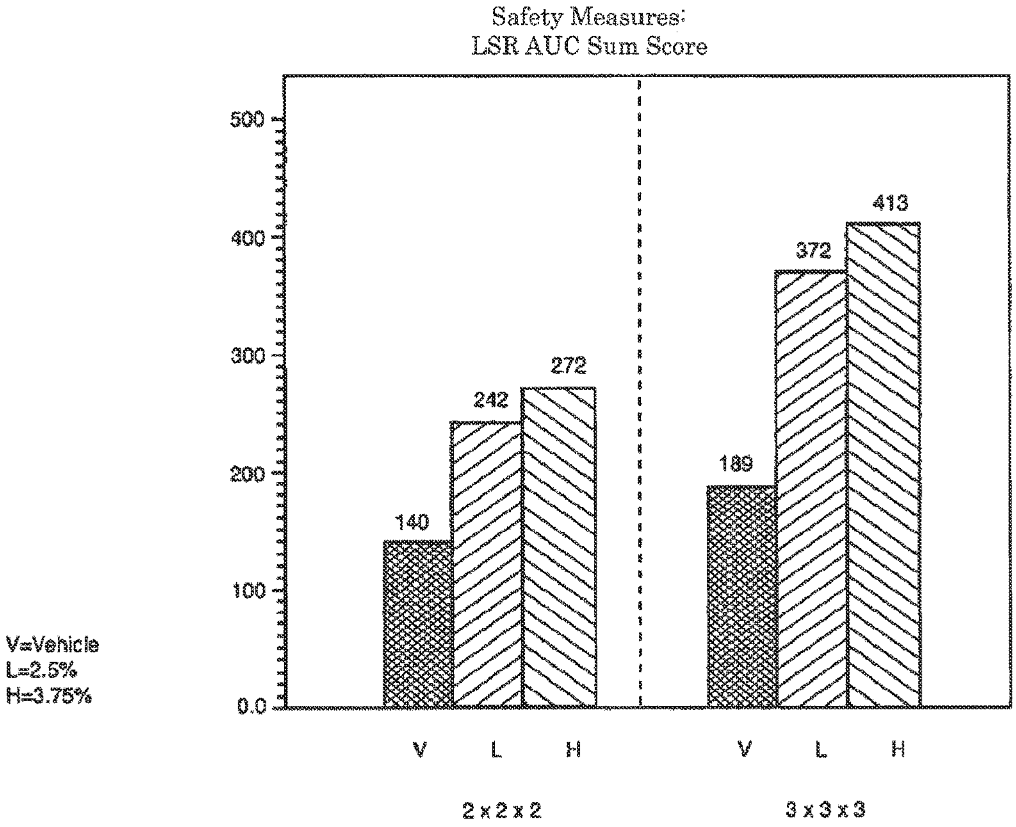
FIG. 17 shows safety measures of LSR AUC sum score for studies GW01-0703, GW01-0702, GW01-0704 and GW01-0705. As used in this FIG. 17, "H" refers to a 3.75% lower dosage strength imiquimod formulation of Examples 23-28 and "L" refers to a 2.5% lower dosage strength imiquimod formulation of Examples 23-28.
Figure 18:
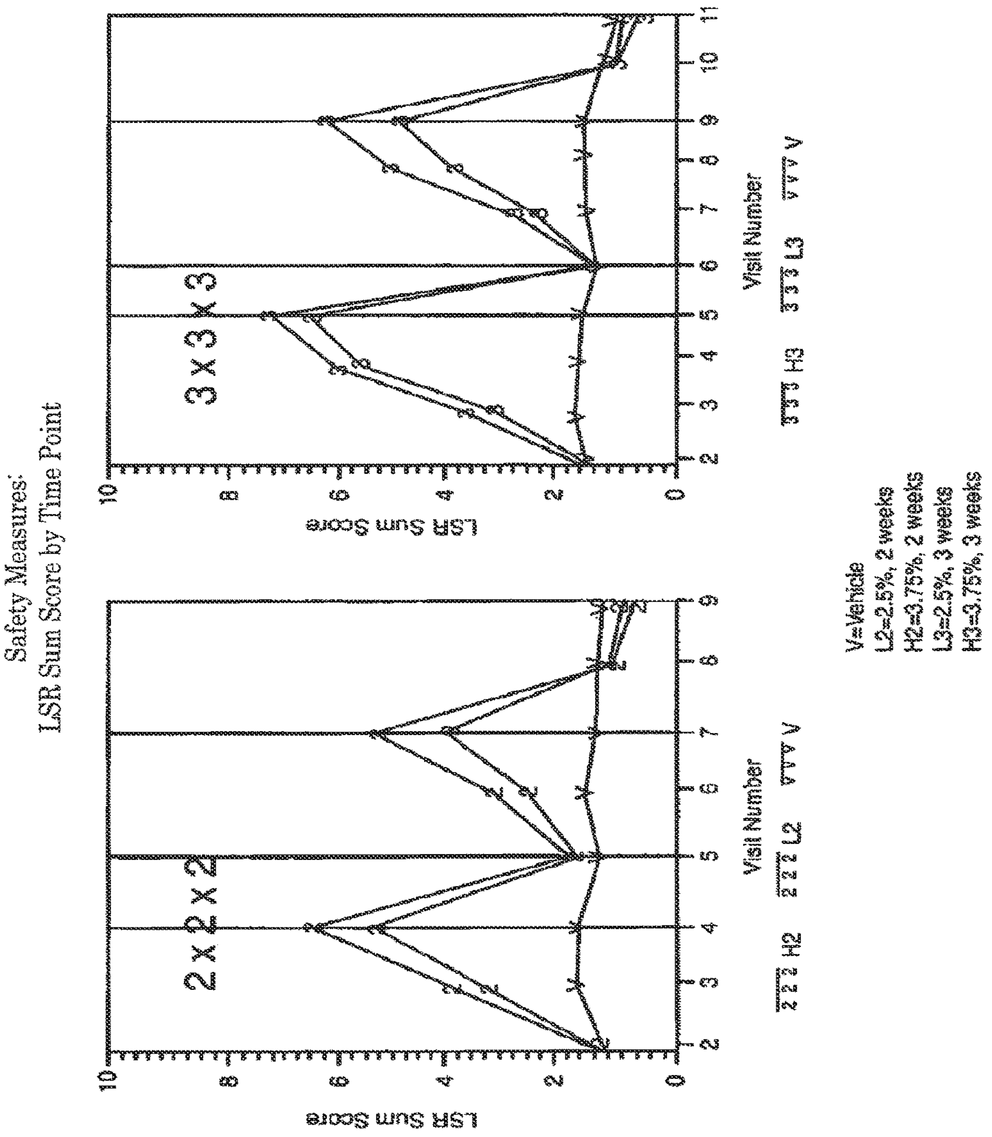
FIG. 18 shows safety measures of LSR sum score, by time point, for studies GW01-0703, GW01-0702, GW01-0704 and GW01-0705.
Figure 18A:
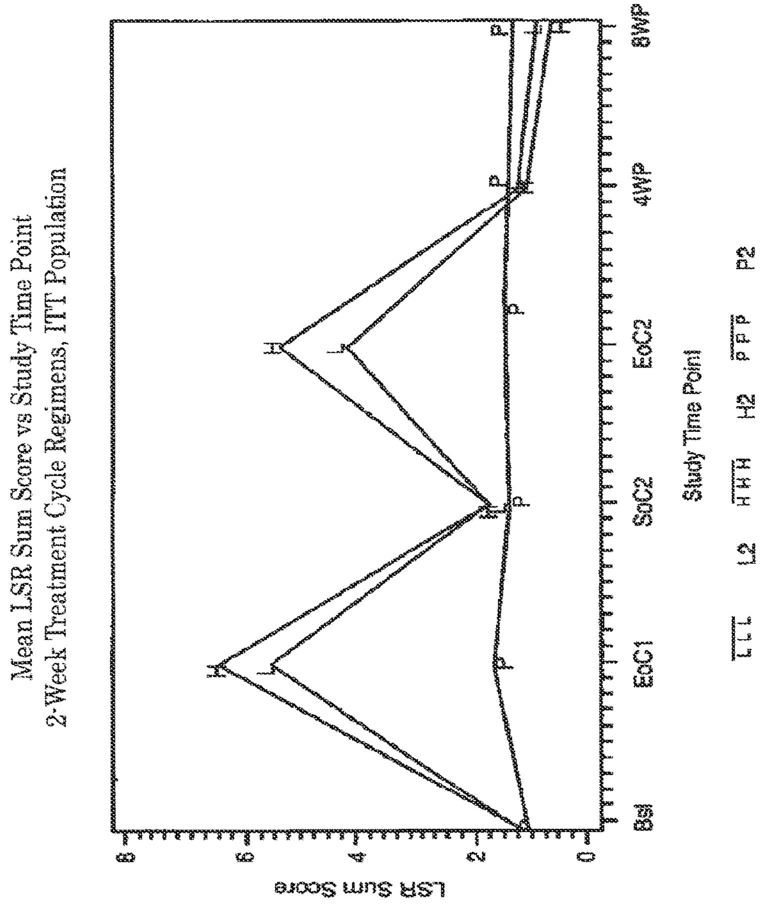
FIG. 18A shows a mean LSR sum score vs. study time point for two-week treatment cycle regimens for an ITT population using a 3.75% lower dosage strength imiquimod formulation of Examples 23-28. Note the following: Bsl=baseline, EoC1=end of cycle 1, SoC2=start of cycle 2, EoC2=end of cycle 2, 4WP=4 weeks post-treatment, 8WP=8 weeks post-treatment, L2=2.5% two-week cycle regimen, H2=3.75% two-week treatment cycle regimen, P2=placebo two-week treatment cycle regimen.
Figure 18B:
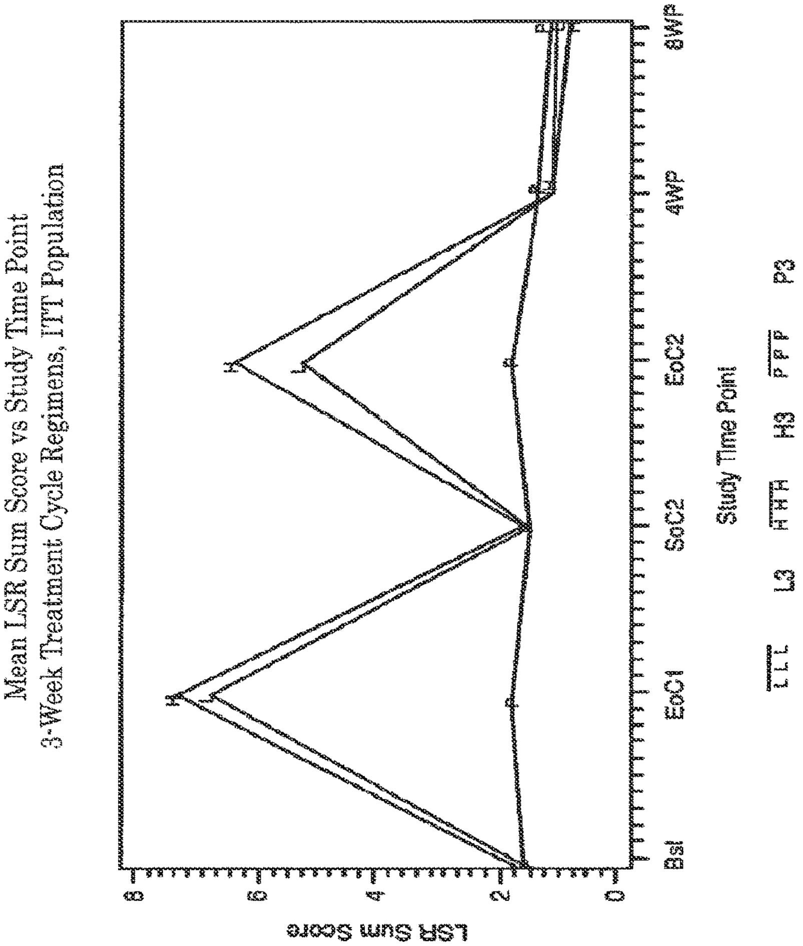
FIG. 18B shows a mean LSR sum score vs. study time point for three-week treatment cycle regimens for an ITT population using a 3.75% lower dosage strength imiquimod formulation of Examples 23-28. Note the following: Bsl=baseline, EoC1=end of cycle 1, SoC2=start of cycle 2, EoC2=end of cycle 2, 4WP=4 weeks post-treatment, 8WP=8 weeks post-treatment, L3=2.5% three-week cycle regimen, H3=3.75% three-week treatment cycle regimen, P32=placebo three-week treatment cycle regimen.
Figure 19:
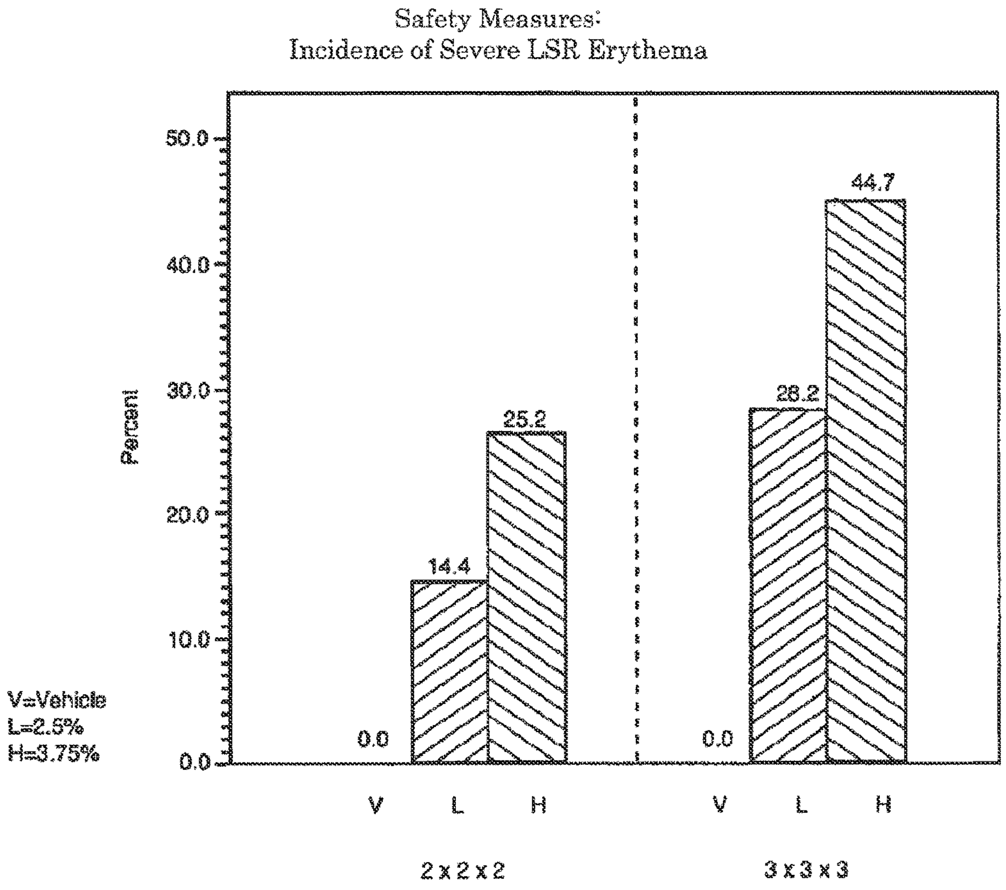
FIG. 19 shows safety measures of incidence of severe LSR erythema for studies GW01-0703, GW01-0702, GW01-0704 and GW01-0705. As used in this FIG. 19, "H" refers to a 3.75% lower dosage strength imiquimod formulation and "L" refers to a 2.5% lower dosage strength imiquimod formulation of Examples 23-28, and "V" refers to vehicle. See also FIGS. 16A-C.
Figure 20:
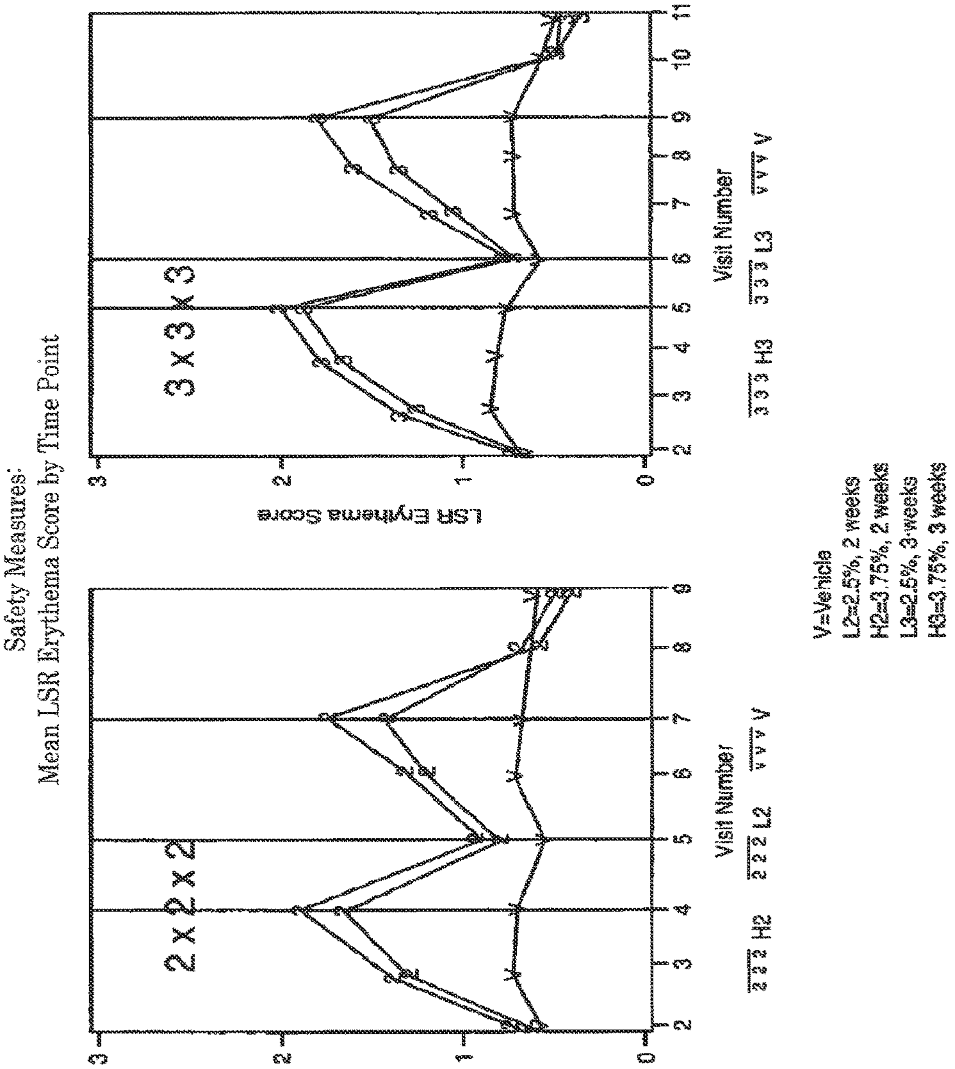
FIG. 20 shows mean LSR erythema score, by time point, for studies GW01-0703, GW01-0702, GW01-0704 and GW01-0705.
Figure 20A:
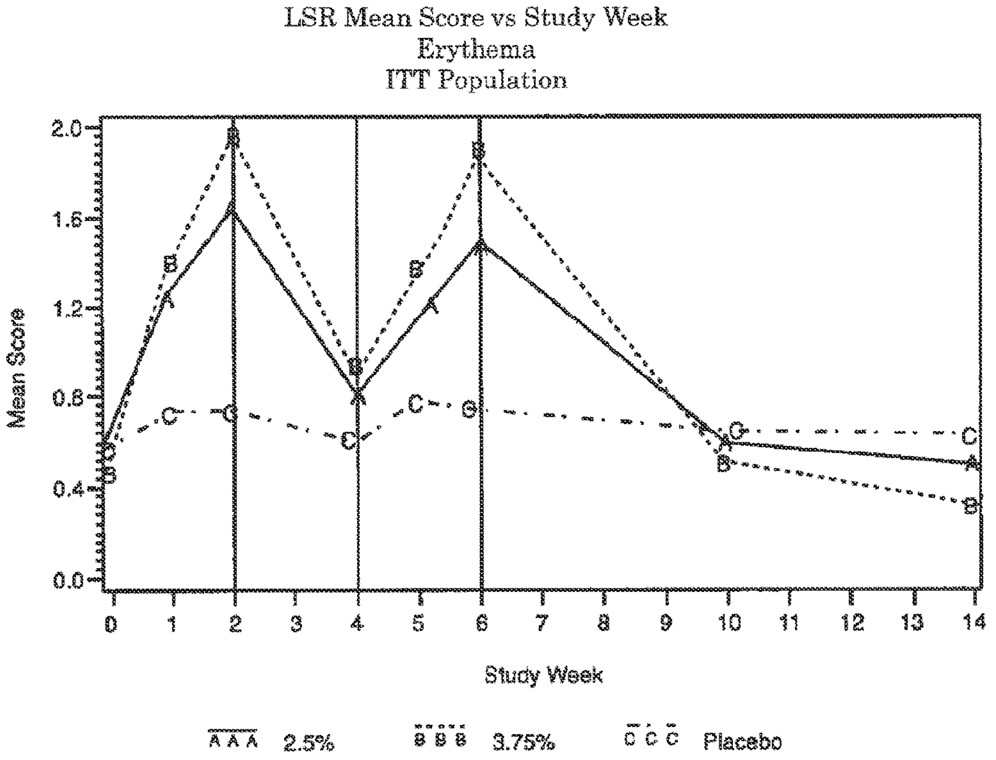
FIG. 20A shows LSR mean score vs. study week for erythema for an ITT population for study GW01-0702. As used in this FIG. 20A, "A" refers to a 2.5% lower dosage strength imiquimod formulation, "B" refers to a 3.75% lower dosage strength imiquimod formulation of Examples 23-28 and C refers to Placebo.
Figure 20B:
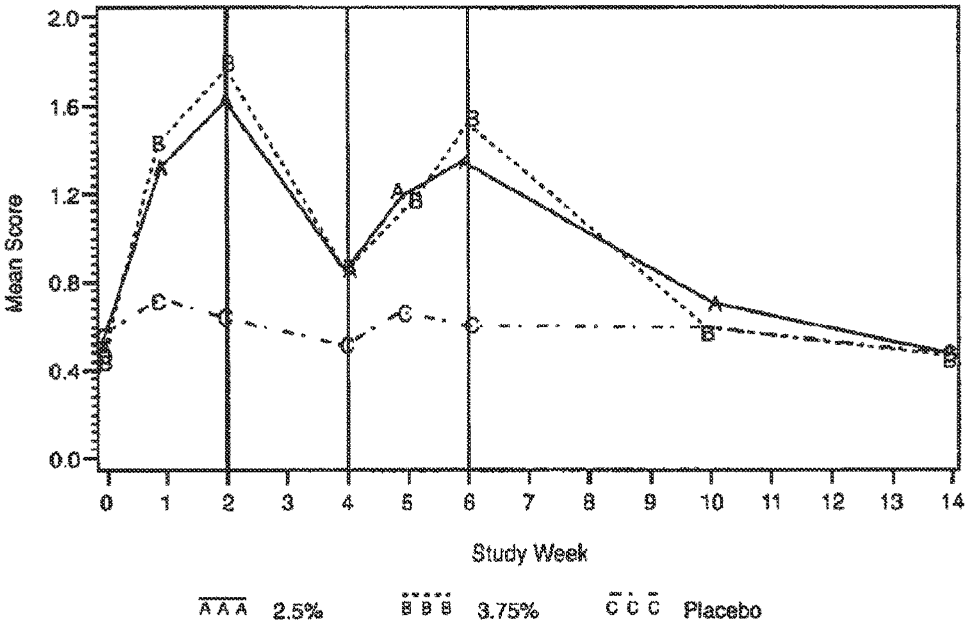
FIG. 20B shows a LSR mean score vs. study week for erythema for an ITT population for study GW01-0704. As used in this FIG. 20B, "A" refers to a 2.5% lower dosage strength imiquimod formulation, "B" refers to a 3.75% lower dosage strength imiquimod formulation of Examples 23-28 and C refers to Placebo.
Figure 21:
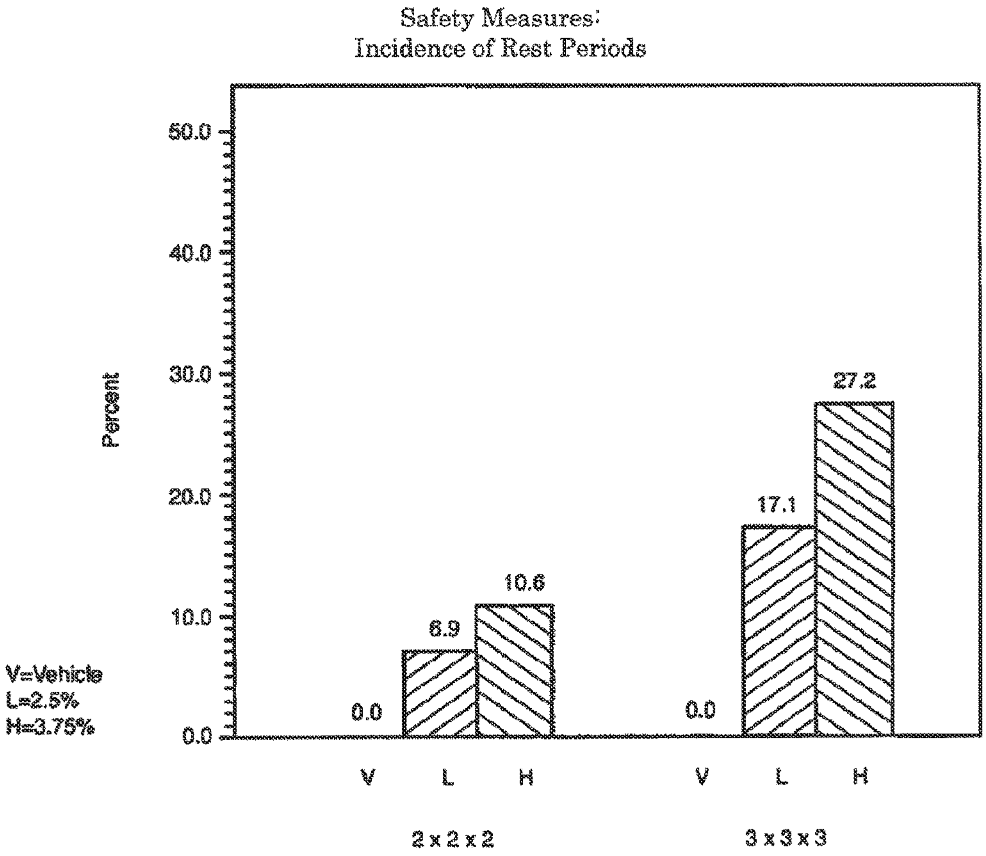
FIG. 21 shows safety measures of incidence of rest periods for studies GW01-0703, GW01-0702, GW01-0704 and GW01-0705. See also FIG. 30.
Figure 22:
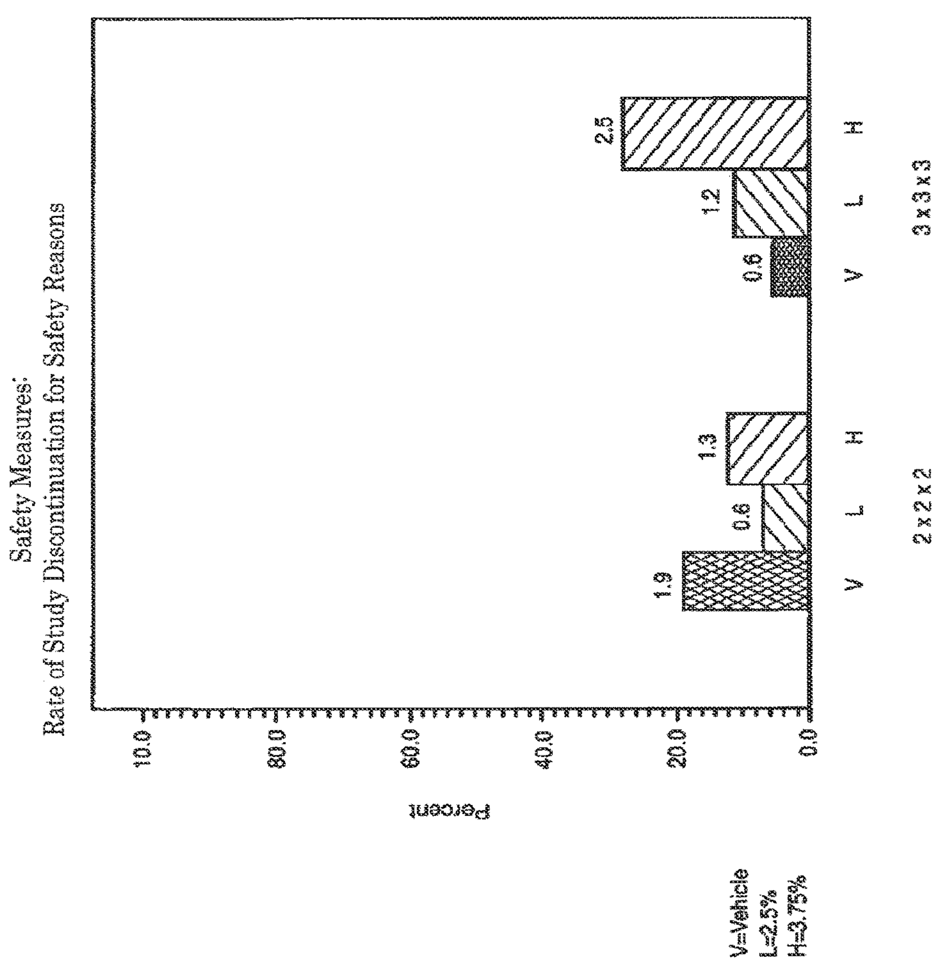
FIG. 22 shows safety measures of rate of study discontinuation, for safety reasons, for studies GW01-0703, GW01-0702, GW01-0704 and GW01-0705. As used in this FIG. 22, "H" refers to a 3.75% lower dosage strength imiquimod formulation of Examples 23-28, "L" refers to a 2.5% lower dosage strength imiquimod formulation of Examples 23-28 and "V" refers to vehicle.

By way of illustrating and providing a more complete appreciation of the present invention and many of the attendant advantages thereof, the following detailed description and examples are given concerning the novel methods and compositions.

In general, the present invention relates to a pharmaceutical composition comprising imiquimod and a pharmaceutically acceptable vehicle for imiquimod, which vehicle comprises a fatty acid. While the present invention may be embodied in many different forms, several specific embodiments are discussed herein with the understanding that the present disclosure is to be considered only as an exemplification of the principles of the invention, and it is not intended to limit the invention to the embodiments described or illustrated.

As used in the specification and claims, the phrase "substantially less-irritating" designates formulations that do not cause unacceptable skin irritation in conventional repeat skin irritation tests in albino rabbits such as that described in Draize et al., "Appraisal of the Safety of Chemicals in Food, Drugs and Cosmetics", prepared by the Division of Pharmacology of the Food and Drug Administration, published originally in 1959 by the Association of Food and Drug Officials of the United States, Topeka, Kans. (2nd printing 1965), incorporated herein by reference.

Unless otherwise indicated, all numbers expressing quantities, ratios, and numerical properties of ingredients, reaction conditions, and so forth used in the specification and claims are to be understood as being modified in all instances by the term "about". All parts, percentages, ratios, etc. herein are by weight unless indicated otherwise.

As used herein, the singular forms "a" or "an" or "the" are used interchangeably and intended to include the plural forms as well and fall within each meaning, unless expressly stated otherwise. Also as used herein, "at least one" is intended to mean "one or more" of the listed element. Singular word forms are intended to include plural word forms and are likewise used herein interchangeably where appropriate and fall within each meaning, unless expressly stated otherwise. Except where noted otherwise, capitalized and non-capitalized forms of all terms fall within each meaning.

By the term "bioequivalence or bioequivalent", as used herein, it refers to lower dosage strength formulations in which they are pharmaceutically equivalent and their bioavailibilities (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which imiquimod becomes available from such formulations at the site of imiquimod action when administered at the same molar dose under similar conditions, e.g., the rate at which imiquimod can leave such a formulation and the rate at which imiquimod can either cross the stratum corneum and/or become available at the site of action to treat actinic keratosis. In other words, there is a high degree of similarity in the bioavailabilities of two imiquimod pharmaceutical products (of the same galenic form) from the same molar dose, that are unlikely to produce clinically relevant differences in therapeutic effects, or adverse reactions, or both. The terms "bioequivalence", as well as "pharmaceutical equivalence" and "therapeutic equivalence" are also used herein as defined and/or used by (a) the FDA, (b) the Code of Federal Regulations ("C.F.R."), Title 21, and/or (c) Health Canada.

By the term "bioavailability or bioavailable", as used herein, it means generally the rate and extent of absorption of imiquimod into the systemic circulation and, more specifically, the rate or measurements intended to reflect the rate and extent to which imiquimod becomes available at the site of action or is absorbed from a drug product and becomes available at the site of action. In other words, and by way of example, the extent and rate of imiquimod absorption from a lower dosage strength formulation of the present invention as reflected by a time-concentration curve of imiquimod in systemic circulation.

By "pharmaceutical equivalence or pharmaceutically equivalent", as used herein, it refers to lower dosage strength imiquimod formulations of the present invention that contain the same amount of imiquimod, in the same dosage forms, but not necessarily containing the same inactive ingredients, for the same route of administration and meeting the same or comparable compendial or other applicable standards of identity, strength, quality, and purity, including potency and, where applicable, content uniformity and/or stability.

By "therapeutic equivalence or therapeutically equivalent", it is meant herein to mean those lower dosage strength imiquimod formulations which (a) will produce the same clinical effect and safety profile when practicing the short durations of therapy, to treat actinic keratosis in accordance with the present invention and (b) are pharmaceutical equivalents, e.g., they contain imiquimod in the same dosage form, they have the same route of administration; and they have the same imiquimod strength. In other words, therapeutic equivalence means that a chemical equivalent of an imiquimod lower dosage strength imiquimod formulation of the present invention (i.e., containing the same amount of imiquimod in the same dosage form) when administered to the same individuals in the same dosage regimen will provide essentially the same efficacy and toxicity.

By "$T_{max}$", it is meant herein to mean the time when the maximum imiquimod serum concentration is reached at steady state following topical application of a lower dosage strength imiquimod formulation of the present invention, i.e., when the rate of imiquimod absorption equals the rate of imiquimod elimination. In other words, the time that $C_{max}$ is observed for imiquimod.

By "$C_{max}$", it is meant herein to refer to the maximum imiquimod serum concentration that is reached at steady state following topical application of a lower dosage strength imiquimod formulation of the present invention, i.e., when the rate of imiquimod absorption equals the rate of imiquimod elimination. In other words, it is the maximum serum concentration; the highest serum concentration observed during the imiquimod dosing or sampling interval.

By "$C_{min}$", it is meant herein to refer to the minimum measurable imiquimod serum concentration; e.g., imiquimod serum concentration that is observed immediately prior to dosing on Days 7, 14, 21 and 22 (24 hours post-dose).

By "$T_{1/2}$", it is meant herein to mean the time required for half of the quantity of maximum imiquimod serum concentration to be eliminated once steady state is achieved following topical application of a lower dosage strength imiquimod formulation of the present invention. For example, the apparent elimination half-life for imiquimod, that is calculated as about $0.693/\lambda_Z$ in accordance with Example 24.

By "$AUC_{0-24}$", it is meant herein to mean the area under the serum imiquimod concentration versus a 24 hour time curve following topical application of a lower dosage strength imiquimod formulation of the present invention, i.e., a measure of imiquimod exposure over a 24 hour period. For example, the area under the imiquimod serum concentration versus time curve, from 0 to 24 hours, that is calculated using the linear trapezoid rule or extrapolated to 24 hours in cases where reportable values are not obtainable up to that time point.

By "$AUC_{0-t}$", it is meant herein to mean the area under the imiquimod serum concentration versus time curve, from 0 to the time of the last non-zero concentration on Day 1; that is calculated using the linear trapezoid rule.

By "$R_{AUC}$", it is meant herein to mean the accumulation ratio; that are calculated as the $AUC_{0-24}$ value during multiple-imiquimod dose administration divided by the $AUC_{0-24}$ value following the first dose (i.e., Day 21/Day 1); or the accumulation ratios that are calculated for an imiquimod metabolite only if sufficient non-zero time points are available to reasonably estimate $AUC_{0-24}$.

By "$AUC_{0-inf}$", it is meant herein to mean the area under the imiquimod serum concentration versus time curve, from 0 to infinity; $AUC_{0-inf}$ that is calculated on Day 1 as $AUC_{(0-inf)}=AUC_{(0-t)}+Ct/K_{el}$ (where $C_t$=the fitted last non-zero concentration, $AUC_{0-t}$=the AUC from time zero to the time of the last non-zero concentration and $K_{el}$=the elimination rate constant).

By "$R_{Cmax}$", it is meant herein to mean the accumulation ratio; calculated as the $C_{max}$ value during multiple-dose administration divided by the $C_{max}$ value following the first dose (i.e., Day 21/Day 1)

By "$\lambda_{z\ EFF}$", it is meant herein to mean the effective elimination rate constant, calculated as $-\ln(1-1/R_{AUC})$/tau.

By "$T_{1/2\ EFF}$", it is meant herein to mean the effective half-life for accumulation; calculated as $0.693/\lambda_{z\ EFF}$.

By "λz", it is meant to refer to an elimination rate constant, i.e., the rate at which imiquimod disappears from the site of measurement once steady state is achieved following topical application of a lower dosage strength imiquimod formulation of the present invention. In other words, the apparent elimination rate constant; that is calculated using linear regression on the terminal portion of the ln concentration versus time profile.

By "geometric mean", it refers a statistical average of a set of transformed numbers often used to represent a central tendency in highly variable data. It is calculated from data transformed using powers or logarithms and then transformed back to original scale after averaging.

By "geometric mean ratio", it refers to a ratio of two geometric means, where the "geometric LS mean test" is the numerator of the geometric mean ratio, and the "geometric LS mean reference" is the denominator of the geometric mean ratio.

By "RH", it refers herein to relative humidity.

By "cPs, it refers herein to centipoise.

By "h", it refers herein to hours.

By "ITT", it refers to an intent-to-treat population.

By "Pbo, it refers to placebo.

By "EOS", it refers to End of Study.

By "V", it refers to vehicle.

Studies GW01-0702 and GW01-0704 are duplicative studies that investigate 2-week treatment cycles, wherein the 2-week treatment cycles are separated by a two week rest period (no treatment) (2×2×2), and studies GW01-0703 and GW01-0705 are duplicative studies that investigate 3-week treatment cycles, wherein the 3-week treatment cycles are separated by a three week rest period (no treatment) (3×3×3). See Table 64 herein below and the flow diagrams depicted in FIG. 70.

By "L2", it refers to a 2.5% lower dosage strength imiquimod formulation that is described in Examples 23-28 and the FIGS. and that is used in connection with studies GW01-0702 and GW01-0704.

By "L3", it refers to a 3.75% lower dosage strength imiquimod formulation that is described in Examples 23-28 and the FIGS. and that is used in connection with studies GW01-0702 and GW01-0704.

By "H2", it refers to a 2.5% lower dosage strength imiquimod formulation that is described in Examples 23-28 and the FIGS. and that is used in connection with studies GW01-0703 and GW01-0705.

By "H3", it refers to a 3.75% lower dosage strength imiquimod formulation that is described in Examples 23-28 and the FIGS. and that is used in connection with studies GW01-0703 and GW01-0705.

By "AE", it refers herein to adverse events.

By "2×2×2", as used herein, it refers to a two-week, 2-cycle AK treatment regimen, wherein (1) during the first 2 weeks (the first cycle of treatment), a lower dosage strength imiquimod formulation of the present invention is applied once daily each day to an AK treatment area, (2) during the second 2 weeks, there is a rest period in which no treatment occurs, and (3) during the third 2 weeks (the second cycle of treatment), the same formulation is again applied once daily each day to the same AK treatment area, In other words, during the first 2 weeks, treatment is on, during the second 2 weeks, treatment is off, and during the third 2 weeks, treatment is on again, By "3×3×3", as used herein, it refers to a three-week, 2-cycle AK treatment regimen, wherein (1) during the first 3 weeks (the first cycle of treatment), a lower dosage strength imiquimod formulation of the present invention is applied once daily each day to an AK treatment area, (2) during the second 3 weeks, there is a rest period in which no treatment occurs, and (3) during the third 3 weeks (the second cycle of treatment), the same formulation is again applied once daily each day to the same AK treatment area, In other words, during the first 3 weeks, treatment is on, during the second 3 weeks, treatment is off, and during the third 3 weeks, treatment is on again, The present invention provides pharmaceutical formulations such as creams, ointments, foams, gels, lotions and adhesive coatings that contain imiquimod and a fatty acid such as isostearic, linoleic, unrefined oleic acid, refined oleic acid, such as Super Refined® oleic acid NF (e.g., a highly purified oleic acid, i.e., an oleic acid which has low polar impurities, such as peroxides, a low peroxide value and is marketed by CRODA; see e.g., www.crodausa.com) and mixtures thereof. The formulations of the invention provide desirable skin penetrability of the imiquimod.

The compound imiquimod is a known antiviral agent that is also known to induce interferon biosynthesis. It can be prepared using the method disclosed in U.S. Pat. No. 4,689,338, the disclosure of which is incorporated herein by reference in its entirety. The compound can be used to treat actinic keratosis. The amount of imiquimod present in a formulation of the present invention will be an effective amount to treat actinic keratosis to achieve total AK lesion clearance or partial AK lesion reduction or clearance, to prevent the recurrence of such a disease and/or to promote immunity against such a disease with an acceptable safety profile. An example of an effective amount of imiquimod in a formulation of the present invention is between about 1.0 percent and about 4.25 percent by weight based on the total weight of a formulation, more preferably between about 1.5%, 1.75%, 2.0%, 2.25%, 2.5%, 2.75%, 3.0%, 3.25%, 3.5%, 3.75%, 4.0% and 4.25%, even more preferably between about 2.0%, 2.25%, 2.5%, 2.75%, 3.0%, 3.25%, 3.5%, 3.75% and 4.0%, and still even more preferably between about 2.5%, 2.75%, 3.0%, 3.25%, 3.5% and 3.75%. Imiquimod formulations of the present invention that contain about 2.5% imiquimod or about 3.75% imiquimod by weight based on the total weight of the formulation are most preferred.

Likewise, a shortened period or duration, as contemplated by the present invention, will be for reduced periods of time effective to treat actinic keratosis as discussed herein above, e.g., up to six weeks, again depending upon the lower dosage strength imiquimod formulation of the present invention that is selected for daily application, and preferably up to four weeks. By way of example, short periods of treatment with lower dosage strength imiquimod formulations for treating actinic keratosis, include:

(a) applying an effective amount of imiquimod, such as via the lower dosage strength imiquimod formulations of the present invention to the area affected with actinic keratosis, as follows: applying an effective amount once per day for fourteen (14) consecutive days, followed by a rest period of for fourteen (14) days (no treatment), followed by again applying an effective amount once per day for fourteen (14) days for a total of twenty-eight (28) doses or four weeks to treat actinic keratosis (2-cycle therapy); or (b) applying an effective amount of imiquimod, such as via the lower dosage strength imiquimod formulations of the present invention to the area affected with actinic keratosis, as follows: applying an effective amount once per day for twenty one (21) days, followed by a rest period of twenty one (21) days (no treatment, followed by again applying an effective amount once per day for twenty one (21) consecutive days for a total of forty-two (42) doses or six weeks to treat actinic keratosis (2-cycle therapy); or (c) applying an effective amount of imiquimod, such as via a suitable lower dosage strength imiquimod formulation of the present invention to the area affected with actinic keratosis, once per day for up to about forty-two (42) days or less and, preferably, for up to about twenty-eight days (28) or less (1-cycle therapy).

A fatty acid such as isostearic acid, palmitic acid, stearic acid, linoleic acid, refined oleic acid, such as Super Refined® oleic acid NF (e.g., a highly purified oleic acid, i.e., an oleic acid which has low polar impurities, such as peroxides, a low peroxide value and is marketed by CRODA; see e.g., www.crodausa.com), an unrefined oleic acid blended with effective amounts of antioxidants or mixtures thereof are incorporated into formulations of the present invention. The total amount of fatty acid present in a formulation is preferably between about 3 percent and about 45 percent by weight based on the total weight of a formulation. It should be understood that when oleic acid is selected as a fatty acid, that stability may present issue. Thus, stabilizers, such as anti-oxidants and the like, may be required to preserve pharmaceutical elegance and stability over the life of the oleic acid formulation.

A pharmaceutical formulation of the invention can be in a form such as a cream, an ointment, a foam, a gel, a lotion, a pressure-sensitive adhesive composition, or other forms known to those skilled in the art, each particular form containing imiquimod and fatty acid in particular amounts, and optionally containing various additional elements. The preferred amounts of drug and fatty acid, and the amounts and types of optional elements used in formulations of the invention are discussed below with particular reference to creams, ointments and adhesive compositions.

A cream according to the invention contains 1-isobutyl-1H-imidazo[4,5-c]quinolin-4-amine and fatty acid.

The amount of 1-isobutyl-1H-imidazo[4,5-c]-quinolin-4-amine present in a cream is preferably about 0.5 percent to about 9 percent by weight, and more preferably about 1 percent to about 5 percent by weight, based on the total weight of the cream.

The total amount of fatty acid present in a cream of the invention is preferably about 3 percent to about 45 percent by weight, and more preferably about 5 percent to about 25 percent by weight, based on the total weight of the cream.

Optionally, a cream of the present invention can contain emollients, emulsifiers, thickeners, and/or preservatives.

Emollients such as long chain alcohols, e.g., cetyl alcohol, stearyl alcohol and cetearyl alcohol; hydrocarbons such as petrolatum and light mineral oil; or acetylated lanolin can be included in a cream of the invention. A cream can contain one or more of these emollients. The total amount of emollient in a cream of the invention is preferably about 5 percent to about 30 percent, and more preferably about 5 percent to about 10 percent by weight based on the total weight of the cream.

Emulsifiers such as nonionic surface active agents, e.g., polysorbate 60 (available from ICI Americas), sorbitan monostearate, polyglyceryl-4 oleate, and polyoxyethylene (4)lauryl ether or trivalent cationic a cream of the invention. A cream can contain one or more emulsifiers. Generally the total amount of emulsifier is preferably about 2 percent to about 14 percent, and more preferably about 2 percent to about 6 percent by weight based on the total weight of the cream.

Pharmaceutically acceptable thickeners, such as Xanthum gum, Guar gum, Veegum Gum™K (available from R. T. Vanderbilt Company, Inc.), and long chain alcohols (i.e. cetyl alcohol, stearyl alcohol or cetearyl alcohol) can be used. A cream can contain one or more thickeners. The total amount of thickener present is preferably about 3 percent to about 12 percent by weight based on the total weight of the cream.

Preservatives such as methylparaben, propylparaben and benzyl alcohol can be present in a cream of the invention. The appropriate amount of such preservative(s) is known to those skilled in the art.

Optionally, an additional solubilizing agent such as benzyl alcohol, lactic acid, acetic acid, stearic acid, salicylic acid, any alpha-hydroxy acid such as glycolic acid, or hydrochloric acid can be included in a cream of the invention.

If an additional solubilizing agent is used, the amount present is preferably about 1 percent to about 12 percent by weight based on the total weight of the cream.

Optionally, a cream of the invention can contain a humectant such as glycerin, skin penetration enhancers such as butyl stearate, and additional solubilizing agents.

Generally, a cream consists of an oil phase and a water phase mixed together to form an emulsion. Preferably, the amount of water present in a cream of the invention is about 45 percent to about 85 percent by weight based on the total weight of the cream. The oil phase of a cream of the invention can be prepared by first combining the 1-isobutyl-1H-imidazo[4,5-c]quinolin-4-amine or 1-(2-methylpropyl)-1H-imidazo[4,5-c]quinolin-4-amine and the fatty acid (if the cream contains benzyl alcohol it can also be added at this point) and heating with occasional stirring to a temperature of about 50° C. to 85° C. When the 1-isobutyl-1H-imidazo[4,5-c]quinolin-4-amine or 1-(2-methylpropyl)-1H-imidazo[4,5-c]quinolin-4-amine appears to be completely dissolved, the remaining oil phase ingredients are added and heating is continued until dissolution appears to be complete.

The water phase can be prepared by combining all other ingredients and heating with stirring until dissolution appears to be complete.

The creams of the invention are generally prepared by adding the water phase to the oil phase with both phases at a temperature of about 65° C. to 75° C. The resulting emulsion is mixed with a suitable mixer apparatus to give the desired cream.

An ointment of the invention contains an ointment base in addition to 1-isobutyl-1H-itnidazo[4,5-c]quinolin-4-amine and fatty acid.

The amount of 1-isobutyl-1H-imidazo[4,5-c]-quinolin-4-amine present in an ointment of the invention is preferably about 0.5 percent to about 9 percent, and more preferably about 0.5 percent to about 5 percent by weight based on the total weight of the ointment.

The total amount of fatty acid present in an ointment of the invention is preferably about 3 percent to about 45 percent, and more preferably about 3 percent to about 25 percent based on the total weight of the ointment.

A pharmaceutically acceptable ointment base such as petrolatum or polyethylene glycol 400 (available from Union Carbide) in combination with polyethylene glycol 3350 (available from Union Carbide) can be used. The amount of ointment base present in an ointment of the invention is preferably about 60 percent to about 95 percent by weight based on the total weight of ointment.

Optionally, an ointment of the invention can also contain emollients, emulsifiers and thickeners. The emollients, emulsifiers, and thickeners and the preferred amounts thereof described above in connection with creams are also generally suitable for use in an ointment of the invention.

An ointment according to the invention can be prepared by combining 1-isobutyl-1H-imidazo[4,5-c]quinolin-4-amine with fatty acid and heating with occasional stirring to a temperature of about 65° C. When the 1-isobutyl-1H-imidazo[4,5-c]-quinolin-4-amine or 1-(2-methylpropyl)-1H-imidazo[4,5-c]quinolin-4-amine appears to be completely dissolved, the remaining ingredients are added and heated to about 65.° C. The resulting mixture is mixed with a suitable mixer while being allowed to cool to room temperature.

A pressure-sensitive adhesive composition of the invention contains 1-isobutyl-1H-imidazo[4,5-c]-quinolin-4-amine or 1-(2-methylpropyl)-1H-imidazo[4,5-c]quinolin-4-amine, fatty acid, and a pressure sensitive adhesive polymer.

The amount of 1-isobutyl-1H-imidazo[4,5-c]-quinolin-4-amine or 1-(2-methylpropyl)-1H-imidazo[4,5-c]quinolin-4-amine present in a pressure sensitive adhesive composition of the invention is preferably about 0.5 percent to about 9 percent by weight, and more preferably about 3 percent to about 7 percent by weight based on the total weight of the adhesive composition. The amount of fatty acid present is preferably about 10 percent to about 40 percent by weight, more preferably about 15 percent to about 30 percent by weight, and most preferably about 20 percent to about 30 percent by weight, based on the total weight of the adhesive composition.

Preferably, the adhesive polymer utilized in a pressure sensitive adhesive composition of the invention is substantially chemically inert to 1-isobutyl-1H-imidazo[4,5-c]-quinolin-4-amine or 1-(2-methylpropyl)-1H-imidazo[4,5-c]quinolin-4-amine. The adhesive polymer is preferably present in an amount of about 55 percent to about 85 percent by weight based on the total weight of the composition. Suitable adhesive polymers include acrylic adhesives that contain, as a major constituent (i.e., at least about 80 percent by weight of all monomers in the polymer), a hydrophobic monomeric acrylic or methacrylic acid ester of an alkyl alcohol, the alkyl alcohol containing 4 to 10 carbon atoms. Examples of suitable monomers are those discussed below in connection with the “A Monomer”. These adhesive polymers can further contain minor amounts of other monomers such as the “B Monomers” listed below.

Preferred adhesives include acrylic pressure-sensitive adhesive copolymers containing A and B Monomers as follows: Monomer A is a hydrophobic monomeric acrylic or methacrylic acid ester of an alkyl alcohol, the alkyl alcohol containing 4 to 10 carbon atoms, preferably 6 to 10 carbon atoms, more preferably 6 to 8 carbon atoms, and most preferably 8 carbon atoms. Examples of suitable A Monomers are n-butyl, n-pentyl, n-hexyl, isoheptyl, n-nonyl, n-decyl, isohexyl, 2-ethyloctyl, isooctyl and 2-ethylhexyl acrylates. The most preferred A Monomer is isooctyl acrylate.

Monomer B is a reinforcing monomer selected from the group consisting of acrylic acid; methacrylic acid; alkyl acrylates and methacrylates containing 1 to 3 carbon atoms in the alkyl group; acrylamide; methacrylamide; lower alkyl-substituted acrylamides (i.e., the alkyl group containing 1 to 4 carbon atoms) such as tertiary-butyl acrylamide; diacetone acrylamide; n-vinyl-2-pyrrolidone; vinyl ethers such as vinyl tertiary-butyl ether; substituted ethylenes such as derivatives of maleic anhydride, dimethyl itaconate and monoethyl formate and vinyl perfluoro-n-butyrate. The preferred B Monomers are acrylic acid, methacrylic acid, the above-described alkyl acrylates and methacrylates, acrylamide, methacrylamide, and the above-described lower alkyl substituted acrylamides. The most preferred B Monomer is acrylamide.

In one embodiment of a pressure-sensitive adhesive composition of the invention, the pressure-sensitive adhesive copolymer containing A and B Monomers as set forth above preferably contains the A Monomer in an amount by weight of about 80 percent to about 98 percent of the total weight of all monomers in the copolymer. The A Monomer is more preferably present in an amount by weight of about 88 percent to about 98 percent, and is most preferably present in an amount by weight of about 91 percent to about 98 percent. The B Monomer in such a copolymer is preferably present in the pressure-sensitive adhesive copolymer in an amount by weight of about 2 percent to about 20 percent, more preferably about 2 percent to about 12 percent, and most preferably 2 to 9 percent of the total weight of the monomers in the copolymer.

In another embodiment of a pressure-sensitive adhesive composition of the invention, the adhesive copolymer comprises about 60 to about 80 percent by weight (and preferably about 70 to about 80 percent by weight) of the above-mentioned hydrophobic monomeric acrylic or methacrylic acid ester of an alkyl alcohol (i.e., Monomer A described above) based on the total weight of all monomers in the copolymer; about 4 to about 9 percent by weight based on the total weight of all monomers in the copolymer of a reinforcing monomer selected from the group consisting of acrylic acid, methacrylic acid, an alkyl acrylate or methacrylate containing 1 to 3 carbon atoms in the alkyl group, acrylamide, methacrylamide, a lower alkyl-substituted acrylamide, diacetone acrylamide and N-vinyl-2-pyrrolidone; and about 15 to about 35 percent by weight (and preferably about 15 to about 25 percent by weight) of vinyl acetate based on the total weight of all monomers in the copolymer. In this embodiment the preferred acrylic or methacrylic acid ester is isooctyl acrylate and the preferred reinforcing monomer is acrylamide.

The above described adhesive copolymers are known, and methods of preparation therefore are well known to those skilled in the art, having been described for example, in U.S. Pat. No. 24,906 (Ulrich), the disclosure of which is incorporated herein by reference. The polymerization reaction can be carried out using a free radical initiator such as an organic peroxide (e.g., benzoylperoxide) or an organic azo compound (e.g., 2,2'-azobis(2,4-dimethylpentanenitrile), available under the trade designation “Vazo 52” from DuPont).

Since pressure-sensitive adhesives such as those described above are inherently rubbery and tacky and are suitably heat and light stable, there is no need to add tackifiers or stabilizers. However, such can be added if desired.

Optionally, a pressure sensitive adhesive composition of the invention can also contain one or more skin penetration enhancers such as glyceryl monolaurate, ethyl oleate, isopropyl myristate, diisopropyl adipate and N,N-dimethyldodecylamine-N-oxide, either as a single ingredient or as a combination of two or more ingredients. The skin penetration enhancer(s) preferably form a substantially homogeneous mixture with the pressure sensitive adhesive polymer or copolymer. The total amount of skin penetration enhancer (s) present in a pressure sensitive adhesive composition of the invention is preferably about 3 percent to about 25 percent by weight, more preferably about 3 percent to about 10 percent by weight based on the total weight of the adhesive composition.

When the skin penetration enhancer is a single ingredient, it is preferably a skin penetration enhancer such as isopropyl myristate, diisopropyl adipate, ethyl oleate, or glyceryl monolaurate.

When a combination skin penetration enhancer is used, it is preferably a combination such as: ethyl oleate with glyceryl monolaurate; ethyl oleate with N,N-dimethyldodecylamine-N-oxide; glyceryl monolaurate with N,N-dimethyldodecylamine-N-oxide; and ethyl oleate with both glyceryl monolaurate and N,N-dimethyldodecylamine-N-oxide.

A pressure-sensitive adhesive composition of the invention can be prepared by combining dry adhesive, 1-isobutyl-1H-imidazo[4,5-c]quinolin-4-amine, fatty acid, and skin penetration enhancer(s) with an organic solvent. The preferred organic solvents are methanol and ethyl acetate. The total solids content of the adhesive coating is preferably in the range of about 15 percent to about 40 percent, and more preferably in the range of about 20 to about 35 percent based on the total weight of the adhesive coating. The resulting mixture is shaken or mixed for a period of about 20 to 72 hours. When this method is used it is preferred that the 1-isobutyl-1H-imidazo[4,5-c]-quinolin-4-amine be in micronized form (i.e., particle size of 1-2 microns in diameter). Optionally, the mixture can be heated during shaking.

In a preferred method, the 1-isobutyl-1H-imidazo[4,5-c]-quinolin-4-amine or 1-(2-methylpropyl)-1H-imidazo[4,5-c] quinolin-4-amine is combined with the fatty acid and shaken at 40° C. until there appears to be complete dissolution. The remaining ingredients are added and the mixture is shaken for a period of about 20 to 72 hours.

The pressure-sensitive adhesive compositions described above are preferably coated onto one surface of a suitable backing of sheet material, such as a film, to form a pressure-sensitive adhesive coated sheet material. A pressure-sensitive adhesive coated sheet material of the invention can be prepared by knife coating a suitable release liner to a predetermined uniform thickness with a wet adhesive formulation. This adhesive coated release liner is then dried and laminated onto a backing using conventional methods. Suitable release liners include conventional release liners comprising a known sheet material, such as a polyester web, a polyethylene web, or a polystyrene web, or polyethylene-coated paper, coated with a suitable silicone-type coating such as that available under the trade designation Daubert 164Z, from Daubert Co. The backing can be occlusive, non-occlusive or a breathable film as desired. The backing can be any of the conventional materials for pressure-sensitive adhesive tapes, such as polyethylene, particularly low density polyethylene, linear low density polyethylene, high density polyethylene, randomly-oriented nylon fibers, polypropylene, ethylene-vinylacetate copolymer, polyurethane, rayon and the like. Backings that are layered, such as polyethylene-aluminum-polyethylene composites are also suitable. The backing should be substantially non-reactive with the ingredients of the adhesive coating. The presently preferred backing is low density polyethylene.

The pressure-sensitive adhesive coated sheet material of the invention can be made in the form of an article such as a tape, a patch, a sheet, a dressing or any other form known to those skilled in the art.

Preferably, an article in the form of a patch is made from an adhesive coated sheet material of the invention and applied to the skin of a mammal. The patch is replaced as necessary with a fresh patch to maintain the particular desired therapeutic effect of the 1-isobutyl-1H-imidazo[4,5-c]quinolin-4-amine.

The inherent viscosity values reported in the Examples below were obtained by the conventional method used by those skilled in the art. The measurement of the viscosity of dilute solutions of the adhesive, when compared to controls run under the same conditions, clearly demonstrates the relative molecular weights. It is the comparative values that are significant; absolute figures are not required. In the examples, the inherent viscosity values were obtained using a Cannon-Fenske #50 viscometer to measure the flow time of 10 ml of a polymer solution (0.2 g polymer/deciliter tetrahydrofuran, in a water bath controlled at 25° C.). The examples and the controls were run under identical conditions. The test procedure followed and the apparatus used are explained in detail in the Textbook of Polymer Science, F. W. Billmeyer, Wiley-Interscience, 2nd Edition, 1971 under: Polymer chains and their characterization, D. Solution Viscosity and Molecular Size, pp 84-85, the disclosure and textbook of which is incorporated by reference.

As indicated herein above, and in accordance with the present invention, the present invention contemplates bioequivalent or interchangeable lower dosage strength imiquimod formulations. By way of an example, bioequivalent or interchangeable 3.75% lower dosage strength imiquimod topical formulations, as contemplated by the present invention, include those 3.75% imiquimod formulations that have comparable in-vivo serum profiles, i.e., wherein the following in-vivo parameters are either the same or may vary up to about ±25% or more (See also FIG. 54), when such 3.75% formulations are topically administered daily to the same individuals in the same dosage regimen in accordance with the short durations of therapy, such as the two-cycle therapies, of the present invention:

(a) a Day 21 $T_{max}$ of from about 4 hours to about 16 hours and preferably a mean $T_{max}$ of about 7.4 hours with a standard deviation ("SD") of about 3.5, a median $T_{max}$ of about 9 hours and a geometric mean $T_{max}$ of about 6.6 hours and a coefficient of variation ("CV") of about 48%;

(b) a Day 21 $C_{max}$ of from about 0.07 to about 0.6 ng/ml and preferably a mean $C_{max}$ of about 0.3 ng/ml with a standard deviation of about 0.16, a median $C_{max}$ of about 0.35 and a geometric mean $C_{max}$ of about 0.27 ng/ml and a coefficient of variation of about 49%;

(c) a Day 21 $T_{1/2}$ of from about 9.7 to about 84 hours and preferably a mean $T_{1/2}$ of about 29.3 hours with a standard deviation of about 17, a median $T_{1/2}$ of about 25.6 hours and a geometric mean $T_{1/2}$ of about 26 hours and a coefficient of variation of about 58%;

(d) a Day 21 $AUC_{0-24}$ of from about 1.1 to about 12 nghr/ml and preferably a mean $AUC_{0-24}$ of about 6 nghr/ml with a standard deviation of about 3, a median $AUC_{0-24}$ of about 7 nghr/ml and a geometric mean $AUC_{0-24}$ of about 5 nghr/ml and a coefficient of variation of about 52%;

(e) a Day 21 $\lambda z$ of from about 0.008 $hr^{-1}$ to about 0.07 $hr^{-1}$ and preferably a mean $\lambda z$ of about 0.03 $hr^{-1}$ with a standard deviation of about 0.01, a median $\lambda z$ of about 25.6 $hr^{-1}$ and a geometric mean $\lambda z$ of about 0.03 $hr^{-1}$ and a coefficient of variation of about 49%;

(f) a Day 21 $C_{min}$ of from about 0.06 to about 0.4 and preferably a mean $C_{min}$ of about 0.20 with an SD of about 0.11, a median $C_{min}$ of about 0.19 and a geometric mean $C_{min}$ of about 0.17 and a coefficient of variation of about 55%;

(g) at Day 14/7 (a ratio of the trough concentration at Day 14 over the trough concentration at Day 7), a trough concentration geometric mean ratio of about 1.09 with a 90% confidence interval ("CI") within a range of between about 0.8 and about 1.5;

(h) at Day 21/14 (a ratio of the trough concentration at Day 21 over the trough concentration at Day 14), a trough concentration geometric mean ratio of about 1.33 with a 90% confidence interval ("CI") within a range of between about 0.9 and about 1.9;

(i) at Day 22/21 (a ratio of the trough concentration at Day 22 over the trough concentration at Day 21) a trough concentration geometric mean ratio of about 0.93 with a 90% confidence interval ("CI") within a range of between about 0.6 and about 1.3;

(j) a mean peak imiquimod serum concentration of about 0.323 ng/ml at Day 21;

(k) a Day 21 RAUC of from about 1 to about 7 and preferably a mean RAUC of about 4 with a standard deviation of about 2, a median RAUC of about 3.5 and a geometric mean RAUC of about 3.3 and a coefficient of variation of about 56%;

(l) a Day 21 $RC_{max}$ of from about 0.5 to about 5 and preferably a mean $RC_{max}$ of about 3 with a standard deviation of about 1.5, a median $RC_{max}$ of about 2.7 and a geometric mean $RC_{max}$ of about 2.4 and a coefficient of variation of about 54%;

(m) a Day 21 $L\lambda z_{eff}$ of from about 0.006 $hr^{-1}$ to about 0.08 $hr^{-1}$ and preferably a mean $L\lambda z_{eff}$ of about 0.02 $hr^{-1}$ with a standard deviation of about 0.02, a median $L\lambda z_{eff}$ of about 0.01 $hr^{-1}$ and a geometric mean $L\lambda z_{eff}$ of about 0.16 $hr^{-1}$ and a coefficient of variation of about 97%; and (n) a Day 21 $T^{1/2}{}_{eff}$ of from about 8 hr to about 110 hr and preferably a mean $T^{1/2}{}_{eff}$ of about 55 hr with a standard deviation of about 36, a median $T^{1/2}{}_{eff}$ of about 50 hr and a geometric mean $T^{1/2}{}_{eff}$ of about 42 $hr^{-1}$ and a coefficient of variation of about 66%.

While the lower dosage strength imiquimod pharmaceutical formulations of the present invention can be formulated into any form known to the art, such as a cream, an ointment, a foam, a gel, a lotion or a pressure-sensitive adhesive composition or patch, it should be understood that the creams, ointments, foams, gels and lotions may be packaged into any suitable container, such as unit-dose sachets or packets or multi-dose tubes or containers. A packaged amount of an imiquimod pharmaceutical formulation contemplated by the present invention includes any suitable amount, such as about 250 mg to about 500 mg or more, and preferably about 250 mg, about 300 mg, about 350 mg, about 400 mg, about 450 mg or about 500 mg unit-dose sachets or packets.

Examples of various embodiments of the present invention will now be further illustrated with reference to the following examples. Thus, the following examples are provided to illustrate the invention, but are not intended to be limiting thereof. Parts and percentages are by weight unless otherwise specified. Examples of creams, ointments and pressure sensitive adhesive compositions contemplated by the present invention are described in U.S. Pat. Nos. 4,689,338 and 5,238,944, which are incorporated herein by reference in their entireties. Percent modifications for, e.g., imiquimod and vehicle, to generate imiquimod formulations as described herein are likewise contemplated by the present invention. In addition, the formulations described and disclosed in U.S. Patent Publication No. 2007/0123558, Ser. No. 11/276,324, U.S. Patent Publication No. 2007/0264317, Ser. No. 433,471, and US2007/0900550, Publication No. WO2008098232 (A1), are also contemplated by the present invention and are incorporated herein by reference in their entireties.

Preparative Method 1

Laboratory Scale Preparation of Isooctylacrylate/Acrylamide Copolymer

To a 114 gram narrow-mouth glass bottle were added: 18.6 g isooctyl acrylate, 1.4 g acrylamide, 0.04 g benzoyl peroxide, 27.0 g ethyl acetate and 3.0 g methanol. The solution was purged for thirty five seconds with nitrogen at a flow rate of one liter per minute. The bottle was sealed and placed in a rotating water bath at 55° C. for twenty-four hours to effect essentially complete polymerization. The polymer was diluted with ethyl acetate/methanol (90/10) to 23.2 percent solids and had a measured inherent viscosity of 1.26 dl/g in ethyl acetate.

Preparative Method 2

Pilot Plant Scale Preparation of Isooctylacrylate/Acrylamide Copolymer 155 kg isooctylacrylate, 11.6 kg acrylamide, 209.1 kg ethyl acetate and 23.2 kg methanol were charged to a clean, dry reactor. Medium agitation was applied. The batch was deoxygenated with nitrogen while heating to an induction temperature of 55° C. 114 g Lucidol™ 70 initiator (available from Pennwalt Corp.) mixed with 2.3 kg ethyl acetate was charged to the reactor. The temperature was maintained at 55° C. throughout the reaction. After 5.5 hours reaction time, 114 g Lucidol™ 70 mixed with 2.3 kg ethyl acetate were charged to the reactor. After 9.0 hours reaction time, an additional 114 g Lucidol™ 70 initiator mixed with 2.3 kg ethyl acetate were charged to the reactor. The reaction was continued until the percent conversion was greater than 98 percent as measured by gas chromatographic evaluation of residual monomer concentration. The resulting polymer solution was diluted to 25-28 percent solids with ethyl acetate/methanol (90/10) and had a measured Brookfield viscosity of 17,000-21,000 centipoises using spindle #4 at 12 rpm. The polymer had a measured inherent viscosity of 1.3-1.4 dllg in ethyl acetate.

The above-mentioned procedure was found to provide a pressure-sensitive adhesive that is equivalent in the practice of the present invention to a pressure-sensitive adhesive prepared according to Preparative Method 1.

A 25-30 percent solids solution of the isooctyl acrylate: acrylamide (93:7) adhesive copolymer in ethyl acetate/methanol (90:10) was coated onto a two-sided release liner using a knife-coater and coating at 0.5 mm in thickness. The adhesive-coated laminate was dried first at 82° C. for 3 minutes and then at 116° C. for 3 minutes. The dried adhesive coating was then stripped off the release liner and placed in a glass bottle. The foregoing procedure results in a reduction of the amount of any residual monomer in the adhesive copolymer.

Preparative Method 3

Preparation of Isooctyl Acrylate:Acrylamide:Vinyl Acetate (75:5:20) Copolymer

The procedure of Preparative Method 1 above acrylate, 8.0 g acrylamide, 32.0 g vinyl acetate, 0.32 g benzoyl peroxide, 216.0 g ethyl acetate and 24.0 g methyl alcohol. The resulting polymer was diluted with the ethyl acetate/methyl alcohol mixture to 21.52% solids. The adhesive polymer had a measured inherent viscosity of 1.40 dl/g in ethyl acetate at a concentration of 0.15 g/dl. Its Brookfield viscosity was 2,300 centipoise.

Preparative Method 4

Preparation of Isooctyl Acrylate Acrylamide:Vinyl Acetate (75:5:20) Copolymer

A master batch was prepared by combining 621.0 g of isooctyl acrylate, 41.4 g of acrylamide, 165.6 g of vinyl acetate, 1.656 g of 2,2'-azobis(2,4-dimethylpentanenitrile) (available from the DuPont Company as Vazo™52), 884.52 g of ethyl acetate and 87.48 g of methanol. A 400 g portion of the resulting solution was placed in an amber quart bottle. The bottle was purged for two minutes with nitrogen at a flow rate of one liter per minute. The bottle was sealed and placed in a rotating water bath at 45° C. for twenty-four hours to effect essentially complete polymerization. The copolymer was diluted with 250 g of ethyl acetate/methanol (90/10) to 26.05% solids and had a measured inherent viscosity of 1.27 dl/g in ethyl acetate at a concentration of 0.15 g/dl. Its Brookfield viscosity was 5580 centipoise.

Example 1

A cream according to the present invention is prepared from the following ingredients:

| | % by Weight | Amount |
|---|---|---|
| Oil Phase | | |
| 1-isobutyl-1H-imidazo[4,5-c]-quinolin-4-amine | 1.0 | 40.0 g |
| Isostearic acid | 10.0 | 400.0 g |
| Benzyl alcohol | 2.0 | 80.0 g |
| Cetyl alcohol | 2.2 | 88.0 g |
| Stearyl alcohol | 3.1 | 124.0 g |
| Polysorbate 60 | 2.55 | 102.0 g |
| Sorbitan monostearate | 0.45 | 18.0 g |
| Aqueous Phase | | |
| Glycerin | 2.0 | 80.0 g |
| Methylparaben | 0.2 | 8.0 g |
| Propylparaben | 0.02 | 0.8 g |
| Purified water | 76.48 | 3059.2 g |

The materials listed above were combined according to the following procedure:

The glycerin, methylparaben, propylparaben and water were weighed into a 4 liter glass beaker then heated on a hot plate with stirring until the parabens isostearic acid and 1-isobutyl-1H-imidazo[4,5-c]-quinolin-4-amine were weighed into an 8 liter stainless steel beaker and heated on a hot plate until the amine was in solution (the temperature reached 69° C.). The benzyl alcohol, cetyl alcohol, stearyl alcohol, polysorbate 60 and sorbitan monostearate were added to the isostearic acid solution and heated on a hot plate until all material was dissolved (the temperature reached 75° C.). With both phases at approximately the same temperature (65°-75° C.), the water phase was added to the oil phase. The mixture was mixed with a homogenizer for 13 minutes then put into a cool water bath and mixed with a 3 inch propeller for 40 minutes (the temperature was 29° C.). The resulting cream was placed in glass jars.

Examples 2-9

Using the general method of Example 1, the cream formulations shown in Tables 1 and 2 are prepared.

TABLE 1

| | % by Weight | | | |
|---|---|---|---|---|
| | Example 2 | Example 3 | Example 4 | Example 5 |
| Oil Phase | | | | |
| 1-isobutyl-1H-imidazo-[4,5-c]quinolin-4-amine | 1.0 | 1.0 | 1.0 | 1.0 |
| Isostearic acid | 10.0 | 10.0 | 5.0 | 5.0 |
| Benzyl alcohol | | 2.0 | | |
| Cetyl alcohol | | 1.7 | | |
| Stearyl alcohol | | 2.3 | | |
| Cetearyl alcohol | 6.0 | | 6.0 | 6.0 |
| Polysorbate 60 | 2.55 | 2.55 | 2.55 | 2.55 |
| Sorbitan monostearate | 0.45 | 0.45 | 0.45 | 0.45 |
| Brij ™ 30[a] | | | | 10.0 |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 77.78 | 77.78 | 82.78 | 72.78 |

[a]Brij ™ 30 (polyoxyethylene(4) lauryl ether) is available from ICI Americas, Inc.

TABLE 2

| | % by Weight | | | |
|---|---|---|---|---|
| | Example 6 | Example 7 | Example 8 | Example 9 |
| Oil Phase | | | | |
| 1-isobutyl-1H-imidazo-[4,5-c]quinolin-4-amine | 1.0 | 1.0 | 1.0 | 1.0 |
| Isostearic acid | 10.0 | 25.0 | 10.0 | 6.0 |
| Benzyl alcohol | | 2.0 | | 2.0 |
| Cetyl alcohol | | 2.2 | 1.7 | |
| Stearyl alcohol | | 3.1 | 2.3 | |
| Cetearyl alcohol | 6.0 | | | 6.0 |
| Polysorbate 60 | 2.55 | 3.4 | 2.55 | 2.55 |
| Sorbitan monostearate | 0.45 | 0.6 | 0.45 | 0.45 |
| Brij ™ 30[a] | 10.0 | | | |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 67.78 | 60.48 | 79.78 | 79.78 |

[a]Brij ™ 30 (polyoxyethylene(4) lauryl ether) is available from ICI Americas, Inc.

Example 10

A cream according to the present invention is prepared from the following ingredients in the following Table 3:

TABLE 3

| | % by Weight | Amount |
|---|---|---|
| Oil Phase | | |
| 1-isobutyl-1H-imidazo[4,5-c]quinolin-4-amine | 1.0 | 3.00 g |
| Isostearic acid | 5.0 | 15.0 g |
| White petrolatum | 15.0 | 45.0 g |
| Light mineral oil | 12.8 | 38.4 g |

TABLE 3-continued

| | % by Weight | Amount |
|---|---|---|
| Aluminum stearate | 8.0 | 24.0 g |
| Cetyl alcohol | 4.0 | 12.0 g |
| Witconol ™ 14[a] | 3.0 | 9.00 g |
| Acetylated lanolin | 1.0 | 3.0 g |
| Propylparaben | 0.063 | 0.19 g |
| Aqueous Phase | | |
| Veegum ™ K[b] | 1.0 | 3.0 g |
| Methylparaben | 0.12 | 0.36 g |
| Purified water | 49.017 | 147.05 g |

[a]Witconol ™ 14 (polyglyceryl4 oleate) is available from Witco Chemical Corp. Organics Division
[b]Veegum ™ K (colloidal magnesium aluminum silicate) is available from R. T. Vanderbilt Company Inc.

The materials listed above were combined according to the following procedure:

The 1-isobutyl-1H-imidazo[4,5-c]quinolin-4-amine and the isostearic acid were weighed into a glass jar and heated with occasional stirring until the amine was dissolved (the temperature reached 68° C.). To this solution was added, the petrolatum, mineral oil, aluminum stearate, cetyl alcohol, Witconol™ 14, acetylated lanoline and propylparaben. The mixture was heated to 75° C. In a separate beaker, the methylparaben and water were combined and heated until the paraben dissolved (the temperature reached 61° C.). The Veegum™ K was added to the aqueous solution and heated at 75° C. for 30 minutes while mixing with a homogenizer. With both phases at 75° C., the aqueous phase was slowly added to the oil phase while mixing with a homogenizer. Mixing was continued for 30 minutes while maintaining a temperature to about 80° C. The jar was then capped and the formulation was allowed to cool.

Example 11

An ointment according to the present invention is prepared from the ingredients in the following Table 4:

TABLE 4

| | % by Weight | Amount |
|---|---|---|
| 1-isobutyl-1H-imidazo[4,5-c]quinolin-4-amine | 1.0 | 0.20 g |
| Isostearic acid | 5.0 | 1.00 g |
| Mineral oil | 12.8 | 2.56 g |
| White petrolatum | 65.2 | 13.04 g |
| Cetyl alcohol | 4.0 | 0.80 g |
| Acetylated lanolin | 1.0 | 0.20 g |
| Witconol ™ | 143.0 | 0.60 g |
| Aluminum stearate | 8.0 | 1.60 g |

The materials listed above are combined according to the following procedure:

The 1-isobutyl-1H-imidazo[4,5-c]quinolin-4-amine and the isostearic acid were placed in a glass jar and heated with stirring until the amine was dissolved. The remaining ingredients were added and the resulting mixture was heated to 65° C. and then mixed while being allowed to cool to room temperature.

Example 12

Using the general procedure of Example 11 an ointment containing the ingredients in the following Table 5 is prepared.

TABLE 5

| | % by Weight | Amount |
|---|---|---|
| 1-Tsobutyl-1H-imidazo[4,5-c]quinolin-4-amine | 1.0 | 0.20 g |
| Isostearic acid | 6.0 | 1.20 g |
| Polyethylene Glycol 400 | 55.8 | 11.16 g |
| Polyethylene Glycol 3350 | 32.6 | 6.52 g |
| Stearyl alcohol | 4.6 | 0.92 g |

Examples 13-15

Creams of the present invention are prepared using the ingredients shown in Table 6. The Example 1 except that benzyl alcohol was used with the isostearic acid to dissolve the 1-isobutyl-1H-imidazo [4,5-c] quinolin-4-amine.

TABLE 6

| | Example 13 Amount % by Weight | Example 14 Amount % by Weight | Example 15 Amount % by Weight |
|---|---|---|---|
| Oil Phase | | | |
| 1-isobutyl-1H-imidazo[4,5-c]quinolin-4-amine | 50 | 5.0 | 4.85 |
| Isostearic acid | 25.0 | 25.0 | 24.3 |
| Benzyl alcohol | 2.0 | 2.0 | 1.94 |
| Cetyl alcohol | 2.2 | 2.2 | 1.16 |
| Stearyl alcohol | 3.1 | 3.1 | 1.75 |
| Petrolatum | 3.0 | | 2.91 |
| Polysorbate 60 | 3.4 | 3.4 | 4.13 |
| Sorbitan monostearate | 0.6 | 0.6 | 0.73 |
| Stearic acid | | | 9.71 |
| Aqueous Phase | | | |
| Glycerin | 2.0 | 2.0 | 1.94 |
| Methylparaben | 0.2 | 0.2 | 0.19 |
| Propylparaben | 0.02 | 0.02 | 0.02 |

Example 16

A cream according to the present invention is prepared from the ingredients in the following Table 7:

TABLE 7

| | % by Weight Amount | % by Weight Amount |
|---|---|---|
| Oil Phase | | |
| 1-isobutyl-1H-imidazo[4,5-c]quinolin-4-amine | 4.0 | 0.80 g |
| Isostearic acid | 20.0 | 4.00 g |
| Benzyl alcohol | 2.0 | 0.40 g |
| Cetyl alcohol | 2.2 | 0.49 g |
| Stearyl alcohol | 3.1 | 0.62 g |
| Polysorbate 60 | 3.4 | 0.68 g |
| Sorbitan monostearate | 0.6 | 0.12 g |
| Aqueous Phase | | |
| 1-isobutyl-1H-imidazo [4,5-c]quinolin-4-amine | 1.0 | 0.2 g |
| Glycerin | 2.0 | 0.4 g |
| 85% Lactic acid | 1.0 | 0.22 g |
| Methylparaben | 0.2 | 0.04 g |
| Propylparaben | 0.02 | 0.004 g |
| Purified water | 60.48 | 12.0 g |

The materials listed above are combined according to the following procedure:

The isostearic acid and 0.8 g of 1-isobutyl-1H-imidazo [4,5-c]quinolin-4-amine or 1-(2-methylpropyl)-1H-imidazo [4,5-c]quinolin-4-amine were combined in a glass jar and heated with stirring until the amine had dissolved. The remaining oil phase ingredients were added to this solution and the mixture was heated to about 70° C. The aqueous phase ingredients were weighed into a separate beaker and heated with stirring until the amine and the parabens had dissolved. With both phases at about 70° C., the water phase was added to the oil phase and mixed with a propeller until the mixture cooled to room temperature.

Example 17

A mixture of 5.9415 g of the 93:7 isooctyl acrylate: acrylamide adhesive copolymer prepared in PREPARATIVE METHOD 2 above, 1.5126 g isostearic acid, 2.0075 g ethyl oleate, 0.3021 g glyceryl monolaurate, 0.2936 1-isobutyl-1H-imidazo[4,5-c]quinolin-4-amine (micronized) and 23.7 g of 90:10 ethyl acetate: methanol was placed in a small glass jar. The jar was placed on a horizontal shaker and shaken at room temperature for about 13 hours. The formulation was coated at a thickness of 20 mils onto a 5 mil Daubert 164Z liner. The laminate was oven dried for 3 minutes at 105° F., for 2 minutes at 185° F., and for 2 minutes at 210° F. The resulting adhesive coating contained 59.1 percent 93:7 isooctyl acrylate:acylamide adhesive copolymer, 15.0 percent isostearic acid, 20.0 percent ethyl oleate, 3.0 percent glyceryl monolaurate and 2.9 percent 1-isobutyl-1H-imidazo[4,5-c]quinolin-4-amine. The material was then laminated with 3 mil low density polyethylene backing and die cut into 2.056 cm.sup.2 patches.

Examples 18-20

Pressure-Sensitive Adhesive Coated Sheet Materials Prepared Using Unmicronized 1-isobutyl-1H-imidazo[4,5-c]quinolin-4-amine Using the general method of Example 17 the formulations shown below are prepared. 1-Isobutyl-1H-imidazo[4,5-c] quinolin-4-amine or 1-(2-methylpropyl)-1H-imidazo [4,5-c] quinolin-4-amine that had been ground with a mortar and pestle was used. The adhesive was the 93:7 isooctyl acrylate: acrylamide copolymer prepared in Preparative Method 1 above. The solvent was 90:10 ethyl acetate:methanol. All formulations in the following Table 8 were mixed at room temperature.

TABLE 8

| | Example 18 | Example 19 | Example 20 |
|---|---|---|---|
| 1-isobutyl-1H-imidazo[4,5-c]quinolin-4-amine | 5.0 | 3.0 | 3.0 |
| Ethyl oleate | 5.1 | 5.0 | 8.0 |
| Isostearic acid | 10.0 | 10.0 | 6.0 |
| Oleic acid | 20.0 | 20.0 | 13.0 |
| Glyceryl monolaurate | 1.5 | 1.5 | 1.5 |
| N,N-dimethyldodecylamine-N-oxide Adhesive | 1.0<br>57.4 | 1.1<br>59.3 | 3.0<br>65.4 |

Example 21

A formulation with the same components in the same proportions as Example 18 is prepared using a different method. The 1-isobutyl-1H-imidazo[4,5-c]-quinolin-4-amine or 1-(2-methylpropyl)-1H-imidazo[4,5-c]quinolin-4-amine was combined with the oleic and isostearic acids and shaken at 40° C. until there was complete dissolution of the 1-isobutyl-1H-imidazo-[4,5-c]quinolin-4-amine or 1-(2-methylpropyl)-1H-imidazo[4,5-c]quinolin-4-amine. The remaining ingredients were added and shaken a 40° C. for 72 hours. Patches measuring 2.056 cm.sup.2 were prepared by the general method of Example 17.

Example 22

A mixture of 2.4734 g 1-isobutyl-1H-imidazo[4,5-c]-quinolin-4-amine or 1-(2-methylpropyl)-1H-imidazo[4,5-c] quinolin-4-amine, 3.3315 g isostearic acid and 6.6763 g oleic acid is prepared. To 1.8738 g of the above mixture was added 2.8750 g of the 93:7 isooctyl acrylate:acryamide adhesive copolymer prepared in Preparative Method 2 above, 0.2548 g of ethyl oleate, 0.0510 g N,N-dimethyldodecylamine-N-oxide, 0.0820 g glyceryl monolaurate (from Lauricidin, Inc.) and 14.0457 g of 90:10 ethyl acetate/ methanol. The above was shaken for 30 hours at room temperature on a horizontal shaker. Transdermal patches were then prepared generally according to the procedures of Example 17.

Example 23

Topical Imiquimod Pharmaceutical Cream Formulations

Creams are prepared in accordance with the present invention using the ingredients shown in this Example 23.

The materials listed below in this Example 23 are combined according to the following procedure to make cream formulations in the following Table 9 of this Example 23:

TABLE 9

Lower Dosage Strength Imiquimod Formulations

| | % w/w | % w/w | % w/w | % w/w | % w/w | % w/w |
|---|---|---|---|---|---|---|
| | Formulation | | | | | |
| Excipients | 1 | 2 | 3 | 4 | 5 | 6 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.98 | 66.98 | 64.98 | 61.98 | 60.73 | 60.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |
| | % w/w | % w/w | % w/w | % w/w | % w/w | % w/w |
| | Formulation | | | | | |
| Excipients | 7 | 8 | 9 | 10 | 11 | 12 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |

TABLE 9-continued

Lower Dosage Strength Imiquimod Formulations

| | | | | | | |
|---|---|---|---|---|---|---|
| Xanthan gum | 0.50 | 0.50 | 0.50 | 0.50 | 0.50 | 0.50 |
| Purified water | 66.98 | 60.98 | 60.98 | 57.08 | 58.98 | 55.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 13 | 14 | 15 | 16 | 17 | 18 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.48 | 67.08 | 59.98 | 58.98 | 56.98 | 61.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 19 | 20 | 21 | 22 | 23 | 24 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.73 | 66.73 | 64.73 | 61.73 | 60.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 25 | 26 | 27 | 28 | 29 | 30 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.73 | 60.73 | 60.73 | 56.83 | 58.73 | 55.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

TABLE 9-continued

Lower Dosage Strength Imiquimod Formulations

| | % w/w | % w/w | % w/w | % w/w | % w/w | % w/w |
|---|---|---|---|---|---|---|
| | Formulation | | | | | |
| Excipients | 31 | 32 | 33 | 34 | 35 | 36 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.23 | 66.83 | 59.73 | 58.73 | 56.73 | 61.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 37 | 38 | 39 | 40 | 41 | 42 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.48 | 66.48 | 64.48 | 61.48 | 60.23 | 60.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 43 | 44 | 45 | 46 | 47 | 48 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.48 | 60.48 | 60.48 | 56.58 | 58.48 | 55.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 49 | 50 | 51 | 52 | 53 | 54 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |

TABLE 9-continued

Lower Dosage Strength Imiquimod Formulations

| | | | | | | |
|---|---|---|---|---|---|---|
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.98 | 66.58 | 59.48 | 58.48 | 56.48 | 61.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| | % w/w Formulation | % w/w | % w/w | % w/w | % w/w | % w/w |
|---|---|---|---|---|---|---|
| Excipients | 55 | 56 | 57 | 58 | 59 | 60 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.23 | 66.23 | 64.23 | 61.23 | 59.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| | % w/w Formulation | % w/w | % w/w | % w/w | % w/w | % w/w |
|---|---|---|---|---|---|---|
| Excipients | 61 | 62 | 63 | 64 | 65 | 66 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 6.00 | 6.00 | 3.00 | 5.00 | 3.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.23 | 60.23 | 60.23 | 56.33 | 58.23 | 55.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| | % w/w Formulation | % w/w | % w/w | % w/w | % w/w | % w/w |
|---|---|---|---|---|---|---|
| Excipients | 67 | 68 | 69 | 70 | 71 | 72 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.73 | 66.33 | 59.23 | 58.23 | 56.23 | 61.23 |
| Benzyl alcohol | 2.00 | 2.00 | 2.00 | 2.00 | 2.00 | 2.00 |

TABLE 9-continued

Lower Dosage Strength Imiquimod Formulations

| | | | | | | |
|---|---|---|---|---|---|---|
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| | % w/w Formulation | % w/w | % w/w | % w/w | % w/w | % w/w |
|---|---|---|---|---|---|---|
| Excipients | 73 | 74 | 75 | 76 | 77 | 78 |
| Fatty acid* | 10.00 | 12.50 | 25.00 | 10.00 | 15.00 | 20.00 |
| Cetyl alcohol | 2.20 | 2.20 | 2.70 | 4.00 | 4.00 | 2.20 |
| Stearyl alcohol | 3.10 | 3.10 | 3.80 | 2.00 | 2.00 | 3.10 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.00 |
| Sorbitan Monostearate | 0.60 | 0.60 | 0.60 | 1.00 | 1.00 | 1.00 |
| Glycerin | 5.00 | 5.00 | 2.00 | 1.00 | 0.70 | 0.75 |
| Xantham gum | 0.50 | 0.50 | 0.50 | 0.30 | 0.70 | 0.75 |
| Purified water | 65.98 | 63.48 | 54.78 | 70.28 | 64.28 | 59.73 |
| Benyzl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| | % w/w Formulation | % w/w | % w/w | % w/w | % w/w | % w/w |
|---|---|---|---|---|---|---|
| Excipients | 79 | 80 | 81 | 82 | 83 | 84 |
| Fatty acid* | 10.00 | 12.50 | 25.00 | 10.00 | 15.00 | 25.00 |
| Cetyl alcohol | 2.20 | 2.20 | 2.70 | 4.00 | 4.00 | 2.70 |
| Stearyl alcohol | 3.10 | 3.10 | 3.80 | 2.00 | 2.00 | 3.80 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.40 |
| Sorbitan Monostearate | 0.60 | 0.60 | 0.60 | 1.00 | 1.00 | 0.60 |
| Glycerin | 5.00 | 5.00 | 2.00 | 1.00 | 3.00 | 2.00 |
| Xanthan gum | 0.50 | 0.50 | 0.50 | 0.30 | 0.70 | 0.50 |
| Purified water | 65.98 | 63.48 | 54.78 | 70.28 | 64.28 | 54.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| | % w/w Formulation | % w/w | % w/w | % w/w | % w/w | % w/w |
|---|---|---|---|---|---|---|
| Excipients | 85 | 86 | 87 | 88 | 89 | 90 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.48 | 66.08 | 58.98 | 57.98 | 55.98 | 60.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

TABLE 9-continued

Lower Dosage Strength Imiquimod Formulations

| | % w/w | % w/w | % w/w | % w/w | % w/w | % w/w |
|---|---|---|---|---|---|---|
| | Formulation | | | | | |
| Excipients | 91 | 92 | 93 | 94 | 95 | 96 |
| Fatty acid* | 15.00 | 12.50 | 25.00 | 15.00 | 10.00 | 20.00 |
| Cetyl alcohol | 2.20 | 2.20 | 2.20 | 2.00 | 2.00 | 2.20 |
| Stearyl alcohol | 3.10 | 3.10 | 3.10 | 2.00 | 2.40 | 3.10 |
| White petrolatum | 5.00 | 3.00 | 3.40 | 2.80 | 3.00 | 6.00 |
| Polysorbate 60 | 3.00 | 3.00 | 3.40 | 3.80 | 3.80 | 3.00 |
| Sorbitan Monostearate | 1.00 | 1.00 | 0.60 | 0.20 | 1.00 | 1.00 |
| Glycerin | 5.00 | 5.00 | 2.00 | 3.00 | 3.00 | 3.00 |
| Xanthan gum | 1.00 | 0.50 | 1.00 | 0.30 | 0.30 | 0.75 |
| Purified water | 60.23 | 63.23 | 55.23 | 66.83 | 70.23 | 59.48 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 97 | 98 | 99 | 100 | 101 | 102 |
| Fatty acid* | 15.00 | 12.50 | 25.00 | 15.00 | 10.00 | 25.00 |
| Cetyl alcohol | 2.20 | 2.20 | 2.20 | 2.00 | 2.00 | 2.70 |
| Stearyl alcohol | 3.10 | 3.10 | 3.10 | 2.00 | 2.40 | 3.80 |
| White petrolatum | 5.00 | 3.00 | 3.40 | 2.80 | 3.00 | 6.00 |
| Polysorbate 60 | 3.00 | 3.00 | 3.40 | 3.80 | 3.80 | 3.40 |
| Sorbitan Monostearate | 1.00 | 1.00 | 0.60 | 0.20 | 1.00 | 0.60 |
| Glycerin | 5.00 | 5.00 | 2.00 | 3.00 | 3.00 | 2.00 |
| Xanthan gum | 1.00 | 0.50 | 1.00 | 0.30 | 0.30 | 0.50 |
| Purified water | 60.23 | 63.23 | 55.23 | 66.83 | 70.23 | 54.53 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 103 | 104 | 105 | 106 | 107 | 108 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.23 | 65.83 | 58.73 | 57.73 | 55.73 | 60.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 109 | 110 | 111 | 112 | 113 | 114 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 3.00 | 2.00 | 3.00 | 6.00 | 3.00 | 2.50 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.98 | 65.48 | 63.48 | 60.48 | 59.23 | 59.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 115 | 116 | 117 | 118 | 119 | 120 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 6.00 | 6.00 | 3.00 | 5.00 | 3.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 65.48 | 59.48 | 59.48 | 55.58 | 57.48 | 54.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 121 | 122 | 123 | 124 | 125 | 126 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.98 | 65.58 | 58.48 | 57.48 | 55.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 127 | 128 | 129 | 130 | 131 | 132 |
| Fatty acid* | 15.00 | 18.00 | 15.00 | 20.00 | 12.50 | 20.00 |
| Cetyl alcohol | 2.00 | 2.00 | 2.00 | 2.00 | 2.20 | 2.20 |
| Stearyl alcohol | 2.00 | 2.00 | 2.40 | 2.40 | 3.10 | 3.10 |
| White petrolatum | 2.80 | 3.40 | 2.80 | 5.00 | 3.00 | 3.40 |
| Polysorbate 60 | 3.00 | 3.80 | 3.00 | 3.00 | 3.40 | 3.00 |
| Sorbitan Monostearate | 1.00 | 1.00 | 0.20 | 0.20 | 0.60 | 1.00 |
| Glycerin | 3.00 | 2.00 | 1.00 | 3.00 | 6.00 | 3.00 |
| Xanthan gum | 0.30 | 0.70 | 0.70 | 0.30 | 0.50 | 0.75 |
| Purified water | 65.08 | 62.48 | 67.08 | 61.08 | 61.48 | 58.73 |
| Benzyl alcohol | 2.00 | 2.00 | 2.00 | 2.00 | 2.00 | 2.00 |

TABLE 9-continued

Lower Dosage Strength Imiquimod Formulations

| | | | | | | |
|---|---|---|---|---|---|---|
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 133 | 134 | 135 | 136 | 137 | 138 |
| Fatty acid* | 15.00 | 18.00 | 15.00 | 20.00 | 12.50 | 25.00 |
| Cetyl alcohol | 2.00 | 2.00 | 2.00 | 2.00 | 2.20 | 2.70 |
| Stearyl alcohol | 2.00 | 2.00 | 2.40 | 2.40 | 3.10 | 3.80 |
| White petrolatum | 2.80 | 3.40 | 2.80 | 5.00 | 3.00 | 3.40 |
| Polysorbate 60 | 3.00 | 3.80 | 3.00 | 3.00 | 3.40 | 3.40 |
| Sorbitan Monostearate | 1.00 | 1.00 | 0.20 | 0.20 | 0.60 | 0.60 |
| Glycerin | 3.00 | 2.00 | 1.00 | 3.00 | 6.00 | 2.00 |
| Xanthan gum | 0.30 | 0.70 | 0.70 | 0.30 | 0.50 | 0.50 |
| Purified water | 65.08 | 62.48 | 67.08 | 61.08 | 61.48 | 53.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 139 | 140 | 141 | 142 | 143 | 144 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.48 | 65.08 | 57.98 | 56.98 | 54.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 145 | 146 | 147 | 148 | 149 | 150 |
| Fatty acid* | 15.00 | 20.00 | 15.00 | 20.00 | 10.00 | 0.00 |
| Cetyl alcohol | 2.00 | 2.00 | 4.00 | 4.00 | 2.20 | 2.20 |
| Stearyl alcohol | 2.00 | 2.40 | 2.40 | 2.40 | 3.10 | 3.10 |
| White petrolatum | 2.80 | 2.50 | 3.40 | 5.00 | 3.00 | 3.40 |
| Polysorbate 60 | 3.00 | 3.00 | 3.00 | 3.80 | 3.40 | 3.00 |
| Sorbitan Monostearate | 1.00 | 0.20 | 1.00 | 1.00 | 0.60 | 1.00 |
| Glycerin | 3.00 | 3.00 | 1.00 | 3.00 | 5.00 | 3.00 |
| Xanthan gum | 0.30 | 0.30 | 0.30 | 0.70 | 0.50 | 0.75 |
| Purified water | 64.83 | 60.83 | 65.33 | 57.23 | 64.73 | 58.48 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

TABLE 9-continued

Lower Dosage Strength Imiquimod Formulations

| | % w/w | % w/w | % w/w | % w/w | % w/w | % w/w |
|---|---|---|---|---|---|---|
| | Formulation | | | | | |
| Excipients | 151 | 152 | 153 | 154 | 155 | 156 |
| Fatty acid* | 15.00 | 20.00 | 15.00 | 20.00 | 10.00 | 25.00 |
| Cetyl alcohol | 2.00 | 2.00 | 4.00 | 4.00 | 2.20 | 2.70 |
| Stearyl alcohol | 2.00 | 2.40 | 2.40 | 2.40 | 3.10 | 3.80 |
| White petrolatum | 2.80 | 2.50 | 3.40 | 5.00 | 3.00 | 3.40 |
| Polysorbate 60 | 3.00 | 3.00 | 3.00 | 3.80 | 3.40 | 3.40 |
| Sorbitan Monostearate | 1.00 | 0.20 | 1.00 | 1.00 | 0.60 | 0.60 |
| Glycerin | 3.00 | 3.00 | 1.00 | 3.00 | 5.00 | 2.00 |
| Xanthan gum | 0.30 | 0.30 | 0.30 | 0.70 | 0.50 | 0.50 |
| Purified water | 64.83 | 60.83 | 65.33 | 57.23 | 64.73 | 53.53 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 157 | 158 | 159 | 160 | 161 | 162 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.40 | 5.00 | 3.00 | 5.00 | 3.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.23 | 64.83 | 59.98 | 56.73 | 54.73 | 59.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 163 | 164 | 165 | 166 | 167 | 168 |
| Fatty acid* | 15.00 | 10.00 | 12.50 | 19.00 | 20.00 | 20.00 |
| Cetyl alcohol | 2.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 5.00 | 5.00 | 3.00 | 3.00 | 3.00 | 3.40 |
| Polysorbate 60 | 3.00 | 3.40 | 4.00 | 3.40 | 3.40 | 3.00 |
| Sorbitan Monostearate | 0.20 | 0.60 | 0.60 | 0.60 | 0.60 | 1.00 |
| Glycerin | 1.00 | 4.00 | 5.00 | 2.00 | 6.00 | 3.00 |
| Xanthan gum | 0.70 | 0.50 | 0.50 | 0.50 | 0.50 | 0.75 |
| Purified water | 66.58 | 65.48 | 61.38 | 60.48 | 56.48 | 58.23 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 169 | 170 | 171 | 172 | 173 | 174 |
| Fatty acid* | 15.00 | 10.00 | 12.50 | 19.00 | 20.00 | 25.00 |
| Cetyl alcohol | 2.00 | 2.20 | 2.20 | 2.20 | 2.20 | 2.70 |
| Stearyl alcohol | 2.40 | 3.10 | 3.10 | 3.10 | 3.10 | 3.80 |

TABLE 9-continued

Lower Dosage Strength Imiquimod Formulations

| | | | | | | |
|---|---|---|---|---|---|---|
| White petrolatum | 3.40 | 5.00 | 5.00 | 3.00 | 3.00 | 3.00 |
| Polysorbate 60 | 3.00 | 3.40 | 4.00 | 3.40 | 3.40 | 3.40 |
| Sorbitan Monostearate | 0.20 | 0.60 | 0.60 | 0.60 | 0.60 | 0.60 |
| Glycerin | 1.00 | 4.00 | 5.00 | 2.00 | 6.00 | 2.00 |
| Xanthan gum | 0.70 | 0.50 | 0.50 | 0.50 | 0.50 | 0.50 |
| Purified water | 66.58 | 65.48 | 61.38 | 60.48 | 56.48 | 53.28 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 175 | 176 | 177 | 178 | 179 | 180 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.98 | 64.58 | 57.48 | 56.48 | 54.48 | 59.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 181 | 182 | 183 | 184 | 185 | 186 |
| Fatty acid* | 20.00 | 20.00 | 25.00 | 18.75 | 20.00 | 21.25 |
| Cetyl alcohol | 4.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 2.80 | 3.00 | 3.00 | 5.00 | 5.00 | 3.75 |
| Polysorbate 60 | 3.00 | 3.40 | 3.40 | 3.00 | 3.40 | 3.40 |
| Sorbitan Monostearate | 1.00 | 0.60 | 0.60 | 1.00 | 0.60 | 0.60 |
| Glycerin | 1.00 | 2.00 | 2.00 | 5.00 | 5.00 | 5.00 |
| Xanthan gum | 0.30 | 0.50 | 0.50 | 0.50 | 0.50 | 0.50 |
| Purified water | 64.53 | 59.23 | 54.23 | 55.48 | 54.23 | 54.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 187 | 188 | 189 | 190 | 191 | 192 |
| Fatty acid* | 20.00 | 20.00 | 20.00 | 25.00 | 18.75 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 59.23 | 53.23 | 53.23 | 54.33 | 55.48 | 53.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 193 | 194 | 195 | 196 | 197 | 198 |
| Fatty acid* | 25.00 | 20.00 | 20.00 | 20.00 | 20.00 | 21.00 |
| Cetyl alcohol | 2.20 | 4.00 | 2.20 | 2.20 | 2.20 | 2.20 |
| Stearyl alcohol | 3.10 | 2.40 | 3.10 | 3.10 | 3.10 | 3.10 |
| White petrolatum | 3.00 | 3.40 | 5.00 | 3.00 | 5.00 | 5.00 |
| Polysorbate 60 | 3.40 | 3.80 | 3.40 | 3.40 | 3.40 | 3.40 |
| Sorbitan Monostearate | 0.60 | 1.00 | 0.60 | 0.60 | 0.60 | 0.60 |
| Glycerin | 2.00 | 3.00 | 2.00 | 5.00 | 5.00 | 5.00 |
| Xanthan gum | 1.00 | 0.70 | 0.50 | 0.50 | 0.50 | 0.50 |
| Purified water | 53.73 | 55.73 | 57.23 | 56.23 | 54.23 | 53.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 199 | 200 | 201 | 202 | 203 | 204 |
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| | % w/w | % w/w | % w/w | % w/w | % w/w | % w/w |
|---|---|---|---|---|---|---|
| | Formulation | | | | | |
| Excipients | 205 | 206 | 207 | 208 | 209 | 210 |
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

TABLE 9-continued

Lower Dosage Strength Imiquimod Formulations

| Excipients | % w/w | % w/w | % w/w Formulation | % w/w | % w/w | % w/w |
|---|---|---|---|---|---|---|
| | 211 | 212 | 213 | 214 | 215 | 216 |
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.48 | 64.08 | 56.98 | 55.98 | 53.98 | 58.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients | % w/w | % w/w | % w/w Formulation | % w/w | % w/w | % w/w |
|---|---|---|---|---|---|---|
| | 217 | 218 | 219 | 220 | 221 | 222 |
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.73 | 63.73 | 61.73 | 58.73 | 57.48 | 57.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

| Excipients | % w/w | % w/w | % w/w Formulation | % w/w | % w/w | % w/w |
|---|---|---|---|---|---|---|
| | 223 | 224 | 225 | 226 | 227 | 228 |
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 63.73 | 57.73 | 57.73 | 53.83 | 55.73 | 52.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

| Excipients | % w/w | % w/w | % w/w Formulation | % w/w | % w/w | % w/w |
|---|---|---|---|---|---|---|
| | 229 | 230 | 231 | 232 | 233 | 234 |
| Fatty acid* | 25.00 | 15.00 | 20.00 | 20.00 | 20.0 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.20 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.23 | 63.83 | 56.73 | 55.73 | 53.73 | 58.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

*The Fatty acid referenced in this Table 9 can be, for example, linoleic acid (la), Stearic acid (sa), palmitic acid (pa), isostearic acid (isa), unrefined oleic acid, (uoa), refined oleic acid, such as SUPER REFINED ® oleic acid (roa), or mixtures thereof.

The work area, all vessels and equipment is initially cleaned prior to commencing manufacture. A 2 L glass container and paddle stirrer blade are placed onto a balance and the weight is recorded. The paddle is then removed from the vessel. The isostearic acid and benzyl alcohol are weighed directly into the 2 L glass container. The imiquimod is then weighed into the 2 L glass container and a spatula is used to ensure the imiquimod is wetted with the isostearic acid and benzyl alcohol mixture. The 2 L container is then heated in a water bath to about 55±5° C. while stirring with a Heidolph mixer (Note: aluminum foil is placed around the top of the vessel and the paddle for the mixer, to limit evaporation). The solution is visually inspected to confirm the imiquimod has fully dissolved prior to mixing with cetyl alcohol, stearyl alcohol, white petrolatum, polysorbate 60 and sorbitan monostearate. Cetyl alcohol, stearyl alcohol, white petrolatum, polysorbate 60 and sorbitan monostearate are then weighed directly into the 2 L container and mixing is continued at about 55±5° C. until the oil phase is completely in solution. Separately, about 2 L of water are placed into a beaker and heated to 55±5° C. while stirring with a magnetic follower. Briefly, about 500 ml of the heated water is transferred into a 1 L beaker and placed into the water bath maintained at about 55±5° C. Half of the amount of glycerin required for the final formulation is then weighed into the beaker along with the total amount of methylparaben and propylparaben to the water (where both methyl and propyl paraben are weighed into weighing boats first, a pipette is used to remove a portion of the heated water to wash out the weighing boats to ensure total transfer of both the propyl- and methylparaben into the aqueous phase). The mixture is continuously stirred at about 55±5° C. (this is the aqueous phase). The remaining glycerin is then added to a 28 ml vial and the xanthan gum is added and mixed using a small overhead mixer (IKA®-Werke Lab Egg) with paddle attachment for about 10 min. The glycerin and xanthan mixture are then added slowly into the vortex of the aqueous phase, and a further aliquot of about 20 ml of heated water is used to rinse the vessel out into the water phase to ensure complete transfer. The water phase is then heated and mixed at about 55±5° C. until the xanthan gum mixture is fully and evenly dispersed into the aqueous phase. The temperatures of both the water phase and oil phase are both maintained at about 55±5° C. The aqueous phase is then transferred into the oil phase and the speed of the Heidolph mixer is increased during addition. The mixture is then homogenized on high speed for about 3 min and transferred immediately back to the Heidolph mixture; however, the contents of the homogenized sample, about 2 L, are mixed at about room temperature and allowed to cool to about 35° C. The container and contents and the paddle from the overhead mixer are then re-weighed and the weight of the paddle and 2 L beaker, as determined above, are subtracted to determine the total weight of the formulation remaining. The total weight (about 1 kg) of the cream is then made up to weight with heated water (Note: water evaporated during heating, which needs to be corrected at this point). The mixture is then transferred back onto the Heidolph mixer at about room temperature and mixed until the temperature of the formulation is below about 28° C. The lid of the container is then placed onto the vessel and stored at room temperature.

The lower dosage strength formulations of this Example 23 are believed to be stable and consistent with the specifications for the commercially available Aldara® 5% imiquimod cream. More preferably, low dosage formulations of this Example 23, especially as to those lower dosage strength formulations wherein the vehicle comprises an isostearic acid as the fatty acid, are believed to have the following:

(1) Stability. The imiquimod formulations of the present invention, when they are measured on HPLC at 25° C./60% RH, 30° C./65% RH and 40° C./75% RH over, one, two, three and six months, demonstrate stability consistent with the Aldara® 5% imiquimod cream;

(2) Degradation Products. No degradation products are detected in the formulations of the present invention, at its current recommended storage temperatures of about 4-25° C. In addition, there are no degradation products detected at any of the temperatures or time points mentioned under "Stability" above, when analyzed at about 318 nm;

(3) Homogeneity. The amount of imiquimod that is recovered from the formulations at any of the above-mentioned temperatures and time points is between about 90 to about 110% w/w thereby demonstrating good homogeneity;

(4) Benzyl Alcohol Content. The formulations of the present invention are also within specifications for the Aldara® 5% imiquimod cream, i.e., between 1.0% w/w and 2.1% w/w, at any of the above-mentioned temperatures and time points as to benzyl alcohol content.

(5) Microscopic Stability. There is no change in the particle size and no crystals are detected in the formulations of the present invention when they are stored at 25° C./60% RH and analyzed over a six month period;

(6) Macroscopic Stability. There are no obvious physical changes in the formulations of the present invention when they are stored at 25° C./60% RH and analyzed over a six month period;

(7) Viscosity. The formulations of the present invention are within the range of the specifications for the Aldara® 5% imiquimod cream, i.e., between 2000 cPs and 35,000 cPs, when they are stored at 25° C./60% RH and analyzed over a six month period; pH Stability. The formulations of the present invention are within the range of the specifications for the Aldara® 5% imiquimod cream, i.e., between pH 4.0 and pH 5.5) when they are stored at 25° C./60% RH and analyzed over a six month period;

(8) Preservative Efficacy Test ("PET"). The formulations of the present invention demonstrate sufficient reductions in colony forming unit counts for each of the organisms with which the formulations are inoculated, i.e., *S. aureus, E. coli*, Ps. *Aeruginosa, C. albicans*, and *A. niger*, at 2-8° C. and 40° C. over a 28 day test period and meet the requirements specified in both the USP and EP.

(9) Imiquimod In vitro Release. The Aldara® 5% imiquimod cream releases statistically significant ($p<0.05$) higher amounts of imiquimod over a 3 hour time period in comparison to the lower dosage strength formulations of the present invention through a synthetic membrane, e.g., Microporous polyethylene film 3M No. 9711 CoTran™. There is no statistical difference ($p<0.05$) in the total cumulative amount of imiquimod that is released from any of the 3.75% w/w imiquimod formulations. There is no statistical difference ($p<0.05$) in the total cumulative amount of imiquimod that is released from any of the 2.5% w/w imiquimod formulations. The Aldara® 5% imiquimod cream also statistically significantly ($p<0.05$) releases imiquimod at a faster rate over a 3 hour time period in comparison to the lower dosage strength formulations of the present invention through a synthetic membrane, e.g., Microporous polyethylene film 3M No. 9711 CoTran™. There is no statistical difference ($p<0.05$) between the imiquimod release rates for any of the 3.75% w/w imiquimod formulations. There is no statistical difference ($p<0.05$) between the imiquimod release rates for any of the 2.5% w/w imiquimod formulations. Thus, the greater the amount of imiquimod in a formulation, the faster and greater the total amount of imiquimod that is released from such formulation that the amount and rate of release of imiquimod are concentration dependant and that the rates and amounts of release of imiquimod from the formulations of the present invention are linear and dose proportionate to the Aldara® 5% imiquimod cream;

(10) Imiquimod In vitro Skin Permeation (Franz Cell Study). With respect to statistical analyses, there is no statistical difference between the lower dosage strength formulations of the present invention and the Aldara® 5% imiquimod cream as to the amount of imiquimod recovered from the receiver fluid, epidermis and dermis combined. Nonetheless, there is a statistically significant ($p<0.05$) dose proportionate difference between the amount of imiquimod recovered from each of the matrices with respect to the concentration of imiquimod in the lower dosage strength formulations of the present invention and the Aldara® 5% imiquimod cream for both un-absorbed and stratum corneum. Thus there is a linear dose release between the amount of imiquimod that is applied and recovered in each of the matrices, i.e., receiver fluid, unabsorbed dose, stratum corneum, epidermis and dermis.

ANOVA statistical analysis at 95% confidence level is used to analyze the stability data generated, including the data generated for the membrane and skin permeation experiments.

It is also believed that the formulations of the present invention, including the formulations identified in this Example 23, have Hydrophilic-lipophilic balance (HLB) values between about 12 and 15, and more preferably between about 12.4 and about 13.4.

I. Physical Characterization and Testing

The following is conducted for physical characterization of lower dosage strength imiquimod formulations, e.g., formulations identified in Table 12 and Table 18, and for testing lower dosage strength imiquimod formulations, e.g., imiquimod formulations identified in Tables 13-17.

(A) Analytical Method—HPLC Assay

A summary of an HPLC method is provided in Table 10.

TABLE 10

Summary of HPLC Methodology

| | |
|---|---|
| HPLC System | HPLC 9. Waters 265 (Alliance Separations module), Water 996 (Photodiode array detector), CPU (Compaq), Software - Microsoft Windows |

TABLE 10-continued

| Summary of HPLC Methodology | |
|---|---|
| | NT Version 4.00.1381 and Analysis software - Millenium[32] Version 4.00.00.00 |
| Column | Supelcosil LC-8-DB (5 mm, 15 × 0.46 cm) |
| Guard Column | Supelguard LC-8-DB 2 cm |
| Detection | UV at 258 nm |
| Sample Temperature | 25° C. |
| Column Temperature | 25° C. |
| Flow Rate | 2 ml/min |
| Mobile Phase | 72:28 aqueous:ACN (1% TEA solution, 0.2% Octyl Sodium Sulfate, adjusted to pH 2.0 with $H_3PO_4$ |
| Injection Volume | 20 μl |
| Run Time | 12 min |
| Needle Wash | 10:90 0.1N HCI:water |

(B) Preparation of HPLC Reagents (1) Mobile Phase:

About 2.0 g octyl sodium sulfate (OSS) is weighed into a large beaker and is mixed with about 990 ml Milli-Q ultrapure water and about 10.0 ml of triethylamine (TEA). The mixture is sonicated and stirred for about 5 min to dissolve the solids. A pH meter is then placed in the mixture and the pH of the OSS/TEA solution is adjusted to about 2.0 with concentrated $H_3PO_4$, stirring continuously during the adjusting procedure. The entire mixture is then filtered through a 0.2 μm filter. The filtrate is mixed with acetonitrile (HPLC grade) in the ratio of about 72:28 aqueous: acetonitrile by volume.

(2) Sample Diluent

About 250 ml acetonitrile (HPLC grade), about 740 ml purified water and about 10 ml of concentrated HCl are mixed together in a 1 L volumetric flask.

(3) Receiver Fluid

About 100 ml of a commercially available standardized 1N HCl solution is diluted to about 1000 ml with Milli-Q ultra pure water.

(4) Standards

Imiquimod standards are prepared, as described under Sample Diluent and Receiver Fluid, for stability test and receiver for membrane release tests. Initially, a stock solution of imiquimod is prepared by dissolving about 25 mg of imiquimod into about 50 ml of solvent (either Sample Diluent or Receiver Fluid) to give a concentration of about 500 μg/ml in Sample Diluent or Receiver Fluid.

A calibration range as shown in Table 11 is prepared for each HPLC run.

TABLE 11

| Preparation of Calibration Standards | | |
|---|---|---|
| Volume of stock solution (ml) | Volume of diluent | Final concentration of Test Item (μg/m1) |
| 10 | 0 | 500 |
| 5 | 5 | 250 |
| 4 | 6 | 200 |
| 2 | 8 | 100 |
| 1 | 9 | 50 |
| 0.5 | 9.5 | 25 |
| 0.2 | 9.8 | 10 |
| 0.1 | 9.9 | 5 |

(5) Combination Standard

The following combination standard solution is also prepared; whereby, about 500 mg of methylparaben and about 50 mg propylparaben are weighed into a single 250 ml volumetric flask and is diluted to volume with sample diluent above, to form the parabens solution. In addition, about 500 mg of imiquimod and about 200 mg benzyl alcohol are also weighed into a single 100 ml volumetric flask and about 10 ml of the parabens solution is then transferred into the imiquimod/benzyl alcohol volumetric which is made up to volume with diluent and is sonicated to dissolve fully.

(6) Impurity Standards

Impurity standards are prepared separately at a concentration of about 50 μg/ml in Sample Diluent and are analyzed in each HPLC run. The impurity standards that are included in each HPLC run are as follows:

N-propyl imiquimod

N-methyl imiquimod 4-hydroxyimiquimod 4-chloro imiquimod

TABLE 12

| | 2.5% Imiquimod Formulations | | | | | | 3.75% Imiquimod Formulations | | | | | |
|---|---|---|---|---|---|---|---|---|---|---|---|---|
| Excipients | 235 % w/w | 236 % w/w | 237 % w/w | 238 % w/w | 239 % w/w | 240 % w/w | 241 % w/w | 242 % w/w | 243 % w/w | 244 % w/w | 181 % w/w | 245 % w/w |
| Isostearic acid | 15 | 10 | 15 | 10 | 15 | 15 | 15 | 20 | 15 | 20 | 15 | 20 |
| Cetyl alcohol | 2 | 4 | 4 | 2 | 2 | 4 | 2 | 2 | 2 | 2 | 4 | 4 |
| Stearyl alcohol | 2 | 2 | 2 | 2.4 | 2.4 | 2.4 | 2 | 2 | 2.4 | 2.4 | 2.4 | 2.4 |
| White petrolatum | 3.4 | 3.4 | 2.8 | 2.8 | 3.4 | 2.8 | 3.4 | 2.8 | 3.4 | 2.8 | 2.8 | 3.4 |
| Polysorbate 60 | 3.8 | 3.8 | 3 | 3.8 | 3 | 3.8 | 3 | 3.8 | 3 | 3 | 3 | 3.8 |
| Sorbitan Monostearate | 0.2 | 1 | 1 | 1 | 1 | 0.2 | 1 | 1 | 0.2 | 0.2 | 1 | 1 |
| Glycerine | 3 | 1 | 3 | 3 | 1 | 1 | 3 | 1 | 1 | 3 | 1 | 3 |
| Xanthan gum | 0.3 | 0.3 | 0.7 | 0.3 | 0.7 | 0.3 | 0.3 | 0.7 | 0.7 | 0.3 | 0.3 | 0.7 |
| Purified water | 65.58 | 69.78 | 63.78 | 69.98 | 66.78 | 65.78 | 64.33 | 60.73 | 66.33 | 60.33 | 64.53 | 55.73 |
| Benzyl alcohol | 2 | 2 | 2 | 2 | 2 | 2 | 2 | 2 | 2 | 2 | 2 | 2 |
| Methylparaben | 0.2 | 0.2 | 0.2 | 0.2 | 0.2 | 0.2 | 0.2 | 0.2 | 0.2 | 0.2 | 0.2 | 0.2 |
| Propylparaben | 0.02 | 0.02 | 0.02 | 0.02 | 0.02 | 0.02 | 0.02 | 0.02 | 0.02 | 0.02 | 0.02 | 0.02 |
| Imiquimod | 2.50 | 2.50 | 2.50 | 2.50 | 2.50 | 2.50 | 3.75 | 3.75 | 3.75 | 3.75 | 3.75 | 3.75 |
| Total amount (g) | 100.00 | 100.00 | 100.00 | 100.00 | 100.00 | 100.00 | 100.00 | 100.00 | 100.00 | 100.00 | 100.00 | 100.00 |
| HLB Values | 14.4 | 12.8 | 12.4 | 12.8 | 12.4 | 14.4 | 12.4 | 12.8 | 14.3 | 14.3 | 12.4 | 12.8 |

In Table 13, fifteen 2.5% w/w imiquimod formulations are manufactured in 100 g batches. Each of the fifteen formulations are assessed for macroscopic and microscopic appearance, as discussed hereinafter.

TABLE 13

| | Imiquimod Formulations | | | | | | | |
|---|---|---|---|---|---|---|---|---|
| Excipients | 246 % w/w | 110 % w/w | 116 % w/w | 247 % w/w | 117 % w/w | 248 % w/w | 249 % w/w | 250 % w/w |
| Cetyl alcohol | 2.20 | 2.20 | 2.20 | 2.20 | 2.20 | 2.20 | 2.20 | 2.20 |
| Stearyl alcohol | 3.10 | 3.10 | 3.10 | 3.10 | 3.10 | 3.10 | 3.10 | 3.10 |
| White petrolatum | 15.50 | 3.00 | 6.00 | 8.50 | 6.00 | 6.00 | 8.50 | 3.00 |
| Polysorbate 60 | 3.40 | 3.40 | 3.40 | 3.40 | 3.00 | 4.25 | 3.00 | 3.40 |
| Sorbitan Monostearate | 0.60 | 0.60 | 0.60 | 0.60 | 1.00 | 0.75 | 1.00 | 0.60 |
| Glycerine | 2.00 | 2.00 | 5.00 | 5.00 | 5.00 | 5.00 | 5.00 | 2.00 |
| Xanthan gum | 0.50 | 0.50 | 0.50 | 0.50 | 0.50 | 0.50 | 0.50 | 0.50 |
| Purified water | 52.98 | 65.48 | 59.48 | 61.98 | 59.48 | 58.48 | 61.98 | 55.48 |
| Benzyl alcohol | 2.00 | 2.00 | 2.00 | 2.00 | 2.00 | 2.00 | 2.00 | 2.00 |
| Methylparaben | 0.20 | 0.20 | 0.20 | 0.20 | 0.20 | 0.20 | 0.20 | 0.20 |
| Propylparaben | 0.02 | 0.02 | 0.02 | 0.02 | 0.02 | 0.02 | 0.02 | 0.02 |
| Imiquimod | 2.50 | 2.50 | 2.50 | 2.50 | 2.50 | 2.50 | 2.50 | 2.50 |
| Total amount (g) | 100.00 | 100.00 | 100.00 | 100.00 | 100.00 | 100.00 | 100.00 | 100.00 |
| HLB Values | 13.4 | 13.4 | 13.4 | 13.4 | 12.4 | 13.4 | 12.4 | 13.4 |

| | Imiquimod Formulations | | | | | | |
|---|---|---|---|---|---|---|---|
| Excipients | 113 % w/w | 251 % w/w | 252 % w/w | 253 % w/w | 254 % w/w | 120 % w/w | 121 % w/w |
| Cetyl alcohol | 2.20 | 2.20 | 2.20 | 2.20 | 2.20 | 2.70 | 2.20 |
| Stearyl alcohol | 3.10 | 3.10 | 3.10 | 3.10 | 3.10 | 3.80 | 3.10 |
| White petrolatum | 6.00 | 6.00 | 5.00 | 5.00 | 5.00 | 3.00 | 3.00 |
| Polysorbate 60 | 3.00 | 3.00 | 3.40 | 3.40 | 3.00 | 3.40 | 3.40 |
| Sorbitan Monostearate | 1.00 | 1.00 | 0.60 | 0.60 | 1.00 | 0.60 | 0.60 |
| Glycerine | 5.00 | 5.00 | 5.00 | 5.00 | 5.00 | 2.00 | 2.00 |
| Xanthan gum | 0.75 | 1.00 | 0.50 | 0.50 | 0.60 | 0.50 | 1.00 |
| Purified water | 59.23 | 58.98 | 65.48 | 62.98 | 62.98 | 54.28 | 54.98 |
| Benzyl alcohol | 2.00 | 2.00 | 2.00 | 2.00 | 2.00 | 2.00 | 2.00 |
| Methylparaben | 0.20 | 0.20 | 0.20 | 0.20 | 0.20 | 0.20 | 0.20 |
| Propylparaben | 0.02 | 0.02 | 0.02 | 0.02 | 0.02 | 0.02 | 0.02 |
| Imiquimod | 2.50 | 2.50 | 2.50 | 2.50 | 2.50 | 2.50 | 2.50 |
| Total amount (g) | 100.00 | 100.00 | 100.00 | 100.00 | 100.00 | 100.00 | 100.00 |
| HLB Values | 12.4 | 12.4 | 13.4 | 13.4 | 12.4 | 13.4 | 13.4 |

TABLE 14

| | 2.5% Imiquimod Formulations | | | | | | | | | | | |
|---|---|---|---|---|---|---|---|---|---|---|---|---|
| Excipients | 110 % w/w | 116 % w/w | 117 % w/w | 250 % w/w | 254 % w/w | 120 % w/w | 121 % w/w | 235 % w/w | 123 % w/w | 124 % w/w | 125 % w/w | 126 % w/w |
| Isostearic acid | 15.00 | 15.00 | 15.00 | 25.00 | 12.5 | 25.00 | 25.00 | 15 | 20.00 | 20.00 | 20.00 | 20.00 |
| Cetyl alcohol | 2.20 | 2.20 | 2.20 | 2.20 | 2.20 | 2.70 | 2.20 | 2 | 2.20 | 2.20 | 2.20 | 2.20 |
| Stearyl alcohol | 3.10 | 3.10 | 3.10 | 3.10 | 3.10 | 3.80 | 3.10 | 2 | 3.10 | 3.10 | 3.10 | 3.10 |
| White petrolatum | 3.00 | 6.00 | 6.00 | 3.00 | 5.00 | 3.00 | 3.00 | 3.4 | 5.00 | 3.00 | 5.00 | 3.00 |
| Polysorbate 60 | 3.40 | 3.40 | 3.00 | 3.40 | 3.00 | 3.40 | 3.40 | 3.8 | 3.40 | 3.40 | 3.40 | 3.40 |
| Sorbitan Monostearate | 0.60 | 0.60 | 1.00 | 0.60 | 1.00 | 0.60 | 0.60 | 0.2 | 0.60 | 0.60 | 0.60 | 0.60 |
| Glycerine | 2.00 | 5.00 | 5.00 | 2.00 | 5.00 | 2.00 | 2.00 | 3 | 2.00 | 5.00 | 5.00 | 2.00 |
| Xanthan gum | 0.50 | 0.50 | 0.50 | 0.50 | 0.50 | 0.50 | 1.00 | 0.3 | 0.50 | 0.50 | 0.50 | 0.50 |
| Purified water | 65.48 | 59.48 | 59.48 | 55.48 | 62.98 | 54.28 | 54.98 | 65.58 | 58.48 | 57.48 | 55.48 | 60.48 |
| Benzyl alcohol | 2.00 | 2.00 | 2.00 | 2.00 | 2.00 | 2.00 | 2.00 | 2 | 2.00 | 2.00 | 2.00 | 2.00 |
| Methylparaben | 0.20 | 0.20 | 0.20 | 0.20 | 0.20 | 0.20 | 0.20 | 0.2 | 0.20 | 0.20 | 0.20 | 0.20 |
| Propylparaben | 0.02 | 0.02 | 0.02 | 0.02 | 0.02 | 0.02 | 0.02 | 0.02 | 0.02 | 0.02 | 0.02 | 0.02 |
| Imiquimod | 2.50 | 2.50 | 2.50 | 2.50 | 2.50 | 2.50 | 2.50 | 2.50 | 2.50 | 2.50 | 2.50 | 2.50 |
| Total | 100.00 | 100.00 | 100.00 | 100.00 | 100.00 | 100.00 | 100.00 | 100.00 | 100.00 | 100.00 | 100.00 | 100.00 |
| HLB Values | 13.4 | 13.4 | 12.4 | 13.4 | 12.4 | 13.4 | 13.4 | 14.4 | 13.4 | 13.4 | 13.4 | 13.4 |

TABLE 15

| | 3.75% Imiquimod Formulations | | | | | | | | | | |
|---|---|---|---|---|---|---|---|---|---|---|---|
| Excipients | 182 % w/w | 188 % w/w | 189 % w/w | 183 % w/w | 184 % w/w | 255 % w/w | 193 % w/w | 245 % w/w | 195 % w/w | 256 % w/w | 197 % w/w |
| Isostearic acid | 20.00 | 20.00 | 20.00 | 25.00 | 18.75 | 25.00 | 25.00 | 20 | 20.00 | 20.00 | 20.00 |
| Cetyl alcohol | 2.20 | 2.20 | 2.20 | 2.20 | 2.20 | 2.70 | 2.20 | 4 | 2.20 | 2.20 | 2.20 |
| Stearyl alcohol | 3.10 | 3.10 | 3.10 | 3.10 | 3.10 | 3.80 | 3.10 | 2.4 | 3.10 | 3.10 | 3.10 |
| White petrolatum | 3.00 | 6.00 | 6.00 | 3.00 | 5.00 | 3.00 | 3.00 | 3.4 | 5.00 | 3.00 | 5.00 |
| Polysorbate 60 | 3.40 | 3.40 | 3.00 | 3.40 | 3.00 | 3.40 | 3.40 | 3.8 | 3.40 | 3.40 | 3.40 |
| Sorbitan Monostearate | 0.60 | 0.60 | 1.00 | 0.60 | 1.00 | 0.60 | 0.60 | 1 | 0.60 | 0.60 | 0.60 |
| Glycerine | 2.00 | 5.00 | 5.00 | 2.00 | 5.00 | 2.00 | 2.00 | 3 | 2.00 | 5.00 | 5.00 |
| Xanthan gum | 0.50 | 0.50 | 0.50 | 0.50 | 0.50 | 1.00 | 1.00 | 0.7 | 0.50 | 0.50 | 0.50 |
| Purified water | 59.23 | 53.23 | 53.23 | 54.23 | 55.48 | 53.73 | 53.73 | 55.73 | 57.23 | 58.23 | 54.23 |
| Benzyl alcohol | 2.00 | 2.00 | 2.00 | 2.00 | 2.00 | 2.00 | 2.00 | 2 | 2.00 | 2.00 | 2.00 |
| Methylparaben | 0.20 | 0.20 | 0.20 | 0.20 | 0.20 | 0.20 | 0.20 | 0.2 | 0.20 | 0.20 | 0.20 |
| Propylparaben | 0.02 | 0.02 | 0.02 | 0.02 | 0.02 | 0.02 | 0.02 | 0.02 | 0.02 | 0.02 | 0.02 |
| Imiquimod | 3.75 | 3.75 | 3.75 | 3.75 | 3.75 | 3.75 | 3.75 | 3.75 | 3.75 | 3.75 | 3.75 |
| Total | 100.00 | 100.00 | 100.00 | 100.00 | 100.00 | 100.00 | 100.00 | 100.00 | 100.00 | 100.00 | 100.00 |
| HLB Values | 13.4 | 13.4 | 12.4 | 13.4 | 12.4 | 13.4 | 13.4 | 12.8 | 13.4 | 13.4 | 13.4 |

In Table 16, compositions for Aldara® 5% imiquimod cream and 1% imiquimod cream formulations are shown. Also shown in the Table 16, are four placebo formulations Pbo1, Pbo2, Pbo3 and formulation Pbo4.

TABLE 16

| | Formulations | | | | | |
|---|---|---|---|---|---|---|
| | 3M Aldara ® | 257 | Placebos | | | |
| Excipients | (5% Bulk) % w/w | (1%) % w/w | Pbo1 % w/w | Pbo2 % w/w | Pbo3 % w/w | Pbo4 % w/w |
| Isostearic acid | 25.00 | 25.00 | 20.00 | 20.00 | 20.00 | 20.00 |
| Cetyl alcohol | 2.20 | 2.40 | 2.20 | 2.20 | 2.20 | 2.20 |
| Stearyl alcohol | 3.10 | 3.40 | 3.10 | 3.10 | 3.10 | 3.10 |
| White petrolatum | 3.00 | 3.00 | 5.00 | 3.00 | 5.00 | 3.00 |
| Polysorbate 60 | 3.40 | 3.40 | 3.40 | 3.40 | 3.40 | 3.40 |
| Sorbitan Monostearate | 0.60 | 0.60 | 0.60 | 0.60 | 0.60 | 0.60 |
| Glycerin | 2.00 | 2.00 | 2.00 | 5.00 | 5.00 | 2.00 |
| Xanthan gum | 0.50 | 0.50 | 0.60 | 0.60 | 0.50 | 0.50 |
| Purified water | 52.98 | 58.48 | 80.98 | 59.98 | 57.98 | 62.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 5.00 | 1.00 | 0.00 | 0.00 | 0.00 | 0.00 |
| Total | 100.00 | 100.00 | 100.00 | 100.00 | 100.00 | 100.00 |
| HLP Values | 13.37 | 13.37 | 13.37 | 13.37 | 13.37 | 13.37 |

(C) Uniformity/Homogeneity

Following a 1 kg batch manufacturing process as described in this Example 23, 3×150 mg samples (top, middle and bottom) are removed from each 1 kg bulk batch using a positive displacement pipette and are extracted and are analyzed as described in Section, entitled "Imiquimod Content" described hereinafter.

(D) Preparation of Stability Samples

Each of the 1 kg batches are sub-aliquoted individually into 21×60 ml glass powder jars, where:

5×50 g (25° C./60% RH t=0 h, 1 month, 2 months, 3 months, 6 months)

5×50 g (30°/65% RH–t=0 h, 1 month, 2 months, 3 months, 6 months)

5×50 g (40° C./75% RH–t=0 h, 1 month, 2 months, 3 months, 6 months)

1×60 g (PET sample, placed at 2-8° C.)

1×20 g (placed at 2-8° C.)

1×20 g (placed at −20° C.)

The remaining formulation, is divided into 3 additional aliquots and each is placed at 25° C./60% RH, 30°/65% RH and 40° C./75% RH.

All batches are characterised based on the protocols that are shown in Section entitled Protocol for the Assessment of Formulations. Once each aliquot is removed from the relevant stability conditions at each time point; the remaining aliquot from each sample is placed in a fridge at 2-8° C. for future reference if required.

Following the 1 month stability time point, the benzyl alcohol content of the formulations are monitored; for all subsequent time points, the placebo formulations are analyzed by HPLC. Thus, there are no t=0 measurements for benzyl alcohol content for placebo formulations Pbo1, Pbo2 and Pbo3.

(E) Protocol for the Assessment of Formulations

The protocols that are used for the assessment of the formulations are as follows:

(1) Macroscopic Appearance

Macroscopic appearance is determined by visual examination of the physical characteristics which include appearance and texture of each cream. Macroscopic appearance is performed at each time point (t=0, 1, 2, 3 and 6 months) for the 25° C. stability samples, as follows:

Using a medium Granton® pallet knife, a small aliquot of sample (approximately 1 to 2 g) is removed from its container and is placed on the surface of a large Granton® pallet knife.

The medium Granton® pallet knife is then used to smooth the cream over the surface of the large Granton® pallet knife, by using a backward and forward motion of the spatula until a visually uniform layer of cream is obtained on the large Granton® pallet knife.

Visual observations of the cream are recorded which are based on, the presence of lumps, graduals or ease of spread over the surface of the spatula.

(2) Microscopic Appearance

Formulations are viewed under a light microscope (Leica DME FD198536 Light Microscope), to determine particle size, uniformity and the absence of particulates. Digital images of each formulation are taken at each time point (t=0, 1, 2, 3 and 6 months) for the 25° C. stability samples, as follows:

The microscope is set up so that the camera (Nikkon Cool Pix 4500 digital camera) is attached to the relay lens of the microscope and the 40× objective lens is set into place to view the sample. Camera settings: Image size: 1280×960 pixels, Image quality: Fine.

A small droplet of the formulation to be viewed is placed onto a microscope slide (Fisher-brand microscope slides, Cat No. 7101) using a micro-spatula. The microscope slide is then covered using a cover glass (Fisher-brand cover glass, width: 22-32 mm, thickness: 0.13-0.17 mm).

The microscope slide with the formulation is then placed under the 40× objective. Using the fine adjustment knob of the light microscope, the slide is brought into sharper focus to get a clear view.

Once a clear distinct view is obtained, pictures are taken (×400 magnification).

Figure 55:
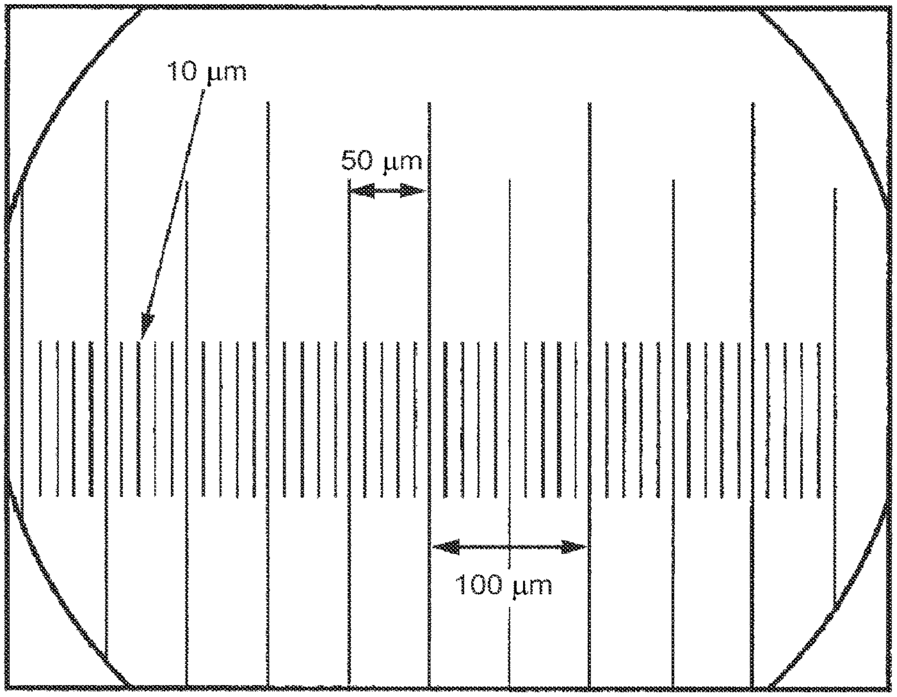
FIG. 55 shows a calibrated graticule scale at ×400 magnification; where the 10 μm, 50 μm and 100 μm divisions are indicated.

The particle sizes of formulations prepared are determined using a graticule (Olympus, Objective Micrometer, 0.01 mm). Overall uniformity and particle size are measured using the scale on the calibrated graticule shown in FIG. 55. Five random locations on each slide for each formulation are chosen to assess uniformity and particle size.

(3) Imiquimod Content

The imiquimod content of the formulations is measured at each time point (t=0, 1, 2, 3 and 6 months) for the 25° C. and 40° C. stability samples. The 30° C. stability samples are removed from the stability cabinet at each time point and placed at about 2-8° C. for future reference, as follows:

About 150 mg of the formulation is removed from each sample and is transferred into a 50 ml volumetric flask.

About 30-40 ml of diluent (about 250 ml acetonitrile (HPLC grade), about 740 ml purified water and about 10 ml of concentrated HCl are mixed together in a 1 L volumetric flask) is then added to the volumetric flask containing the aliquot of the formulation.

The sample is then vortex mixed for approximately 1 min or until the formulation has visibly completely dispersed into the diluent.

The sample is then sonicated for about 5 min and then is left to cool to room temperature.

The sample is then filled to volume with diluent and is mixed by inverting the volumetric flask.

This step is followed by filtration through a 0.45 mm filter directly into a 2 ml HPLC vial and the cap crimped.

The sample is then analysed on the HPLC using the method described in Section entitled Analytical Method—HPLC Assay described above, with the standard solutions as described above in Sections entitled Standards Combination Standard and Impurity Standard. This method also allows for the detection and measurement of benzyl alcohol.

(4) Related Substances/Degradation Products

Following the extraction and analysis, as described above under Imiquimod Content, the chromatograms for each formulation are compared to those generated for the impurity standards, as described above under Impurity Standards, to identify if there are any degradation peaks present. As the preservatives have similar retention times as the degradation products, the chromatograms are viewed at an absorbance of 318 nm wavelength at which the preservatives do not absorb to confirm the absence of degradation products.

(5) pH Measurements

The pH of the formulations are measured at each time point (t=0, 1, 2, 3 and 6 months). The pH measurement protocol is as follows:

A small sample of the formulation is applied on to the surface of a strip of pH paper (Fisher-brand pH paper: FB33045, Range pH 0.5-5.5) and is spread evenly over the surface using a spatula.

The pH paper with the formulation on it is then left for 10 min to ensure that the paper does absorb the cream (which is confirmed by a color change).

The pH of the formulation is then determined by comparing the color on the strip of pH paper with a range of colors (color chart) that are provided with the Fisher-brand pH paper.

(6) Viscosity from Flow Curve (Rheology Bohlin CVO Measurements)

The rheology of the formulations are measured at each time point (t=0, 1, 2, 3 and 6 months) for the 25° C. stability samples.

(7) Rheology Oscillation Methodology (Bohlin CVO)

The Crossover and $G^1$ values of the ICH stability samples are measured for all the t=0 samples. See e.g., Tables 18 and 26. The 'crossover' point is an indication of the elastic structure of the formulation and a high cross over point indicates that more force is required to breakdown the formulation thus providing an indication for longer term stability of the cream formulations. The $G^1$ value is a measurement of the elastic part of the formulation, whereby a high $G^1$ value indicates a more rigid formulation which 'recovers' more easily from applied shear stress.

(8) Viscosity (Brookfield) Measurements

The viscosity of the formulations is measured at each time point (t=0, 1, 2, 3 and 6 months) for the 25° C. stability samples.

(9) Preservative Efficacy Test Protocol

The preservative efficacy test is performed on formulations 110, 126, Pbo4 and 182 which are stored at about 2-8° C. and about 40° C. for about 3 months. Preservative efficacy testing is carried out according to the procedure described in line with the methodology described in the USP 2007 and EP 2007. The time points, at which the inoculated samples are tested are: 0 h, 24 h, 48 h, 7 days, 14 days, 21 days and 28 days.

Method validation is performed using *Staphylococcus aureus* cultures to confirm the neutralizing effect of D/E broth, for this purpose 110 and 182 are used to confirm neutralization of the preservatives.

Figure 56:
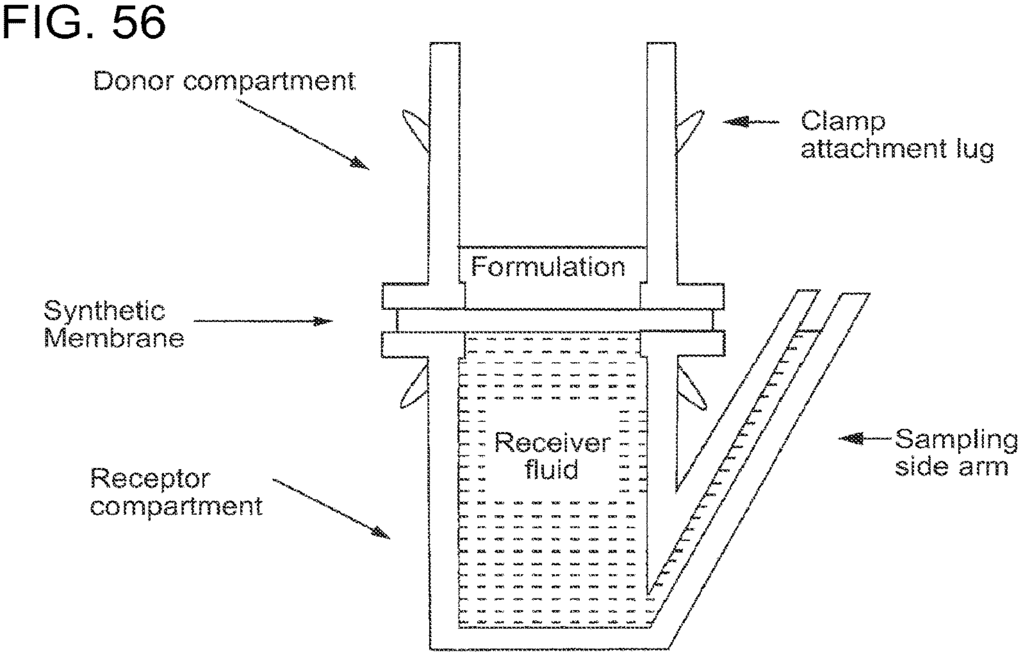
FIG. 56 shows a schematic representation of a Franz cell.

II. Test Item Release Studies Through Synthetic Membranes (A) In Vitro Screening of Release Profiles Through Synthetic Membranes The release of imiquimod from 13 formulations (n=4 for each) are compared using methodology based on the principles of the FDA, SUPAC-SS guidelines. The formulations that are tested included: 3M's Aldara® 5% imiquimod cream 1 kg bulk sample, Aldara® 5% imiquimod cream sachet (commercial product), Graceway's Aldara® 5% imiquimod cream 1 kg batch, and formulations 257 (1%), 123, 250, 125, 110, 182, 195, 256, 197 and 183. The protocol for the investigation is as follows:

A synthetic membrane (Microporous polyethylene film 3M No. 9711 CoTran™) is mounted in a small Franz cell (refer to FIG. 56) with a receiver fluid (0.1 N HCI) to ensure sink conditions (is equilibrated for a minimum of 30 min prior to dosing). An infinite dose of formulation (230 to 250 μl is dispensed using a calibrated positive displacement pipette) is applied to the membrane (using the pipette tip to gently spread over the surface) and the diffusion of imiquimod that is measured over time (n=4 per formulation). Briefly 200 μl of the receiver fluid is removed using a 250 μl Hamilton syringe at each time point (0, 15, 30, 60, 120 and 240 min) and is analysed on the HPLC using the method, as described under Analytical Method—HPLC Assay. The sample of receiver fluid is removed at each time point and is replaced with fresh pre-warmed (32° C.) receiver fluid.

III. In Vitro Skin Permeation Study (A) Analytical Methods (1) Liquid Scintillation Method Details Samples are added to a scintillation vial and about 4 ml of scintillation cocktail (Hionic-fluor) is added. The vial is capped and is shaken using a vortex mixer until the sample is mixed with the scintillation cocktail. The scintillation vials are then loaded into racks before analysing on the scintillation counter, using the settings listed as follows.

Model of scintillation counter: Beckman LS 5000 CE
Isotope setting: $C_{14}$
Counting time: 5 min
Calculation mode: SL DPM
Count samples: 1 times
Replicates: 1
Quench monitor: Yes (B) Radioactive Purity of Imiquimod $^{14}C$ 1. Preparation of Stock The radio-labelled material is as follows:

Imiquimod stock ($^{C}14$): Specific activity of about 57 mCl/mmol with a radiochemical purity of about 99.2% is supplied as a powder in a borosilicate multi-dose vial with additional screw cap.

Working stock solutions are prepared by addition of 1 ml isostearic acid to the imiquimod powder using a needle and syringe inserted through the septum of the vial. The screw cap is then replaced securely and the vial shaken on a vortex mixer until all the imiquimod dissolves in the isostearic acid. The homogeneity is also confirmed. This results in a stock solution containing about 1000 Ci/ml.

(C) Preparation of Formulations

The method for the preparation of about a 100 g radioactive batch is as follows:

- The glass container and mixer paddle attachment are placed onto a balance and the weight is recorded before the container and paddle are removed.
- The amount of imiquimod required for the formulation is added by weight and the remaining isostearic acid (minus 1.38 g) and benzyl alcohol are added to the container.
- The entire mixture is heated in a water bath at about 55±5° C. while stirring with a small over head mixer (IKA®-Werke Lab Egg) and paddle attachment.
- Cetyl alcohol, stearyl alcohol, white petrolatum, polysorbate 60 and sorbitan monostearate are added into the beaker and mixed at about 55±5° C. until the oil phase is completely in solution.
- Separately, about 200 ml of water is heated in a beaker to about 55±5° C. while stirring with a magnetic follower.
- About 50 ml of the heated water is transferred into a beaker and is placed in a water bath maintained at about 55±5° C. and half the glycerine, methyl hydroxyparabens and propyl hydroxyparabens are added (where both methyl and propyl parabens are weighed into weighing boats first) to the water and is stirred at about 55±5° C. (this is the aqueous phase).
- The remaining glycerine is added to a 28 ml vial with the xanthan gum and is mixed using a small over head mixer (IKA®-Werke Lab Egg) with paddle attachment for about 10 min.
- The glycerine and xanthan mixture are then added into the vortex of the aqueous phase, using about a 5 ml aliquot of heated water to rinse the vessel out into the water phase.
- Mixing of the water phase is continued for at least about 5 min.
- The aqueous phase is transferred into the oil phase, increasing the stirring speed during addition.
- The mixture is stirred on high speed maintaining the temperature at about 55±5° C. for 30 min.
- The vessel is removed from the mixer and is homogenised using the 1 cm head for about 3 min.
- Mixing is continued while cooling to about 35° C. and the total weight of the cream is made up to weight with heated water. The mixture is transferred to the overhead stirrer and cooling and stirring is continued to about 25° C.
- The formulations are then aliquoted in to screw top vials and are sealed with Parafilm® placed around the screw top lid.
- About 9.862 g of the formulation is weighed into a vial and is placed in a water bath at about 5° C. About 138 mg of radio-labelled working stock solution is then added to the formulation and the formulation is thoroughly mixed using a spatula while cooling.

(D) Homogeneity Control

Following manufacturing of the formulations, the following test is performed:

For each of the formulations, three aliquots (top, middle and bottom of batch) of approximately 5 mg is exactly weighed directly into a scintillation vial, where about 4 ml of scintillation cocktail is added. All of the samples are then directly quantified on the Liquid Scintillation Counter ("LSC") to confirm homogeneity within ±10%.

(E) Franz Cell Study

The method involves the use of full thickness human skin that is mounted in a Franz cell with about a 0.01 N hydrochloric acid as receiver fluid to ensure sink conditions. A dose of formulation equivalent to about 10 mg/cm$^2$ is applied to the membrane and the diffusion of imiquimod is measured over time. Human skin from cosmetic reduction surgery is used. Subcutaneous fat is removed mechanically prior to preparation of the skin section for the study. The formulations (6 ɥ ) are applied to the surface of the membrane using a positive displacement pipette. The investigation is performed in several experiments. Two skin donors are used randomly and are assigned across all experiments so that each formulation is tested on both skin donors. Each experiment consists of two randomly assigned formulations (n=6 cells per formulation) and two comparator formulations (n=6 cells per comparator). The receptor compartment of the Franz cells is then filled with the receiver fluid and the cells are fixed in a water bath maintained at about 37° C. The receptor compartment contents are continuously agitated by small magnetic followers. At t=1, 8 and 24 h, samples of receiver fluid are taken from the receptor compartment, and are replaced with fresh receiver fluid and are assayed by scintillation counting.

(F) Mass Balance

At the end of the experiment, a mass balance experiment is carried out, where the amount of $^{14}$C imiquimod remaining in the donor compartment, surface residue, Stratum corneum (SC), remaining epidermis, dermis and receiver compartment is quantified. This method involves removal of the SC by tape stripping and processing of the remaining epidermal layer and dermis using standard procedures. The protocol for the mass balance is as follows:

Unabsorbed dose: The surface of each Franz cell donor chamber is wiped gently with a cotton bud using 5 clockwise and anti-clockwise movements. This procedure is repeated on 4 occasions using alternate wet (receiver fluid) and dry cotton buds. The cotton buds are added to scintillation cocktail before analysis. Two tape strips are removed from the skin and these are regarded as unabsorbed formulation and included in the total surface activity. The Stratum corneum) (SC) is removed by carefully tape stripping the membrane ten times using Scotch adhesive tape. Collectively, each tape is placed into a scintillation vial to which 4 ml of scintillation cocktail are added before analysis. Epidermal layer: The remaining section of the epidermis (following tape stripping) is carefully removed from the dermis with a scalpel. The epidermis is placed into a glass vial containing 2 ml of Soluene 350 and is incubated at about 50° C. for about 72 h before analysis by LSC. The remaining dermal layer is placed in to a glass vial containing about 2 ml of Soluene 350 and is incubated at about 50° C. for about 72 h before analysis by LSC.

(G) Analysis of Data

ANOVA statistical analysis at a 95% confidence level is used to analyse the data generated for the membrane release and skin permeation experiments.

An example of the ANOVA statistical analysis is as follows:

| Individual 95% CIs For Mean Base on Pooled StDev | | | | |
|---|---|---|---|---|
| Level | N | Mean | StDev | +------------+------------+------------+------------ |
| Formulation X | 4 | 4605.5 | 626.9 | (---*---) |
| Formulation Y | 4 | 1862.8 | 185.9 | (---*----) |
| Formulation Z | 4 | 1845.6 | 206.4 | (---*---) |
| | | | | +------------+------------+------------+------------<br>0 1500 3000 4500 |

Whereby, no significance (p>0.05) is shown by two overlapping histograms (e.g. Y and Z), whereas a significant difference (P≤0.05) can be identified by two histograms which don't overlap (e.g. X and Y and X and Z). The width of the each histogram is a reflection of the pooled standard deviation from all data sets.

IV. Results and Discussion (A) Degradation Product Analysis

It is discovered that the preservatives (benzyl alcohol, methylparaben and propylparaben) at about 318 in the imiquimod formulations can not be detected. Thus, by analysing the imiquimod formulations at this wavelength, it permits the detection of degradation products, if any, in the presence of preservatives. However, no degradation products are identified at about 318 nm for any of the imiquimod formulations tested up to and including the 6 month stability time point at about 25° C. and about 40° C.

Figure 57:
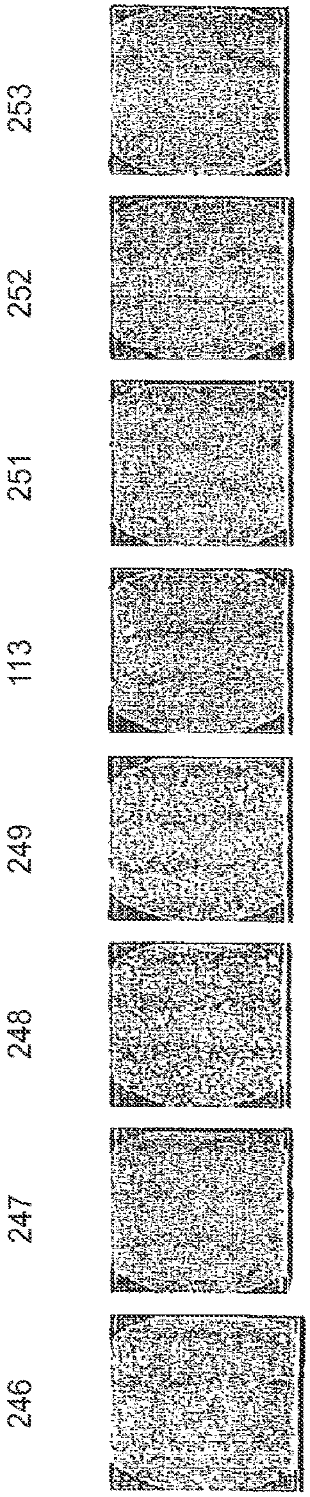
FIG. 57 shows a summary of microscope pictures of eight 2.5% w/w imiquimod formulations, i.e., formulations 113, 246, 247, 248, 249, 251, 252 and 253 (the formulations continued into the stability program are included for the 1 kg batches in TABLE 18 and FIG. 64)

In Table 17 and FIG. 57, they show a summary of the findings, whereby simple microscopic analysis of the imiquimod formulations identify formulations with inconsistent particle size and large aggregation of material. Summary and composition of lower dosage strength imiquimod formulations are listed in Table 13 and Table 14.

TABLE 17

| | 246 % w/w | 110 % w/w | 116 % w/w | 247 % w/w | 117 % w/w | 248 % w/w | 249 % w/w | 250 % w/w |
|---|---|---|---|---|---|---|---|---|
| Viscosity (visual) | high | High | high | high | high | high | high | low |
| Appearance (spatula) | lumpy | Smooth | smooth | smooth | smooth | smooth | smooth | smooth |
| pH | 5 | 5 | 5 | 5 | 4.5 | 4.5 | 5 | 4 |
| $G^1$ (Pa) | 3639 | 1150.5 | 1504 | 1093 | 1740.5 | 5235 | 1364.5 | 171.5 |
| crossover ($o^1$) | 29.5 | 14.5 | 20.5 | 16 | 21.5 | none | 21.5 | 13 |
| Microscope | v. bad | Ok | good | bad | good | v. bad | bad | good |

| | 113 % w/w | 251 % w/w | 252 % w/w | 253 % w/w | 254 % w/w | 120 % w/w | 121 % w/w |
|---|---|---|---|---|---|---|---|
| Viscosity (visual) | high | high | high | Medium-high | high | very high | medium-low |
| Appearance (spatula) | slightly textured | Textured | smooth | smooth | matt, smooth | matt, smooth | smooth |
| pH | 5 | 5 | 5 | 5 | 5 | 4.5 | 4.5 |
| $G^1$ (Pa) | 642 | 943 | 626.5 | 567 | 2285.5 | 5231 | 304.5 |
| crossover ($o^1$) | 21.5 | 29.25 | 19 | 15 | 21.5 | 20.5 | 29.75 |
| Microscope | bad | bad | ok | bad | ok | ok | good |

TABLE 18

Physical Characteristics of 12 Lower Dosage Strength Imiquimod Formulations, i.e., Formulations 181, 235, 236, 237, 238, 239, 240, 241, 242, 243, 244 and 245.

| Excipients | 235 % w/w | 236 % w/w | 237 % w/w | 238 % w/w | 239 % w/w | 240 % w/w |
|---|---|---|---|---|---|---|
| Isostearic acid | 15 | 10 | 15 | 10 | 15 | 15 |
| Cetyl alcohol | 2 | 4 | 4 | 2 | 2 | 4 |
| Stearyl alcohol | 2 | 2 | 2 | 2.4 | 2.4 | 2.4 |
| White petroleum | 3.4 | 3.4 | 2.8 | 2.8 | 3.4 | 2.8 |
| Polysorbate 60 | 3.8 | 3.8 | 3 | 38 | 3 | 3.8 |
| Sorbitan Monostearate | 0.2 | 1 | 1 | 1 | 1 | 0.2 |
| Glycerin | 3 | 1 | 3 | 3 | 1 | 1 |
| Xanthan gum | 0.3 | 0.3 | 0.7 | 0.3 | 0.7 | 0.3 |
| Purified water | 65.58 | 69.78 | 63.78 | 69.98 | 66.78 | 65.78 |
| Benzyl alcohol | 2 | 2 | 2 | 2 | 2 | 2 |
| Methylparaben | 0.2 | 0.2 | 0.2 | 0.2 | 0.2 | 0.2 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total amount (g) | 100.00 | 100.00 | 100.00 | 100.00 | 100.00 | 100.00 |
| HLB Values | 14.39 | 12.78 | 12.35 | 12.78 | 12.35 | 14.39 |
| Modification: | multi | multi | multi | multi | multi | multi |
| Viscosity | low/med | high | high | medium | med/high | high |
| pH | 4.7 | 4.7 | 4.7 | 6 | 4.7 | 4.7 |
| G | 294.37 | 1527.65 | 639.345 | 467.78 | 552.61 | 924.075 |
| crossover | 9.5 | 25.25 | 10.5 | 17.75 | 12 | 25.5 |
| microscope | v. good | ok, but particles? | bad | good, but particles? | bad | bad - particles? |
| Appearance/Spatula | glossy, v. slight texture, matt, does smooth out | smooth, matt, slightly aerated | slight texture, matt does smooth out | glossy, smooth | v. glossy & v. smooth | smooth, matt |

| Excipients | 241 % w/w | 242 % w/w | 243 % w/w | 244 % w/w | 181 % w/w | 245 % w/w |
|---|---|---|---|---|---|---|
| Isostearic acid | 15 | 20 | 15 | 20 | 15 | 20 |
| Cetyl alcohol | 2 | 2 | 2 | 2 | 4 | 4 |
| Stearyl alcohol | 2 | 2 | 2.4 | 2.4 | 2.4 | 2.4 |
| White petroleum | 3.4 | 2.8 | 3.4 | 2.8 | 2.8 | 3.4 |
| Polysorbate 60 | 3 | 3.8 | 3 | 3 | 3 | 3.8 |
| Sorbitan Monostearate | 1 | 1 | 0.2 | 0.2 | 1 | 1 |
| Glycerin | 3 | 1 | 1 | 3 | 1 | 3 |
| Xanthan gum | 0.3 | 0.7 | 0.7 | 0.3 | 0.3 | 0.7 |
| Purified water | 64.33 | 60.73 | 66.33 | 60.33 | 86.53 | 55.73 |

TABLE 18-continued

Physical Characteristics of 12 Lower Dosage Strength Imiquimod Formulations, i.e., Formulations 181, 235, 236, 237, 238, 239, 240, 241, 242, 243, 244 and 245.

| | | | | | | |
|---|---|---|---|---|---|---|
| Benzyl alcohol | 2 | 2 | 2 | 2 | 2 | 2 |
| Methylparaben | 0.2 | 0.2 | 0.2 | 0.2 | 0.2 | 0.2 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total amount (g) | 100.00 | 100.00 | 100.00 | 100.00 | 100.00 | 100.00 |
| HLB Values | 12.35 | 12.78 | 14.26 | 14.26 | 12.35 | 12.78 |
| Modification: | multi | multi | multi | multi | multi | multi |
| Viscosity | Medium-High | Medium | Medium-Low | Medium-high | Very High | High |
| pH | 5.0 | 4.7 | 4.7 | 4.5 | 4.7 | 4.5 |
| G | 116.18 | 416.65 | 8767 | 65.425 | 2514.25 | 1280.05 |
| crossover | 13.75 | 18.5 | none | 11.75 | 36 | 22.5 |
| microscope | good with bubbles | very good | ok | good | very good | good |
| Appearance/Spatula | glossy, slightly textured with some aeration | glossy, textured with some aeration | glossy, slightly textured, very aerated | glossy, very slightly textured | smooth with a matt appearance | glossy, smooth, with some aeration |

(B) Scale-Up and ICH Stability

1. Homogeneity

In Table 19, formulations 245, 121 and 193 show signs of phase separation. All the other formulations in Table 19 show good homogeneity, and are subsequently sub-aliquoted and placed on stability as described above under Preparation of Stability Samples.

TABLE 19

Homogeneity Results from 1 kg batches, where Samples are Removed from Top Middle and the Bottom of the Batch for Comparison of Homogeneity.

| Formulation | % Recovery | % CV |
|---|---|---|
| 3M Aldara ® 5% Batch | 102.69 ± 2.29 | 2.23 |
| 257 (1%) | 100.29 ± 0.68 | 0.68 |
| 197 | 96.81 ± 2.15 | 2.22 |
| 183 | 97.56 ± 0.48 | 0.50 |
| 245 | 91.08 ± 12.80 | 14.06 |
| 182 | 97.68 ± 0.73 | 0.75 |
| 189 | 98.32 ± 0.92 | 0.94 |
| 184 | 98.37 ± 1.61 | 1.63 |
| 193 | 97.21 ± 0.22 | 0.23 |
| 188 | 98.95 ± 2.48 | 2.51 |
| 195 | 99.66 ± 0.70 | 0.70 |
| 255 | 99.46 ± 0.49 | 0.49 |
| 256 | 98.80 ± 0.75 | 0.76 |
| Graceway Aldara ® 5% Imiquimod | 102.74 ± 1.26 | 1.23 |
| 110 | 101.43 ± 0.63 | 0.62 |
| 116 | 100.39 ± 0.18 | 0.18 |
| 117 | 100.49 ± 0.64 | 0.64 |
| 250 | 99.98 ± 0.37 | 0.37 |
| 254 | 98.70 ± 0.21 | 0.21 |
| 120 | 100.02 ± 0.34 | 0.34 |
| 121 | 106.22 ± 0.09 | 0.09 |
| 235 | 101.04 ± 0.21 | 0.21 |
| 123 | 101.75 ± 0.28 | 0.28 |

TABLE 19-continued

Homogeneity Results from 1 kg batches, where Samples are Removed from Top Middle and the Bottom of the Batch for Comparison of Homogeneity.

| Formulation | % Recovery | % CV |
|---|---|---|
| 124 | 95.00 ± 0.32 | 0.34 |
| 125 | 101.12 ± 0.12 | 0.12 |
| 126 | 102.37 ± 0.58 | 0.57 |
| Pbo1 | N/A | N/A |
| Pbo2 | N/A | N/A |
| Pbo3 | N/A | N/A |
| Pbo4 | N/A | N/A |

(C) Stability

1. Stability of Imiquimod in Formulations

In Table 20, imiquimod in the formulations is stable at both about 25° C. and about 40° C. over an about six month period, although the results for three and six months at both about 25° C. and about 40° C. look consistently higher than previous time points. This could be attributed to a small amount of water evaporation from the containers. In addition, all samples are consistent with the commercially supplied Aldara® 5% imiquimod cream sample. There are no degradation products detected in any of the samples in Table 20 at any of the temperatures and time points when analyzed at about 318 nm. With reference to formulation specification, the specification amount of imiquimod that is recovered from the samples in Table 20 is between about 90%-110% w/w, thereby confirming that the samples fall within their target specification. In other words, and by way of example, the specification amount of imiquimod that is recovered from preferred 2.5% imiquimod formulations of the present invention will fall within between about 2.25% and about 2.75% w/w and the amount of imiquimod that is recovered from preferred 3.7.5% imiquimod formulations of the present invention will fall within between about 3.38% and about 4.12% w/w. Thus, in accordance with the present invention, the amount of imiquimod recovery from preferred formulations will fall within about the 100%±10% w/w specification of their target concentrations.

TABLE 20

Percentage of Imiquimod that is Recovered from the Formulations as Compared to Theoretical when the Formulations are Stored at 25° C. and 40° C. over a 6 Month Period. Highlighted Grey Areas Indicate Time Points Which Are Not Tested Due To Rejection/Omission Of Formulations (n = 3 ± sd).

| Imiquimod Formulations | T = 0 Mean SD | T = 1 month 25° C. Mean SD | T = 1 month 40° C. Mean SD | T = 2 months 25° C. Mean SD | T = 2 months 40° C. Mean SD |
|---|---|---|---|---|---|
| Aldara ® 5% 3M | 100.38 ± 0.25 | 100.60 ± 0.10 | 100.41 ± 0.04 | 100.58 ± 0.10 | 101.40 ± 0.29 |
| 257 (1%) | 100.29 ± 0.12 | 104.36 ± 0.18 | 104.98 ± 2.41 | 102.31 ± 0.46 | 102.42 ± 0.10 |
| 197 | 96.81 ± 0.17 | 97.74 ± 0.20 | 99.22 ± 0.33 | 99.28 ± 0.14 | 101.47 ± 0.22 |
| 183 | 97.69 ± 0.21 | 99.73 ± 0.32 | 99.43 ± 2.77 | 99.61 ± 0.33 | 100.01 ± 0.05 |
| 245 | | | | | |
| 182 | 96.76 ± 0.25 | 102.01 ± 0.01 | 98.46 ± 0.15 | 99.00 ± 0.12 | 98.07 ± 0.10 |
| 189 | 98.73 ± 0.19 | 100.72 ± 0.17 | 99.20 ± 0.25 | | |
| 184 | 100.09 ± 0.08 | 101.71 ± 0.14 | 96.86 ± 0.20 | | |
| 193 | | | | | |
| 188 | 100.28 ± 0.02 | 99.39 ± 0.17 | 97.04 ± 0.21 | | |
| 195 | 99.39 ± 0.32 | 99.33 ± 0.07 | 97.84 ± 0.25 | 101.13 ± 0.10 | 103.13 ± 0.10 |
| 255 | 98.87 ± 0.42 | 100.67 ± 0.02 | 98.73 ± 0.13 | | |
| 256 | 97.58 ± 0.03 | 100.06 ± 0.22 | 98.05 ± 0.12 | 99.74 ± 0.07 | 99.28 ± 0.24 |
| Graceway Aldara ® 5% Imiquimod | 98.62 ± 0.11 | 102.32 ± 0.28 | 96.66 ± 0.18 | 101.65 ± 0.06 | 101.02 ± 0.10 |
| 110 | 101.06 ± 0.35 | 102.17 ± 0.95 | 99.48 ± 0.19 | 101.46 ± 0.09 | 99.03 ± 0.14 |
| 116 | 98.63 ± 0.25 | 99.15 ± 0.13 | 96.87 ± 0.09 | | |
| 117 | 99.00 ± 0.73 | 102.06 ± 0.10 | 98.42 ± 0.09 | | |
| 250 | 97.67 ± 0.11 | 101.88 ± 0.06 | 99.37 ± 1.05 | 99.43 ± 0.20 | 99.74 ± 0.13 |
| 254 | 96.29 ± 0.27 | 99.75 ± 0.09 | 97.11 ± 0.25 | | |
| 120 | 99.79 ± 0.27 | 100.61 ± 0.03 | 98.82 ± 0.17 | | |
| 121 | | | | | |
| 235 | 99.25 ± 0.25 | 102.80 ± 0.20 | 100.78 ± 0.11 | | |
| 123 | 99.71 ± 0.17 | 101.49 ± 0.10 | 99.52 ± 0.34 | 102.08 ± 0.34 | 101.11 ± 0.27 |
| 124 | 93.17 ± 0.07 | 94.26 ± 0.04 | 92.93 ± 0.14 | | |
| 125 | 98.37 ± 0.23 | 102.33 ± 0.29 | 99.14 ± 0.14 | 99.99 ± 0.21 | 100.38 ± 0.09 |
| 126 | 102.37 ± 0.58 | 102.84 ± 0.45 | 104.11 ± 0.04 | 100.02 ± 0.95 | 101.32 ± 0.40 |
| Pbo4 | 0 ± 0 | 0 ± 0 | 0 ± 0 | 0 ± 0 | 0 ± 0 |
| Pbo1 | 0 ± 0 | 0 ± 0 | 0 ± 0 | 0 ± 0 | 0 ± 0 |
| Pbo2 | 0 ± 0 | 0 ± 0 | 0 ± 0 | 0 ± 0 | 0 ± 0 |
| Pbo3 | 0 ± 0 | 0 ± 0 | 0 ± 0 | 0 ± 0 | 0 ± 0 |

| Imiquimod Formulations | T = 3 month 25° C. Mean SD | T = 3 month 40° C. Mean SD | T = 6 month 25° C. Mean SD | T = 6 month 40° C. Mean SD |
|---|---|---|---|---|
| Aldara ® 5% 3M | 104.12 ± 0.23 | 104.12 ± 0.79 | 106.78 ± 4.64 | 105.41 ± 0.60 |
| 257 (1%) | 103.16 ± 0.37 | 105.79 ± 0.27 | 107.09 ± 1.63 | 103.76 ± 3.59 |
| 197 | 102.69 ± 0.92 | 102.69 ± 0.92 | 100.39 ± 1.04 | 101.11 ± 2.66 |
| 183 | 100.80 ± 1.07 | 103.70 ± 1.58 | 100.75 ± 1.82 | 102.19 ± 1.33 |
| 245 | | | | |
| 182 | 101.48 ± 0.27 | 104.39 ± 1.55 | 102.91 ± 1.16 | 99.21 ± 4.25 |
| 189 | | | | |
| 184 | | | | |
| 193 | | | | |
| 188 | | | | |
| 195 | 103.00 ± 0.15 | 106.25 ± 0.99 | 106.84 ± 1.38 | 106.28 ± 1.22 |
| 255 | | | | |
| 256 | 101.74 ± 0.37 | 101.71 ± 0.44 | 105.42 ± 2.10 | 105.55 ± 3.20 |
| Graceway Aldara ® 5% Imiquimod | 103.58 ± 0.19 | 103.64 ± 0.15 | 101.70 ± 0.79 | 103.20 ± 1.85 |
| 110 | 102.73 ± 0.64 | 103.36 ± 0.38 | 102.42 ± 1.16 | 102.38 ± 2.82* |
| 116 | | | | |
| 117 | | | | |
| 250 | 101.57 ± 0.35 | 105.32 ± 2.42 | 102.45 ± 0.50 | 101.14 ± 2.23 |
| 254 | | | | |
| 120 | | | | |
| 121 | | | | |
| 235 | | | | |
| 123 | 103.27 ± 0.31 | 102.35 ± 0.47 | 105.49 ± 1.11 | 103.34 ± 1.44 |
| 124 | | | | |
| 125 | 103.28 ± 0.76 | 104.87 ± 2.65 | 102.48 ± 1.27 | 103.87 ± 1.37 |
| 126 | 99.28 ± 3.25 | 98.43 ± 0.55 | 101.95 ± 0.37 | 103.02 ± 1.89 |
| Pbo4 | 0 ± 0 | 0 ± 0 | 0 ± 0 | 0 ± 0 |

TABLE 20-continued

Percentage of Imiquimod that is Recovered from the Formulations as Compared to Theoretical when the Formulations are Stored at 25° C. and 40° C. over a 6 Month Period. Highlighted Grey Areas Indicate Time Points Which Are Not Tested Due To Rejection/Omission Of Formulations (n = 3 ± sd).

| | | | | |
|---|---|---|---|---|
| Pbo1 | 0 ± 0 | 0 ± 0 | 0 ± 0 | 0 ± 0 |
| Pbo2 | 0 ± 0 | 0 ± 0 | 0 ± 0 | 0 ± 0 |
| Pbo3 | 0 ± 0 | 0 ± 0 | 0 ± 0 | 0 ± 0 |

*30° C. sample analysed, as 40° C. had shown signs of phase separation.

2. Stability of Benzyl Alcohol in Formulations

In Table 21, Benzyl alcohol content is found to fall over the duration of the stability tests. The greatest loss observed is in the placebo's; Pbo4 (1.08±0.02% w/w), Pbo1 (1.01±0.03% w/w), Pbo2 (1.04±0.08% w/w) and Pbo3 (1.11±0.00% w/w) and the active formulation 257 (1%) (1.37±0.01% w/w) which shows a loss in benzyl alcohol at about 40° C. for about 6 months down from 2.0% w/w. The specified range for benzyl alcohol in the Aldara® 5% imiquimod cream formulations (1.0 to 2.1% w/w), are within specification for Aldara® 5% imiquimod cream. The decrease in benzyl alcohol content from the formulations is possibly the result of the formation of an ester (benzyl isostearate), whereby there is a reaction between the excipients of benzyl alcohol and isostearic acid.

TABLE 21

Amount of Benzyl Alcohol that is Recovered from the Formulations when the formulations that are Stored at 25° C. and 40° C. over a 6 Month Period. Highlighted Grey Areas Indicate Time Points Which Are Not Tested Due To Rejection/Omission Of Formulations (N = 3 ± Sd).

| Imiquimod Formulations | T = 0 Mean SD | T = 1 month 25° C. Mean SD | T = 1 month 40° C. Mean SD | T = 2 months 25° C. Mean SD | T = 2 months 40° C. Mean SD |
|---|---|---|---|---|---|
| Aldara ® 5% 3M | 2.11 ± 0.02 | 2.04 ± 0.01 | 1.86 ± 0.01 | 2.04 ± 0.01 | 1.84 ± 0.06 |
| 257 (1%) | 2.06 ± 0.01 | 2.01 ± 0.01 | 1.74 ± 0.02 | 2.00 ± 0.04 | 1.07 ± 0.03 |
| 197 | 2.06 ± 0.00 | 2.06 ± 0.01 | 1.86 ± 0.01 | 2.05 ± 0.00 | 1.91 ± 0.02 |
| 183 | 2.05 ± 0.01 | 2.01 ± 0.01 | 1.85 ± 0.12 | 2.00 ± 0.01 | 1.81 ± 0.00 |
| 245 | | | | | |
| 182 | 2.17 ± 0.00 | 2.17 ± 0.00 | 1.95 ± 0.01 | 2.11 ± 0.04 | 1.97 ± 0.00 |
| 189 | 2.11 ± 0.01 | 2.06 ± 0.02 | 1.88 ± 0.02 | | |
| 184 | 2.13 ± 0.01 | 2.09 ± 0.01 | 1.86 ± 0.01 | | |
| 193 | | | | | |
| 188 | 2.15 ± 0.02 | 2.05 ± 0.02 | 1.84 ± 0.01 | | |
| 195 | 2.12 ± 0.02 | 2.04 ± 0.01 | 1.85 ± 0.02 | 2.07 ± 0.03 | 1.95 ± 0.03 |
| 255 | 2.09 ± 0.01 | 2.04 ± 0.00 | 1.81 ± 0.02 | | |
| 256 | 2.07 ± 0.01 | 2.05 ± 0.00 | 1.85 ± 0.00 | 2.06 ± 0.02 | 1.87 ± 0.03 |
| Graceway Aldara ® 5% Imiquimod | 2.06 ± 0.01 | 2.06 ± 0.00 | 1.80 ± 0.00 | 2.05 ± 0.00 | 1.91 ± 0.02 |
| 110 | 2.09 ± 0.01 | 2.04 ± 0.01 | 1.84 ± 0.01 | 2.04 ± 0.02 | 1.91 ± 0.02 |
| 116 | 2.08 ± 0.01 | 2.05 ± 0.01 | 1.87 ± 0.01 | | |
| 117 | 2.11 ± 0.01 | 2.06 ± 0.01 | 1.82 ± 0.05 | | |
| 250 | 2.03 ± 0.01 | 2.00 ± 0.01 | 1.78 ± 0.07 | 1.96 ± 0.02 | 1.70 ± 0.01 |
| 254 | 2.07 ± 0.01 | 2.04 ± 0.01 | 1.89 ± 0.01 | | |
| 120 | 2.11 ± 0.00 | 2.00 ± 0.01 | 1.77 ± 0.02 | | |
| 121 | | | | | |
| 235 | 2.10 ± 0.00 | 2.10 ± 0.02 | 1.92 ± 0.02 | | |
| 123 | 2.11 ± 0.01 | 2.05 ± 0.00 | 1.82 ± 0.01 | 2.06 ± 0.01 | 1.85 ± 0.01 |
| 124 | 1.96 ± 0.01 | 1.89 ± 0.01 | 1.71 ± 0.00 | | |
| 125 | 2.08 ± 0.01 | 2.06 ± 0.01 | 1.82 ± 0.00 | 2.02 ± 0.01 | 1.82 ± 0.01 |
| 126 | 2.00 ± 0.02 | 2.02 ± 0.01 | 1.89 ± 0.01 | 1.86 ± 0.02 | 1.65 ± 0.02 |
| PBO4 | 1.93 ± 0.02 | 1.83 ± 0.08 | 1.90 ± 0.03 | 1.91 ± 0.01 | 1.53 ± 0.00 |
| PBO1 | | 1.82 ± 0.01 | 1.65 ± 0.00 | 1.85 ± 0.09 | 1.54 ± 0.10 |
| PBO2 | | 1.83 ± 0.01 | 1.65 ± 0.01 | 1.87 ± 0.19 | 1.70 ± 0.09 |
| PBO3 | | 1.97 ± 0.00 | 1.81 ± 0.01 | 2.09 ± 0.00 | 1.81 ± 0.00 |

| Imiquimod Formulations | T = 3 month 25° C. Mean SD | T = 3 month 40° C. Mean SD | T = 6 month 25° C. Mean SD | T = 6 month 40° C. Mean SD |
|---|---|---|---|---|
| Aldara ® 5% 3M | 1.88 ± 0.02 | 1.67 ± 0.02 | 1.76 ± 0.05 | 1.41 ± 0.00 |
| 257 (1%) | 1.74 ± 0.01 | 1.37 ± 0.01 | 1.58 ± 0.01 | 1.02 ± 0.08 |
| 197 | 1.85 ± 0.01 | 1.70 ± 0.02 | 1.74 ± 0.05 | 1.47 ± 0.02 |
| 183 | 1.78 ± 0.01 | 1.56 ± 0.02 | 1.66 ± 0.04 | 1.24 ± 0.01 |
| 245 | | | | |
| 182 | 1.94 ± 0.01 | 1.82 ± 0.04 | 1.85 ± 0.03 | 1.48 ± 0.05 |
| 189 | | | | |

TABLE 21-continued

Amount of Benzyl Alcohol that is Recovered from the Formulations when the formulations that are Stored at 25° C. and 40° C. over a 6 Month Period. Highlighted Grey Areas Indicate Time Points Which Are Not Tested Due To Rejection/Omission Of Formulations (N = 3 ± Sd).

| | | | | |
|---|---|---|---|---|
| 184 | | | | |
| 193 | | | | |
| 188 | | | | |
| 195 | 1.88 ± 0.01 | 1.74 ± 0.02 | 1.80 ± 0.01 | 1.48 ± 0.01 |
| 255 | | | | |
| 256 | 1.84 ± 0.01 | 1.88 1.68 0.01 | 1.76 ± 0.01 | 1.46 ± 0.01 |
| Graceway Aldara ® 5% Imiquimod | 1.87 ± 0.02 | 1.65 ± 0.01 | 1.73 ± 0.00 | 1.38 ± 0.03 |
| 110 | 1.87 ± 0.02 | 1.75 ± 0.01 | 1.78 ± 0.04 | 1.72 ± 0.02 |
| 116 | | | | |
| 117 | | | | |
| 250 | 1.74 ± 0.01 | 1.47 ± 0.03 | 1.59 ± 0.02 | 1.12 ± 0.02 |
| 254 | | | | |
| 120 | | | | |
| 121 | | | | |
| 235 | | | | |
| 123 | 1.84 ± 0.01 | 1.59 ± 0.00 | 1.73 ± 0.02 | 1.34 ± 0.01 |
| 124 | | | | |
| 125 | 1.85 ± 0.00 | 1.63 ± 0.04 | 1.73 ± 0.02 | 1.32 ± 0.02 |
| 126 | 2.00 ± 0.04 | 1.70 ± 0.04 | 2.01 ± 0.03 | 1.55 ± 0.02 |
| PBO4 | 1.81 ± 0.01 | 1.39 ± 0.01 | 1.71 ± 0.01 | 1.08 ± 0.02 |
| PBO1 | 1.93 ± 0.03 | 1.55 ± 0.04 | 1.58 ± 0.02 | 1.01 ± 0.03 |
| PBO2 | 2.01 ± 0.13 | 1.61 ± 0.08 | 1.65 ± 0.05 | 1.04 ± 0.08 |
| PBO3 | 2.12 ± 0.04 | 1.70 ± 0.00 | 1.73 ± 0.01 | 1.11 ± 0.00 |

Figure 65A:
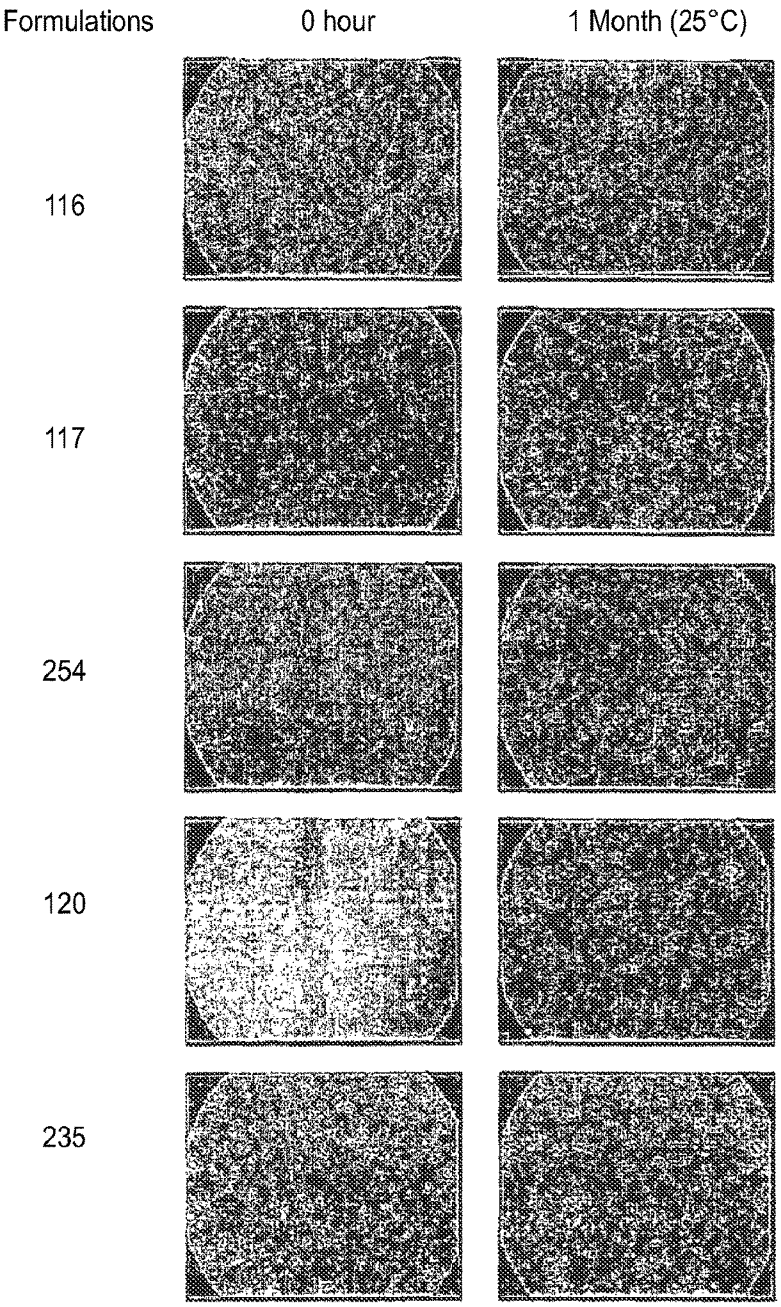
FIGS. 65A-B show microscopic depiction of 10 imiquimod formulations, i.e., formulations, 116, 117, 254, 120, 235, 188, 189, 184, 255, 124, after 1 month stability (t=0 and 1 month)—×400 magnification.
Figure 65B:
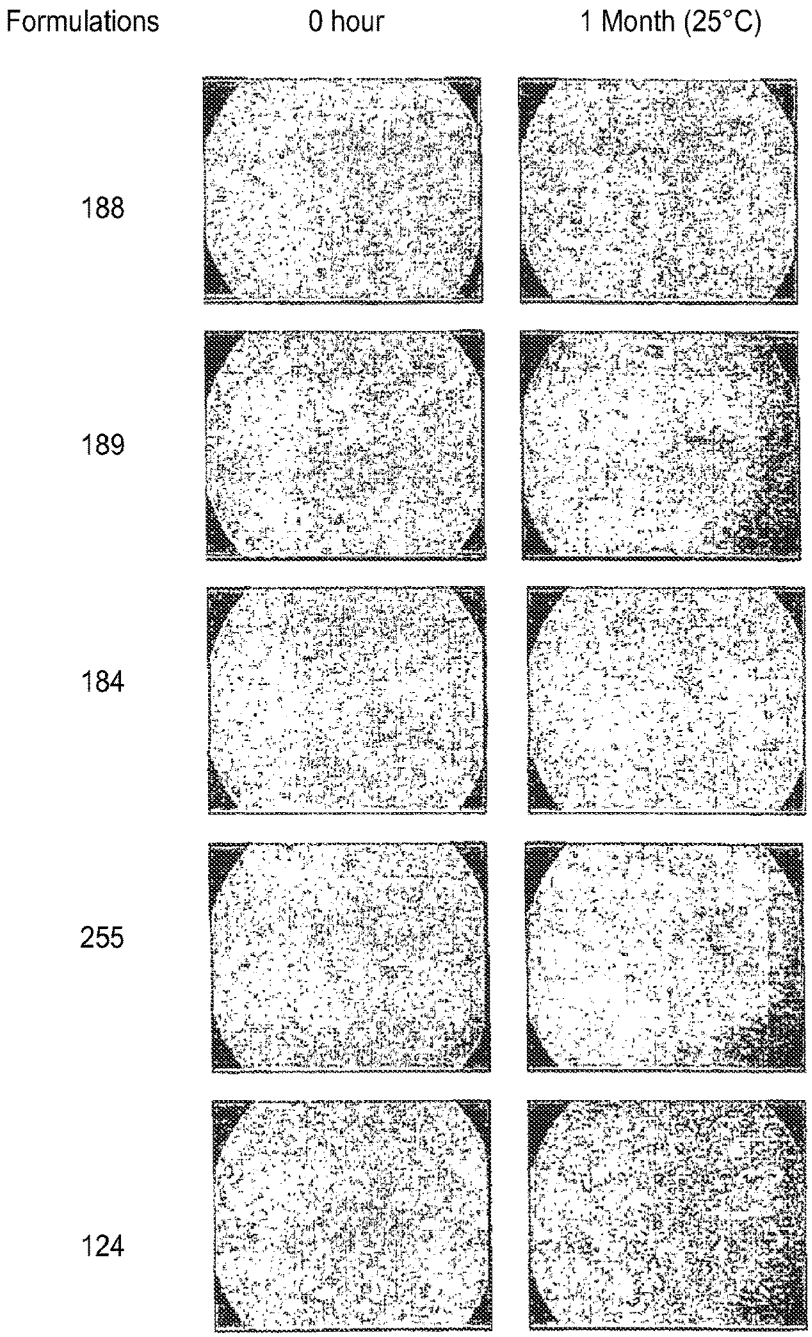

*30° C. sample analysed, as 40° C. had shown signs of phase separation (D) Microscopic Stability of the Formulations In Table 22, there is no change in the particle size in any of the formulations tested at about 25° C. over about a 6 month period. In addition, and with reference to the microscopic photographs presented in FIGS. 63A-C and 64; no crystals are detected. For completeness and reference, the pictures of the formulations rejected after one month stability are shown in FIGS. 65A-B.

TABLE 22

Results of Particle Size of the Formulations when viewed under a Microscope at 25° C. over a 6 Month Period.

| | Particle size (μM) | | | | |
|---|---|---|---|---|---|
| Formulation | T = 0 | t = 1 Month | t = 2 Months | t = 3 Months | t = 6 Months |
| 3M Aldara ® 5% | <10 | <10 | <10 | <10 | <10 |
| GRACEWAY Aldara ® 5% | <10 | <10 | <10 | <10 | <10 |
| 257 (1%) | <10 | <10 | <10 | <10 | <10 |
| 110 | <10 | <10 | <10 | <10 | <10 |
| 250 | <10 | <10 | <10 | <10 | <10 |
| 182 | <10 | <10 | <10 | <10 | <10 |

TABLE 22-continued

Results of Particle Size of the Formulations when viewed under a Microscope at 25° C. over a 6 Month Period.

| | Particle size (μM) | | | | |
|---|---|---|---|---|---|
| Formulation | T = 0 | t = 1 Month | t = 2 Months | t = 3 Months | t = 6 Months |
| 195 | 10 | 10 | 10 | 10 | 10 |
| 123 | 10 | 10 | 10 | 10 | 10 |
| 125 | 10 | 10 | 10 | 10 | 10 |
| 256 | 10 | 10 | 10 | 10 | 10 |
| 197 | 10 | 10 | 10 | 10 | 10 |
| 183 | 10 | 10 | 10 | 10 | 10 |
| 126 | <10 | <10 | <10 | <10 | <10 |
| Pbo1 | <10 | <10 | <10 | <10 | <10 |
| Pbo2 | <10 | <10 | <10 | <10 | <10 |
| Pbo3 | <10 | <10 | <10 | <10 | <10 |
| Pbo4 | <10 | <10 | <10 | <10 | <10 |

(E) Macroscopic Stability of the Formulations

In Table 23, there are no obvious physical changes in the formulations that are tested over the six month stability program, with the exception of the placebos, which become notably less viscous. See also Tables 24-26.

TABLE 23

Macroscopic Appearance when Imiquimod Formulations are stored at about 25° C. over about a 6 Month Period.

| | Appearance spatula Test (25° C. sample only) | | | | | Visual Viscosity (25° C. sample only) | | | | |
|---|---|---|---|---|---|---|---|---|---|---|
| Imiquimod Formulation | t = 0 | t = 1 month | t = 2 months | t = 3 months | t = 6 months | t = 0 | t = 1 month | t = 2 months | t = 3 months | t = 6 months |
| 3M Aldara ® 5% Imiquimod | Glossy, very smooth | Glossy, very smooth | Glossy, very smooth | Glossy, very smooth | Glossy, very smooth | High | Medium-High | Medium | Medium-High | Medium |

TABLE 23-continued

Macroscopic Appearance when Imiquimod Formulations are stored at about 25° C. over about a 6 Month Period.

| Imiquimod Formulation | Appearance spatula Test (25° C. sample only) t = 0 | t = 1 month | t = 2 months | t = 3 months | t = 6 months | Visual Viscosity (25° C. sample only) t = 0 | t = 1 month | t = 2 months | t = 3 months | t = 6 months |
|---|---|---|---|---|---|---|---|---|---|---|
| Graceway Aldara ® 5% Imiquimod | Glossy, very smooth | Glossy, very smooth | Glossy, very smooth | Glossy, very smooth | Glossy, very smooth | High | High | Medium-High | High | Medium |
| 257 (1%) | Glossy and smooth | Glossy and smooth | Glossy, very smooth | Glossy, very smooth | Glossy, very smooth | Medium | Medium-High | Medium-High | Medium-High | Low viscosity |
| 110 | Glossy, very slightly textured | Glossy, very slightly textured | Glossy, slightly textured | Glossy, slightly textured | Glossy, slightly textured | High | High | High | High | Medium |
| 250 | Glossy and smooth, some aeration | Glossy and textured | Glossy, Very slightly textured | Glossy, Very slightly textured | Glossy, Very slightly textured | Medium | Medium-High | Medium-High | Medium-High | Medium |
| 182 | Very glossy and smooth | Very glossy and smooth | Very glossy and smooth | Very glossy and smooth | Very glossy and smooth | High | Medium-High | Medium-High | Medium-High | High |
| 195 | Glossy, slightly textured | Glossy, slightly textured | Glossy, very slightly textured | Glossy, slightly textured | Glossy, slightly textured | High | High | Medium-High | Medium-High | High |
| 123 | Glossy and smooth | Glossy, slightly textured | Glossy, slightly textured, smoothed out | Glossy, slightly textured, smoothed out | Glossy, slightly textured | Medium-High | Medium-High | Medium-High | High | Medium |
| 124 | Glossy and smooth | Glossy and smooth | Glossy, smooth with slight aeration | Glossy, smooth | Glossy, slightly textured | Medium | Medium | Medium | Medium-High | Low |
| 256 | Glossy, slightly textured | Glossy, slightly textured | Glossy, slightly textured | Glossy, slightly textured | Glossy, slightly textured | Medium-High | Medium-High | Medium-High | Medium-High | High |
| 197 | Glossy, slightly textured | Glossy, very slightly textured | Glossy and textured | Glossy and slightly textured | Glossy and slightly textured | Medium | Medium-High | High | High | High |
| 183 | Glossy, smooth slight aeration | Glossy and smooth | Glossy and smooth | Glossy and smooth | Glossy and smooth | High | Medium-High | Medium-High | Medium-High | Low |
| 126 | Glossy, very slightly textured | Smooth, slightly textured, glossy | Glossy and smooth | Slightly textured, sheen | Glossy | Medium | Medium | Medium | Medium | Low viscosity |
| Pbo1 | Glossy and smooth | Very glossy and smooth | Very glossy and smooth | Very glossy and smooth | Glossy and smooth | Low | Medium-Low | Medium-Low | Low | Low |
| Pbo2 | Glossy and smooth | Glossy and smooth | Glossy and smooth | Glossy, very slightly textured | Glossy and smooth | Medium-Low | Medium | Medium-Low | Medium-Low | Low |
| Pbo3 | Glossy and smooth | Glossy and smooth | Glossy, very slightly textured but smoothed out | Glossy, very slightly textured but smoothed out | Glossy and smooth | Low | Medium-Low | Medium-Low | Medium-Low | Medium |
| Pbo4 | Glossy and smooth | Glossy and smooth | Glossy and smooth | Glossy and smooth | Smooth cream high sheen | Medium-Low | Medium | Medium-Low | Low | Low |

TABLE 24

Stability Data for 10 Formulations, i.e., Formulations 116, 117, 120, 124, 188, 184, 189, 235, 254 and 255, rejected after 1 Month Stability, with respect to the Spatula Test, Visual Viscosity and Particle Size (as determined by microscopy).

| | Spatula Test | | Visual Viscosity | | Majority of particle size (μM) | |
|---|---|---|---|---|---|---|
| Formulation | T = 0 | T = 1 Month | T = 0 | T = 1 Month | T = 0 | T = 1 Month |
| 116 | Glossy, textured | Glossy, textured | Medium | Medium-High | 10 | 10 |
| 117 | Glossy, slightly textured | Glossy, slightly textured | Medium-High | Medium-High | <10 | <10 |
| 254 | Smooth with matt appearance | Smooth, matt | High | Medium-High | <10 | <10 |
| 120 | Smooth, matt appearance, some aeration | Smooth, matt | Very High | Very High | <10 | <10 |
| 235 | Glossy, textured but does smooth out | Glossy, very slightly textured but does smooth out | Medium-Low | Medium | <50 | <50 |
| 188 | Glossy and textured | Glossy and textured | Medium-Low | High | <10 | <10 |
| 189 | Glossy, very slightly textured | Glossy, slightly textured | High | Very High | <10 | <10 |
| 184 | Glossy, slightly textured | Glossy, slightly textured | High | High | <10 | <10 |
| 255 | Glossy and smooth | Glossy and smooth | High | High | 10 | <10 |
| 124 | Glossy, very slightly textured | Glossy, very slightly textured | Medium-High | Medium-High | <10 | <10 |

TABLE 25 pH Stability Data for 10 Imiquimod Formulations, i.e., Formulations 116, 117, 120, 124, 188, 184, 189, 235, 254 and 255, Rejected after 1 Month Stability.

| | pH | |
|---|---|---|
| Formulation Identity | T = 0 | T = 1 Month |
| 116 | 5.0 | 4.7 |
| 117 | 4.5 | 4.5 |
| 254 | 4.7 | 4.7 |
| 120 | 4.5 | 4.5 |
| 235 | 4.5 | 4.5 |
| 188 | 4.7 | 4.7 |
| 189 | 4.7 | 4.7 |
| 184 | 4.7 | 4.7 |
| 255 | 4.5 | 4.5 |
| 124 | 4.5 | 4.5 |

TABLE 26

Viscosity Stability Data for 10 Imiquimod Formulations, i.e., Formulations 116, 117, 120, 124, 188, 184, 189, 235, 254 and 255, Rejected after 1 Month Stability

| | Cross- | | Brookfield (cps) | | Bohlin Viscosity (cps) | |
|---|---|---|---|---|---|---|
| Formulation Identity | over T = 0 | G' T = 0 | T = 0 | T = 1 Month | T = 0 | T = 1 Month |
| 116 | 9.0 | 478 | 601867 | 63500 | 15350 | 13300 |
| 117 | 14.0 | 1151 | 1216667 | 1281000 | 17250 | 15600 |
| 254 | 10.3 | 1399 | 1476667 | 1423000 | 19050 | 19000 |
| 120 | 15.3 | 884 | 1416667 | 1393000 | 20250 | 20900 |
| 235 | 6.0 | 134 | 245333 | 313000 | 6350 | 5700 |
| 188 | 14.0 | 708 | 1141333 | 1254000 | 20350 | 20750 |
| 189 | 34.8 | 1037 | 1344333 | 1463000 | 18700 | 18550 |
| 184 | 23.0 | 1054 | 1475667 | 1350000 | 20200 | 21600 |
| 255 | 16.0 | 1488 | 2483333 | 1334000 | 21150 | 25150 |
| 124 | 7.0 | 561 | 849000 | 663000 | 14400 | 14250 |

(F) Brookfield Viscosity Stability Results of Formulations

In Table 27, Brookfield viscosity measurements are notoriously variable and, as such, there are fluctuations in the measurements of the formulations over about a 6 month period when stored at about 25° C. Variations in results are further observed if the spindle or the speed of the spindle rotation is altered. Although the majority of the formulations are measured using the same settings and spindle; the placebo formulations (Pbo1, Pbo2, Pbo3 and Pbo4) result in torque measurements below the threshold required for accurate measurements and subsequently readings are inaccurate. Attempts are made to change the settings and spindles; however, results are vastly different and thus unreliable. See also Tables 24-26.

the viscosity falls by approximately 50%. All formulations are within the range of the specifications for the Aldara® 5% imiquimod cream formulation (2000 to 35,000 cps). See also Tables 24-26.

TABLE 27

Viscosity and Rheology Measurements of Imiquimod Formulations stored at 25° C. over a 6 Month Period.

| Formulation Identity | G(Pa) t = 0 | Crossover (o) t = 0 | Brookfield (cPs) t = 0 | t = 1 Month | t = 2 Months | t = 3 Months | t = 6 Months | Bohlin Viscosity (cPs) (based on 3M method) t = 0 | t = 1 Month | t = 2 Months | t = 3 Months | t = 6 Months |
|---|---|---|---|---|---|---|---|---|---|---|---|---|
| 3M Aldara ® 5% Imiquimod | 507 | 12.5 | 660333 | 623000 | 337000 | 428833 | 166233 | 15700 | 17300 | 17600 | 13296 | 12833 |
| Graceay Aldara ® 5% Imiquimod | 716 | 10.5 | 1108667 | 1109000 | 587667 | 768566 | 252033 | 18250 | 20250 | 19900 | 18697 | 15100 |
| 257 (1%) | 352 | 10.52 | 642667 | 600000 | 220333 | 351566 | * | 13600 | 15050 | 11500 | 6075 | 3139 |
| 110 | 782 | 11.5 | 87100 | 119000 | 782333 | 619300 | 366067 | 16250 | 16400 | 18000 | 16368 | 14076 |
| 250 | 320 | 9 | 695333 | 816000 | 557333 | 394166 | 141400 | 13700 | 16400 | 14950 | 10587 | 5890 |
| 182 | 702 | 8.5 | 693067 | 1097000 | 904667 | 523033 | 273233 | 18050 | 17850 | 18550 | 16820 | 13691 |
| 195 | 692 | 15 | 1141333 | 1293000 | 779333 | 618133 | 381700 | 17000 | 17600 | 16500 | 16208 | 14696 |
| 123 | 510 | 10.8 | 804000 | 773000 | 386333 | 701500 | 199933 | 15800 | 16250 | 15200 | 13095 | 9587 |
| 125 | 485 | 8.5 | 603000 | 707000 | 429667 | 412133 | 127067 | 14900 | 17050 | 15300 | 12069 | 8301 |
| 256 | 667 | 7.3 | 1126000 | 958000 | 697667 | 757523 | 249500 | 19400 | 18300 | 18750 | 15453 | 12379 |
| 197 | 646 | 14 | 1082667 | 1377000 | 613667 | 607366 | 274400 | 17750 | 17850 | 17600 | 15861 | 13524 |
| 183 | 719 | 10.3 | 693333 | 839000 | 596000 | 332900 | 188000 | 18700 | 19100 | 18600 | 15906 | 12120 |
| 126 | AP | . . . | 430100 | 235066 | 228104 | 212500 | 105720 | 16783 | 12739 | 14749 | 10856.5 | 8789.5 |
| PBO1 | 306 | 11 | 85000 | * | • | * | * | 12100 | 14450 | 7500 | 7969 | 2508.3 |
| PBO2 | 263 | 13 | 79500 | . | | | . | 14200 | 13950 | 9100 | 6452.5 | 2617.6 |
| PBO3 | 305 | 11.5 | 117000 | | | | | 12200 | 13850 | 9000 | 8395 | 3256.5 |
| PBO4 | | | 227800 | • | | | | 10350 | 7953 | 5511 | 3550 | 2247 |

• results un-reliable and not presented as the torque was out of range (due to low viscosity) for the Brookfield viscometer using the settings and spindle used for all the other samples. Alternative spindles and settings were investigated; however, the results were vastly different than previous readings.
** no recorded measurements, as test was only required for initial formulations choice and development.

(G) Bohlin Viscosity Results

Also as shown in Table 27, the Bohlin viscosity results are in contrast to the results of the Brookfield viscosity and appear to be more consistent for all formulations. A fall in the viscosity is observed for 257 (1%) and placebo formulations, Pbo1-4, over the 6 month stability study, whereby (H) pH Stability of Formulations In Table 28, it reports that the specification for all formulations that are tested, fall within the Aldara® 5% imiquimod cream specifications (pH 4.0 to 5.5). A slight variation in pH is observed over the 6 month period for all of the formulations. See also Tables 24-26.

TABLE 28 ph for Imiquimod Formulations when Stored at about 25° C. and about 40° C. over a 6 Month Period. Grey Areas Indicate No Test Is Performed.

| Formulation | pH t = 0 25° C. | t = 1 month 25° C. | t = 1 month 40° C. | t = 2 months 25° C. | t = 2 months 40° C. | t = 3 months 25° C. | t = 3 months 40° C. | t = 6 months 25° C. | t = 6 months 40° C. |
|---|---|---|---|---|---|---|---|---|---|
| 3M Aldara ® 5% Imiquimod | 4.5 | 4.5 | | 4.5 | 4.5 | 4.5 | 4.7 | 4.3 | 4.1 |
| Graceway Aldara ® 5% Imiquimod | 4.5 | 4.5 | | 4.5 | 4.5 | 4.5 | 4.5 | 4.3 | 4.5 |
| 257 (1%) | 4.2 | 4.5 | | 4.5 | 4.5 | 4.5 | 4.1 | 4.1 | 3.9 |
| 110 | 5 | 4.7 | | 4.7 | 4.7 | 4.7 | 4.4 | 4.5 | 4.3* |
| 250 | 4.2 | 4.2 | | 4.2 | 4.5 | 4.2 | 4 | 4.2 | 4.1 |
| 182 | 4.5 | 4.5 | | 4.5 | 4.5 | 4.5 | 4.6 | 4.3 | 4.3 |
| 195 | 4.7 | 4.5 | | 4.5 | 4.5 | 4.5 | 4.7 | 4.5 | 4.5 |
| 123 | 4.5 | 4.7 | | 4.7 | 4.7 | 4.7 | 4.3 | 4.1 | 4.3 |
| 125 | 4.5 | 4.5 | | 4.5 | 4.5 | 4.5 | 4.2 | 4.1 | 4.1 |
| 256 | 4.7 | 4.7 | | 4.7 | 4.7 | 4.7 | 4.4 | 4.3 | 4.3 |
| 197 | 4.5 | 4.7 | | 4.7 | 4.7 | 4.7 | 4.6 | 4.5 | 4.3 |
| 183 | 4.5 | 4.5 | | 4.5 | 4.5 | 4.5 | 4.2 | 4.5 | 4.1 |
| 126 | 4.2 | 4.3 | 4.3 | 4.3 | 4.3 | 4.3 | 4.3 | 4.1 | 4.1 |

TABLE 28-continued ph for Imiquimod Formulations when Stored at about 25° C. and about 40° C. over a 6 Month Period. Grey Areas Indicate No Test Is Performed.

| | pH | | | | | | | | |
|---|---|---|---|---|---|---|---|---|---|
| | t = 0 | t = 1 month | | t = 2 months | | t = 3 months | | t = 6 months | |
| Formulation | 25° C. | 25° C. | 40° C. | 25° C. | 40° C. | 25° C. | 40° C. | 25° C. | 40° C. |
| Pbo1 | 4.5 | 4.5 | | 4.5 | 4.5 | 4.2 | 4.5 | 4.0 | 4.0 |
| Pbo2 | 4.5 | 4.5 | | 4.2 | 4.2 | 4.2 | 4.2 | 4.1 | 4.1 |
| Pbo3 | 4.5 | 4.5 | | 4.5 | 4.2 | 4.2 | 4.2 | 4.2 | 4.2 |
| Pbo4 | 4.5 | 4.2 | 4.5 | 4.2 | 4.2 | 4.1 | 4.1 | 4.0 | 4.0 |

*30° C. sample analyzed as the 40° C. sample had phase separated (I) Preservative Efficacy Test Table 29 reports final viable counts of organism inoculations that are added to the formulations.

TABLE 29

Total Viable Counts that are obtained for the Organism Inoculates into the Imiquimod Formulations

| Organism | Mimi for 182 and 110 | Cfu/ml for 126 and Pbo4 |
|---|---|---|
| *Staphylococcus aureus* | 2.4E+08 | 3.1E+08 |
| *Escherichia coli* | 1.7E+08 | 2.1E+08 |
| *Pseudomonas aeruginosa* | 9.0E+07 | 1.1E+08 |
| *Candida albicans* | 1.0E+08 | 1.1E+08 |
| *Aspergillus niger* | 1.7E+07 | 1.6E+08 |

Table 30 shows colony forming unit count (cfu) for *Staphylococcus aureus* after PET validation is performed on two formulations stored at about 2-8° C.

TABLE 30

Viable counts that are obtained for *Staphylococcus aureus* that are Inoculated Formulations after PET Validation

| Imiquimod Formulation | Suspension fluid | Dilution | Viable count (cfu/ml) |
|---|---|---|---|
| 110 | D/E broth | 1 ml in 9 ml | 2.20E+08 |
| | | 0.1 ml in 0.9 ml | 2.80E+08 |
| | Ringer's solution | 1 ml in 9 ml | 1.00E+03 |
| | | 0.1 ml in 0.9 ml | 1.50E+03 |
| 182 | D/E broth | 1 ml in 9 ml | 2.30E+08 |
| | | 0.1 ml in 0.9 ml | 2.60E+08 |
| | Ringer's solution | 1 ml in 9 ml | 1.00E+03 |
| | | 0.1 ml in 0.9 ml | 1.40E+03 |

The preservative efficacy test ("PET") is a procedure used to demonstrate antimicrobial activity of a formulation with respect to the preservative system used. In Table 31, cell counts that are recovered from the inoculated formulations at various time points are reported. The data shows that sufficient log reductions are present in the formulations at about 2-8° C. and about 40° C. and meet the requirements that are specified in both the USP and EP.

TABLE 31

Colony Forming Unit Counts that are recovered (Cfu/Ml) for Each Organism from the Imiquimod Formulations, over 28 Days

| | | Organisms recovered- (cfu/ml) | | | | | | | Pass/ |
|---|---|---|---|---|---|---|---|---|---|
| Formulation | Organism | 0 h | 24 h | 48 h | 7 days | 19 days | 21 days | 28 days | Fail |
| Pbo4 | *S. aureus* | 3.10E+05 | 0.00E+00 | 0.00E+00 | 0.00E+00 | 0.00E+00 | 0.00E+00 | 0.00E+00 | PASS |
| STORAGE: | *E. coil* | 5.00E+03 | 0.00E+00 | 0.00E+00 | 0.00E+00 | 0.00E+00 | 0.00E+00 | 0.00E+00 | PASS |
| 2-8° C. | *Ps. aeruginosa* | 9.00E+03 | 0.00E+00 | 0.00E+00 | 0.00E+00 | 0.00E+00 | 0.00E+00 | 0.00E+00 | PASS |
| | *a albicans* | 5.00E+04 | 1.80E+03 | 0.00E+00 | 0.00E+00 | 0.00E+00 | 0.00E+00 | 0.00E+00 | PASS |
| | *A. niger* | 1.60E+05 | 6.00E+03 | 2.50E+03 | 0.00E+00 | 0.00E+00 | 0.00E+00 | 0.00E+00 | PASS |
| Pbo4 | *S. aureus* | 1.70E+06 | 0.00E+00 | 0.00E+00 | 0.00E+00 | 0.00E+00 | 0.00E+00 | 0.00E+00 | PASS |
| STORAGE: | *E. coil* | 6.00E+03 | 0.00E+00 | G.00E+00 | 0.00E+00 | 0.00E+00 | 0.00E+00 | 0.00E+00 | PASS |
| 40° C. | *Ps. aeruginosa* | 1.30E+04 | 0.00E+00 | 0.00E+00 | 0.00E+00 | 0.00E+00 | 0.00E+00 | 0.00E+00 | PASS |
| | *C. albicans* | 2.60E+04 | 4.10E+03 | 1.30E+03 | 0.00E+00 | 0.00E+00 | 0.00E+00 | 0.00E+00 | PASS |
| | *A. niger* | 3.00E+05 | 1.70E+04 | 3.30E+03 | 0.00E+00 | 0.00E+00 | 0.00E+00 | 0.00E+00 | PASS |
| 126 | *S. aureus* | 5.70E+04 | 0.00E+00 | 0.00E+00 | 0.00E+00 | 0.00E+00 | 0.00E+00 | 0.00E+00 | PASS |
| STORAGE: | *E. coil* | 1.20E+06 | 0.00E+00 | 0.00E+00 | 0.00E+00 | 0.00E+00 | 0.00E+00 | 0.00E+00 | PASS |
| 2-8° C. | *Ps. aeruginosa* | 1.40E+04 | 0.00E+00 | 0.00E+00 | 0.00E+00 | 0.00E+00 | 0.00E+00 | 0.00E+00 | PASS |
| | *C. albicans* | 3.50E+04 | 5.00E+03 | 4.00E+02 | 0.00E+00 | 0.00E+00 | 0.00E+00 | 0.00E+00 | PASS |
| | *A. niger* | 1.00E+05 | 2.10E+04 | 2.50E+03 | 0.00E+00 | 0.00E+00 | 0.00E+00 | 0.00E+00 | PASS |
| 126 | *S. aureus* | 2.10E+04 | 0.00E+00 | 0.00E+00 | 0.00E+00 | 0.00E+00 | 0.00E+00 | 0.00E+00 | PASS |
| STORAGE: | *E. coil* | 5.00E+05 | 0.00E+00 | 0.00E+00 | 0.00E+00 | 0.00E+00 | 0.00E+00 | 0.00E+00 | PASS |
| 40° C. | *Ps. aeruginosa* | 1.50E+04 | 0.00E+00 | 0.00E+00 | 0.00E+00 | 0.00E+00 | 0.00E+00 | 0.00E+00 | PASS |
| | *C. albicans* | 3.80E+04 | 3.60E+03 | 2.50E+03 | 0.00E+00 | 0.00E+00 | 0.00E+00 | 0.00E+00 | PASS |
| | *A. niger* | 1.00E+05 | 2.90E+03 | 1.60E+03 | 0.00E+00 | 0.00E+00 | 0.00E+00 | 0.00E+00 | PASS |

TABLE 31-continued

| Colony Forming Unit Counts that are recovered (Cfu/Ml) for Each Organism from the Imiquimod Formulations, over 28 Days | | | | | | | | | | |
|---|---|---|---|---|---|---|---|---|---|---|
| | | Organisms recovered- (cfu/ml) | | | | | | | Pass/ |
| Formulation | Organism | 0 h | 24 h | 48 h | 7 days | 19 days | 21 days | 28 days | Fail |
| 110 | *S. aureus* | 1.00E+06 | 0.00E+00 | 0.00E+00 | 0.00E+00 | 0.00E+00 | 0.00E+00 | 0.00E+00 | PASS |
| STORAGE: | *E. coli* | 7.00E+05 | 0.00E+00 | 0.00E+00 | 0.00E+00 | 0.00E+00 | 0.00E+00 | 0.00E+00 | PASS |
| 2 - FPG | *Ps. aeruginosa* | 8.00E+04 | 0.00E+00 | 0.00E+00 | 0.00E+00 | 0.00E+00 | 0.00E+00 | 0.00E+00 | PASS |
| | *C. albicans* | 8.00E+05 | 2.60E+04 | 7.00E+03 | 7.00E+01 | 0.00E+00 | 0.00E+00 | 0.00E+00 | PASS |
| | *A. niger* | 6.00E+04 | 9.00E+04 | 2.30E+04 | 7.00E+03 | 3.70E+02 | 0.00E+00 | 0.00E+00 | PASS |
| 110 | *S. aureus* | 6.00E+05 | 0.00E+00 | 0.00E+00 | 0.00E+00 | 0.00E+00 | 0.00E+00 | 0.00E+00 | PASS |
| STORAGE: | *E. coil* | 8.00E+04 | 0.00E+00 | 0.00E+00 | 0.00E+00 | 0.00E+00 | 0.00E+00 | 0.00E+00 | PASS |
| 40° C. | *Ps. aeruginosa* | 7.00E+05 | 0.00E+00 | 0.00E+00 | 0.00E+00 | 0.00E+00 | 0.00E+00 | 0.00E+00 | PASS |
| | *C. albicans* | 1.60E+05 | 1.50E+04 | 4.00E+03 | 2.20E+02 | 0.00E+00 | 0.00E+00 | 0.00E+00 | PASS |
| | *A. niger* | 7.00E+04 | 6.00E+04 | 2.50E+04 | 1.90E+04 | 1.90E+02 | 0.00E+00 | 0.00E+00 | PASS |
| 182 | *S. aureus* | 1.70E+06 | 0.00E+00 | 0.00E+00 | 0.00E+00 | 0.00E+00 | 0.00E+00 | 0.00E+00 | PASS |
| STORAGE: | *E coli* | 1.70E+06 | 0.00E+00 | 0.00E+00 | 0.00E+00 | 0.00E+00 | 0.00E+00 | 0.00E+00 | PASS |
| 2-8° C. | *Ps. aeruginosa* | 7.00E+05 | 0.00E+00 | 0.00E+00 | 0.00E+00 | 0.00E+00 | 0.00E+00 | 0.00E+00 | PASS |
| | *C. albicans* | 3.00E+05 | 2.10E+04 | 1.90E+03 | 3.00E+03 | 0.00E+00 | 0.00E+00 | 0.00E+00 | PASS |
| | *A niger* | 4.00E+05 | 5.00E+03 | 2.40E+03 | 3.00E+03 | 0.00E+00 | 0.00E+00 | 0.00E+00 | PASS |
| 182 | *S. aureus* | 1.50E+06 | 0.00E+00 | 0.00E+130 | 0.00E+00 | 0.00E+00 | 0.00E+00 | 0.00E+00 | PASS |
| STORAGE: | *E. coil* | 1.10E+06 | 0.00E+00 | 0.00E+00 | 0.00E+00 | 0.00E+00 | 0.00E+00 | 0.00E+00 | PASS |
| 40° C. | *Ps. aeruginosa* | 6.00E+05 | 0.00E+00 | 0.00E+00 | 0.00E+00 | 0.00E+00 | 0.00E+00 | 0.00E+OG | PASS |
| | *C. albicans* | 7.00E+05 | 3.00E+04 | 3.00E+03 | 7.00E+03 | 0.00E+00 | 0.00E+00 | 0.00E+00 | PASS |
| | *A. niger* | 7.00E+05 | 6.00E+03 | 2.70E+03 | 1.70E+03 | 1.20E+02 | 0.00E+00 | 0.00E+00 | PASS |

(J) Test Item Release Studies Through Synthetic Membranes

Figure 58:
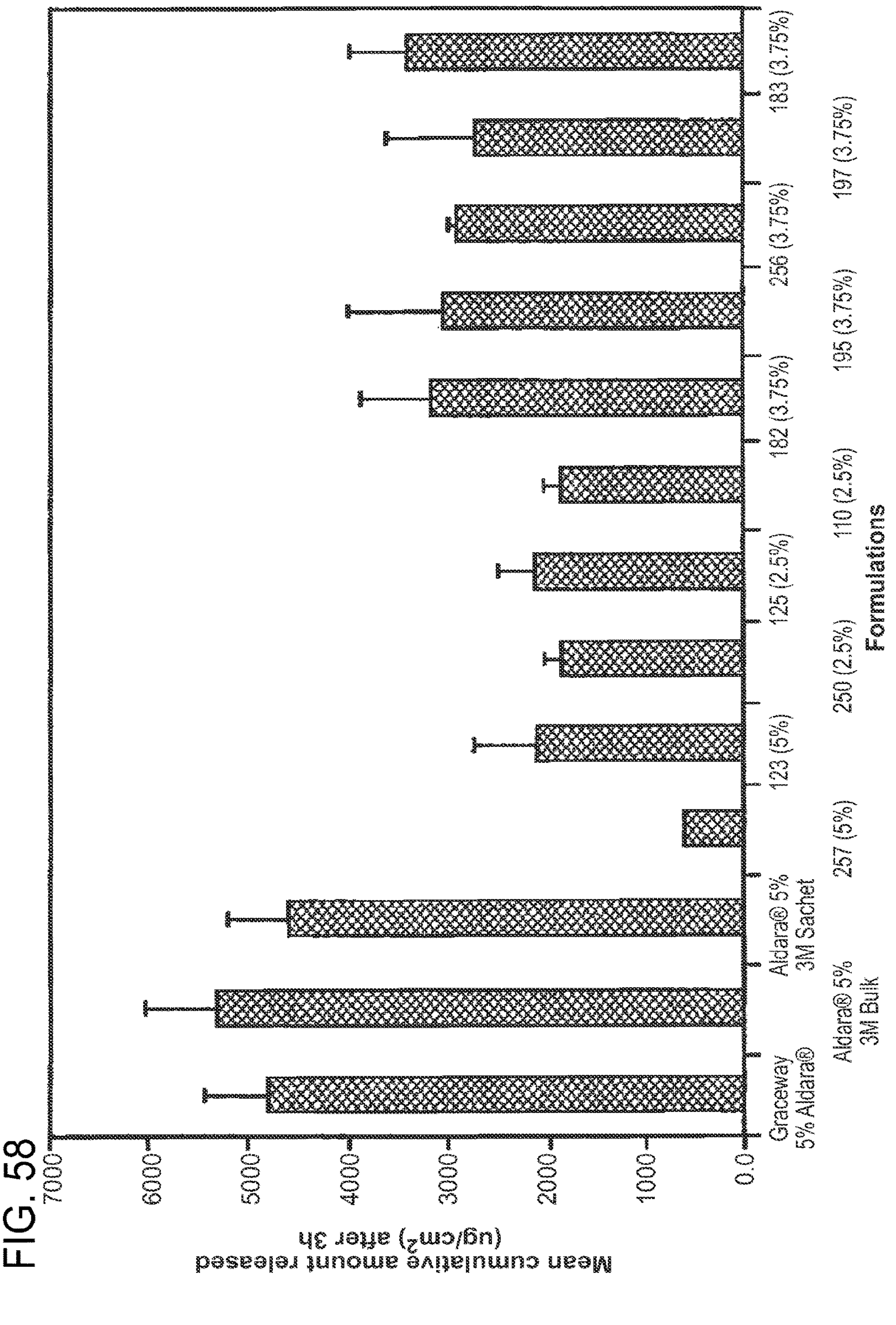
FIG. 58 shows a comparison of the mean cumulative amount of imiquimod released (μg/cm2) after about 3 h for the membrane release studies (for all the formulations selected for Full thickness skin permeation and stability studies) (mean±sd, where n=4)
Figure 59:
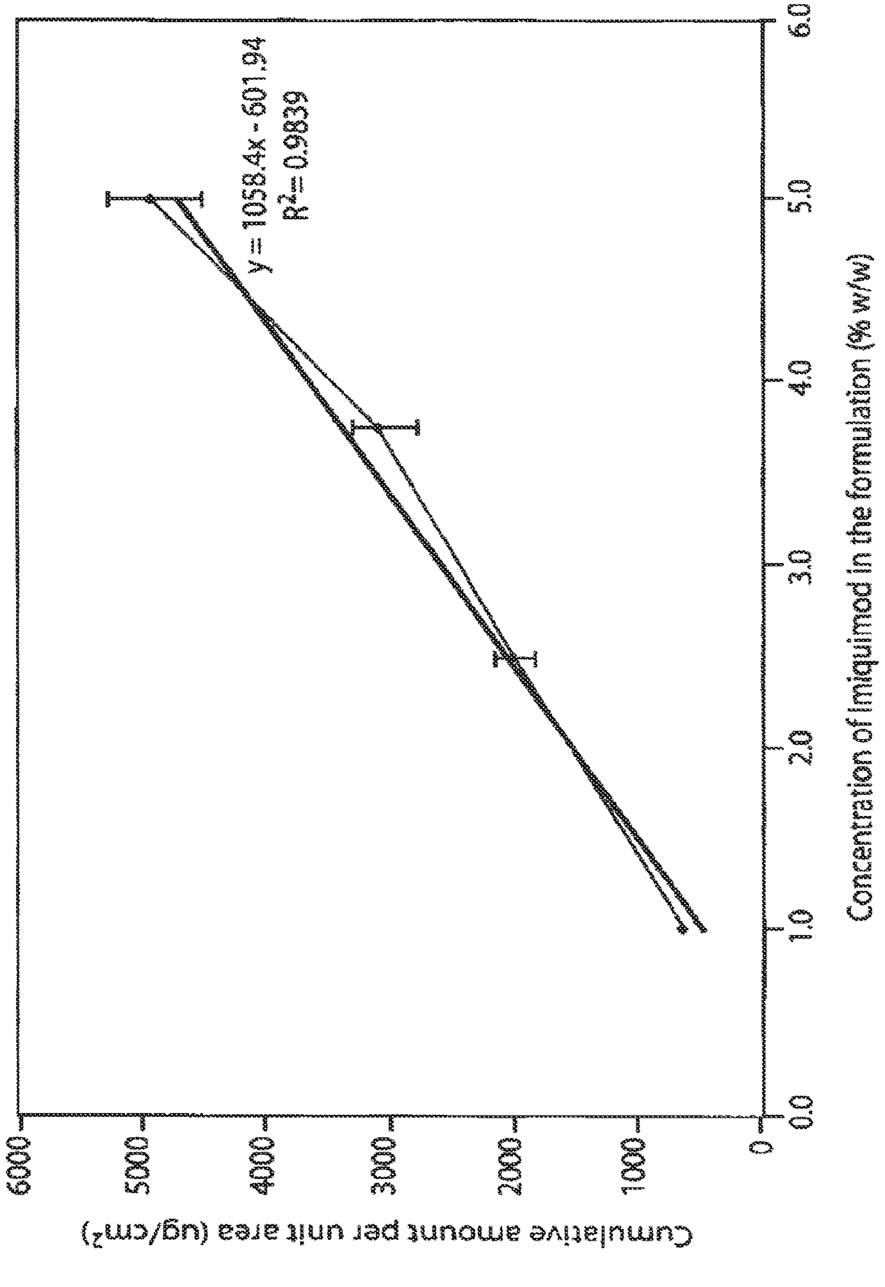
FIG. 59 shows a comparison of the average total cumulative report released (μg/cm2) after 3 h for each concentration of imiquimod in the formulations that are tested (mean □ sd, where n=4 for 1%, n=16 for 2.5%, n=20 for 3.75% and n=12 for 5%)

In FIG. 58, it indicates that there is a trend between the concentrations of imiquimod present in the formulation as compared to the amount that is released. This is supported by the results presented in FIG. 59 and the corresponding statistical analysis, where it can be seen that that the higher the imiquimod concentration in the formulation, the greater the release of imiquimod. However, formulation 183 (3.75% w/w imiquimod) gives a statistically (at a 95% confidence level) greater cumulative release of imiquimod when it is compared to the 2.5% w/w formulations. All of the 5% w/w formulations, i.e., Aldara® 5% imiquimod cream batch, Aldara® 5% imiquimod cream Graceway batch, and Aldara® 5% imiquimod cream Sachet), result in significantly ($p<0.05$) higher amounts of imiquimod released over a 3 h time period in comparison to 1%, 2.5% and 3.75% w/w imiquimod formulations. There is no statistical difference ($p>0.05$) in the total cumulative amount of imiquimod that is released from any of the 3.75% w/w imiquimod formulations; likewise there is also no statistical difference ($p<0.05$) from the 2.5% w/w imiquimod formulations.

ANOVA statistical analysis (95% confidence level): mean total cumulative amount that is released (μg/$cm^2$) after 3 h (from results that are presented in FIG. 58):

| Source | DF | SS | MS | F | P |
|---|---|---|---|---|---|
| Formulation | 12 | 86439222 | 7203268 | 19.40 | 0.000 |
| Error | 39 | 14484370 | 371394 | | |
| Total | 51 | 100923592 | | | |

S = 609.4

R-Sq = 85.65%

R-Sq (adj) = 81.23%

| | | | | Individual 95% CIs For Mean Based on Pooled StDev |
|---|---|---|---|---|
| Level | N | Mean | St. Dev | +---------------+---------------+--------------+---------- |
| Aldara 3M 5% | 4 | 5332.8 | 734.2 | (----*---) |
| Aldara sachet | 4 | 4605.5 | 626.9 | (---*---) |
| 110 | 4 | 1862.8 | 185.9 | (---*----) |
| 250 | 4 | 1845.6 | 206.4 | (---*---) |
| 182 | 4 | 3161.3 | 774.9 | (---*---) |
| 195 | 4 | 3046.2 | 988.2 | (---*---) |

-continued

| Individual 95% CIs For Mean Based on Pooled StDev | | | | |
|---|---|---|---|---|
| Level | N | Mean | St. Dev | +----------------+---------------+--------------+---------- |
| 123 | 4 | 2094.9 | 674.6 | (---*---) |
| 125 | 4 | 2134.1 | 369.0 | (---*---) |
| 256 | 4 | 2918.7 | 59.5 | (---*----) |
| 197 | 4 | 2766.0 | 929.1 | (---*----) |
| 183 | 4 | 3453.2 | 564.4 | (---*---) |
| MedPharm Aldara | 4 | 4813.3 | 660.7 | (---*---) |
| 257% | 4 | 586.9 | 170.2 | (---*---) |
| | | | | +---------------+--------------+--------------+------------ |
| | | | | 0 1500 3000 4500 |

Pooled StDev = 609.4

ANOVA statistical analysis (95% confidence level): mean total cumulative amount that is released (μg/$cm^2$) after 3 h for each concentration of imiquimod in the formulations that are tested (from results that are presented in FIG. 59):

| Source | DF | SS | MS | F | P |
|---|---|---|---|---|---|
| Formulation | 3 | 83957708 | 27985903 | 79.18 | 0.000 |
| Error | 48 | 16965878 | 353456 | | |
| Total | 51 | 100923586 | | | |

S = 594.5
R-Sq = 83.19%
R-Sq (adj) = 82.14%

| Individual 95% CIs For Mean Based on Pooled StDev | | | | |
|---|---|---|---|---|
| Level | N | Mean | St. Dev | +----------------+---------------+--------------+---------- |
| 1% | 4 | 586.9 | 170.2 | (---*---) |
| 2.50% | 16 | 1984.4 | 389.9 | (-*-) |
| 3.75% | 20 | 3069.1 | 702.3 | (*-) |
| 5.00% | 12 | 4917.2 | 689.4 | (--*-) |
| | | | | +---------------+--------------+--------------+------------ |
| | | | | 0 1500 3000 4500 |

Pooled StDev = 594.5

Figure 66:
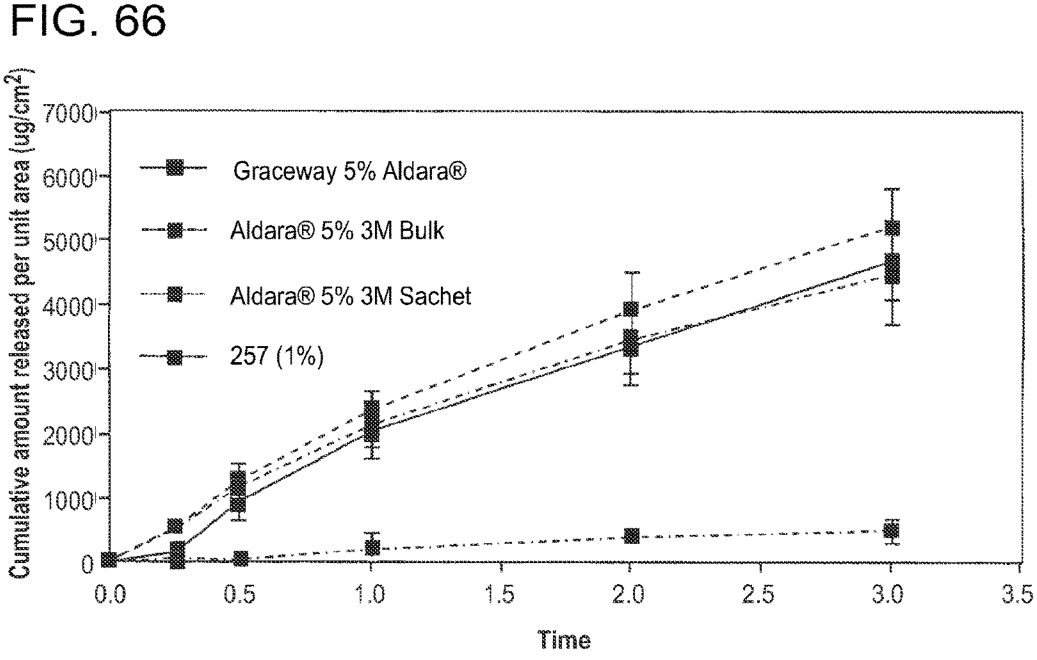
FIG. 66 shows a comparison of the mean amount of imiquimod that is released (μg/cm2) over a 3 hour period for the 3M Aldara® imiquimod cream 1 kg batch, the 3M Aldara® imiquimod cream sachet, the Graceway 3M Aldara® imiquimod cream 1 kg batch and formulation 257, a 1% Imiquimod formulation (mean±sd, where n=4)
Figure 67:
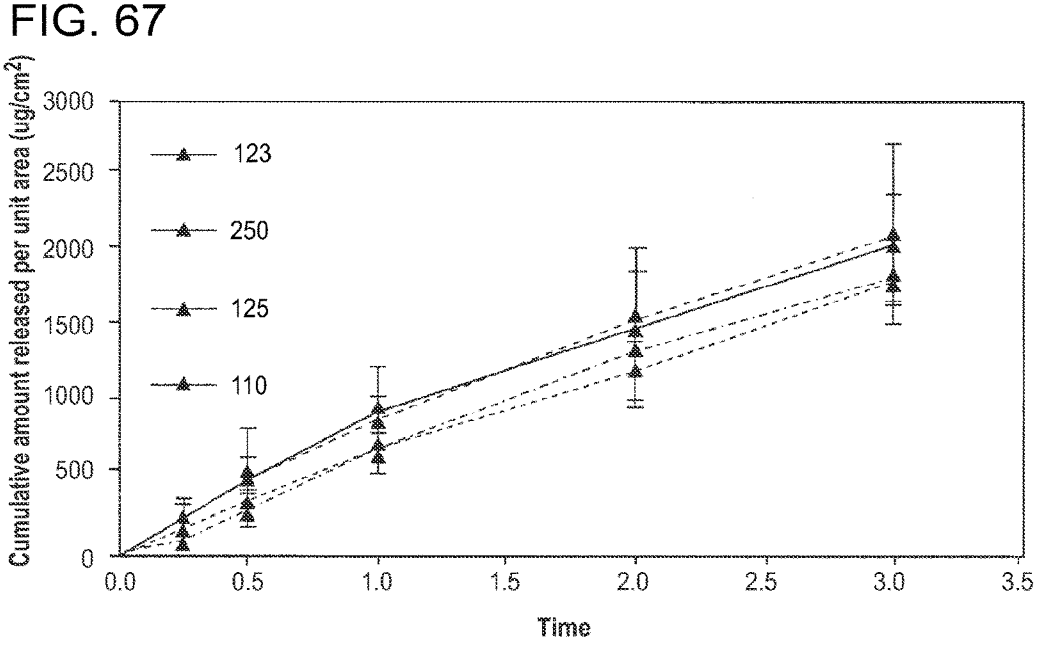
FIG. 67 shows a comparison of the mean amount of imiquimod that is released (μg/cm2) over a 3 hour period for four 2.5% imiquimod formulations, i.e., formulations 110, 123, 125 and 250 (mean+sd, where n=4).
Figure 68:
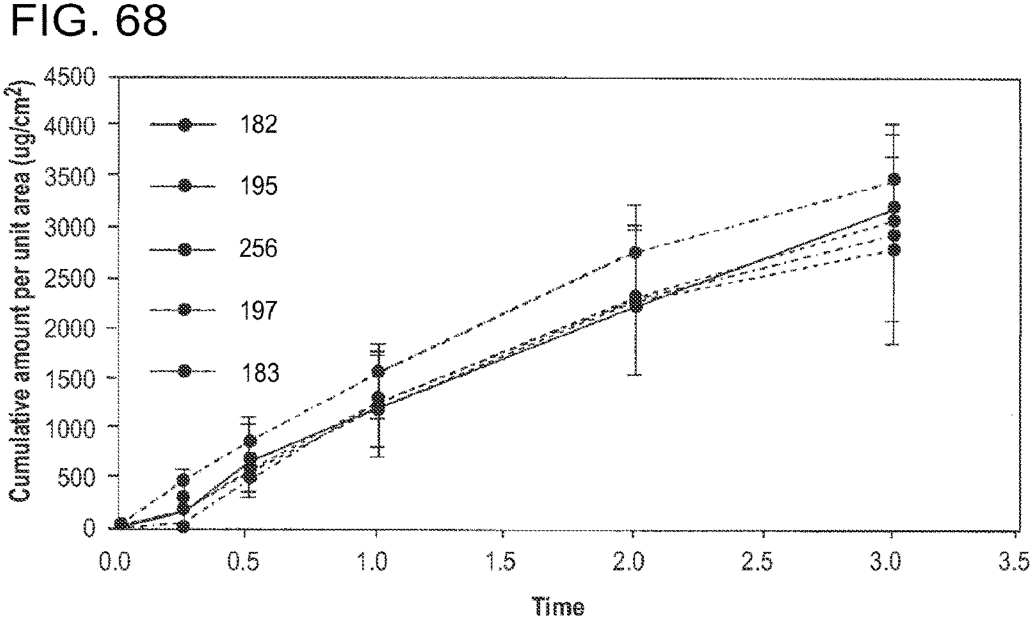
FIG. 68 shows a comparison of the mean amount of imiquimod that is released (μg/cm2) over a 3 hour period for five 3.75% imiquimod formulations, i.e., formulations 182, 183, 195, 197 and 256 (mean+sd, where n=4)

The result for the rate of release presented in Table 32, indicate that the higher the amount of imiquimod in the formulation, the faster the rate of release of imiquimod. Similar to the results of the cumulative amount permeated, there is no statistical difference (p>0.05) between the results for the 2.5% w/w imiquimod formulations (Table 32 and FIG. 67) and likewise for the 3.75% w/w imiquimod formulations (Table 32 and FIG. 68). See also FIGS. 66 and 69.

TABLE 32

Comparison of Mean Flux of Imiquimod (μg/Cm$^2$) over a 3 H Period for Membrane Release Tests (Mean ± Sd, Where N = 4) that are Presented as a Function of √Time from 15 Min To 3 H. Flux √time

| Formulations | Mean ± sd |
|---|---|
| Graceway Aldara ® 5% Imiquimod | 3720.65 ± 569.38 |
| 3M Aldara ® 5% Imiquimod Cream Bulk | 3873.38 ± 479.64 |
| 3M Aldara ® 5% Imiquimod Cream sachet | 3319.56 ± 494.32 |
| 257 (1%) | 504.40 ± 148.43 |
| 123 (2.5%) | 1539.39 ± 482.36 |
| 250 (2.5%) | 1396.68 ± 173.65 |
| 125 (2.5%) | 1592.98 ± 324.51 |
| 110 (2.5%) | 1518.29 ± 151.17 |
| 182 (3.75%) | 2410.03 ± 599.08 |
| 195 (3.75%) | 2310.06 ± 597.59 |
| 256 (3.75%) | 2424.87 ± 28.09 |
| 197 (3.75%) | 2116.53 ± 723.60 |
| 183 (3.75%) | 2516.84 ± 357.41 |

ANOVA statistical analysis (95% confidence level): mean amount of imiquimod released (μg/cm$^2$) over a 3 hour period for the membrane release studies (mean±sd, where n=4) presented as a function of √time from 15 min to 3 h (from results presented in Table 32):

| Source | DF | SS | MS | F | P |
|---|---|---|---|---|---|
| Formulation | 12 | 45353042 | 3779420 | 19.05 | 0.000 |
| Error | 39 | 7739267 | 198443 | | |
| Total | 51 | 53092309 | | | |

S = 445.5
R-Sq = 85.42%
R-Sq (adj) = 80.94%

| Level | N | Mean | St. Dev | Individual 95% CIs For Mean Based on Pooled StDev<br>+----------------+---------------+--------------+---------- |
|---|---|---|---|---|
| 3 M Aldara ® 5% Imiquimod Cream Bulk | 4 | 3873.4 | 479.6 | (--*---) |
| 3 M Aldara ® 5% Imiquimod Cream Sachet | 4 | 3319.6 | 494.3 | (---*--) |
| 110 | 4 | 1518.3 | 151.2 | (---*--) |
| 250 | 4 | 1396.7 | 173.6 | (---*--) |
| 182 | 4 | 2410.0 | 599.1 | (---*---) |
| 195 | 4 | 2310.1 | 597.6 | (---*---) |
| 123 | 4 | 1539.4 | 482.4 | (---*---) |
| 125 | 4 | 1593.0 | 324.5 | (--*---) |
| 256 | 4 | 2424.9 | 28.1 | (---*---) |
| 197 | 4 | 2116.5 | 723.6 | (---*---) |

-continued

| Level | N | Mean | St. Dev | Individual 95% CIs For Mean Based on Pooled StDev<br>+---------------+---------------+--------------+---------- |
|---|---|---|---|---|
| 183 | 4 | 2516.8 | 357.4 | (---*---) |
| Graceway ® 5% | 4 | 3720.6 | 569.4 | (---*---) |
| Imiquimod Cream 257 1% | 4 | 504.4 | 148.4 | (---*---) |
| | | | | +---------------+---------------+--------------+----------<br>0 1200 2400 3600 |

Pooled StDev = 445.5

ANOVA statistical analysis (95% confidence level): Comparison of the mean amount of imiguimod released (μg/$cm^2$) over a 3 hour period for the 3M Aldara® 5% imiquimod cream 1 kg batch, the 3M Aldara® 5% imiquimod cream sachet, the Graceway Aldara® 5% imiquimod cream 1 kg batch and 257, 1% Imiquimod formulation (mean±sd, where n=4)—refer to FIG. 66:

| Source | DF | SS | MS | F | P |
|---|---|---|---|---|---|
| Formulation | 3 | 57378855 | 19126285 | 54.74 | 0.000 |
| Error | 12 | 4192460 | 349372 | | |
| Total | 15 | 61571315 | | | |

S = 591.1
R-Sq = 93.19%
R-Sq (adj) = 91.49%

| Level | N | Mean | St.Dev | Individual 95% CIs For Mean Based on Pooled StDev<br>+---------------+---------------+--------------+---------- |
|---|---|---|---|---|
| Aldara 3 M 5% | 4 | 5332.8 | 734.2 | (---*---) |
| Aldara sachet | 4 | 4605.5 | 626.9 | (---*---) |
| MedPharm Aldara ® | 4 | 4813.3 | 660.7 | (---*---) |
| U2F 1% | 4 | 586.9 | 170.2 | (---*---) |
| | | | | +---------------+---------------+--------------+----------<br>0 1600 3200 4800 |

Pooled StDev = 591.1

ANOVA statistical analysis (95% confidence level): Comparison of the mean amount of imiquimod released (μg/$cm^2$) over a 3 hour period for 2.5% imiquimod formulations 123, 250, 125 and 110 (mean±sd, where n=4)—refer to FIG. 67:

| Source | DF | SS | MS | F | P |
|---|---|---|---|---|---|
| Formulation | 3 | 274778 | 91593 | 0.55 | 0.659 |
| Error | 12 | 2004990 | 167083 | | |
| Total | 15 | 2279769 | | | |

S = 408.8
R-Sq = 12.05%
R-Sq (adj) = 0.00%

| Level | N | Mean | St. Dev | Individual 95% Os For Mean Based on Pooled StDev<br>---+---------+---------+---------+------ |
|---|---|---|---|---|
| GW002 | 4 | 1862.8 | 185.9 | (---------------*---------------) |
| GW008 | 4 | 1845.6 | 206.4 | (---------------*---------------) |
| GW037 | 4 | 2094.9 | 674.6 | (---------------*---------------) |
| GW039 | 4 | 2134.1 | 369.0 | (---------------*---------------) |
| | | | | ---+---------+---------+---------+------<br>1500 1800 2100 2400 |

Pooled StDev = 408.8

ANOVA statistical analysis (95% confidence level): Comparison of the mean amount of imiquimod released (μg/cm$^2$) over a 3 hour period for 3.75% imiquimod formulations 182, 195, 256, 197 and 183 (mean±sd, where n=4)—refer to FIG. 68:

| Source | DF | SS | MS | F | P |
|---|---|---|---|---|---|
| Formulation | 4 | 1084063 | 271016 | 0.49 | 0.743 |
| Error | 15 | 8286917 | 552461 | | |
| Total | 19 | 9370981 | | | |

S = 743.3
R-Sq = 11.57%
R-Sq (adj) = 0.00%

| Level | N | Mean | StDev | Individual 95% CIs For Mean Based on Pooled St. Dev<br>-------+---------+---------+---------+-- |
|---|---|---|---|---|
| GW030 | 4 | 3161.3 | 774.9 | (-------------*------------) |
| GW033 | 4 | 3046.2 | 988.2 | (-------------*------------) |
| GW040 | 4 | 2918.7 | 59.5 | (-------------*------------) |
| GW041 | 4 | 2766.0 | 929.1 | (-------------*------------) |

-continued

| Level | N | Mean | StDev | Individual 95% CIs For Mean Based on Pooled St. Dev<br>-------+---------+---------+---------+-- |
|---|---|---|---|---|
| GW042 | 4 | 3453.2 | 564.4 | -------+---------+---------+---------+--<br>2400 3000 3600 4200 |

Pooled StDev = 743.3

Figure 69:
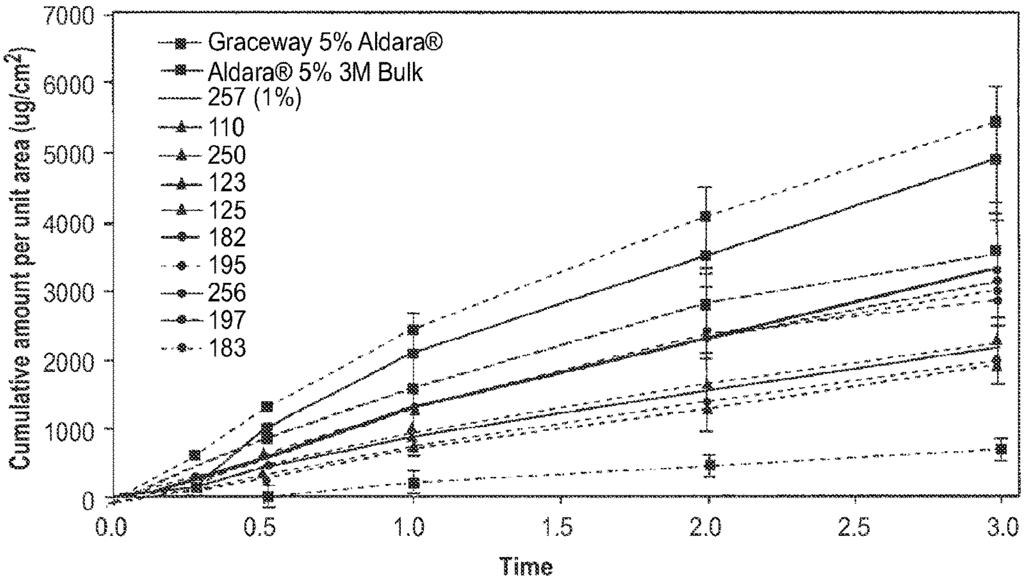
FIG. 69 shows a comparison of the mean amount of imiguimod released (μg/$cm^2$) over a 3 hour period for the 2.5% (▲), 3.75% (●), 3M Aldara® imiquimod cream batch (■), Graceway Aldara® imiquimod cream 1 kg batch (■) and formulation 257 Imiquimod formulations (■) (mean±sd, where n=4).

As discussed under FIG. 69 in the Brief Description of the Drawings, FIG. 69 shows a comparison of the mean amount of imiguimod released (μg/cm$^2$) over a 3 hour period for the 2.5% (▲), 3.75% (●), 3M Aldara® imiquimod cream batch (■), Graceway Aldara® imiquimod cream 1 kg batch (■) and formulation 257 Imiquimod formulations (■) (mean±sd, where n=4).

Based on the results; it appears that the greater the amount of imiquimod in the formulation, the faster and greater the total amount of imiquimod that is released, suggesting that the amount and rate of release are concentration dependant.

(K) In vitro Skin Permeation Study (1) Homogeneity

Manufacture of the formulations (about 100 g batches) is first performed, which batches are then mixed with the radioactive labelled material. The batches are prepared by omitting about 1.38 g of isostearic acid which is added with the radio-labelled imiquimod. The homogeneity of the test formulations, see Table 33, is measured as described in under Homogeneity Control above and all compositions are confirmed to meet the criterion (<10% CV).

TABLE 33

Homogeneity of Radioactivity for Imiquimod Formulations

| Formulation | % CV |
|---|---|
| Graceway Aldara ® 5% Imiquimod Cream | 0.93 |
| 3M Aldara ® 5% Imiquimod Cream | 1.50 |
| 182 | 0.80 |
| 195 | 2.39 |
| 256 | 1.17 |
| 197 | 0.07 |
| 183 | 1.54 |
| 110 | 0.71 |
| 250 | 2.53 |
| 123 | 1.89 |
| 125 | 1.53 |
| 126 | 2.55 |
| 257 (1%) | 2.30 |

(2) Franz Cell Study

Figure 60:
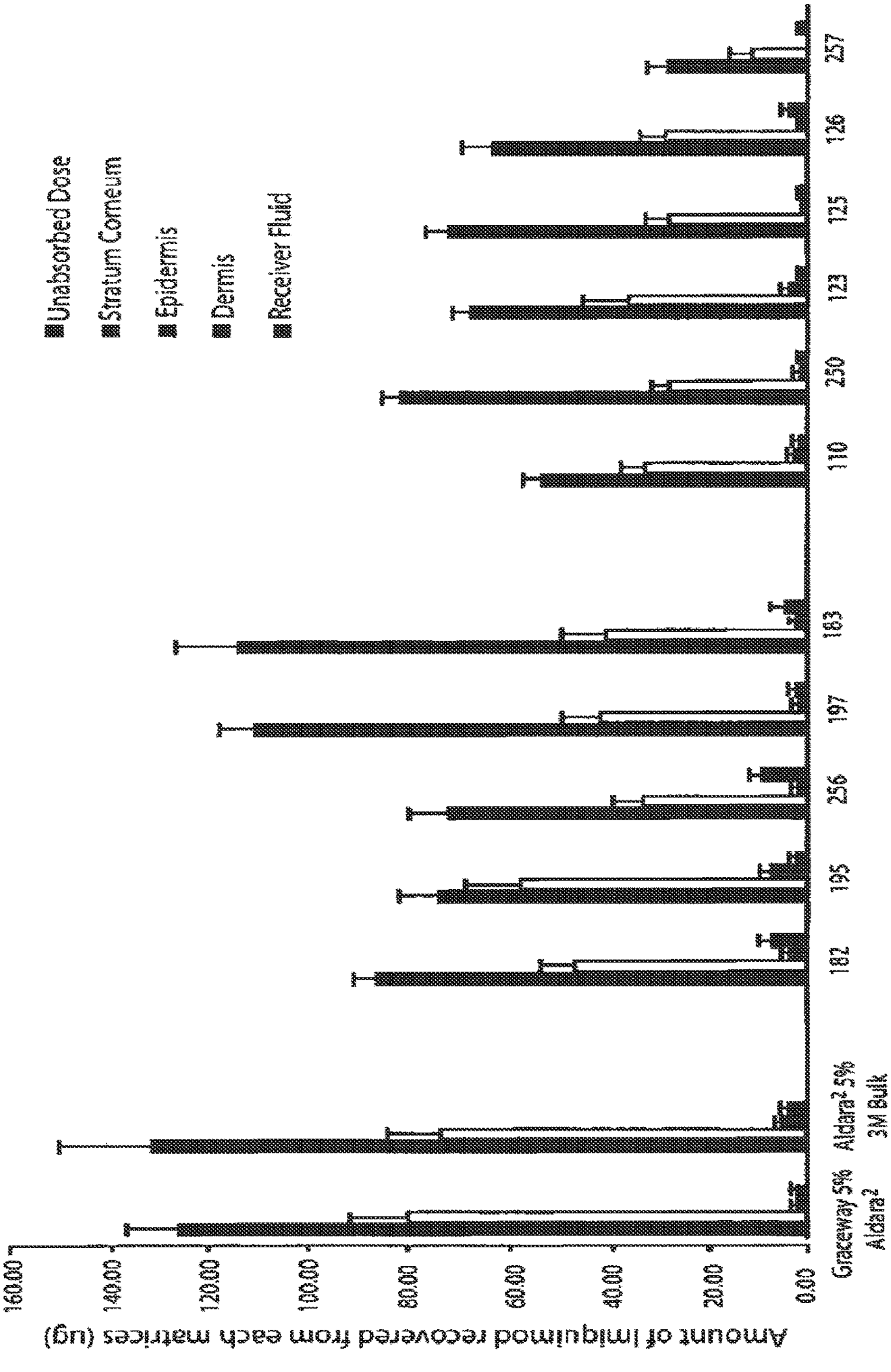
FIG. 60 shows a total amount of imiguimod that is recovered following mass balance for each formulation (See also Tables 35-40 for statistical analysts) (mean±sd, refer to Table 34 for n numbers of each sample)
Figure 61:
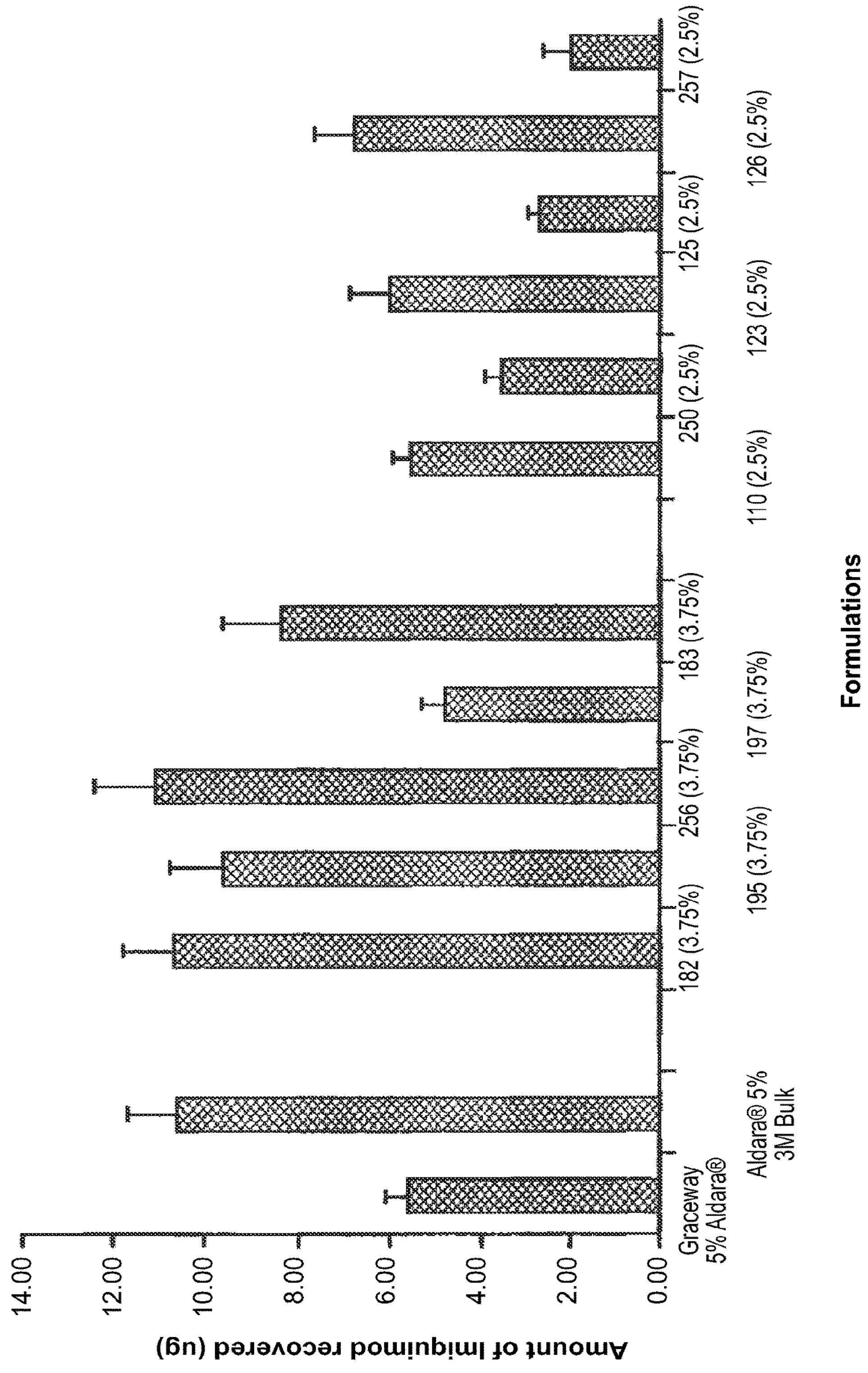
FIG. 61 shows a total amount of imiquimod recovered for each formulation in the receiver fluid, epidermis and dermis combined (mean±sd, refer to Table 34 for n numbers of each sample)

The data that is shown in Table 34 is the actual amount of imiquimod that is recovered for each formulation from the various matrices, which is also represented graphically in FIG. 60. FIG. 61 represents the total amount of imiquimod that is recovered for each formulation in the epidermis, dermis and receiver fluid combined.

TABLE 34

Amount of Imiquimod that is Recovered following Mass Balance Investigation

| | | | Amount of imiquimod recovered ± SEM (μg) | | | | | |
|---|---|---|---|---|---|---|---|---|
| Formulations | Percentage imiquimod | Repli-cates (n) | Receiver Fluid | Unabsorbed Dose | Stratum Corneum | Epidermis | Dermis | Percentage total recovered |
| Graceway Aldara ® 5% Imiquimod Cream | 5% | 6 | 0.03 ± 0.01 | 127.06 ± 9.58 | 80.78 ± 11.67 | 2.90 ± 0.72 | 2.76 ± 0.70 | 85.24 ± 5.15 |

TABLE 34-continued

Amount of Imiquimod that is Recovered following Mass Balance Investigation

| Formulations | Percentage imiquimod | Repli-cates (n) | Amount of imiquimod recovered ± SEM (μg) Receiver Fluid | Unabsorbed Dose | Stratum Corneum | Epidermis | Dermis | Percentage total recovered |
|---|---|---|---|---|---|---|---|---|
| 3M Aldara ® 5% Imiquimod Cream | 5% | 4 | 0.05 0.03 | 132.75 ± 17.62 | 74.37 ± 10.59 | 6.60 ± 1.91 | 3.96 ± 0.41 | 86.92 ± 4.16 |
| 182 3.75% | 3.75% | 6 | 0.08 ± 0.06 | 85.75 ± 3.93 | 46.85 ± 5.51 | 3.65 ± 0.85 | 6.94 2.22 | 76.25 ± 1.82 |
| 195 3.75% | 3.75% | 4 | 0.08 ± 0.07 | 74.19 ± 6.90 | 57.41 ± 11.46 | 7.06 2.29 | 2.47 ± 0.87 | 75.16 ± 5.12 |
| 256 3.75% | 3.75% | 5 | 0.16 ± 0.06 | 71.73 ± 7.22 | 33.41 ± 4.77 | 1.99 ± 0.71 | 9.03 ± 2.37 | 61.91 ± 3.95 |
| 197 3.75% | 3.75% | 5 | 0.06 ± 0.03 | 110.54 6.22 | 41.61 ± 6.54 | 2.21 ± 0.36 | 2.53 ± 0.91 | 83.54 ± 3.92 |
| 183 3.75% | 3.75% | 4 | 0.02 ± 0.01 | 113.84 ± 11.63 | 40.99 ± 6.99 | 3.26 ± 0.53 | 5.11 ± 2.32 | 86.88 ± 6.68 |
| 110 2.5% | 2.5% | 6 | 0.00 ± 0.00 | 52.92 3.96 | 33.96 ± 3.43 | 3.25 ± 0.70 | 2.32 ± 0.44 | 73.82 ± 4.64 |
| 250 2.5% | 2.5% | 5 | 0.00 ± 0.00 | 82.46 ± 2.94 | 28.30 ± 3.67 | 2.35 ± 0.68 | 1.17 ± 0.30 | 91.25 ± 3.93 |
| 123 2.5% | 2.5% | 5 | 0.01 ± 0.01 | 68.33 ± 3.18 | 35.93 ± 10.40 | 4.20 ± 1.69 | 1.80 ± 0.32 | 88.04 ± 7.95 |
| 125 2.5% | 2.5% | 6 | 0.02 ± 0.01 | 72.82 ± 3.92 | 28.88 ± 4.41 | 1.12 ± 0.42 | 1.52 ± 0.42 | 83.32 ± 2.44 |
| 126 2.5% | 2.5% | 5 | 0.01 ± 0.00 | 64.00 ± 5.27 | 29.59 ± 4.97 | 2.36 ± 0.40 | 4.44 ± 1.62 | 80.15 ± 6.61 |
| 257 1% | 1% | 4 | 0.01 ± 0.00 | 28.88 ± 4.60 | 12.49 ± 3.75 | 0.42 ± 0:14 | 1.54 ± 1.05 | 86.98 ± 3.40 |

The only data rejected from that presented in Table 34, FIG. 60 and FIG. 61 are obvious outliers that are observed on the basis of cell failure.

Figure 62:
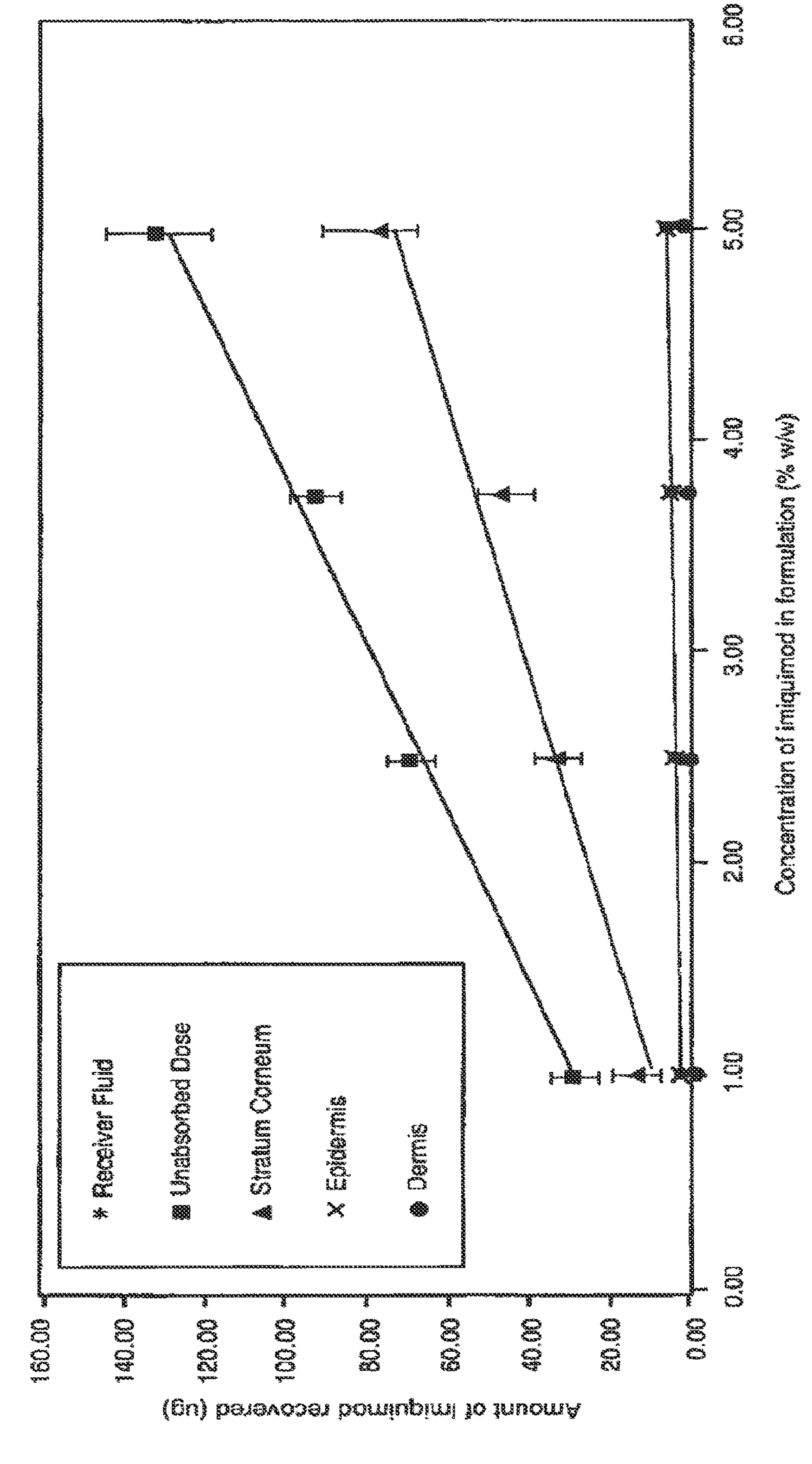
FIG. 62 shows a total amount of imiquimod recovered for the averages of each imiquimod concentration from each of the skin matrices.
Figure 63A:
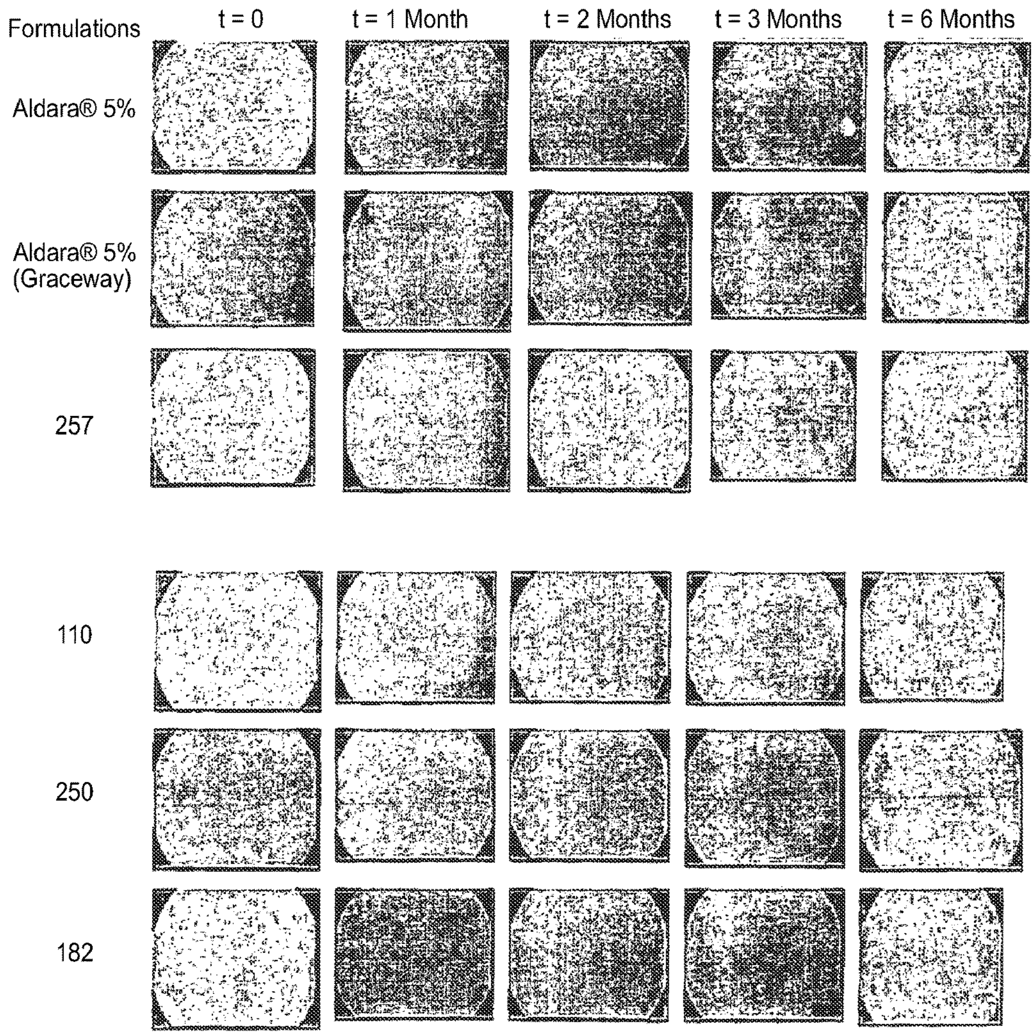
FIGS. 63A-C show microscopic depiction of 13 imiquimod formulations, i.e., 3M Aldara® imiquimod cream 1 kg batch, Graceway 3M Aldara® imiquimod cream 1 kg batch and formulations 110, 123, 125, 126, 182, 183, 195, 197, 250, 256 and 257 (t=0, 1, 2, 3 and 6 months)—×400 magnification.
Figure 63B:
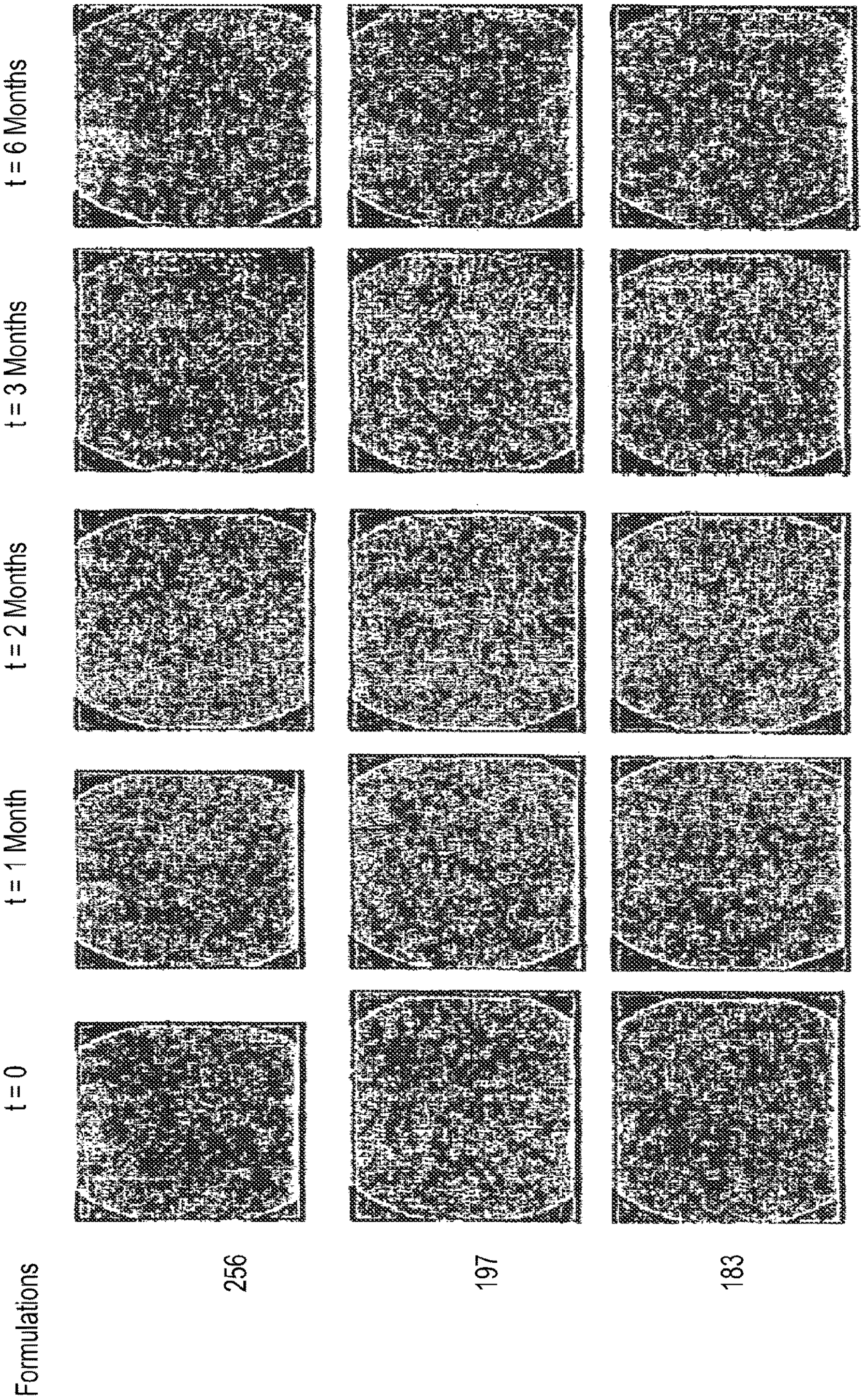
Figure 63C:
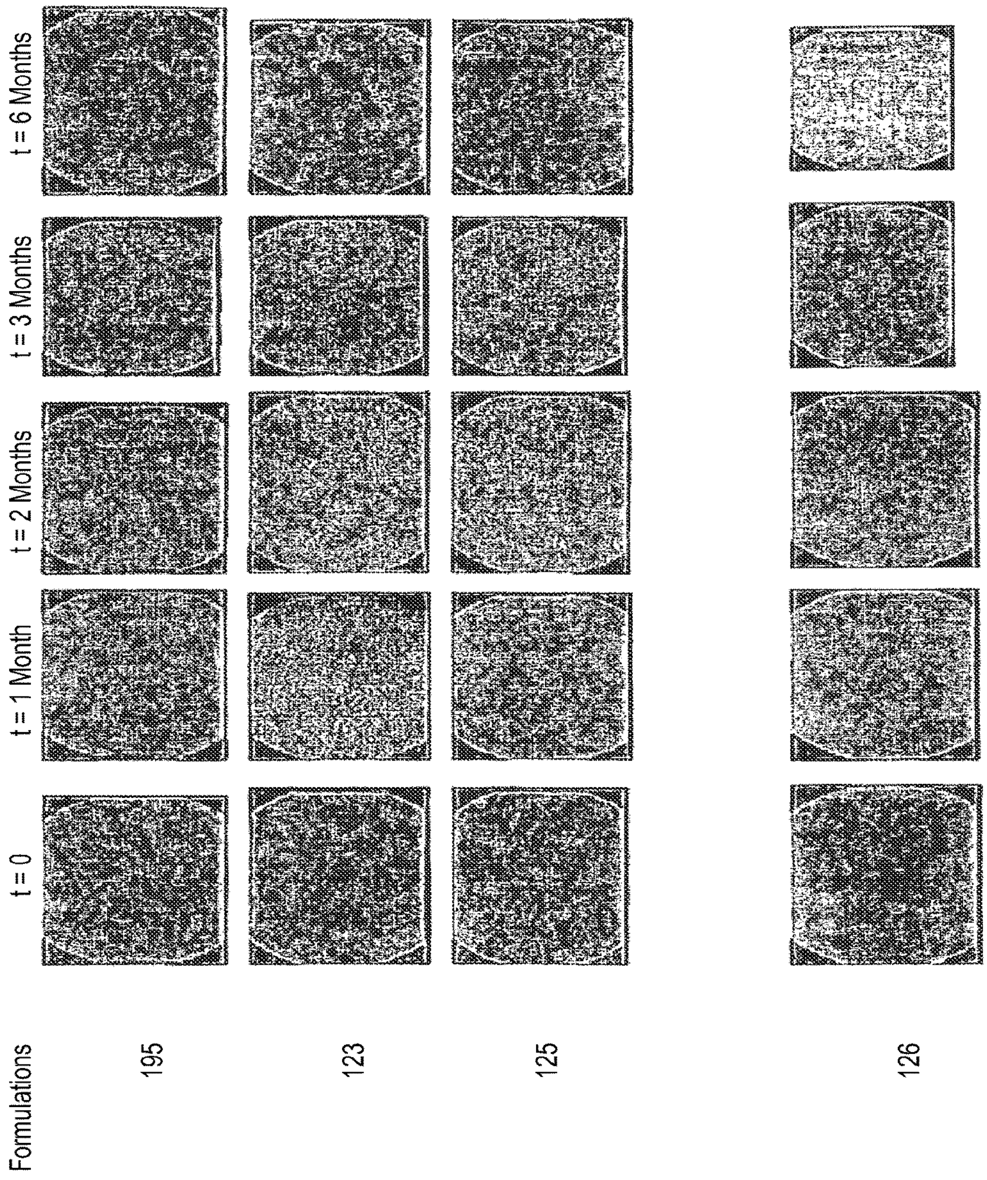
Figure 64:
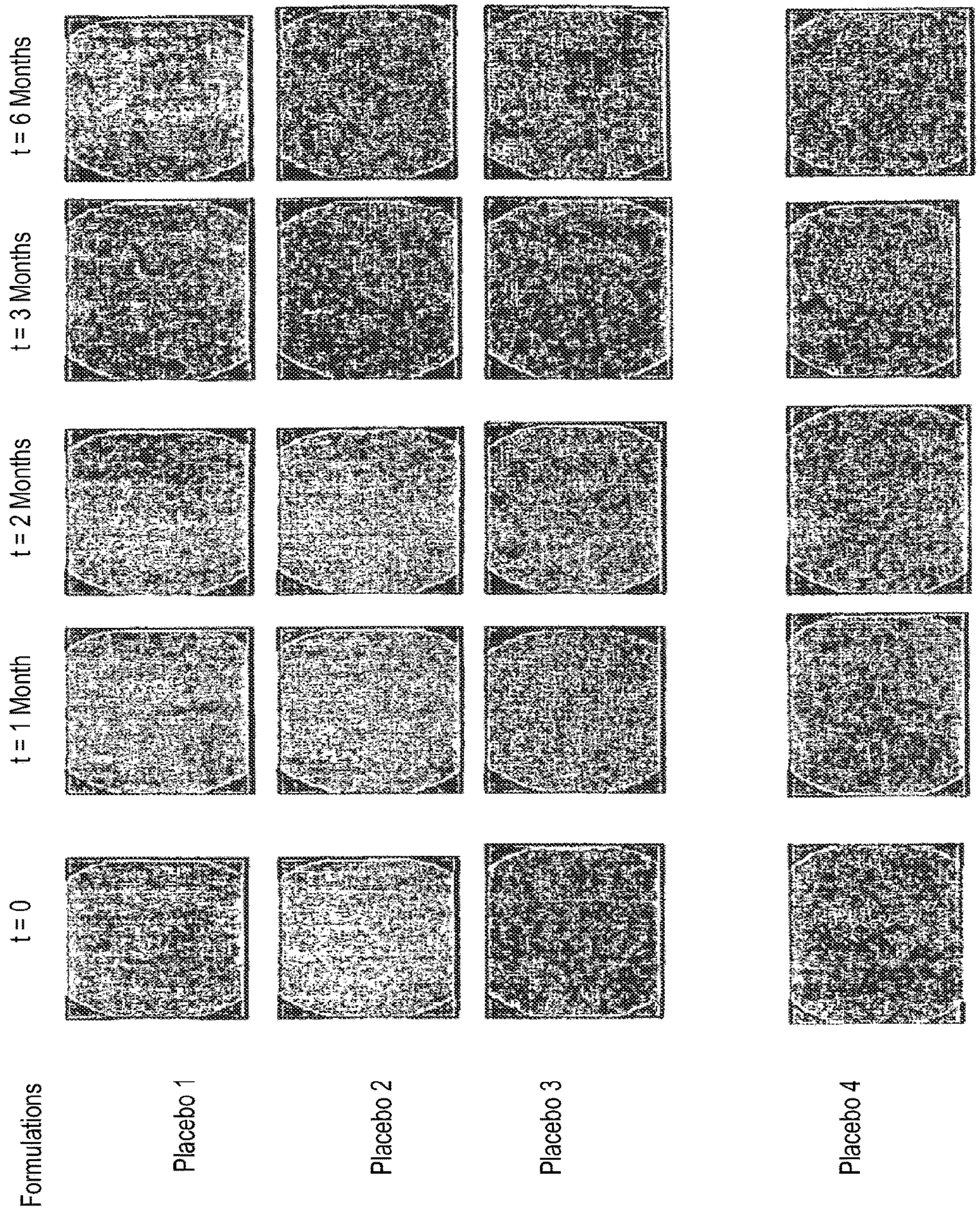
FIG. 64 shows microscopic depiction of placebo formulations Pbo1-Pbo4 (t=0, 1, 2, 3 and 6 months)—×400 magnification.

The average data for the 5%, 1%, 3.75% and 2.5% w/w formulations showing the amount of imiquimod that is recovered from the unabsorbed fraction, in the Stratum corneum and in the epidermis, dermis and receiver fluid combined are shown in FIG. 62. This data shows that there is a linear dose release between the amount of imiquimod applied and recovery in each of the matrices. See also Table 35 for stability of calibration standards in spent receiver fluid and Tables 36-40—for statistical analysis.

TABLE 35

Stability of Calibration Standards in Spent Receiver Fluid (Stored In HPLC Crimp Top Vials at Each Temperature (Where Recovery was Compared To T = 0)

| Standard (μg/ml) | Spent receiver fluid: | 48 h % recovered in Spent receiver fluid Fridge | RT | 37° C. |
|---|---|---|---|---|
| 105.5 | Full thickness + placebo | 88.242 | 88.546 | 91.704 |
| 84.4 | | 84.561 | 84.421 | 85.629 |
| 52.75 | | 91.776 | 92.027 | 93.779 |
| 42.2 | | 83.976 | 84.144 | 86.439 |
| 21.1 | | 84.584 | 85.162 | 88.000 |
| 10.55 | | 88.307 | 86.897 | 90.798 |
| 5.275 | | 90.260 | 87.973 | 86.134 |
| 105.5 | Full thickness | 90.545 | 92.275 | 92.278 |
| 84.4 | | 98.841 | 99.790 | 101.010 |
| 52.75 | | 92.317 | 92.152 | 95.282 |
| 42.2 | | 95.103 | 95.805 | 95.939 |
| 21.1 | | 91.876 | 91.968 | 93.847 |
| 10.55 | | 94.989 | 93.522 | 97.826 |
| 5.275 | | 94.586 | 95.232 | 90.611 |
| 105.5 | Epidermal sheet + placebo | 83.833 | 84.515 | 84.903 |
| 84.4 | | 95.620 | 96.033 | 98.178 |
| 52.75 | | 85.635 | 88.169 | 86.906 |
| 42.2 | | 93.077 | 92.904 | 95.095 |
| 21.1 | | 101.831 | 105.389 | 105.213 |
| 10.55 | | 84.046 | 85.095 | 89.945 |
| 5.275 | | 88.881 | 86.540 | 86.828 |

TABLE 35-continued

Stability of Calibration Standards in Spent Receiver Fluid (Stored In HPLC Crimp Top Vials at Each Temperature (Where Recovery was Compared To T = 0)

| Standard (μg/ml) | Spent receiver fluid: | 48 h % recovered in Spent receiver fluid Fridge | RT | 37° C. |
|---|---|---|---|---|
| 105.5 | Epidermal sheet | 90.465 | 92.089 | 91.501 |
| 84.4 | | 81.350 | 82.276 | 82.694 |
| 52.75 | | 87.669 | 89.096 | 90.943 |
| 42.2 | | 85.716 | 86.340 | 89.641 |
| 21.1 | | 95.828 | 97.098 | 97.470 |
| 10.55 | | 93.180 | 94.971 | 97.099 |
| 5.275 | | 88.938 | 91.447 | 85.995 |

Tables 36-40. Statistical Analysis for Amount of Imiquimod that is Recovered following Mass Balance Test ANOVA statistical analysis (95% confidence level): Amount of imiquimod that is recovered following mass balance test from receiver fluid (from results that are presented in FIG. 60) is shown in Table 36:

TABLE 36

| Source | DF | SS | MS | F | P |
|---|---|---|---|---|---|
| Cl | 14 | 0.12075 | 0.01006 | 1.84 | 0.066 |
| Error | 52 | 0.28455 | 0.00547 | | |
| Total | 64 | 0.40530 | | | |

S = 0.07397
R-Sq = 29.79%
R-Sq (adj) = 13.59%

| Level | N | Mean | St. Dev | Individual 95% CIs For Mean Based on Pooled StDev ---------+---------+---------+---------+ |
|---|---|---|---|---|
| 3 M Aldara ® 5% | 4 | 0.05250 | 0.05909 | (---------*---------) |
| Imiquimod Cream 110 2.5% | 6 | 0.00000 | 0.00000 | (-------*-------) |
| 250 2.5% | 5 | 0.00400 | 0.00894 | (-------*-------) |
| 182 3.75% | 6 | 0.07833 | 0.14400 | (---------*---------) |
| 195 3.75% | 4 | 0.08250 | 0.14500 | (----------*----------) |
| 123 2.5% | 5 | 0.01200 | 0.01095 | (--------*-------) |
| 125 2.5% | 6 | 0.02333 | 0.02503 | (-------*------) |
| 256 3.75% | 5 | 0.15600 | 0.14064 | (-------*-------) |
| 197 3.75% | 5 | 0.05800 | 0.06611 | (-------*--------) |
| 183 3.75% | 4 | 0.01750 | 0.01708 | (--------*--------) |
| 126 | 5 | 0.00600 | 0.00894 | (---------*---------) |
| Graceway Aldara ® | 6 | 0.02833 | 0.03312 | (---------*---------) |
| 5% Imiquimod Cream 257 (1%) | 4 | 0.00500 | 0.00577 | (---------*---------) |
| | | | | ---------+---------+---------+---------+ 0.000 0.080 0.160 0.240 |

Pooled StDev = 0.07397

ANOVA statistical analysis (95% confidence level): Amount of imiquimod that is recovered following mass balance test from un-absorbed dose (from results that are presented in FIG. 60) is shown in Table 37:

TABLE 37

| Source | DF | SS | MS | F | P |
|---|---|---|---|---|---|
| Cl | 12 | 50777 | 4231 | 16.83 | 0.000 |
| Error | 52 | 13071 | 251 | | |
| Total | 64 | 63848 | | | |

S = 15.85
R-Sq = 79.53%
R-Sq (adj) = 74.80%

| Level | N | Mean | St. Dev | Individual 95% CIs For Mean Based on Pooled StDev ------------+---------------+--------------+----------+-- |
|---|---|---|---|---|
| 3 M Aldara ® 5% | 4 | 132.75 | 35.25 | (----*---) |
| Imiquimod Cream 1102.5% | 6 | 52.93 | 9.69 | (---*---) |

-continued

| Level | N | Mean | St. Dev | Individual 95% CIs For Mean Based on Pooled StDev ------------+---------------+--------------+----------+-- |
|---|---|---|---|---|
| 2502.5% | 5 | 82.46 | 6.57 | (----*---) |
| 182 3.75% | 6 | 85.75 | 9.63 | (--*---) |
| 195 3.75% | 4 | 74.19 | 13.80 | (---*----) |
| 123 2.5% | 5 | 68.33 | 7.10 | (----*---) |
| 125 2.5% | 6 | 72.82 | 9.61 | (---*---) |
| 256 3.75% | 5 | 71.73 | 16.15 | (---*----) |
| 197 3.75% | 5 | 110.54 | 13.91 | (---*---) |
| 183 3.75% | 4 | 113.85 | 23.27 | (----*---) |
| 126 | 5 | 63.98 | 11.78 | (---*---) |
| Graceway Aldara ® | 6 | 127.06 | 23.46 | (--*---) |
| 5% Imiquimod Cream 257 (1%) | 4 | 28.88 | 9.20 | (---*----) |
| | | | | ------------+---------------+--------------+----------+-- 35 70 105 140 |

Pooled StDev = 15.85

ANOVA statistical analysis (95% confidence level): Amount of imiquimod that is recovered following mass balance test from Stratum corneum (from results that are presented in FIG. 60) is shown in Table 38:

TABLE 38

| Source | DF | SS | MS | F | P |
|---|---|---|---|---|---|
| Cl | 12 | 21479 | 1790 | 6.72 | 0.000 |
| Error | 52 | 13848 | 266 | | |
| Total | 64 | 35327 | | | |

S = 16.32
R-Sq = 60.80%
R-Sq (adj) = 51.75%

| Level | N | Mean | St. Dev | Individual 95% CIs For Mean Based on Pooled StDev --+---------+----------+----------+------ |
|---|---|---|---|---|
| 3 M Aldara ® 5% Imiquimod Cream | 4 | 74.38 | 21.17 | (-----*-----) |
| 110 2.5% | 6 | 33.96 | 8.41 | (-----*----) |
| 250 2.5% | 5 | 28.30 | 8.21 | (------*-----) |

-continued

| Level | N | Mean | St. Dev | Individual 95% CIs For Mean Based on Pooled StDev --+---------+----------+----------+------ |
|---|---|---|---|---|
| 182 3.75% | 6 | 46.85 | 13.50 | (------*-----) |
| 195 3.75% | 4 | 57.41 | 22.92 | (------*-----) |
| 123 2.5% | 5 | 35.93 | 23.25 | (------*-----) |
| 125 2.5% | 6 | 28.88 | 10.80 | (------*-----) |
| 256 3.75% | 5 | 33.41 | 10.67 | (------*-----) |
| 197 3.75% | 5 | 41.61 | 14.62 | (------*-----) |
| 183 3.75% | 4 | 41.00 | 13.97 | (------*-----) |
| 126 | 5 | 29.59 | 11.11 | (------*-----) |
| Graceway Aldara ® | 6 | 80.78 | 28.60 | (------*-----) |
| 5% Imiquimod Cream | | | | |
| 257 (1%) | 4 | 12.49 | 7.49 | (------*-----) |
| | | | | --+---------+----------+----------+------ |
| | | | | 0 25 50 75 |

Pooled StDev = 16.32

ANOVA statistical analysis (95% confidence level): Amount of imiquimod that is recovered following mass balance test from epidermis (from results that are presented in FIG. 60) is shown in Table 39:

TABLE 39

| Source | DF | SS | MS | F | P |
|---|---|---|---|---|---|
| Cl | 12 | 187.78 | 15.65 | 3.26 | 0.002 |
| Error | 52 | 249.79 | 4.80 | | |
| Total | 64 | 437.57 | | | |

S = 2.192
R-Sq = 42.91%
R-Sq (adj) = 29.74%

| Level | N | Mean | St. Dev | Individual 95% CIs For Mean Based on Pooled StDev ------+---------+---------+---------+--- |
|---|---|---|---|---|
| 3 M Aldara ® 5% | 4 | 6.600 | 3.823 | (------*-----) |
| Imiquimod Cream | | | | |
| 110 2.5% | 6 | 3.248 | 1.717 | (------*-----) |
| 250 2.5% | 5 | 2.350 | 1.514 | (------*-----) |
| 182 3.75% | 6 | 3.643 | 2.083 | (------*-----) |

-continued

| Level | N | Mean | St. Dev | Individual 95% CIs For Mean Based on Pooled StDev ------+---------+---------+---------+--- |
|---|---|---|---|---|
| 195 3.75% | 4 | 7.055 | 4.580 | (------*-----) |
| 123 2.5% | 5 | 4.196 | 3.782 | (------*-----) |
| 125 2.5% | 6 | 1.123 | 1.039 | (------*-----) |
| 256 3.75% | 5 | 1.990 | 1.588 | (------*-----) |
| 197 3.75% | 5 | 2.208 | 0.797 | (------*-----) |
| 183 3.75% | 4 | 3.260 | 1.053 | (------*-----) |
| 126 | 5 | 2.360 | 0.903 | (------*-----) |
| Graceway Aldara ® 5% Imiquimod Cream | 6 | 2.895 | 1.752 | (------*-----) |
| 257 (I%) | 4 | 0.415 | 0.273 | (------*-----) |
| | | | | --------------+---------------+-----------+---------+--- 0.0 3.0 6.0 9.0 |

Pooled StDev = 2.192

ANOVA statistical analysis (95% confidence level): Amount of imiquimod that is recovered following mass balance test from dermis (from results that are presented in FIG. 60) is shown in Table 40:

TABLE 40

| Source | DF | SS | MS | F | P |
|---|---|---|---|---|---|
| Cl | 12 | 340.72 | 28.39 | 3.29 | 0.001 |
| Error | 52 | 448.34 | 8.62 | | |
| Total | 64 | 789.06 | | | |

S = 2.936
R-Sq = 43.18%
R-Sq (adj) = 30.07%

| Level | N | Mean | St. Dev | Individual 95% Cls For Mean Based on Pooled StDev ------+---------+---------+---------+--- |
|---|---|---|---|---|
| 3 M Aldara ® 5% Imiquimod Cream | 4 | 3.960 | 0.825 | (--------*-------) |
| 110 2.5% | 6 | 2.323 | 1.068 | (------*------) |
| 250 2.5% | 5 | 1.164 | 0.663 | (------*------) |
| 182 3.75% | 6 | 6.937 | 5.445 | (------*------) |
| 195 3.75% | 4 | 2.473 | 1.733 | (-------*-------) |

-continued

| Level | N | Mean | St. Dev | Individual 95% CIs For Mean Based on Pooled StDev<br>------+---------+---------+---------+--- |
|---|---|---|---|---|
| 123 2.5% | 5 | 1.796 | 0.715 | (-------*-------) |
| 125 2.5% | 6 | 1.518 | 1.020 | (-------*-------) |
| 256 3.75% | 5 | 9.030 | 5.305 | (------*------) |
| 197 3.75% | 5 | 2.532 | 2.036 | (-------*-------) |
| 183 3.75% | 4 | 5.110 | 4.638 | (--------*------) |
| 126 | 5 | 4.436 | 3.626 | (------*------) |
| Graceway Aldara ® Cream | 6 | 2.758 | 1.721 | (------*------) |
| 257 (1%) | 4 | 1.533 | 2.099 | (------*------) |
| | | | | ------+---------------+-----------+---------+-----<br>0.0 3.5 7.0 10.5 |

Pooled StDev = 2.936

The results that are presented in FIG. 61, indicate that the delivery of the imiquimod into the receiver fluid, epidermis and dermis combined from formulations 182, 195 and 256 are similar to the Aldara® 5% imiquimod cream formulation when comparing averages. With respect to the statistical analysis, there is no statistical difference (p>0.05) between 110 (2.5%), 126 (2.5%), 123 (2.5%), 182, (3.75%), 195 (3.75%), 256 (3.75%), 197 (3.75%) and 183 (3.75%) when compared to Aldara® 5% imiquimod cream formulation in the amount of imiquimod that is recovered from the receiver fluid, epidermis and dermis combined.

In Table 41, ANOVA statistical analysis (95% confidence level) are presented: Total amount of imiquimod that is recovered for each formulation in the receiver fluid, epidermis and dermis combined (from the results that are presented in FIG. 61:

TABLE 41

| Source | DF | SS | MS | F | P |
|---|---|---|---|---|---|
| Cl | 12 | 573.2 | 47.8 | 3.28 | 0.001 |
| Error | 52 | 758.2 | 14.6 | | |
| Total | 64 | 1331.4 | | | |

S = 3.819

R-Sq = 43.05%

R-Sq (adj) = 29.91%

| Level | N | Mean | St.Dev | Individual 95% CIs For Mean Based on Pooled StDev<br>----+---------+---------+---------+----- |
|---|---|---|---|---|
| 257 (1%) | 4 | 1.958 | 2.357 | (-------*-------) |
| 110 2.5% | 6 | 5.572 | 2.706 | (-------*-------) |
| 250 2.5% | 5 | 3.524 | 1.445 | (-------*-------) |
| 123 2.5% | 5 | 6.010 | 4.296 | (--------*-------) |
| 125 2.5% | 6 | 2.663 | 0.837 | (-------*------) |
| 126 2.5% | 5 | 6.804 | 3.538 | (--------*--------) |
| 182 3.75% | 6 | 10.662 | 6.441 | (-------*--------) |

-continued

| Level | N | Mean | St.Dev | Individual 95% CIs For Mean Based on Pooled StDev<br>----+---------+---------+---------+----- |
|---|---|---|---|---|
| 195 3.75% | 4 | 9.608 | 5.392 | (-------*--------) |
| 256 3.75% | 5 | 11.180 | 5.770 | (--------*--------) |
| 197 3.75% | 5 | 4.800 | 1.749 | (---------*---------) |
| 183 3.75% | 4 | 8.388 | 3.666 | (---------*---------) |
| Graceway Aldara ® 5% Imiquimod Cream | 6 | 5.682 | 2.671 | (---------*---------) |
| 3M Aldara ® 5% Imiquimod Cream | 4 | 10.613 | 4.211 | (---------*---------) |
| | | | | ----+---------+---------+---------+-----<br>0.0 5.0 10.0 15.0 |

Pooled StDev = 3.819

The results that are presented in FIG. 62 and statistical analysis in Tables 42-46 indicate that there is a distinct dose proportionate trend between the amount of imiquimod that is recovered from each of the matrices with respect to the concentration of imiquimod in the formulation for both un-absorbed and Stratum corneum. The trend in this data, is also observed for the epidermis (with respect to average values in the statistical analysis).

In Tables 42-46, statistical analysis for the total amount of imiquimod recovered from each of the matrices (1%, 2.5%, 3.75% and 5% w/w formulations)

ANOVA statistical analysis (95% confidence level): Total amount of imiquimod that is recovered for imiquimod concentration combined from each of the matrices from un-absorbed dose (from results presented in FIG. 62) in Table 42:

TABLE 42

| Source | DF | SS | MS | F | P |
|---|---|---|---|---|---|
| Cl | 3 | 44198 | 14733 | 35.53 | 0.000 |
| Error | 61 | 25293 | 415 | | |
| Total | 64 | 69491 | | | |

S = 20.36
R-Sq = 63.60%
R-Sq (adj) = 61.81%

| Level | N | Mean | St. Dev | Individual 95% CIs For Mean Based on Pooled StDev<br>--------------+---------------+-----------+---------+- |
|---|---|---|---|---|
| 1% | 4 | 28.88 | 9.20 | (-----*-----) |
| 2.5% | 27 | 64.08 | 16.24 | (-*--) |
| 3.75% | 24 | 90.75 | 22.48 | (-*-) |
| 5% | 10 | 129.33 | 26.99 | (---*---) |
| | | | | --------------+---------------+-----------+---------+-<br>35 70 105 140 |

Pooled StDev = 20.36

ANOVA statistical analysis (95% confidence level): Total amount of imiquimod that is recovered for imiquimod concentration combined from each of the matrices from *Strateum corneum* (from results presented in FIG. 62) in Table 43:

TABLE 43

| Source | DF | SS | MS | F | P |
|---|---|---|---|---|---|
| Cl | 3 | 19744 | 6581 | 25.76 | 0.000 |
| Error | 61 | 15583 | 255 | | |
| Total | 64 | 35327 | | | |

S = 15.98
R-Sq = 55.89%
R-Sq (adj) = 53.72%

| Level | N | Mean | St. Dev | Individual 95% CIs For Mean Based on Pooled StDev<br>-+---------+---------+---------+--------- |
|---|---|---|---|---|
| 1% | 4 | 12.49 | 7.49 | (-----*-----) |
| 2.5% | 27 | 31.34 | 12.57 | (--*-) |
| 3.75% | 24 | 43.74 | 15.85 | (-*--) |
| 5% | 10 | 78.22 | 24.79 | (---*---) |
| | | | | -+---------+---------+---------+---------<br>0 25 50 75 |

Pooled StDev = 15.98

ANOVA statistical analysis (95% confidence level): Total amount of imiquimod that is recovered for imiquimod concentration combined from each of the matrices from epidermis (from results presented in FIG. 62) in Table 44:

TABLE 44

| Source | DF | SS | MS | F | P |
|---|---|---|---|---|---|
| Cl | 3 | 55.25 | 18.42 | 2.94 | 0.040 |
| Error | 61 | 382.32 | 6.27 | | |
| Total | 64 | 437.57 | | | |

S = 2.504
R-Sq = 12.63%
R-Sq (adj) = 8.33%

| Level | N | Mean | St. Dev | Individual 95% CIs For Mean Based on Pooled StDev<br>--------+--------+--------+--------+- |
|---|---|---|---|---|
| 1% | 4 | 0.415 | 0.273 | (---------*---------) |
| 2.5% | 27 | 2.621 | 2.137 | (--*---) |
| 3.75% | 24 | 3.505 | 2.729 | (---*---) |

-continued

| Level | N | Mean | St. Dev | Individual 95% CIs For Mean Based on Pooled StDev<br>--------+--------+--------+--------+- |
|---|---|---|---|---|
| 5% | 10 | 4.377 | 3.200 | (------*-----) |
| | | | | --------+--------+--------+--------+-<br>0.0 2.5 5.0 7.5 |

Pooled StDev = 2.504

ANOVA statistical analysis (95% confidence level): Total amount of imiquimod that is recovered for imiquimod concentration combined from each of the matrices from dermis (from results presented in FIG. 62) in Table 45:

TABLE 45

| Source | DF | SS | MS | F | P |
|---|---|---|---|---|---|
| Cl | 3 | 147.4 | 49.1 | 4.67 | 0.005 |
| Error | 61 | 641.7 | 10.5 | | |
| Total | 64 | 789.1 | | | |

S = 3.243
R-Sq = 18.68%
R-Sq (adj) = 14.68%

| Level | N | Mean | St. Dev | Individual 95% CIs For Mean Based on Pooled StDev<br>-------+---------+---------+---------+-- |
|---|---|---|---|---|
| 1% | 4 | 1.533 | 2.099 | (---------------*---------------) |
| 2.5% | 27 | 2.223 | 1.974 | (----*----) |
| 3.75% | 24 | 5.407 | 4.694 | (-----*----) |
| 5% | 10 | 3.239 | 1.502 | (--------*--------) |
| | | | | -------+---------+---------+---------+--<br>0.0 2.5 5.0 7.5 |

Pooled StDev = 3.243

ANOVA statistical analysis (95% confidence level): Total amount of imiquimod that is recovered for imiquimod concentration combined from each of the matrices from receiver fluid (from results presented in FIG. 62) in Table 46:

TABLE 46

| Source | DF | SS | MS | F | P |
|---|---|---|---|---|---|
| Cl | 3 | 0.07047 | 0.02349 | 4.28 | 0.008 |
| Error | 61 | 0.33483 | 0.00549 | | |
| Total | 64 | 0.40530 | | | |

S = 0.07409
R-Sq = 17.39%
R-Sq (adj) = 13.32%

| Level | N | Mean | St. Dev | Individual 95% CIs For Mean Based on Pooled StDev<br>----+---------+---------+---------+----- |
|---|---|---|---|---|
| 1% | 4 | 0.00500 | 0.00577 | (----------------*----------------) |
| 2.5% | 27 | 0.00926 | 0.01542 | (-----*------) |
| 3.75% | 24 | 0.08083 | 0.11632 | (-----*------) |

-continued

| Level | N | Mean | St. Dev | Individual 95% CIs For Mean Based on Pooled StDev<br>----+---------+---------+---------+----- |
|---|---|---|---|---|
| 5% | 10 | 0.03800 | 0.04392 | (---------*----------) |
| | | | | ----+---------+---------+---------+-----<br>-0.050 0.000 0.050 0.100 |

Pooled StDev = 0.07409

The following Tables 47-59 summarize results for formulations 126, 182 and Pbo4.

TABLE 47

Stability of Imiquimod in the Formulations. Percentage of imiquimod that is recovered from each formulation compared to theoretical when stored at 25° C. and 40° C. over a 6 month period.

| | | t = 1 month | | t = 2 months | |
|---|---|---|---|---|---|
| Formulations | t = 0 h | 25° C. | 40° C. | 25° C. | 40° C. |
| 182 | 96.76 ± 0.25 | 102.01 ± 0.01 | 98.46 ± 0.15 | 99.00 ± 0.12 | 98.07 ± 0.10 |
| PBO4 | 0 | 0 | 0 | 0 | 0 |
| 126 | 102.37 ± 0.58 | 102.84 ± 0.45 | 104.11 ± 0.04 | 100.02 ± 0.95 | 101.32 ± 040 |

| | t = 3 months | | t = 6 months | |
|---|---|---|---|---|
| Formulations | 25° C. | 40° C. | 25° C. | 40° C. |
| 182 | 101.48 ± 0.27 | 104.39 ± 1.55 | 102.91 ± 1.16 | 99.12 ± 0.45 |
| PBO4 | 0 | 0 | 0 | 0 |
| 126 | 99.28 ± 3.25 | 98.43 ± 0.55 | 101.95 ± 0.37 | 103.02 ± 1.89 |

TABLE 48

Stability of Imiquimod in the Formulations. Identification of Imiquimod when the formulations are stored at 25° C. and 40° C. over a 6 month period (confirmed by HPLC).

| | | T = 1 month | | T = 2 months | | T = 3 months | | T = 6 months | |
|---|---|---|---|---|---|---|---|---|---|
| Formulations | T = 0 | 25° C. | 40° C. | 25° C. | 25° C. | 40° C. | 40° C. | 25° C. | 40° C. |
| 182 | Complies | Complies | Complies | Complies | Compiles | Complies | Complies | Compiles | Complies |
| 126 | Complies | Complies | Complies | Complies | Complies | Complies | Complies | Complies | Complies |
| GWO3OP | Complies | Complies | Complies | Complies | Complies | Complies | Complies | Complies | Complies |

TABLE 49

Stability of Benzyl Alcohol in the Formulations. Amount of benzyl alcohol that is recovered from each of the formulations when the formulations are stored at 25° C. and 40° C. over a 6 month period.

| | | t = 1 month | | t = 2 months | | t = 3 months | | t = 6 months | |
|---|---|---|---|---|---|---|---|---|---|
| Formulations | t = 0 h | 25° C. | 40° C. | 25° C. | 40° C. | 25° C. | 40° C. | 25° C. | 40° C. |
| 182 | 2.17 ± 0.00 | 2.17 ± 0.00 | 1.95 ± 0.01 | 2.11 ± 0.04 | 1.97 ± 0.00 | 1.94 ± 0.01 | 1.82 ± 0.04 | 1.85 ± 0.03 | 1.48 ± 0.05 |
| PBO4 | 1.93 ± 0.02 | 1.83 ± 0.06 | 1.90 ± 0.03 | 1.91 ± 0.01 | 1.53 ± 0.00 | 1.81 ± 0.01 | 1.39 ± 0.01 | 1.71 ± 0.01 | 1.08 ± 0.02 |
| 126 | 2.00 ± 0.02 | 2.02 ± 0.01 | 1.89 ± 0.01 | 1.86 ± 0.02 | 1.65 ± 0.02 | 2.00 ± 0.04 | 1.70 ± 0.04 | 2.01 ± 0.03 | 1.55 ± 0.02 |

TABLE 50

Stability of Benzyl Alcohol in the Formulations. Identification of Benzyl alcohol when the formulations are stored at 25° C. and 40° C. over a 6 month period (confirmed by HPLC).

| | | T = 1 month | | T = 2 months | | T = 3 months | | T = 6 months | |
|---|---|---|---|---|---|---|---|---|---|
| Formulations | T = 0 | 25° C. | 40° C. | 25° C. | 25° C. | 40° C. | 40° C. | 25° C. | 40° C. |
| 182 | Complies | Complies | Complies | Complies | Compiles | Complies | Complies | Compiles | Complies |
| 126 | Complies | Complies | Complies | Complies | Compiles | Complies | Complies | Compiles | Complies |
| PBO4 | Complies | Complies | Complies | Complies | Complies | Complies | Complies | Compiles | Complies |

TABLE 51

Stability of Methylparabens in the Formulations. Amount of Methylparabens that are recovered from each of the formulations when the formulations are stored at 25° C. and 40° C. over a 6 month period.

| | | t = 1 month | | t = 2 months | | t = 3 months | | t = 6 months | |
|---|---|---|---|---|---|---|---|---|---|
| Formulations | t = 0 h | 25° C. | 40° C. | 25° C. | 40° C. | 25° C. | 40° C. | 25° C. | 40° C. |
| 182 | 0.18 ± 0.00 | 0.18 ± 0.00 | 0.19 ± 0.00 | 0.20 ± 0.00 | 0.20 ± 0.00 | 0.19 ± 0.00 | 0.20 ± 0.00 | 0.19 ± 0.00 | 0.19 ± 0.001 |
| PBO4 | 0.19 ± 0.00 | 0.19 ± 0.00 | 0.18 ± 0.00 | 0.20 ± 0.00 | 0.20 ± 0.000 | 0.20 ± 0.00 | 0.20 ± 0.00 | 0.20 ± 0.00 | 0.20 ± 0.002 |
| 126 | 0.20 ± 0.00 | 0.20 ± 0.00 | 0.19 ± 0.00 | 0.19 ± 0.00 | 0.21 ± 0.00 | 0.21 ± 0.00 | 0.20 ± 0.00 | 0.20 ± 0.00 | 0.20 ± 0.001 |

TABLE 52

Stability of Methylparabens in the Formulations. Identification of Methylparabens when the formulations are stored at 25° C. and 40° C. over a 6 month period (confirmed by HPLC).

| | | T = 1 month | | T = 2 months | | T = 3 months | | T = 6 months | |
|---|---|---|---|---|---|---|---|---|---|
| Formulations | T = 0 | 25° C. | 40° C. | 25° C. | 25° C. | 40° C. | 40° C. | 25° C. | 40° C. |
| 182 | Complies | Complies | Complies | Complies | Compiles | Complies | Complies | Compiles | Complies |
| 126 | Complies | Complies | Complies | Complies | Compiles | Complies | Complies | Compiles | Complies |
| PBO4 | Complies | Complies | Complies | Complies | Complies | Complies | Complies | Compiles | Complies |

TABLE 53

Stability of Propylparabens in the Formulations. Amount of Propylparabens that are recovered from each of the formulations when the formulations are stored at 25° C. and 40° C. over a 6 month period.

| | | t = 1 month | | t = 2 months | |
|---|---|---|---|---|---|
| Formulations | t = 0 h | 25° C. | 40° C. | 25° C. | 40° C. |
| 182 | 0.019 ± 0.000 | 0.020 ± 0.001 | 0.018 ± 0.000 | 0.018 ± 0.000 | 0.018 ± 0.000 |
| PBO4 | 0.018 ± 0.001 | 0.018 ± 0.001 | 0.16 ± 0.001 | 0.19 ± 0.000 | 0.020 ± 0.000 |
| 126 | 0.018 ± 0.000 | 0.019 ± 0.001 | 0.021 ± 0.001 | 0.018 ± 0.000 | 0.019 ± 0.001 |

| | t = 3 months | | t = 6 months | |
|---|---|---|---|---|
| Formulations | 25° C. | 40° C. | 25° C. | 40° C. |
| 182 | 0.021 ± 0.002 | 0.022 ± 0.001 | 0.019 ± 0.000 | 0.019 ± 0.0010 |
| PBO4 | 0.020 ± 0.002 | 0.020 ± 0.002 | 0.018 ± 0.000 | 0.020 ± 0.001 |
| 126 | 0.020 ± 0.001 | 0.010 ± 0.001 | 0.020 ± 0.000 | 0.020 ± 0.001 |

TABLE 54

Stability of Propylparabens in the Formulations. Identification of Propylparabens when the formulations are stored at 25° C. and 40° C. over a 6 month period (confirmed by HPLC).

| | | T = 1 month | | T = 2 months | | T = 3 months | | T = 6 months | |
|---|---|---|---|---|---|---|---|---|---|
| Formulations | T = 0 | 25° C. | 40° C. | 25° C. | 25° C. | 40° C. | 40° C. | 25° C. | 40° C. |
| 182 | Complies | Complies | Complies | Complies | Compiles | Complies | Complies | Compiles | Complies |
| 126 | Complies | Complies | Complies | Complies | Complies | Complies | Complies | Complies | Complies |
| PBO4 | Complies | Complies | Complies | Complies | Complies | Complies | Complies | Complies | Complies |

TABLE 55

Microscopic Stability of the Formulations. The results of the particle size for each formulation which is determined by optical microscopy at 25° C. over a 6 month period.

| | Particle size (μM) | | | | |
|---|---|---|---|---|---|
| Formulation | t = 0 | t = 1 Month | t = 2 Months | t = 3 Months | t = 6 Months |
| 182 | <10 | <10 | <10 | <10 | <10 |
| PBO4 | <10 | <10 | <10 | <10 | <10 |
| 126 | <10 | <10 | <10 | <10 | <10 |

TABLE 56 pH stability of the Formulations. The results of the pH test for each of the formulations when the formulations are stored at 25° C. and 40° C. over a 6 month period. Grey area indicate no test was performed.

| | pH | | | | | | | | |
|---|---|---|---|---|---|---|---|---|---|
| | t = 0 | t = 1 month | | t = 2 months | | t = 3 months | | t = 6 months | |
| Formulation | 25° C. | 25° C. | 40° C. | 25° C. | 40° C. | 25° C. | 40° C. | 25° C. | 40° C. |
| 182 | 4.5 | 4.5 | | 4.5 | 4.5 | 4.5 | 4.6 | 4.3 | 4.3 |
| PBO4 | 4.5 | 4.2 | 4.5 | 4.2 | 4.2 | 4.1 | 4.1 | 4.0 | 4.0 |
| 126 | 4.2 | 4.3 | 4.3 | 4.3 | 4.3 | 4.3 | 4.3 | 4.1 | 4.1 |

TABLE 57

Macroscopic stability of the Formulations. The results of the macroscopic appearance test when the formulations are stored at 25° C. over a 6 month period.

| | Appearance spatula Test (25° C. sample only) | | | | | Visual Viscosity (25° C. sample only) | | | | |
|---|---|---|---|---|---|---|---|---|---|---|
| Formulation | t = 0 | t = 1 month | t = 2 months | t = 3 months | t = 6 months | t = 0 | t = 1 month | t = 2 months | t = 3 months | t = 6 months |
| 182 | Very glossy and smooth | Very glossy and smooth | Very glossy and smooth | Very glossy and smooth | Very glossy and smooth | High | Medium-High | Medium-High | Medium-High | High |
| 126 | Glossy, very slightly textured | Smooth, slightly textured, glossy | Glassy and smooth | Slightly textured, sheen | Glossy | Medium | Medium | Medium | Medium | Low viscosity |
| PBO4 | Glossy and smooth | Glossy and smooth | Glossy and smooth | Glossy and smooth | Smooth cream high sheen | Medium-Low | Medium | Medium-Low | Low | Low |

TABLE 58

Brookfield and Bohlin Viscosity. The results of the viscosity and rheology measurements for the formulations that are stored at 25° C. over a 6 month period.

| | | Cross-over | Brookfield (cPs) | | | | | Bohlin Viscosity (cPs) (based on 3M method) | | | | |
|---|---|---|---|---|---|---|---|---|---|---|---|---|
| Formulation Identity | G *(Pa) t = 0 | (o *) t = 0 | t = 0 | t = 1 Month | t = 2 Months | t = 3 Months | t = 6 Months | t = 0 | t = 1 Month | t = 2 Months | t = 3 Months | t = 6 Months |
| 182 | 702 | 8.5 | 693067 | 1097000 | 904667 | 523033 | 273233 | 18050 | 17850 | 18550 | 16820 | 13691 |
| 126 | ** | ** | 430100 | 235066 | 228104 | 212500 | 105720 | 16783 | 12739 | 14749 | 10856.5 | 8789.5 |
| PBO4 | ** | ** | 227800 | * | * | * | * | 10350 | 7953 | 5511 | 3550 | 2247 |

* Results not presented as the torque is out of range (due to low viscosity) for the Brookfields viscometer based on the setting and spindle that are used for all the other samples. Alternative spindles and settings are investigated; however, the results are vastly different compared to previous readings.
** no recorded measurements.

TABLE 59

Identification of 4-hydroxy Imiquimod when the formulations are stored at 25° C. and 40° C. over a 6 month period (confirmed by HPLC at 318 nm).

| | t = 0 | t = 1 month | | t = 2 months | | t = 3 months | | t = 6 months | |
|---|---|---|---|---|---|---|---|---|---|
| Formulations | 25° C. | 25° C. | 40° C. | 25° C. | 40° C. | 25° C. | 40° C. | 25° C. | 40° C. |
| 182 | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| PBO4 | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| 126 | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |

Example 24

Four Phase 3 Randomized, Double-Blinded, Multicenter, Placebo-Controlled Clinical Studies In this Example 24, four Phase 3 randomized, double-blinded, multicenter, placebo-controlled clinical studies comparing the efficacy and safety of a 3.75% imiquimod cream of Example 23 and a 2.5% imiquimod cream of Example 23 to placebo in the treatment of typical visible or palpable actinic keratoses of the face or balding scalp. Subjects, who are determined to be eligible during the screening phase, are randomized in a 1:1:1 ratio to receive either 2.5% imiquimod cream, 3.75% imiquimod cream or placebo cream once daily during the treatment cycles. Studies GW01-0702 and GW01-0704 are duplicative studies that investigate 2-week treatment cycles, wherein the 2-week treatment cycles are separated by a two week rest period (no treatment), and studies GW01-0703 and GW01-0705 are duplicative studies that investigate 3-week treatment cycles, wherein the 3-week treatment cycles are separated by a three week rest period (no treatment). See flow diagrams depicted in FIG. 70 and see Table 64 herein below. The study entry criteria and endpoints are identical for all four studies. Each study has the same length of a post treatment follow-up period in which the primary endpoint in all four studies is at 8 weeks following the last treatment application. Thus, four Phase 3 clinical studies with two formulations (2.5% and 3.75% imiquimod creams) and one pharmacokinetic study (Example 25) with one formulation of 3.75% imiquimod cream are conducted for the treatment of actinic keratosis diagnosed on the face or balding scalp. See also the FINAL LABEL and the PRODUCT MONOGRAPH, which are filed contemporaneously herewith and incorporated herein by reference in their entireties. Also incorporated herein by reference in their entireties are the following studies identified as follows: (1) Sponsored and information provided by: Graceway Pharmaceuticals, LLC, Study entitled "Safety and Effectiveness Study of Imiquimod Creams for Treatment of Actinic Keratoses [Aks]", and ClinicalTrials.gov Identifier No.: NCT00605176; (2) Sponsored and information provided by: Graceway Pharmaceuticals, LLC, Study entitled "Safety and Effectiveness Study of Imiquimod Creams for Treatment of Actinic Keratoses [Aks]", and ClinicalTrials.gov Identifier No.: NCT00603798; and (3) Sponsored and information provided by: Graceway Pharmaceuticals, LLC, Study entitled "Follow-up Study to Evaluate Sustained Clearance Rates of Actinic Keratoses up to One Year", and ClinicalTrials.gov Identifier No.: NCT00668733. The four Phase 3 clinical studies with two formulations (2.5% and 3.75% imiquimod creams) and the one pharmacokinetic study (Example 25) are summarized as follows:

In Example 25, a pharmacokinetic study conducted under maximal use conditions (Study GW01-0706) is described as indicated above.

Four randomized, double-blinded, placebo-controlled Phase 3 clinical studies (differing only in the duration of treatment and interval cycles) are characterized as follows:

1. Studies GW01-0702 & GW01-0704 (2-week treatment cycle regimen): two identical studies evaluating 2.5% imiquimod cream, 3.75% imiquimod cream or placebo cream which is applied daily for two 2-week treatment cycles. The first treatment cycle consists of two weeks of daily treatment followed by two weeks of no treatment, and the second treatment cycle consists of an additional two weeks of daily treatment followed by eight weeks of post treatment follow-up period (total study duration 14 weeks); and 2. Studies GW01-0703 & GW01-0705 (3-week treatment cycle regimen): two identical studies evaluating 2.5% imiquimod cream, 3.75% imiquimod cream or placebo cream which is applied daily for two 3-week treatment cycles. The first treatment cycle consists of three weeks of daily treatment followed by three weeks of no-treatment, and the second treatment cycle consists of an additional three weeks of daily treatment followed by eight weeks of post treatment follow-up period (total study duration 17 weeks).

The clinical studies are displayed in Table 61 below. All 4 Phase 3 studies are conducted at separate study sites to provide independent confirmatory evidence of safety and efficacy. The results from these studies are evaluated and based on the safety and efficacy results from all four studies.

TABLE 61

Summary of Studies of Imiquimod for the Actinic Keratosis

| Study Number/ Status | Number of Subjects | Treatments | Brief Study Description/ Comments |
|---|---|---|---|
| GW01-0706 | 19 | Two 250 mg packets of 3.75% imiquimod is applied to the entire face or balding scalp every day for 3 weeks | Pharmacokinetic study is conducted under maximal use conditions in AK subjects. Study designed to demonstrate steady-state conditions. |
| GW01-0702 | 242 | Up to two 250 mg packets are applied to the entire face or balding scalp 2.5% imiquimod cream every day for two 2-week treatment cycles 3.75% imiquimod cream every day for two 2-week treatment cycles Placebo every day for two 2-week treatment cycles | Phase 3 study of the 2-week treatment cycle regimen (2 weeks on treatment, 2 weeks of no treatment, followed by 2 weeks on treatment). Primary endpoint of complete clearance at 8 weeks after treatment (Week 14; End Of Study—EOS) |
| GW01-0704 | 237 | Same treatments as Study 02 | Duplicate of study 02 is conducted at independent study centers. |
| GW01-0703 | 240 | Up to two 250 mg packets are applied to the entire face or balding scalp 2.5% imiquimod every day for two 3-week treatment cycles 3.75% imiquimod every day for two 3-week treatment cycles Placebo every day for two 3-week treatment cycles | Phase 3 study of the 3-week treatment cycle regimen (3 weeks on treatment, 3 weeks of no treatment, followed by 3 weeks on treatment). Primary endpoint of complete clearance at 8 weeks after treatment (Week 17; EOS) |
| GW01-0705 | 250 | Same treatments as Study 03 | Duplicate of Phase 3 study 03 is conducted at independent study centers. |

All four Phase 3 studies are randomized, double-blinded, multicenter, placebo-controlled studies comparing the efficacy and safety of 3.75% imiquimod cream and 2.5% imiquimod cream to placebo in the treatment of typical visible or palpable actinic keratoses of the face or balding scalp. Subjects determined to be eligible during the screening phase are randomized in a 1:1:1 ratio to receive either 3.75% imiquimod cream, 2.5% imiquimod cream or placebo cream once daily during the treatment cycles. Studies GW01-0702 and GW01-0704 investigate two 2-week treatment cycles that are separated by a two weeks of no treatment, and studies GW01-0703 and GW01-0705 investigate two 3-week treatment cycles that are separated by three weeks of no treatment.

Studies GW01-0702 and GW01-0704 are conducted concurrently according to identical protocols. A total of approximately 479 subjects are randomized in a 1:1:1 ratio (approximately 240 to each treatment arm) to achieve approximately 450 subjects completing the study. The treatment arms are:

2.5% imiquimod cream 3.75% imiquimod cream placebo cream

Eligible subjects for the study are at least 18 years of age, with about 5 to 20 typical visible or palpable actinic keratosis lesions (AKs) in an area that exceeded 25 $cm^2$ on either the face or the balding scalp. The treatment area could be either the entire face, excluding the ears, or the balding scalp, but not both. Apart from the primary diagnosis, the subjects are to be in good general health, and free of conditions which might put them at undue risk during study procedures. They must not use imiquimod cream on the face or scalp within 1 year of study entrance, nor use other potentially interfering medications within pre-specified washout intervals prior to study entrance.

The randomized, blinded study product is used in 2 treatment cycles each of 2 weeks duration, separated by a 2-week period without treatment. Once a day during the treatment cycles, subjects apply the study cream in a thin layer to the entire treatment area. A maximum of 2 packets (i.e., up to 500 mg) could be applied for a given dose. The study cream is applied prior to normal sleeping hours and is removed approximately 8 hours later with mild soap and water.

During the 2 treatment cycles of 2 weeks, subjects are scheduled for a total of 9 study visits:

Visit 1, Screening

Visit 2, Baseline, Cycle 1 Treatment Initiation

Visit 3, Week 1

Visit 4, Week 2, End of Cycle 1

Visit 5, Week 4, Cycle 2 Treatment Initiation

Visit 6, Week 5

Visit 7, Week 6, End of Cycle 2 (End of Treatment)

Visit 8, Week 10, Follow-up

Visit 9, Week 14, End of Study, Primary Efficacy Endpoint

The objective of the studies is to compare the safety and efficacy of 2.5% imiquimod cream and 3.75% imiquimod cream vs. placebo in the treatment of actinic keratosis when the cream is applied once daily for two 2-week treatment cycles separated by a 2-week no-treatment period.

The two additional Phase 3 studies, GW01-0703 and GW01-0705, are conducted concurrently according to identical protocols. These studies are also randomized, double-blind, multicenter, placebo-controlled trials identical to the pivotal studies in all respects except for the duration of the treatment regimens and corresponding differences in visit schedules. The planned number of subjects, randomization methodology, entrance criteria, and study drug formulations are the same as in the two Phase 3 GW01-0702 and GW01-0704 studies trials.

As in the GW01-0702 and GW01-0704 studies, the randomized, blinded study products are used in two 2-week treatment cycles, but in GW01-0703 and GW01-0705, the treatment cycles are of three weeks duration, separated by a 3-week period without treatment.

During the two treatment cycles of three weeks, subjects are scheduled for a total of 11 study visits:

Visit 1, Screening
Visit 2, Baseline, Cycle 1 Treatment Initiation
Visit 3, Week 1
Visit 4, Week 2
Visit 5, Week 3, End of Cycle 1
Visit 6, Week 6, Cycle 2 Treatment Initiation
Visit 7, Week 7
Visit 8, Week 8
Visit 9, Week 9, End of Cycle 2 (End of Treatment)
Visit 10, Week 13, Follow-up
Visit 11, Week 17, End of Study, Primary Efficacy Endpoint Thus, two pairs of 2 identical Phase 3 studies (four Studies) regarding efficacy and safety of four and six weeks of treatment with imiquimod formulations for actinic keratosis are conducted. See Table 62. Each pair evaluates a different treatment regimen and each individual study contains two imiquimod concentrations, i.e., 2.5% and 3.75% imiquimod formulations with comparisons to placebo (double-blinded).

TABLE 62

Four Clinical Trials

| | | | |
|---|---|---|---|
| 2 × 2 × 2 wks | GW01-0702 | | |
| | 2.5% | (N = 81) | L2 |
| | 3.75% | (N = 81) | H2 |
| | Vehicle | (N = 80) | V |
| 2 × 2 × 2 wks | GW01-0704 | | |
| | 2.5% | (N = 79) | L2 |
| | 3.75% | (N = 79) | H2 |
| | Vehicle | (N = 79) | V |
| 3 × 3 × 3 wks | GW01-0703 | | |
| | 2.5% | (N = 82) | L3 |
| | 3.75% | (N = 80) | H3 |
| | Vehicle | (N = 78) | V |
| 3 × 3 × 3 wks | GW01-0705 | | |
| | 2.5% | (N = 82) | L3 |
| | 3.75% | (N = 82) | H3 |
| | Vehicle | (N = 82) | V |

The study design is as summarized in Table 63—Study Designs below.

TABLE 63

Study Designs
2 Cycles + 8 wks Follow-up

| Cycle 1 | | Cycle 2 | |
|---|---|---|---|
| Daily TX | No TX<br>Rest Period | Daily TX | No TX<br>Follow up |
| 2 or 3 wks | 2 or 3 wks | 3 × 3 × 3 study | 8 wks - Endpoint is determined at end of week 14 for the 2 × 2 × 2 study or week 17 for the |

In contrast, the FDA approved treatment regimen for treating actinic keratosis with Aldara® 5% imiquimod cream is two times per week for 16 weeks and end point is determined at end of week 24.

The key entry criteria for these four studies are: (1) 18 years of age or greater; (2) 5-20 AKs in treatment area; (3) the treatment area exceeds 25 $cm^2$; and (4) the treatment area is either full face or balding scalp, but not both. As a historical reference, the FDA approved treatment area for Aldara® 5% imiquimod cream is 25 $cm^2$ and the number of AK lesions treated in the treatment area is generally between 4 and 8.

Key efficacy measures for these four studies are a reduction of AK lesions from Baseline to End of Study (Week 14 or 17):

Primary: complete clearance (yes/no)*
Secondary: at least 75% reduction in number of AK lesions (partial clearance yes/no)*
Secondary: percent reduction in number of AK lesions analyzed as a continuous variable

* All AK lesions that are cleared including newly arising sub-clinical lesions

The protocol for the two pairs of identical phase three studies (4 Studies) includes: (1) voluntary rest periods of any length during treatment cycles are permitted; (2) the subjects keep to original study schedule irrespective of rest periods or missed doses; and (3) the subjects apply the imiquimod formulation in Cycle 2 irrespective of clearance in Cycle 1.

The key safety measures for the study are: (1) adverse events; (2) local skin reactions (LSRs), including (a) area under the curve (AUCsum) and (b) erythema (includes severe); (3) rest periods; and (4) study discontinuations.

Figure 70:
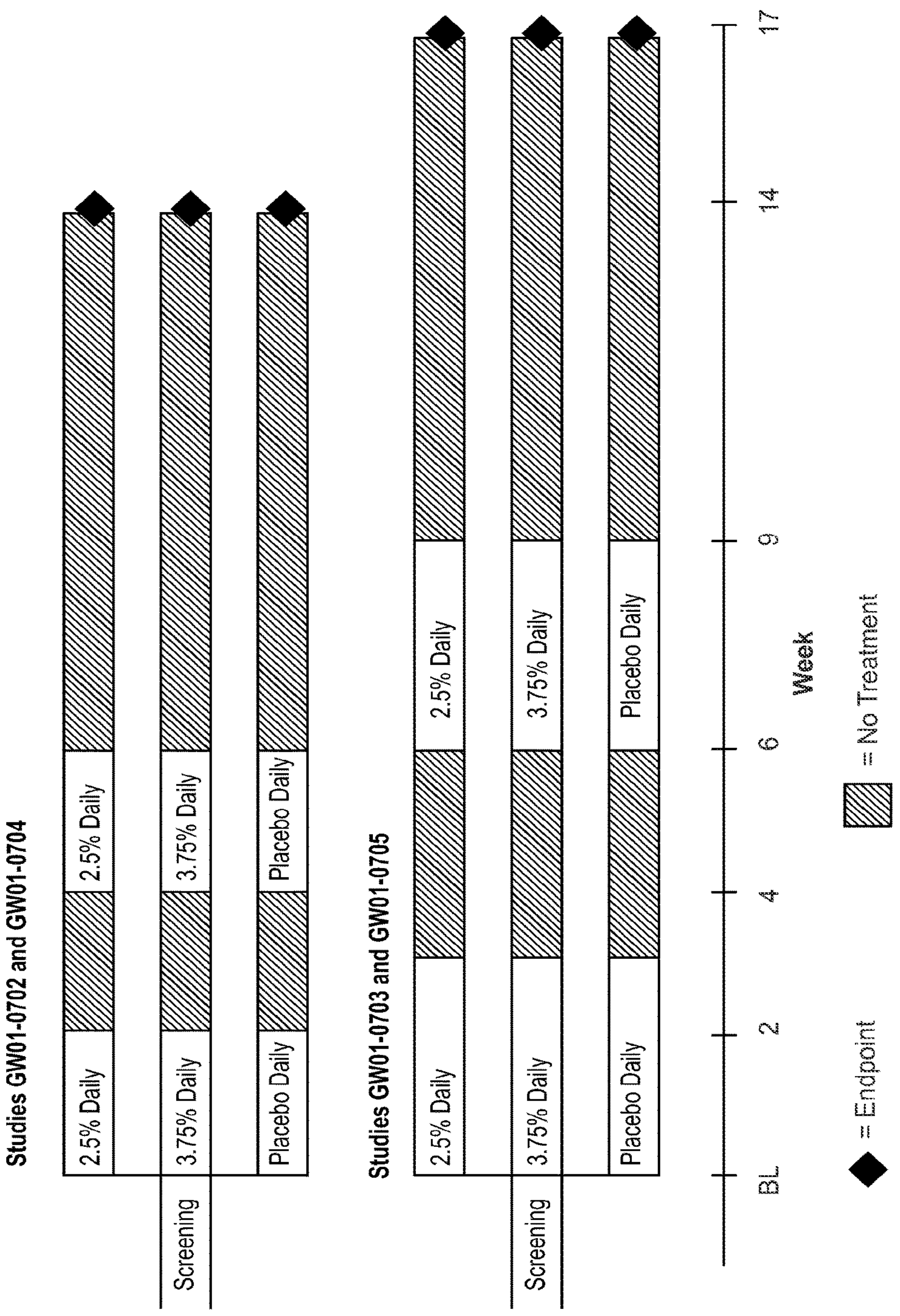
FIG. 70 includes flow diagrams illustrating the treatment regimen for studies GW01-0702, GW01-0703, GW01-0704 and GW01-0705.

The study treatment regimens are described in Table 64 and depicted in the flow diagram(s) illustrated in FIG. 70.

TABLE 64

Study Treatment Regimen

| Study | Treatment Regimen |
|---|---|
| GW01-0702 | 2.5% Daily, 2 × 2 × 2 weeks, see FIG. 70 |
| GW01-0704 | 3.75% Daily, 2 × 2 × 2 weeks, see FIG. 70 |
| GW01-0703 | 2.5% Daily, 3 × 3 × 3 weeks, see FIG. 70 |
| GW01-0704 | 3.75% Daily, 3 × 3 × 3 weeks, see FIG. 70 |

The LSR AUC sum is defined as follows:

(1) LSRs (0-3 scale)
Erythema
Edema
Weeping/exudate
Scabbing/crusting
Flaking/scaling/dryness
Erosion/ulceration*

*0-2 scale (2) $AUC_{sum}$
Sum of individual LSR Scores
Over study duration (14 or 17 weeks; includes 4 or 6 weeks on treatment)

The population of the study is summarized in the Table 65—Population below and as follows:

(1) 969 AK subjects enrolled to 4 studies;
(2) 646 subjects are randomized to active imiquimod cream:
160 to 2.5% imiquimod cream, 2-week cycles
160 to 3.75% imiquimod cream, 2-week cycles
164 to 2.5% imiquimod cream, 3-week cycles
162 to 3.75% imiquimod cream, 3-week cycles; and (3) The subjects are enrolled at 51 sites geographically distributed in the USA, wherein:

Median number of subjects enrolled per site: 18

Range: 2 to 34.

TABLE 65

| Population | | | | | |
|---|---|---|---|---|---|
| | L2 2.5% 2 W (N = 160) | H2 3.75% 2 W (N = 160) | L3 2.5% 3 W (N = 164) | H 3.75% 3 W (N = 162) | V Vehicle (N = 323) |
| Age, Mean (Range) | 64 (39-90) | 64 (36-89) | 66 (33-87) | 64 (40-90) | 64 (37-89) |
| Sex, % male | 79 | 83 | 78 | 76 | 82 |
| Race % white | 100 | 100 | 100 | 99 | 99 |
| Treatment Area, % Face/Scalp | 73/27 | 76/2 | 70/30 | 71/2 | 75/25 |
| Skin Type, % I, II, and III | 84 | 87 | 88 | 90 | 86 |
| Baseline Count, Mean/Median | 10.9/10.0 | 11.0110.0 | 10.6/10.0 | 11.1/9.0 | 10.8/10.0 |

A summary of drug exposure and compliance is set forth in the Table 66 Drug Exposure/Compliance below.

TABLE 66

| Drug Exposure/Compliance | | | | | |
|---|---|---|---|---|---|
| | L2 2.5% 2 Week (N = 160) | H2 3.75% 2 Week (N = 160) | L3 2.5% 3 Week (N = 164) | H 3.75% 3 Week (N = 162) | V Vehicle (N = 323) |
| Average Number of Packets Used Per Application | 1.71 | 1.62 | 1.68 | 1.67 | 1.70 |
| Number (%) Subjects Noncompliant* | 2 (1.3) | 9 (5.6) | 69 (3.7) | 9 (5.6) | 14 (4.4) |

The following efficacy and safety results are observed and reported in FIGS. 1-24 and 51-52:

(1) all active treatment groups show statistically significant differences from vehicle in all efficacy measures; and (2) there are no consistent statistically significant differences between the 2.5% and 3.75% treatment groups (*) within each of the studies;

Partial clearance is significantly different between L2 and H2 in the GW01-0704 study, but not in the GW01-0702 study;

Percent reduction between L2 and H2 in PP GW01-0704 study and PP GW01-0702 study, not in ITT population.

Percent reduction between L3 and H3 in PP GW01-0705 study, not in ITT population and not in GW01-07023 study.

Primary analysis populations are defined prospectively for the analysis. The primary population to be analyzed for efficacy and safety is the Intent-To-Treat ("ITT") population, including all randomized subjects. The Per Protocol ("PP") population includes subjects who complete the study without any protocol violations. Subjects are excluded from the PP population if any of the following criteria are met.

Failure to meet Inclusion/Exclusion criteria

Took restricted medications/treatments

Nonadherence to the visit schedule

Noncompliance with study treatment

The investigators determine the treatment area for the studies at baseline (either the entire face or the balding scalp, but not both). Subjects are instructed to apply a thin layer of study medication to the treatment area, up to two packets (up to 500 mg) of product, avoiding the periocular areas, lips and nares. Subjects return for clinic visits over the course of the study for efficacy and safety measurements.

Actinic keratosis lesions arise on a background of UV-damaged skin, and therefore, usually occur over an extensive area or field of sun-exposed skin. The creams are applied to the entire face or balding scalp, and not just the 5-20 individual lesions required for study entry. Application to the full face of balding scalp provides clear direction to subjects regarding the area to be treated without reference to the exact location of lesions; additionally application to the full face or balding scalp has the potential to treat sub-clinical or incipient lesions. Two concentrations of imiquimod cream (2.5% and 3.75%) are used and compared to placebo for each study regimen, allowing a direct comparison of the concentrations for study outcomes.

As indicated above, treatment cycles of two or three weeks are chosen for these Phase three studies. It is observed that sizable numbers of subjects receiving the 5% imiquimod cream two or three times a week take rest periods typically at the 4-6 week point in therapy. The need for rest periods is usually preceded by an increase at ~2-3 weeks in signs and symptoms of local skin reactions. Cycle treatment (two cycles of three times a week for four consecutive weeks) appears to reduce but not eradicate the need for rest periods among subjects. The current Phase three studies investigate daily dosing (for two or three weeks) followed by an interval of two or three weeks of no treatment before repeating another two- or three-week treatment cycle. This 'no treatment period' is expected to occur after the initial onset of signs and symptoms which herald the onset of pharmacodynamic effects of imiquimod treatment.

Subjects were instructed to apply the cream for a second treatment cycle irrespective of the degree of lesion clearance with the initial treatment cycle. This is consistent with the current Aldara® package insert, which mandates a full 16 weeks of treatment irrespective of interim treatment response. The use of two treatment cycles allows for a uniform assessment point for all subjects at 8 weeks following the termination of the second treatment cycle, irrespective of initial treatment response. The two-cycle treatment course is anticipated to have a beneficial effect on 'sub-clinical' lesions. Previous studies suggest that these lesions may become visible approximately two weeks into a treatment course. A second treatment cycle has the potential to treat both residual clinically evident AK lesions as well as any sub-clinical lesions.

AK lesions are counted at study visits to derive the one primary (Complete Clearance) and two secondary (Partial Clearance, Percent AK reduction) efficacy endpoints. To meet the Complete Clearance primary efficacy endpoint, subjects needed to be clear of all lesions in the treatment area, irrespective of whether those lesions were identified at baseline or later.

The primary efficacy variable is subject status with respect to complete clearance of AK lesions at the end of study (EOS; 8 weeks following the last scheduled dose). The EOS visits occurred at Week 14 for the GW01-0702/GW01-0704 studies, and at Week 17 for the GW01-0703/GW01-0705 studies. Complete clearance was defined as the absence of clinically visible or palpable AK lesions in the treatment area.

The secondary efficacy variables are:

Subject status with respect to partial clearance of AK lesions at EOS, defined as at least about a 75% reduction in the number of AK lesions in the treatment area compared with Baseline;

Percent change (reductions) from Baseline to EOS in investigator counts of AK lesions.

The statistical methods for efficacy analyses are the same in all four Phase 3 studies.

Efficacy analyses are conducted on the ITT population and on the PP population. For the primary efficacy variable, imputations are made for missing data points using last observation carried forward (LOCF, primary analysis), taking all missed observations as failure (sensitivity analysis), and using observed cases only (supportive analysis). The PP population analysis uses only cases that are observed. For analysis of secondary efficacy variables, only the LOCF method is used for the ITT population, and only cases that are observed for the PP population. All data from interim visits (before EOS/Early Termination) are analyzed at their nominal time points.

The allowed visit window at EOS, is any time more than 42 days after the date of last dose (or last rest). Subjects with no EOS visit are excluded from the PP population. In the ITT population, subjects without an in-window EOS visit are analyzed using the LOCF.

All pairwise comparisons of active treatment versus placebo are made using Hochberg's modified Bonferroni procedure. If either test is significant at a 0.025 level of significance, then that test is considered significant. Otherwise, if both tests are significant at 0.05, then both tests are considered significant. The 3.75% and 2.5% imiquimod treatment groups are compared to each other at the 0.05 level of significance if at least one of these treatment groups is found to be different than the placebo using the Hochberg's test.

In this way, complete clearance rates, partial clearance rates, change from Baseline AK lesion counts, and percent change from baseline AK lesion counts are analyzed using Cochran-Mantel-Haenszel (CMH) statistics, stratifying on center.

If at least one of the active arms is found to be superior to placebo in the primary efficacy variable of complete clearance, the secondary efficacy variable of partial clearance is compared between each of the active arms and placebo using Hochberg's modified Bonferroni procedure. If the secondary efficacy variable of partial clearance is found to be superior to placebo in either of the active treatment groups, then the secondary efficacy variable of percent reduction is tested. Tertiary efficacy variables are tested without adjustment for multiplicity at the nominal 5% level.

In order to obtain at least 6 subjects per center per treatment group, investigational centers yielding fewer than 18 subjects are combined together in order of geographical proximity. The exact composition of these "analysis centers" is determined and documented prior to breaking the study blind. The stratification for CMH analyses is based on the analysis centers, not on the actual investigational centers.

In the primary analysis of complete clearance rate, the Breslow-Day statistic is tested at the 10% level for heterogeneity of the odds ratios across analysis centers. A finding of statistical significance in this test is followed by exploratory analyses to characterize the source of the heterogeneity.

The primary efficacy variable is summarized without statistical testing by success frequency by investigator center, by analysis center, by gender, by age subgroup, by skin type subgroup, by baseline lesion count subgroup, and by treatment area (face or balding scalp).

Subjects who show a greater number of AK lesions at any time post-baseline compared to the baseline lesion count are of particular interest since the new lesions may represent sub-clinical lesions which are present but unobserved at the baseline visit. The proportion of subjects who show new lesions while on treatment are presented by treatment group, and the primary efficacy variable is summarized in this subject subgroup.

All safety measures are analyzed using the ITT data set. Safety is assessed by collection of adverse events which are fully characterized as to intensity, seriousness and relationship to study drug. Additionally, local skin reactions (LSRs) are anticipated adverse events related to the pharmacodynamic activity of the drug; therefore, LSRs are assessed by the investigator at each study visit. Six LSRs (erythema, edema, weeping/exudate, flaking/scaling/dryness, scabbing/crusting, and erosion/ulceration) are rated by the investigator at each study visit on a 0-3 scale (save erosion/ulceration rated 0-2). Data relating to rest periods are collected. Vital signs and laboratory data are collected prestudy or baseline and at end of study.

Adverse events (AEs) are coded using Medical Dictionary for Regulatory Activities (MedDRA) terminology. Treatment-emergent AEs are summarized for each treatment group by the overall incidence of at least one event, incidence by system organ class, and incidence by system organ class and preferred term. Treatment-emergent. AEs are also summarized by severity, and by relationship to study product. The AE incidence is summarized by gender, by age subgroup, by skin type subgroup, by baseline lesion count subgroup, and by location of treatment area (face or balding scalp). Serious AEs and discontinuations due to AEs are listed by subject.

The intensity of each local skin reaction (LSR) type (erythema, edema, weeping/exudate, flaking/scaling/dryness, scabbing/crusting, and erosion/ulceration) and the most intense reaction (post-baseline) for each type are summarized by frequency counts and mean scores by treatment group and study visit. An LSR sum score is computed at each study visit, and 3 areas under the curve (AUC, in days) are calculated; from Baseline to beginning of Treatment Cycle 2, from beginning of Treatment Cycle 2 to End of Study (EOS), and from Baseline to EOS. These values are compared pairwise between treatment groups using Fisher's least significant differences in the 1-way analysis of variance (treatment group).

The number and percentage by treatment group of subjects who require a rest period (1 or more, by treatment cycle and overall) are analyzed using CMH statistics. A similar analysis summarized the number and percentage of subjects by treatment group (1) who require a rest period in both treatment cycles, (2) who require a rest period in Cycle 1 only, and (3) who require a rest period in Cycle 2 only. The number of dosing days missed due to rest periods and the number of dosing days prior to the beginning of the first rest period are analyzed using nonparametric CMH methods for each treatment cycle and overall.

Clinical laboratory values are listed, and frequency counts in alert status shifts are tabulated.

The preliminary results from each of the Phase 3 clinical studies are summarized in the sections below, with the results of paired identical studies (GW01-0702/GW01-0704 and GW01-0703/GW01-0705 presented side by side). Overall, a total of 969 subjects are enrolled into the four Phase 3 studies. Fifty-one independent sites in the United States enrolled subjects in the Phase 3 studies. The number of subjects that are included in the ITT Data sets are tabulated in Table 67.

TABLE 67

| Number of Subjects Included in the ITT Data Sets | | | | |
|---|---|---|---|---|
| Study | 3.75% IMIQ | 2.5% IMIQ | Placebo | Overall |
| GW01-0702 | 81 | 81 | 80 | 242 |
| GW01-0704 | 79 | 79 | 79 | 237 |
| Combined 2-Week Treatment Cycle Regimen Studies | 160 | 160 | 159 | 479 |
| GW01-0703 | 80 | 82 | 78 | 240 |
| GW01-0705 | 82 | 82 | 86 | 250 |
| Combined 3-Week Treatment Cycle Regimen Studies | 162 | 164 | 164 | 490 |

Studies of Two-Week Treatment Cycles

Preliminary data from the Two-week Treatment Cycle Studies (GW01-0702 and GW01-0704) are presented below.

Subject Disposition for studies GW01-0702 and GW01-0704 is tabulated in Table 68.

TABLE 68

Subject Disposition; Two-Week Treatment Cycle Regimen Studies

| | GW01-0702 | | | GW01-0704 | | |
|---|---|---|---|---|---|---|
| | 2.5% IMIQ | 3.75% IMIQ | Placebo | 2.5% IMIQ | 3.75% IMIQ | Placebo |
| Total no. of subjects, n (%) | | | | | | |
| Randomized | 81 | 81 | 80 | 79 | 79 | 79 |
| Completed Study[a] | 78 (96.3) | 74 (91.4) | 75 (93.8) | 76 (96.2) | 75 (94.9) | 75 (94.9) |
| Discontinued Study | 3 (3.7) | 7 (8.6) | 5 (6.3) | 3 (3.8) | 4 (5.1) | 4 (5.1) |
| Reasons for discontinuation from the study, n (%[b]) | | | | | | |
| Safety reasons (AEs) | 1 (1.2) | 1 (1.2) | 2 (2.5) | 0 | 1 (1.3) | 1 (1.3) |
| Investigator's request | 0 | 0 | 0 | 0 | 0 | 0 |
| Subject's request (not AE) | 1 (1.2) | 3 (3.7) | 2 (2.5) | 1 (1.3) | 1 (1.3) | 2 (2.5) |
| Noncompliance | 0 | 0 | 0 | 0 | 1 (1.3) | 0 |
| Use of concomitant therapy | 0 | 1 (1.2) | 0 | 0 | 0 | 1 (1.3) |
| Lost to follow-up | 1 (1.2) | 2 (2.5) | 1 (1.3) | 1 (1.3) | 0 | 0 (0.0) |
| Other (not AE) | 0 | 0 | 0 | 1 (1.3) | 1 (1.3) | 0 |

AE = adverse event;
IMIQ = Imiquimod
[a]Includes subjects who complete both the treatment periods and the post-treatment follow-up period.
[b]Percentage of randomized population.

Subject demographics for each study are tabulated in Table 69, and the number of baseline AK lesions for each study are tabulated in Table 70.

TABLE 69

Demographic Summary - Two-Week Treatment Cycle Regimen Studies; ITT Population

| | GW01-0702 | | | GW01-0704 | | |
|---|---|---|---|---|---|---|
| | 2.5% IMIQ (N = 81) | 3.75% IMIQ (N = 81) | Placebo (N = 80) | 2.5% IMIQ (N = 79) | 3.75% IMIQ (N = 79) | Placebo (N = 79) |
| Age in years | | | | | | |
| Mean ± SD | 63.7 ± 10.7 | 63.8 ± 11.1 | 63.6 ± 8.3 | 65.0 ± 10.3 | 65.3 ± 10.0 | 65.0 ± 9.5 |
| Median | 63.3 | 63.9 | 63.4 | 64.4 | 65.3 | 63.7 |
| Minimum, Maximum | 43.8, 88.7 | 36.5, 89.8 | 42.7, 83.1 | 39.6, 90.0 | 36.3, 86.4 | 46.4, 89.1 |
| Sex, n (%) | | | | | | |
| Male | 59 (72.8) | 69 (85.2) | 70 (87.5) | 68 (86.1) | 63 (79.7) | 60 (75.9) |
| Female | 22 (27.2) | 12 (14.8) | 10 (12.5) | 11 (13.9) | 16 (20.3) | 19 (24.1) |
| Race, n (%) | | | | | | |
| White | 81 (100) | 81 (100) | 80 (100) | 79 (100) | 79 (100) | 78 (98.7) |
| Non-White | 0 | 0 | 0 | 0 | 0 | 1 (1.3) |
| Ethnicity, n (%) | | | | | | |
| Hispanic | 4 (4.9) | 5 (6.2) | 5 (6.3) | 0 | 1 (1.3) | 0 |
| Non-Hispanic | 77 (95.1) | 76 (93.8) | 75 (93.8) | 79 (100) | 78 (98.7) | 79 (100) |

TABLE 69-continued

Demographic Summary - Two-Week Treatment Cycle Regimen Studies; ITT Population

| | GW01-0702 | | | GW01-0704 | | |
|---|---|---|---|---|---|---|
| | 2.5% IMIQ (N = 81) | 3.75% IMIQ (N = 81) | Placebo (N = 80) | 2.5% IMIQ (N = 79) | 3.75% IMIQ (N = 79) | Placebo (N = 79) |
| Fitzpatrick skin type, n (%) | | | | | | |
| I | 9 (11.1) | 5 (6.2) | 6 (7.5) | 20 (25.3) | 17 (21.5) | 13 (16.5) |
| II | 35 (43.2) | 43 (53.1) | 25 (31.3) | 27 (34.2) | 31 (39.2) | 33 (41.8) |
| III | 23 (28.4) | 17 (21.0) | 37 (46.3) | 20 (25.3) | 26 (32.9) | 26 (32.9) |
| IV | 11 (13.6) | 15 (18.5) | 11 (13.8) | 11 (13.9) | 5 (6.3) | 5 (6.3) |
| V | 3 (3.7) | 1 (1.2) | 1 (1.3) | 1 (1.3) | 0 | 2 (2.5) |
| Location of Treatment Area, n (%) | | | | | | |
| Face | 61 (75.3) | 66 (81.5) | 60 (75.0) | 56 (70.9) | 55 (69.9) | 59 (74.7) |
| Balding Scalp | 20 (24.7) | 15 (18.5) | 20 (25.0) | 23 (29.1) | 24 (30.4) | 20 (25.3) |

SD = standard deviation;

IMIQ = Imiquimod

Fitzpatrick skin type: I = burns easily, never tans; II = burns easily, tans minimally with difficulty; III = burns moderately, tans moderately and uniformly; IV = burns minimally, tans moderately and evenly; V = rarely burns, tans profusely; VI = never burns, tans profusely.

TABLE 70

Actinic Keratosis Lesions at Baseline - Two-Week Treatment Cycle Regimen Studies; ITT Population

| | GW01-0702 | | | GW01-0704 | | |
|---|---|---|---|---|---|---|
| Baseline values | 2.5% IMIQ (N = 81) | 3.75% IMIQ (N = 81) | Placebo (N = 80) | 2.5% IMIQ (N = 79) | 3.75% IMIQ (N = 79) | Placebo (N = 79) |
| Mean (SD) | 11.11 (4.42) | 10.89 (4.90) | 11.74 (4.77) | 10.77 (4.44) | 11.16 (4.81) | 10.82 (4.64) |
| Median | 10 | 9 | 10 | 10 | 11 | 10 |
| Minimum, Maximum | 5, 20 | 5, 20 | 5, 20 | 5, 20 | 5, 29 | 5, 20 |
| P value vs Placebo[a] | 0.376 | 0.256 | NA | 0.864 | 0.542 | NA |
| P value vs 3.75% imiquimod cream[a] | 0.818 | NA | NA | 0.688 | NA | NA |

SD = Standard deviation

[a]P values are from Cochran-Mantel-Haenszel test, are stratified by investigator center, taking 2 treatment groups at a time.

Subjects in studies GW01-0702 and GW01-0704 are compliant with the administration of study medication; greater than 91% of the subjects are compliant with the dosing regimen. Compliance is defined as applying more than 75% of the prescribed doses; 'rest' days are considered as application days.

Primary and secondary efficacy results for the GW01-0702 and GW01-0704 studies are presented in Table 71, Table 72 and Table 73. The primary efficacy variable is the rate of complete clearance at EOS (Week 14). The secondary efficacy variables are the rate of partial clearance (at least 75% reduction in AKs from baseline) at EOS, and the percent change from Baseline to EOS in investigator counts of AK lesions. Both active treatment arms demonstrate greater efficacy than placebo, which is statistically significant for all primary and secondary endpoints.

TABLE 71

ITT (LOCF) Complete Clearance Rates at EOS for Individual Two-Week Treatment Cycle Regimen Studies

| Study | 3.75% IMIQ | 2.5% IMIQ | Placebo |
|---|---|---|---|
| GW01-0702 | 25.9% (21/81) | 23.5% (19/81) | 2.5% (2/80) |
| GW01-0704 | 45.6% (36/79) | 38.0% (30/79) | 10.1% (8/79) |
| Combined | 35.6% (57/160) | 30.6% (49/160) | 6.3% (10/159) |

TABLE 72

ITT (LOCF) Partial Clearance Rates at EOS for Individual Two-Week Treatment Cycle Regimen Studies

| Study | 3.75% IMIQ | 2.5% IMIQ | Placebo |
|---|---|---|---|
| GW01-0702 | 45.7% (37/81) | 42.0% (34/81) | 18.8% (15/80) |
| GW01-0704 | 73.4% (58/79) | 54.4% (43/79) | 26.6% (21/79) |
| Combined | 59.4% (95/160) | 48.1% (77/160) | 22.6% (36/159) |

TABLE 73

ITT (LOCF) Median Percent Change from Baseline in AK Lesion Count at EOS for Individual Two-Week Treatment Cycle Regimen Studies

| Study | 3.75% IMIQ | 2.5% IMIQ | Placebo |
|---|---|---|---|
| GW01-0702 | −72.7% | −60.0% | −21.1% |
| GW01-0704 | −90.9% | −76.5% | −30.0% |
| Combined | −81.8% | −71.8% | −25.0% |

The incidence rates for selected safety parameters for the combined Two-Week Treatment Cycle Regimen studies are displayed in Table 74.

TABLE 74

Summary of Incidence Rates for Selected Safety Parameters (Combined Two-Week Treatment Cycle Regimen Studies)

| | 3.75% IMIQ (N = 160) | 2.5% IMIQ (N = 160) | Placebo (N = 159) |
|---|---|---|---|
| Discontinued study prematurely due to safety reasons, n (%) | 2 (1.3%) | 1 (0.6%) | 3 (1.9%) |
| Treatment-related AEs, n (%) | 31 (19.4%) | 19 (11.9%) | 4 (2.5%) |
| Rest periods, n (%) | 17 (10.6%) | 11 (6.9%) | 0 (0%) |

The most common treatment-related adverse events are displayed in Table 75 below.

TABLE 75

Incidence of Most Common* Treatment-Related Adverse Events (Combined Two-Week Treatment Cycle Regimen Studies)

| MedDRA Term | 3.75% IMIQ (N = 160) | 2.5% IMIQ (N = 160) | Placebo (N = 159) |
|---|---|---|---|
| Application site pruritus | 7 (4.4%) | 6 (3.8%) | 1 (0.6%) |
| Application site pain | 5 (3.1%) | 2 (1.3%) | 0% |
| Application site irritation | 5 (3.1%) | 4 (2.5%) | 0% |
| Fatigue | 4 (2.5%) | 0% | 0% |
| Headache | 4 (2.5%) | 1 (0.6%) | 2 (1.3%) |
| Dizziness | 3 (1.9%) | 0% | 0% |
| Lymphadenopathy | 3 (1.9%) | 3 (1.9%) | 0% |
| Nausea | 3 (1.9%) | 1 (0.6%) | 0% |
| Pyrexia | 2 (1.3%) | 0% | 0% |
| Application site swelling | 2 (1.3%) | 0% | 0% |
| Arthralgia | 2 (1.3%) | 0% | 0% |

*>1% in the 3.75% imiquimod treatment group

For each of the two-week treatment cycle regimen studies, LSRs appear to be dose-dependent. The combined AUC of $LSR_{sum}$ Scores are 272, 242 and 140 for the 3.75% imiquimod, 2.5% imiquimod, and placebo treatment groups, respectively. Erythema is the most intense LSR during the treatment cycles, and on average all LSRs return to baseline at the first observation post-treatment cycle (within either two or four weeks, following cycles 1 and 2, respectively). The combined incidence of severe erythema is 26.3%, 14.4%, and 0% for the 3.75% imiquimod, 2.5% imiquimod, and placebo treatment groups, respectively.

There were 12 subjects with 15 serious adverse events reported in the two-week treatment cycle regimen studies, of which one of the serious adverse events for one of the subjects is considered related to treatment (diarrhea with secondary nausea/fatigue reported in the 3.75% treatment group).

In the two-week treatment cycle regimen studies, both 2.5% and 3.75% imiquimod creams demonstrate substantial efficacy for the treatment of AKs that is consistently significantly greater than that of placebo cream, with a trend toward greater efficacy in the 3.75% group. Both products are well-tolerated as evidence by measures of adverse events, ability of subjects to remain in the study, incidence of rest periods, and compliance with study regimen. Both active products result in increases in local skin reactions versus the placebo cream. For both active creams, the LSRs rapidly reduces with the completion of each treatment cycle and these LSRs are associated with relatively few reported application site reactions.

Studies of Three-Week Treatment Cycles

Preliminary data from the Three-Week Treatment Cycle Regimen Studies (GW01-0703 and GW01-0705) are presented as follows.

Subject Disposition for Studies GW01-0703 and GW01-0705 is tabulated in Table 76.

TABLE 76

Subject Disposition; Three-Week Treatment Cycle Regimen Studies

| | GW01-0703 | | | GW01-0705 | | |
|---|---|---|---|---|---|---|
| | 2.5% IMIQ | 3.75% IMIQ | Placebo | 2.5% IMIQ | 3.75% IMIQ | Placebo |
| Total no. of subjects, n (%) | | | | | | |
| Randomized | 82 | 80 | 78 | 82 | 82 | 86 |
| Completed Study[a] | 77 (93.9) | 76 (95.0) | 73 (93.6) | 80 (97.6) | 76 (92.7) | 81 (94.2) |
| Discontinued Study | 5 (6.1) | 4 (5.0) | 5 (6.4) | 2 (2.4) | 6 (7.3) | 5 (5.8) |
| Reasons for discontinuation from the study, n (%[b]) | | | | | | |
| Safety reasons (AEs) | 1 (1.2) | 2 (2.5) | 0 | 1 (1.2) | 2 (2.4) | 1 (1.2) |
| Investigator's request | 0 | 0 | 0 | 0 | 0 | 0 |

TABLE 76-continued

| Subject Disposition; Three-Week Treatment Cycle Regimen Studies | GW01-0703 | | | GW01-0705 | | |
|---|---|---|---|---|---|---|
| | 2.5% IMIQ | 3.75% IMIQ | Placebo | 2.5% IMIQ | 3.75% IMIQ | Placebo |
| Subject's request (not AE) | 3 (3.7) | 2 (2.5) | 4 (5.1) | 0 | 2 (2.4) | 0 |
| Noncompliance | 1 (1.2) | 0 (0.0) | 0 (0.0) | 0 | 0 | 0 |
| Use of concomitant therapy | 0 | 0 | 0 | 0 | 0 | 0 |
| Lost to follow-up | 0 | 0 | 0 | 0 (0.0) | 1 (1.2) | 1 (1.2) |
| Other (not AE) | 0 (0.0) | 0 (0.0) | 1 (1.3) | 1 (1.2) | 1 (1.2) | 3 (3.5) |

AE = adverse event;
IMIQ = Imiquimod
[a]Includes subjects who complete both the treatment periods and the post-treatment follow-up period.
[b]Percentage of randomized population.

Subject demographics for each study are tabulated in Table 77, and the number of baseline AK lesions for each study are tabulated in Table 78.

TABLE 77

| Demographic Summary - Three-Week Treatment Cycle Regimen Studies; ITT Population | GW01-0703 | | | GW01-0705 | | |
|---|---|---|---|---|---|---|
| | 2.5% IMIQ (N = 82) | 3.75% IMIQ (N = 80) | Placebo (N = 78) | 2.5% IMIQ (N = 82) | 3.75% IMIQ (N = 82) | Placebo (N = 86) |
| Age in years | | | | | | |
| Mean ± SD | 65.7 ± 10.4 | 64.5 ± 10.8 | 63.0 ± 10.1 | 66.4 ± 10.0 | 64.1 ± 9.7 | 64.4 ± 11.5 |
| Median | 66.7 | 64.0 | 63.6 | 65.9 | 63.7 | 65.8 |
| Minimum, Maximum | 85.3, 3.3, | 40.3, 85.5 | 39.8, 83.8 | 45.4, 87.3 | 90.9, 41.6 | 37.9, 87.0 |
| Sex, n (%) | | | | | | |
| Male | 62 (75.6) | 63 (78.8) | 63 (80.8) | 66 (80.5) | 60 (73.2) | 72 (83.7) |
| Female | 20 (24.4) | 17 (21.3) | 15 (19.2) | 16 (19.5) | 22 (26.8) | 14 (16.3) |
| Race, n (%) | | | | | | |
| White | 82 (100) | 78 (97.5) | 77 (98.7) | 82 (100.0) | 82 (100.0) | 86 (100.0) |
| Non-White | 0 | 2 (2.5) | 1 (1.3) | 0 | 0 | 0 |
| Ethnicity, n (%) | | | | | | |
| Hispanic | 2 (2.4) | 1 (1.3) | 0 (0.0) | 6 (7.3) | 6 (7.3) | 6 (7.0) |
| Non-Hispanic | 80 (97.6) | 79 (98.8) | 78 (100) | 76 (92.7) | 76 (92.7) | 80 (93.0) |
| Fitzpatrick skin type, n (%) | | | | | | |
| I | 8 (9.8) | 11 (13.8) | 11 (14.1) | 12 (14.6) | 11 (13.4) | 12 (14.0) |
| II | 35 (42.7) | 31 (38.8) | 28 (35.9) | 28 (34.1) | 47 (57.3) | 39 (45.3) |
| III | 28 (34.1) | 24 (30.0) | 26 (33.3) | 33 (40.2) | 21 (25.6) | 23 (26.7) |
| IV | 9 (11.0) | 13 (16.3) | 10 (12.8) | 8 (9.8) | 3 (3.7) | 9 (10.5) |
| V | 2 (2.4) | 1 (1.3) | 3 (3.8) | 1 (1.2) | 0 | 3 (3.5) |
| Location of Treatment Area, n (%) | | | | | | |
| Face | 63 (76.8) | 54 (67.5) | 60 (76.9) | 52 (63.4) | 61 (74.4) | 62 (72.1) |
| Balding Scalp | 19 (23.2) | 26 (32.5) | 18 (23.1) | 30 (36.6) | 21 (25.6) | 24 (27.9) |

SD = standard deviation;

IMIQ = Imiquimod

Fitzpatrick skin type: I = burns easily, never tans; II = burns easily, tans minimally with difficulty; III = burns moderately, tans moderately and uniformly; IV = burns minimally, tans moderately and evenly; V = rarely burns, tans profusely; VI = never burns, tans profusely.

TABLE 78

Actinic Keratosis Lesions at Baseline - Three-Week Treatment Cycle Regimen Studies; ITT Population

| | GW01-0703 | | | GW01-0705 | | |
|---|---|---|---|---|---|---|
| Baseline values | 2.5% IMIQ (N = 82) | 3.75% IMIQ (N = 80) | Placebo (N = 78) | 2.5% IMIQ (N = 82) | 3.75% IMIQ (N = 82) | Placebo (N = 86) |
| Mean (SD) | 10.74 (4.45) | 11.99 (5.47) | 11.24 (4.70) | 10.43 (4.05) | 10.26 (4.12) | 9.49 (3.67) |
| Median | 10 | 11 | 10 | 9 | 9 | 8 |
| Minimum, Maximum | 5, 20 | 5, 23 | 5, 20 | 5, 20 | 5, 20 | 5, 20 |
| P value vs Placebo[a] | 0.408 | 0.359 | NA | 0.094 | 0.197 | NA |
| P value vs 3.75% imiquimod cream[a] | 0.113 | NA | NA | 0.776 | NA | NA |

SD = Standard deviation

[a]P values are from Cochran-Mantel-Haenszel test, stratified by investigator center, taking 2 treatment groups at a time.

Subjects in studies GW01-0703 and GW01-0705 are compliant with the administration of study medication; greater than 92% of the subjects are compliant with the dosing regimen. Compliance is defined as applying more than 75% of the prescribed doses; 'rest' days are considered as application days.

Primary and secondary efficacy results for the GW01-0703 and GW01-0705 studies are presented in Table 79, Table 80, and Table 81. The primary efficacy variable is the rate of complete clearance at EOS (Week 17). The secondary efficacy variables are the rate of partial clearance (at least 75% reduction in AKs from baseline) at EOS, and the percent change from Baseline to EOS in investigator counts of AK lesions. Both active treatment arms demonstrate greater efficacy than placebo, which is statistically significant for all primary and secondary endpoints.

TABLE 79

ITT (LOCF) Complete Clearance Rates at EOS for Individual Three-Week Treatment Cycle Regimen Studies

| Study | 3.75% IMIQ | 2.5% IMIQ | Placebo |
|---|---|---|---|
| GW01-0703 | 32.5% (26/80) | 23.2% (19/82) | 5.1% (4/78) |
| GW01-0705 | 35.4% (29/82) | 26.8% (22/82) | 5.8% (5/86) |
| Combined | 34.0% (55/162) | 25% (41/164) | 5.5% (9/164) |

TABLE 80

ITT (LOCF) Partial Clearance Rates at EOS for Individual Three-Week Treatment Cycle Regimen Studies

| Study | 3.75% IMIQ | 2.5% IMIQ | Placebo |
|---|---|---|---|
| GW01-0703 | 56.3% (45/80) | 46.3% (38/82) | 11.5% (9/78) |
| GW01-0705 | 51.2% (42/82) | 39.0% (32/82) | 14.0% (12/86) |
| Combined | 53.7% (87/162) | 42.7% (70/164) | 12.8% (21/164) |

TABLE 81

ITT (LOCF) Median Percent Change from Baseline in AK Lesion Count at EOS for Individual Three-Week Treatment Cycle Regimen Studies

| Study | 3.75% IMIQ | 2.5% IMIQ | Placebo |
|---|---|---|---|
| GW01-0703 | −82.3% | −66.7% | −23.6% |
| GW01-0705 | −78.9% | −66.7% | −22.5% |
| Combined | −80.0% | −66.7% | −23.6% |

The incidence rates for selected safety parameters for the combined three-week treatment cycle regimen studies are displayed in Table 82.

TABLE 82

Summary of Incidence Rates for Selected Safety Parameters (Combined Three-Week Treatment Cycle Regimen Studies)

| | 3.75% IMIQ (N = 162) | 2.5% IMIQ (N = 164) | Placebo (N = 164) |
|---|---|---|---|
| Discontinued study prematurely due to safety reasons, n (%) | 4 (2.5%) | 2 (1.2%) | 1 (0.6%) |
| Treatment-related AEs, n (%) | 60 (37.0%) | 44 (26.8%) | 4 (2.4%) |
| Rest periods, n (%) | 44 (27.2%) | 28 (17.1%) | 0 (0%) |

The most common treatment-related adverse events are displayed in Table 83.

TABLE 83

Incidence of Most Common* Treatment-Related Adverse Events (Combined Three-Week Treatment Cycle Regimen Studies)

| MedDRA Term | 3.75% IMIQ (N = 162) | 2.5% IMIQ (N = 164) | Placebo (N = 164) |
|---|---|---|---|
| Application site pain | 15 (9.3%) | 11 (6.7%) | 0% |
| Application site pruritus | 14 (8.6%) | 12 (7.3%) | 1 (0.6%) |
| Influenza like illness | 12 (7.4%) | 6 (3.7%) | 0% |
| Application site irritation | 9 (5.6%) | 6 (3.7%) | 1 (0.6%) |
| Fatigue | 7 (4.3%) | 5 (3.0%) | 0% |
| Application site bleeding | 5 (3.1%) | 2 (1.2%) | 0% |
| Lymphadenopathy | 5 (3.1%) | 4 (2.4%) | 0% |
| Pyrexia | 5 (3.1%) | 0% | 0% |
| Headache | 4 (2.5%) | 4 (2.4%) | 0% |
| Cheilitis | 3 (1.9%) | 1 (0.6%) | 1 (0.6%) |
| Myalgia | 3 (1.9%) | 0% | 0% |
| Application site discomfort | 2 (1.2%) | 0% | 0% |
| Application site erythema | 2 (1.2%) | 0% | 0% |
| Chills | 2 (1.2%) | 1 (0.6%) | 0% |
| Dysphonia | 2 (1.2%) | 0% | 0% |
| Herpes simplex | 2 (1.2%) | 2 (1.2%) | 0% |
| Herpes zoster | 2 (1.2%) | 0% | 0% |
| Lethargy | 2 (1.2%) | 0% | 0% |
| Nausea | 2 (1.2%) | 1 (0.6%) | 0% |

*>1% in the 3.75% imiquimod treatment group

For each of the three-week treatment cycle regimen studies, LSRs appear to be dose-dependent. The combined AUC of $LSR_{sum}$ Scores are 413, 372 and 189 for the 3.75% imiquimod, 2.5% imiquimod, and placebo treatment groups, respectively. Erythema is the most intense LSR during the treatment cycles, and on average all LSRs return to baseline at the first observation post-treatment cycle. The combined incidence of severe erythema is 44.7%, 28.2%, and 0% for the 3.75% imiquimod, 2.5% imiquimod, and placebo treatment groups, respectively.

There are 13 subjects who report 18 serious adverse events in the Three-Week Treatment Cycle Regimen studies; one of these serious adverse events is considered related to treatment (pancytopenia reported in the 3.759 treatment group; note that this subject had a previous history of pancytopenia).

In the Three-Week Treatment Cycle Regimen studies, both 2.5% and 3.75% imiquimod creams demonstrate substantial efficacy for the treatment of AKs that is consistently significantly greater than that of placebo cream, with a trend toward greater efficacy with the higher concentration cream. Discontinuation rates for any cause, as well as for safety reasons are low in all treatment groups, and as such, both imiquimod creams can be considered 'well-tolerated'. However, a larger number of subjects that are treated with either the 2.5% or 3.75% imiquimod creams require rest periods from the intended two 3-week treatment cycles. Rest periods and other measures of treatment tolerability (related adverse events, application site reactions, LSRs) demonstrate a dose dependent effect, with the highest incidences in the 3.75% 3-week cycle treatment group.

Selection of the optimal dose/regimen for submission for marketing approval requires the comparisons of both the benefits and risks for each of each dose/regimen combinations that are studied. Studies GW01-0702 and GW01-0704 are duplicate studies investigating two 2-week treatment cycles (aka two-week treatment cycle regimen studies); and studies GW01-0703 and GW01-0705 are duplicate studies investigating two 3-week treatment cycles (aka three-week treatment cycle regimen studies). Data from the four Phase 3 studies are combined as identical pairs (GW01-0702/GW01-0704 and GW01-0703/GW01-0705).

Identical pairs of studies, each including 3 treatment groups, are considered in the analysis of dose/regimen selection:

Two-Week Treatment Cycle Regimen (Studies GW01-0702 and GW01-0704)

3.75% imiquimod 2.5% imiquimod

Placebo

Three-Week Treatment Cycle Regimen (Studies GW01-0703 and GW01-0705)

3.75% imiquimod 2.5% imiquimod

Placebo

To examine the impact of drug concentrations on efficacy, the four imiquimod treatment groups (2.5% and 3.75%, 2-week and 3-week regimens) can be combined by concentration, irrespective of treatment regimen. Data for 2.5% imiquimod (both 2 and 3-Week Treatment Cycle Groups) versus that of 3.75% imiquimod (both 2 and 3-Week Treatment Cycle Groups) are evaluated for efficacy effects of concentration (refer to Table 84 below). Preliminary evaluation suggests an effect of drug concentration in favor of the 3.75% concentration for all three efficacy endpoints: Complete Clearance, Partial Clearance, and Percent Reduction from Baseline of AK lesions. Preliminary evaluation suggests that the two regimens (2-week and 3-week treatment cycles) are comparable in terms of the efficacy endpoints. In addition, all four dosing regimens that are used show statistically and clinically significant effectiveness in the reduction of AK lesions in the target population.

TABLE 84

Analysis of Primary and Secondary Efficacy Endpoints (Combined Studies)

| | 2-Week Cycle Regimen | | | 3-Week Cycle Regimen | | |
|---|---|---|---|---|---|---|
| Parameter | 3.75% | 2.5% | Placebo | 3.75% | 2.5% | Placebo |
| Complete Clearance at EOS | | | | | | |
| n/N, (%) | 57/160 (35.6) | 49/160 (30.6) | 10/159 (6.3) | 55/162 (34.0) | 41/164 (25.0) | 9/164 (5.5) |
| 95% confidence interval | 28.2, 43.6 | 23.6, 38.4 | 3.1, 11.3 | 26.7, 41.8 | 18.6, 32.3 | 2.5, 10.2 |
| Partial Clearance at EOS | | | | | | |
| n/N, (%) | 95/160 (59.4) | 77/160 (48.1) | 36/159 (22.6) | 87/162 (53.7) | 70/164 (42.7) | 21/164 (12.8) |
| 95% confidence interval | 51.3, 67.1 | 40.2, 56.2 | 16.4, 29.9 | 45.7, 61.6 | 35.0, 50.6 | 8.1, 18.9 |
| Percent Change in Number of AK Lesions from Baseline to EOS | | | | | | |
| N | 160 | 160 | 159 | 162 | 164 | 164 |
| Median | −81.8 | −71.8 | −25.0 | −80.0 | −66.7 | −23.6 |
| Mean (SD) | −68.7 (43.4) | −59.2 (41.6) | −27.6 (52.1) | −64.3 (43.0) | −57.0 (45.4) | −24.5 (47.0) |
| 95% confidence interval | −75.4, 61.9 | −65.7, 52.7 | −35.7, 19.4 | −71.0, 57.7 | −64.0, −50.0 | −31.7, 17.2 |

As indicated herein, the efficacy results for the two 2-cycle treatment regimens, i.e., the 2×2×2 weeks and 3×3×3 weeks treatment cycles, suggest that the additional doses provided in the 3-week treatment cycle regimen results in no additional efficacy over that shown for the 2-week treatment cycle regimen. This finding is consistent with the rank order performance of the 3.75% product for all efficacy endpoints in all four individual Phase 3 studies. Therefore, from an efficacy standpoint, the 3.75% imiquimod cream, when applied daily in two 2-week treatment cycles, is believed to be the preferred dose and regimen combination to treat actinic keratosis.

Safety for all four dose regimens is also considered. Since the longer 3-week treatment regimen (with its greater drug exposure) shows no additional efficacy, it is believed that a choice of a 3-week regimen should be based on an improved safety profile.

As with efficacy, safety data are examined from the pooled identical studies (GW01-0702/GW01-0704 and GW01-0703/GW01-0705).

Key safety outcomes are presented above and included:

Incidence of Discontinuation from Study

Incidence of Discontinuation from Study due to Safety Reasons (AEs)

Incidence of Rest Periods

Incidence of Treatment-Related AEs

AUC of LSRsum scores

With the exception of LSRs (which are investigator assessed 'signs'), these measures address symptoms that are experienced by the subject or investigator actions that are related to subject safety (i.e., discontinuations, rest periods, adverse events including LSRs requiring medical intervention).

As can be seen in Table 85 below, discontinuation rates from the four Phase 3 studies for all causes (including safety) are low across all treatment groups, thus supporting the overall tolerability of all dose regimens. Inspection of the incidence rates for Rest Periods and Treatment-Related AEs suggests that the 3-week Treatment Cycle Regimens are relatively less well-tolerated than both 2-week Treatment Cycle Regimens.

The difference in AUC of $LSR_{sum}$ scores by treatment regimen is remarkable. Note that the scores for the 3-week cycle treatment cycle regimens (including placebo) reflect the longer dosing and study duration associated with those study designs. Nonetheless, the data shows pronounced increases in AUC of $LSR_{sum}$ scores for both doses in the 3-week cycle treatment groups. Scores for both of the 2-week cycle treatment groups are lower than the 3-week treatment cycle regimens, with a relatively small increase in the 3.75% AUC of $LSR_{sum}$ score compared to the 2.5% imiquimod treatment group for the 2-week treatment cycle regimen studies.

Looking across the safety parameters, it appears that the short 2-week Treatment Cycle Regimen is relatively better tolerated than the 3-week Treatment Cycle Regimen. Within the 2-week cycle Treatment Cycle Regimen both doses are well-tolerated, although safety incidence rates and scores appear to slightly favor the 2.5% concentration.

As discussed, the 3-week Treatment Cycle Regimens, irrespective of product concentration, demonstrates a less favorable safety profile versus the 2-week Treatment Cycle Regimens with no offsetting efficacy benefit. Within the 2-week Treatment Cycle Regimen studies, the 2.5% imiquimod formulation appear to have a slightly improved safety profile to the 3.75% product, though both products are well-tolerated. However, the 3.75% product shows a consistent incremental efficacy benefit to the 2.5% product.

TABLE 85

Selected Safety Parameters (Combined Studies)

| | Combined Two-Week Treatment Cycle Regimen Studies | | | Combined Three-Week Treatment Cycle Regimen Studies | | |
|---|---|---|---|---|---|---|
| | 3.75% IMIQ (N = 160) | 2.5% IMIQ (N = 160) | Placebo (N = 159) | 3.75% IMIQ (N = 162) | 2.5% IMIQ (N = 164) | Placebo (N = 164) |
| Discontinued study prematurely (any reason) | 11 (6.9%) | 6 (3.8%) | 9 (5.7%) | 10 (6.2%) | 7 (4.3%) | 10 (6.1%) |
| Discontinued study prematurely due to safety reasons, n (%) | 2 (1.3%) | 1 (0.6%) | 3 (1.9%) | 4 (2.5%) | 2 (1.2%) | 1 (0.6%) |
| Treatment-related AEs, n (%) | 31 (19.4%) | 19 (11.9%) | 4 (2.5%) | 60 (37.0%) | 44 (26.8%) | 4 (2.4%) |
| Rest periods, n (%) | 17 (10.6%) | 11 (6.9%) | 0 (0%) | 44 (27.2%) | 28 (17.1%) | 0 (0%) |

For the 2-week treatment cycle regimen, the 2.5% and 3.75% imiquimod creams show similar tolerability. Although the overall incidences of treatment-related adverse events for the 2-week Treatment Cycle Regimens show a dose-related trend (see above 85), the most common treatment-related AEs are application site reactions (see Tables 75 and 83). Inspection of the individual treatment-related AEs reveals low rates for all the individual terms, irrespective of dose group. AEs that may reflect systemic pharmacologic effects of imiquimod's activation of cytokines (e.g., fatigue) are reported; however, systemic AEs occur at a low rate.

Additional to the adverse event data above, the physical signs of anticipated local skin reactions (LSRs) are rated by the investigators via six assessments scores at each study visit. The assessments scores are summated and then integrated across the study duration as AUC of $LSR_{sum}$ scores. The AUC of $LSR_{sum}$ scores for all four treatment groups are presented in Table 86.

TABLE 86

Summary of AUC of $LSR_{sum}$ Scores (Combined Across Studies)

| | 3.75% IMIQ | 2.5% IMIQ | Placebo |
|---|---|---|---|
| Combined Two-Week Treatment Cycle Regimen Studies | 272 | 242 | 140 |
| Combined Three-Week Treatment Cycle Regimen Studies | 413 | 372 | 189 |

In the primary ITT efficacy analysis, missing observations due to early discontinuation are imputed using the last observation carried forward (LOCF). Baseline data are carried forward if no post-Baseline data existed for the subject. The sensitivity of the primary outcome to imputation methods is explored in each of the separate clinical study reports, and the results are found to be robust with respect to changes in imputation methodology. The results of the PP analysis are also found to be entirely consistent with those of the ITT analysis.

Wherever the investigator reported AK lesion count as "indeterminate," the subject is considered not cleared (and not partially cleared), but the numerical lesion count is taken as a missing value.

The demographic and background characteristics of the efficacy study populations by treatment group in all 4 Phase 3 studies are combined by identical study design in pairs (i.e., GW01-0702 and GW01-0704 will be combined in one pair and GW01-0703 and GW01-0705 will be combined in a second pair). The number and percentage by treatment group and overall are presented for subjects randomized, subjects included in the ITT population, subjects completing the study, and subjects discontinuing the study, overall and by reason for discontinuation.

Subject age, height, weight, and Baseline lesion count is summarized by mean, standard deviation, median, and range by treatment group. Sex, race, ethnicity, Fitzpatrick skin type, location of treatment area (face or balding scalp), and prior AK treatment history is characterized by frequency distribution by treatment group.

Descriptive statistics (mean, standard deviation, median, and range) is used to summarize product usage and exposure for the ITT populations by treatment group. Measures of study medication exposure, for each treatment cycle and overall, includes the total duration of treatment (date of last dose minus date of first dose plus 1, excluding the no-treatment period), the total number of applications, the total number of packets used, the total amount of active drug applied, and the average number of packets used per application. The number and percentage of subjects by treatment group who make fewer than 75% of the required applications (fewer than 21 applications and/or rest days in the 2-week treatment cycle regimen, and fewer than 32 applications and/or rest days in the 3-week treatment cycle regimen) is reported.

The primary efficacy variable prospectively defined for all studies is subject status with respect to complete clearance of AK lesions at End of Study. This is defined as the absence of clinically visible or palpable AK lesions in the treatment area.

Secondary efficacy variables are:

Subject status with respect to partial clearance of AK lesions at End of Study, defined as at least a 75% reduction in the number of AK lesions in the treatment area compared with Baseline.

Percent change from Baseline to End of Study in investigator counts of AK lesions.

The comparative and integrated analysis of efficacy focuses on the primary and two secondary efficacy variables. Integrated and comparative summaries is presented at the primary time point of End of Study. The studies are reviewed separately as well as with the identical studies combined in pairs: GW01-0702 and GW01-0704 for the 2-week treatment cycle regimen, and GW01-0703 and GW01-0705 for the 3-week treatment cycle regimen.

In the planned statistical analyses defined prospectively and presented, all pairwise comparisons of active treatment versus placebo are made using Hochberg's modified Bonferroni procedure. If either test is significant at a 0.025 level of significance, then that test is considered significant. Otherwise, if both tests are significant at, 0.05, then both tests are considered significant. The 3.75% and 2.5% treatment groups are compared to each other at the 0.05 level of significance if at least one of these treatment groups is found to be different than the placebo using the Hochberg test.

In this way, complete clearance rates, partial clearance rates, change from Baseline AK lesion counts, and percent change from Baseline AK lesion counts are analyzed using Cochran-Mantel-Haenszel (CMH) statistics, stratifying on site.

In the primary analysis of complete clearance rate, the Breslow-Day statistic is tested at the 10% level for heterogeneity of the odds ratios across analysis sites. There are no findings of statistical significance in these tests for any of the studies.

In order to characterize and explore the efficacy of the proposed drug product in subpopulations of interest, the data from the two pivotal studies is combined and analyzed by age, sex, Fitzpatrick skin type, treatment area, and baseline lesion count. In each case, the ITT population is divided into two subpopulations based on the specific covariate of interest. For age, the subpopulations are selected as less than, or greater than or equal to, 65 years old. For skin type and baseline lesion count, the subpopulations are selected as above or below the approximate median value of the covariate (combining I with II, and combining III, IV, V, and VI) for skin type; taking less than or equal to 10 vs greater than 10 for baseline lesion count). P values for complete clearance and partial clearance are computed using a generalized linear model (PROC GENMOD) assuming a multinomial distribution (DIST=MULT) and a cumulative login link function (LINK=CLOGIT) including effects of treatment, subpopulation, and interaction. P values for percent reduction are derived from the analysis of variance (PROC GLM) including effects of treatment, subpopulation, and interaction. A similar analysis is presented for the subpopulation of subjects who showed increased AK lesion count at any time after baseline. This subpopulation is characterized in current Aldara® labeling as having had "sub-clinical lesions". In these four studies, it is seen that the great majority of subjects are included in this subpopulation.

The LSR intensities are summarized in each study by frequency counts and mean score by treatment group and study visit for each LSR type:

Erythema (0=None, 1=Faint to mild redness, 2=Moderate redness, 3=Intense redness), Edema (0=None, 1=Mild visible or barely palpable swelling/induration, 2=Easily palpable swelling/induration, 3=Gross swelling/induration), Weeping/Exudate (0=None, 1=Minimal exudate, 2=Moderate exudate, 3=Heavy exudate), Flaking/Scaling/Dryness (0=None, 1=Mild dryness/flaking, 2=Moderate dryness/flaking, 3=Severe dryness/flaking), Scabbing/Crusting (0=None, 1=Crusting, 2=Serous scab, 3=Eschar), Erosion/Ulceration (0=None, 1=Erosion, 2=Ulceration).

The most intense reaction (post-baseline) for each type is also presented by frequency distribution and mean score by treatment group.

An LSR sum score is computed at each study visit (addition of six scores). Three areas under the curve (AUC, in days, using the trapezoidal approximation) are calculated for each subject: from Baseline to beginning of Treatment Cycle 2, from beginning of Treatment Cycle 2 to End of Study, and from Baseline to End of Study. These values are compared pair wise between treatment groups using Fisher's least significant differences in the one-way analysis of variance (treatment group). Discontinued subjects are included in this analysis using LOCF. Details of the calculation of AUC are provided in the clinical study reports.

A pooled analysis of is also provided, with P values derived from the analysis of variance (PROC GLM) including effects of concentration, regimen, and interaction. When calculating the AUC over the course of the study period, it is noted that studies GW01-0702 and GW01-0704 are 14 weeks in duration, while GW01-0703 and GW01-0705 are 17 weeks in duration. The additional three weeks in the AUC for the GW01-0703 and GW01-0705 studies correspond to two additional weeks of treatment and one additional week in the no-treatment period between treatment cycles. Nonetheless, subjects in all four studies are followed through eight weeks after the last treatment application in order to allow complete healing of local skin reactions. Thus, the comparison of AUC LSR between the 14-week studies and the 17-week studies, without adjustment, allows an evaluation of the relative duration, as well as the severity of local skin reactions resulting from each of the four dosing regimens.

The number and percentage of subjects by treatment group combining GW01-0702 with GW01-0704 and GW01-0703 with GW01-0705 is presented for each of the following safety indicators.

Requiring Rest Period

Discontinuing the Study Prematurely for Any Reason

Discontinuing the Study Prematurely for Safety Reasons

Any Adverse Event

Any Treatment-Related Event

Any Application Site Reaction

Any Serious Adverse Event

Any Severe Adverse Event

The incidence of subjects requiring rest periods is calculated for each treatment group by Cycle 1, Cycle 2 and Overall.

Adverse events (AEs) is coded using MedDRA (Version 11) terminology. Treatment-emergent AEs is summarized for each treatment group (with the four Phase 3 studies combined in pairs) by:

- n (%) of Subjects in Decreasing Order of Incidence in the 3.75% 2-Week Treatment Cycle Group, Adverse Events with Incidence >1% in the 3.75% 2-Week Treatment Cycle Group;
- n (%) of Subjects in Decreasing Order of Incidence in the 3.75% 2-Week Treatment Cycle Group, Adverse Events Considered Treatment-related by the Investigator;
- n (%) of Subjects in Decreasing Order of Incidence in the 3.75% 2-Week Treatment Cycle Group, Adverse Events Rated Severe;
- n (%) of Subjects in Decreasing Order of Incidence in the 3.75% 2-Week Treatment Cycle Group, All Application Site Reactions.

The incidence of adverse events is summarized by gender, by age subgroup, by skin type, by baseline lesion count, and by location of treatment area (face or balding scalp). For age, the subpopulations is selected as less than or greater than or equal to, 65 years old. For skin type and baseline lesion count, the subpopulations is selected as above or below the approximate median value of the covariate (combining I with II, and combining III, IV, V, and VI for skin type; taking less than or equal to 10 vs greater than 10 for baseline lesion count).

Serious AEs and AEs which led to the discontinuation of the subject from the study is listed by subject.

The frequency counts of shifts in alert status (normal to high, low to normal, etc.) from Screening to End of Study is tabulated by treatment group for each laboratory parameter combining the four Phase 3 studies in pairs.

Example 25

An Open Label, Single Center, Non-Randomized Pharmacokinetic (PK) Study

An open label, single center, non-randomized pharmacokinetic (PK) study in adult subjects diagnosed with actinic keratosis ("AK") is conducted. This PK study is designed to quantify the pharmacokinetic profile of imiquimod and its metabolites following 3 weeks (21 days) of daily applications of a 3.75% imiquimod formulation of Example 23 in adult subjects diagnosed with actinic keratosis (AK). The study is conducted under maximal use conditions (dose, duration, disease severity, and application areas) in a population that had at least 10 AK lesions in the application area. The application area is the entire face (exclusive of nares, vermilion, periocular areas and ears) and/or the entire balding scalp; areas estimated as approximately 200 $cm^2$. If the area of the entire balding scalp is less than 200 $cm^2$, the forehead area is included in order for the entire treatment area to be approximately 200 $cm^2$. The daily dose is 2 packets of 3.75% imiquimod cream for three continuous weeks.

Thus, this PK study is conducted under maximal use conditions: (1) at least 10 clinically typical visible or palpable AK lesions within the treatment area (balding scalp or face); (2) application of 2 full packets (250 mg of formulation per packet) of 3.75% imiquimod formulation once daily for 21 days (maximal dosing regimen); and (3) a skin area of approximately 200 $cm^2$ of the entire face or balding scalp (maximal treatment area).

Subjects stay at the study center overnight at treatment initiation (Day 1, 1st dose), and end of treatment (Day 21, last dose) visits for collection of a 24-hour serum PK profile. During the domicile periods of initiation (Day 1), and end of treatment (Day 20-21) visits, serum PK samples are collected predose and at planned time points through 24 hours post dose. At the end of treatment (Day 21), additional PK samples are taken at approximately 48 and 72 hours post application. Single serum samples for PK analyses of trough concentrations are obtained at Day 7 and Day 14 (in the morning prior to dosing).

Adverse events, study medication accountability, and dosing compliance are reviewed at each visit. Routine clinical laboratory assessments (serum chemistry, hematology and urinalysis) are performed at Screening, Day 1 (predose), and the end of study visits.

Nineteen subjects (14 males/5 females) are enrolled into the study and 18 completed. One female subject discontinues the study prematurely due to concurrent adverse events (moderate body aches and moderate fatigue), and therefore does not have a PK profile at Day 21 (steady-state). For the 19 enrolled subjects, 15 subjects apply the study medication to the entire face, and the remainder apply the study medication to the balding scalp (which may include the upper face if <200 $cm^2$).

A total of 19 subjects have pharmacokinetic profiles (sampling over 24 hours) following the first dose, and 18 subjects have pharmacokinetic profiles (sampling over 72 hours) on Day 21. One subject misses a dose on Day 20, and therefore is excluded from the Day 21 analysis (17 subjects have adequate data for Day 21 analyses of AUC0-24, Cmax and Tmax). Trough serum concentrations are obtained on Days 7, 14, 21, and 22. The trough concentrations on Days 7 and 14 are obtained during outpatient treatment while the trough concentrations on Days 21 and 22 are obtained while the subjects are dosed in the clinical research facility. Trough imiquimod concentrations are summarized in Table 87.

TABLE 87

Summary of Imiquimod Trough Concentrations (ng/mL); Subjects with Paired, Non-zero Data

| | N | Geometric LS Mean Test | Geometric LS Mean Reference | Geometric Mean Ratio | 90% Confidence Interval |
|---|---|---|---|---|---|
| Day 14/7 | 15 | 0.1391 | 0.1277 | 1.0888 | (0.7933-1.4946) |
| Day 21/14 | 16 | 0.1791 | 0.1344 | 1.3328 | (0.9193-1.9325) |
| Day 22/21 | 16 | 0.1671 | 0.1791 | 0.9331 | (0.6612-1.3169) |

Serum concentrations of imiquimod are relatively low in subjects treated with daily applications of an imiquimod 3.75% cream of Example 23 for up to 21 days. While serum concentrations of two imiquimod metabolites (S 26704 and S 27700 combined) are measured throughout the study, very few samples had concentrations above the lower limit of quantitation (LLOQ). Therefore, these data are too sparse to assess.

The ratio of trough concentrations is examined to determine whether steady-state conditions are achieved during 21 days of topical treatment with 3.75% imiquimod cream. Under steady-state treatment conditions, the trough concentrations, aside from variability, demonstrate a stable plateau value (i.e., not significantly increasing over time, as indicated by a ratio significantly >1). Considering the variability in imiquimod trough concentrations (observed CV % ranged from 47.6-58.0%), a ratio <1.43 (following log transformation) is pre-selected to indicate the achievement of steady state; all three ratios meet that criterion. This analysis of trough ratios (i.e., using only those subjects with paired, non-zero data) is also confirmed by an analysis which includes all subjects with paired data by replacing the zero (BQL) values with 0.025 ng/mL (½ of the LLOQ).

The single-dose and steady-state pharmacokinetic parameters for daily application of 3.75% imiquimod cream are summarized in Table 88 and Table 89.

TABLE 88

Preliminary Steady-State (Day 21) Imiquimod Pharmacokinetic Variables

| | $AUC_{0-24}$ (ng · hr/mL) | Cmax (ng/mL) | Tmax (hr) | λz ($hr^{-1}$) | T½ (hr) |
|---|---|---|---|---|---|
| N | 17 | 17 | 17 | 15 | 15 |
| Geometric Mean | 5.029 | 0.274 | 6.623 | 0.027 | 26.11 |
| Mean | 5.974 | 0.323 | 7.356 | 0.029 | 29.26 |
| SD | 3.088 | 0.159 | 3.500 | 0.014 | 16.98 |
| CV % | 51.7% | 49.2% | 47.6% | 48.5% | 58.0% |
| Median | 7.019 | 0.350 | 9 | 0.0271 | 25.56 |
| Min | 1.139 | 0.069 | 4 | 0.0082 | 9.72 |
| Max | 11.800 | 0.588 | 16 | 0.0713 | 84.06 |

TABLE 89

Single-dose and Steady-state Pharmacokinetics of 3.75% Imiquimod Cream of Example 23 (Study GW01-0706)

| Parameter | $N^c$ | Mean (SD) Day 1 | $N^d$ | Mean (SD) Day 21 |
|---|---|---|---|---|
| $C_{max}$ (ng/mL) | 17 | 0.136 (0.059) | 17 | 0.323 (0.159) |
| $C_{min}$ (ng/mL)[a] | — | NA | 17 | 0.199 (0.109) |
| $T_{max}$ (hr)[b] | 17 | 9.0 (4.0-24.03) | 17 | 9.0 (4.0-16.0) |
| $AUC_{0-24}$ (ng · hr/mL) | 17 | 1.831 (0.889) | 17 | 5.974 (3.088) |
| $AUC_{0-t}$ (ng · hr/mL) | 17 | 1.679 (1.056) | — | NA |
| $AUC_{0-inf}$ (ng · hr/mL) | 11 | 4.443 (1.309) | — | NA |
| $\lambda_z$ (1/hr) | 11 | 0.0450 (0.0219) | 15 | 0.0294 (0.0142) |
| $T_{1/2}$ (hr) | 10 | 19.818 (10.125) | 15 | 29.260 (16.979) |
| $R_{AUC}$ | — | NA | 15 | 3.873 (2.153) |
| $R_{Cmax}$ | — | NA | 15 | 2.810 (1.514) |
| $\lambda_{zEFF}$ ($hr^{-1}$) | — | NA | 15 | 0.0235 (0.0229) |
| $T_{1/2EFF}$ (hr) | — | NA | 15 | 55.339 (36.380) |

NA = Not applicable

[a]Pre-dose concentration (t = 0)

[b]Median (minimum-maximum)

[c]Subjects 001-601 and 001-618 were BLQ, therefore unable to calculate PK parameters

[d]Subject 001-619 did not have concentration data on Day 21; Subject 001-608 excluded due to missed dose on Day 20

Peak exposure ($C_{max}$) and total exposure ($AUC_{0\ 24}$) for imiquimod are higher on Day 21 than Day 1 when analyzing all subjects in the pharmacokinetic population. The mean accumulation ratios, $RC_{max}$ and $R_{AUC}$, for all subjects in the pharmacokinetic population are about 2.810 and about 3.873, respectively. The serum concentration profile on Day 21 is relatively flat across the dosage interval, and mean $C_{max}$ (0.323±0.159 ng/mL) is less than twice the level of mean $C_{min}$ (0.199±0.109 ng/mL). The mean effective half life for accumulation is about 55.3 hours and the mean observed elimination half life is about 29.3 hours on Day 21. Analysis of trough concentrations over time indicate that steady state conditions are achieved between Day 7 and Day 14, which is consistent with the time to steady state that is predicted from observed elimination half life (approximately 6 days) and the effective half life for accumulation (approximately 12 days).

In a comparison of female and male subjects who apply an imiquimod 3.75% cream of Example 23 to the face, serum pharmacokinetics for imiquimod are very similar for both groups on Day 21. In a comparison of scalp and face applications in male subjects, imiquimod $C_{max}$ and $AUC_{0\ 24}$ are lower on Day 21 in subjects who apply study medication to balding scalp rather than to the face. Analyses of the subgroups are limited by wide variability in the data, small overall numbers, and a large disparity in group sizes (female/male comparison of 4 versus 10 subjects, and scalp/face comparison of 3 versus 10 subjects).

Under maximal use conditions following daily administration at steady-state, the mean (SD) peak imiquimod serum concentrations are about 0.323 (0.159) ng/mL, and the median time to peak concentration is about 9 hours. Comparison of the mean $C_{max}$ concentrations and the mean trough concentrations indicates a relatively flat concentration-time profile throughout the dosing interval. The observed elimination half-life averaged about 29.26 hours (range 9.72-84.06 hours).

Steady state is believed to be achieved in this study by day 14 or the second week of daily dosing. Subjects in this study apply 2 packets (500 mg of cream—250 mg/packet; 18.75 mg of imiquimod) daily for 3 weeks to the entire face or balding scalp, and the mean peak serum imiquimod concentration ($C_{max}$) is about 0.323 ng/mL. In a previous study of the 5% imiquimod cream, subjects who receive 2 packets (500 mg of cream; 25 mg of imiquimod) 3 times per week for 16 weeks to the scalp, the mean peak serum imiquimod concentration ($C_{max}$) is 0.2 ng/mL. Subjects who receive six packets (1500 mg cream; 75 mg of imiquimod) 3 times per week for 16 weeks to the hand and forearms) have a $C_{max}$ of 3.5 ng/ml. These results are shown below in Table 90.

TABLE 90

Mean Peak Serum Imiquimod Concentration in Adults Following Administration of the Last Topical Dose of Aldara ® 5% Imiquimod Cream During Week 16 (Actinic Keratosis)

| Amount of Aldara ® 5% Imiquimod Cream applied | Mean peak serum imiquimod concentration [$C_{max}$] |
|---|---|
| 12.5 mg (1 packet) | 0.1 ng/mL |
| 25 mg (2 packets) | 0.2 ng/mL |
| 75 mg (6 packets) | 3.5 ng/mL |

Source: Current Aldara ® Package Insert: Section 12.3 Pharmacokinetics: Table 10

Pharmacokinetic data are available from three studies of patients with AK, one using the 3.75% imiquimod formulation of Example 23 (Study GW01-0706), and two studies using the marketed Aldara® 5% imiquimod cream formulation (Study 1520-IMIQ and Study 1402-IMIQ). The dosage, treatment duration, application site and application area in these studies is summarized in Table 91.

TABLE 91

Summary of Dosage, Application Site, and Treated Surface Area for Studies GW01-0706, 1520-IMIQ, and 1402-IMIQ

| Study Dosage | Weekly Dose (imiquimod) | Duration | N [a] | Site | Area |
|---|---|---|---|---|---|
| Study GW01-0706 (3.75% imiquimod cream) | | | | | |
| 2 packets (18.75 mg) daily | 131.25 mg | 21 days | 17 | Face or Scalp | 200 $cm^2$ |
| Study 1520-IMIQ (5% imiquimod cream) | | | | | |
| 6 packets (75 mg) 2 x weekly | 150 mg | 16 wks [d] | 13 | NS | >25% of BSA |
| Study 1402-IMIQ (5% imiquimod cream) | | | | | |
| 1 packet (12.5 mg) 3 x weekly | 37.5 mg | 16 wks | 23 | Face | 25 $cm^2$ |
| 2 packets (25 mg) 3 x weekly | 75 mg | 16 wks | 11 | Scalp | >25 $cm^2$ |
| 6 packets (75 mg) 3 x weekly | 225 mg | 16 wks | 24 | Hands/Arms [b] | NS [c] |

NS = not specified;
BSA= Body surface area
[a] Number of subjects in PK population at steady-state
[b] Applied to dorsal surface of forearms and hands, 3 packets applied to each side
[c] Not specified; estimated in the range of 300-400 $cm^2$ based on the protocol description
[d] Data from one 16-week treatment cycle, subjects could receive up to 3 cycles of treatment over 18 months.

While studies 1402-IMIQ and GW01-0706 are primarily pharmacokinetic studies, the data from Study 1520-IMIQ is a large long-term safety trial (551 subjects enrolled), and the pharmacokinetic data comes from subset of subjects representing a cohort receiving maximal exposure to imiquimod (6 packets of 5% cream applied twice weekly to >25% of their body surface area). Subjects in this study could participate in up to three 16-week treatment cycles during the 18-month study. In Study 1520-IMIQ, 71.9% of subjects (396 of 551) in the safety population have completed the trial. Subjects in the safety population average 466.9 days in the study and apply an estimated average of 214.6 packets of study drug (2682.5 mg of imiquimod). At study initiation, the median prescribed dose is about 3.3 packets twice weekly, and 380 of 551 subjects (69%) have received a dose of 3 or more packets twice weekly, and 182 subjects have received the maximal exposure of 6 packets twice weekly.

Based on the total amount of drug administered during one week of treatment, the weekly dose of the an 3.75% imiquimod lower dosage strength formulation of Example 23 and the novel two week 2-cycle dosage regimen (2 packets daily or 131.25 mg imiquimod weekly) is similar to the weekly dose that was used in the 1520-IMIQ study, and falls between the two higher doses used in Study 1402-IMIQ. In addition, the novel two week 2-cycle dosage regimen treats a larger surface area (about 200 $cm^2$) than the previously approved regimens for AK on the face and balding scalp (25 $cm^2$). Systemic exposure at steady-state is summarized in Table 92.

TABLE 92

Summary of Systemic Exposure at Steady-State Following Administration of 3.75% or 5% Imiquimod Cream [Mean(SD) Serum Imiquimod Cmax and AUCss]

| | Cmax (ng/mL) | | AUC (ng · hr/mL) | |
|---|---|---|---|---|
| | Mean (SD) | Ratio [a] | Mean (SD) | Ratio [a] |
| Study GW01-0706 | | | | |
| 2 pkts (18.75 mg) daily to face/scalp | 0.323 (0.159) | | 5.974 (3.088) | |
| Study 1520-IMIQ [b] | | | | |
| 6 pkts (75 mg) 2x weekly to >25% BSA | 0.958 (1.18) | 2.96 | 24.3 (26.9) | 4.07 |
| Study 1402-IMIQ | | | | |
| 1 pkts (12.5 mg) 3x/ week to face | 0.120 (0.0629) | 0.37 | 2.06 (1.70) | 0.34 |
| 2 pkts (25 mg) 3x/ week to scalp | 0.214 (0.0968) | 0.66 | 4.89 (4.41) | 0.82 |
| 6 pkts (75 mg) 3x/ week to hand/ forearms [c] | 1.35 (0.841) | 4.18 | 29.1 (17.1) | 4.87 |
| 6 pkts (75 mg) 3x/ week to hand/ forearms [d] | 3.53 (6.52) | 10.92 | 55.4 (76.0) | 9.27 |

Pkts = packets;
BSA = Body surface area
[a] 5% imiquimod regimen/3.75% imiquimod regimen
[b] Month 4 data
[c] Data from Harrison et al, 2004[1] (rejecting outliers that were >5X the SD of their respective means)
[d] Data from the 1402-IMIQ[2] report that includes outliers The mean $C_{max}$ and AUC in Study GW01-0706 at steady state are substantially lower than those that are observed following administration of the high dose used in the large safety trial (6 packets, 75 mg, twice weekly, Study 1520-IMIQ). Based on these results, it is believed that the novel treatment regimen, i.e., an 3.75% imiquimod lower dosage strength formulation of Example 23 applied daily in a two week 2-cycle dosage regimen (2 packets daily or 131.25 mg imiquimod weekly) has about an 3- to 4-fold safety margin for systemic exposure relative to the high-dose exposure in Study 1520-IMIQ. Thus, these results indicate that the intended dose of an 3.75% imiquimod cream product of Example 23 has less systemic exposure than what is observed in the high dose group for the 5% imiquimod cream product in the long-term safety Study 1520-IMIQ.

Pharmacokinetic profiles were obtained following single-dose and repeat-dose administration of 3.75% imiquimod cream in Study GW01-0706 (see Table 89 above). The mean (SD) accumulation ratios that are calculated from $C_{max}$ and $AUC_{0-24}$ are about 2.810 (1.514) and about 3.873 (2.153), respectively. The mean effective half-life for accumulation is about 55.3 hours and the mean observed elimination half-life is about 29.3 hours on Day 21. Analysis of trough concentrations over time indicate that steady-state conditions are achieved between Day 7 and Day 14.

In summary, the amount of imiquimod that is absorbed into systemic circulation after topical application of an imiquimod 3.75% cream of Example 23 to the face and/or scalp once daily for up to 21 days is low; peak and total serum imiquimod concentrations are increased by about 3 to 4 fold between Day 1 and Day 21. Steady state is achieved by Day 14. Cmax and $AUC_{0\ 24}$ on Day 21 appear to be similar in female and male subjects and lower in male subjects who apply an imiquimod 3.75% cream of Example 23 to balding scalp rather the face.

Thus, the mean peak serum imiquimod concentration that is observed with the daily application of the 3.75% imiquimod product (about 0.323 ng/mL) is within the mean peak serum imiquimod concentrations previously observed with Aldara® 5% imiquimod cream.

Example 26

Meta-Analysis—Efficacy, Adverse Events, Local Skin Reactions and Rest Periods A meta analysis is conducted across the four clinical studies described in Example 24. Data for Aldara® 5% imiquimod cream is displayed for comparative purposes. See, e.g., FIGS. 25-30. Of course, the Aldara® data concerned much smaller size treatment areas and a smaller number of AK lesions per treatment than the clinical studies that are described in Example 24.

Figure 25:
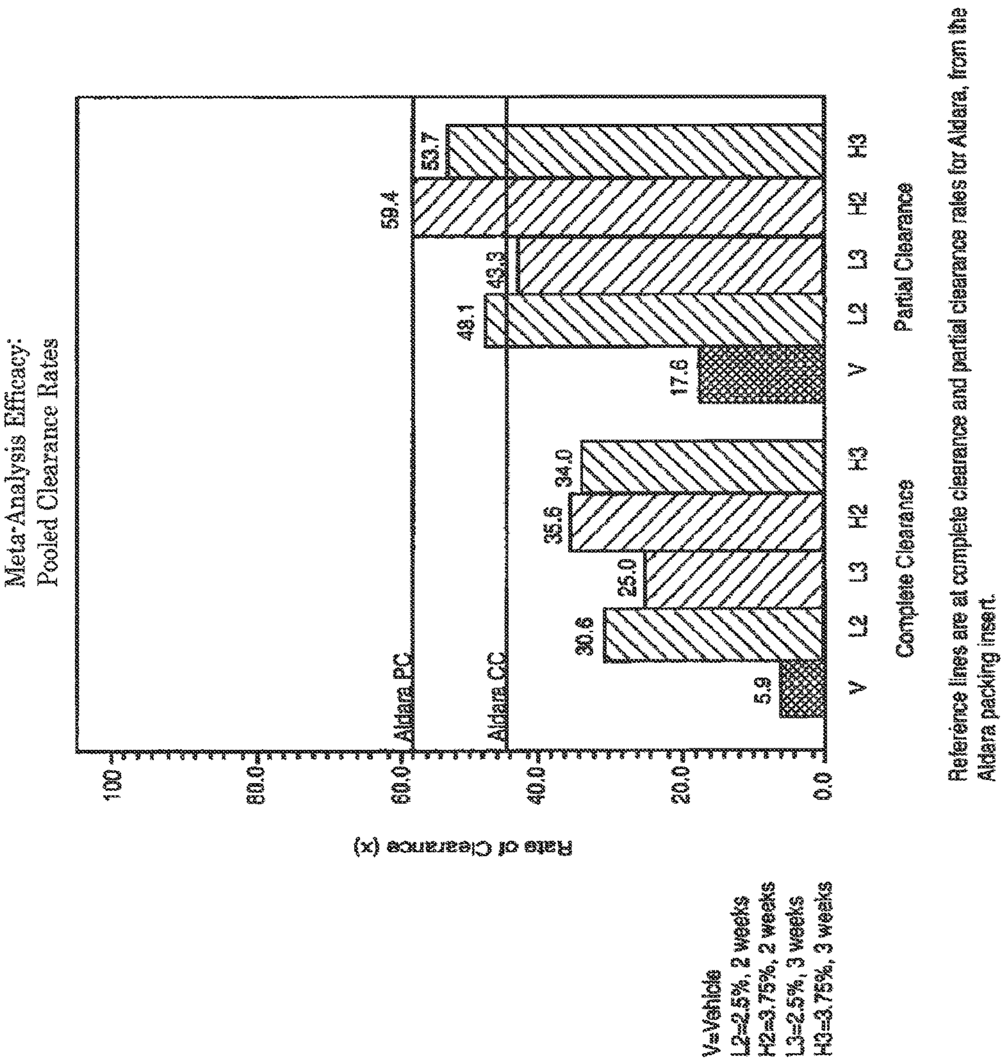
FIG. 25 shows meta-analysis efficacy of pooled clearance rates for studies GW01-0703, GW01-0702, GW01-0704 and GW01-0705.

Turning now to FIGS. 25 and 25A, they show the pooled actinic keratosis lesion clearance rates, i.e., complete and partial clearance rates for the 2.5% and 3.75% imiquimod formulations of Example 23 that are used in the short duration therapies (2×2×2 weeks and 3×3×3 weeks), are about as equally effective as the Aldara® 5% imiquimod cream treatment, even though Aldara® was applied twice a week for 16 weeks on treatment areas no greater than about 25 $cm^2$ and to no more than between about 4 and 8 AK lesions.

Figure 26:
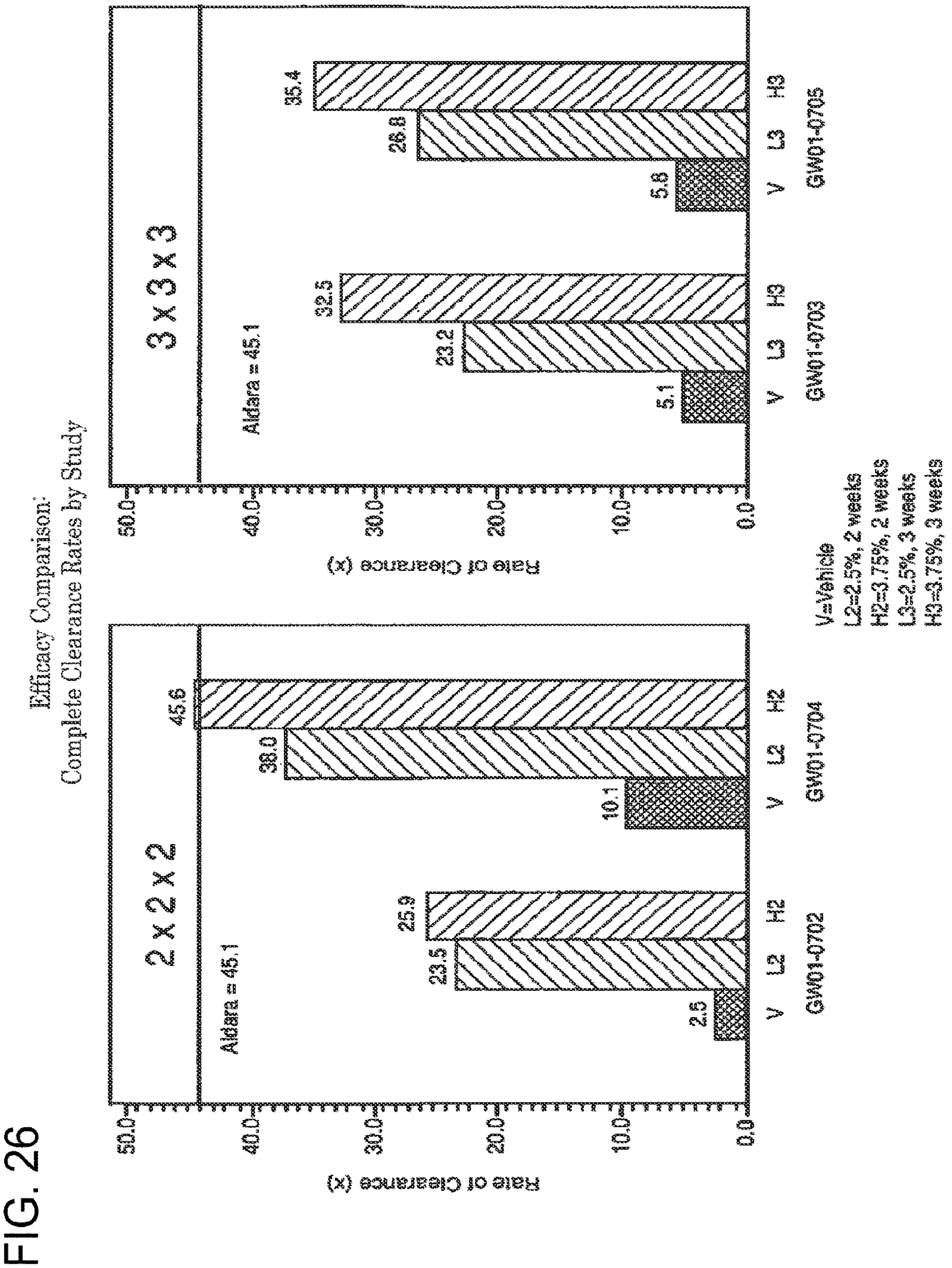
FIG. 26 shows an efficacy comparison of complete clearance rates, by study, for studies GW01-0703, GW01-0702, GW01-0704 and GW01-0705. As used in this FIG. 26, "2×2×2" refers to a two week, 2-cycle therapy and "3×3×3" refers to a three week, 2-cycle therapy. See also FIG. 25A.

In FIG. 26, it shows the complete clearance rates for the 2.5% and 3.75% imiquimod formulations of Example 23, that are used in the short duration therapies, i.e., 2×2×2 weeks and 3×3×3 weeks, are about as equally effective as the Aldara® 5% imiquimod cream treatment, even though Aldara® was applied twice a week for 16 weeks on treatment areas no greater than about 25 $cm^2$ and to no more than between about 4 and 8 AK lesions.

Figure 27:
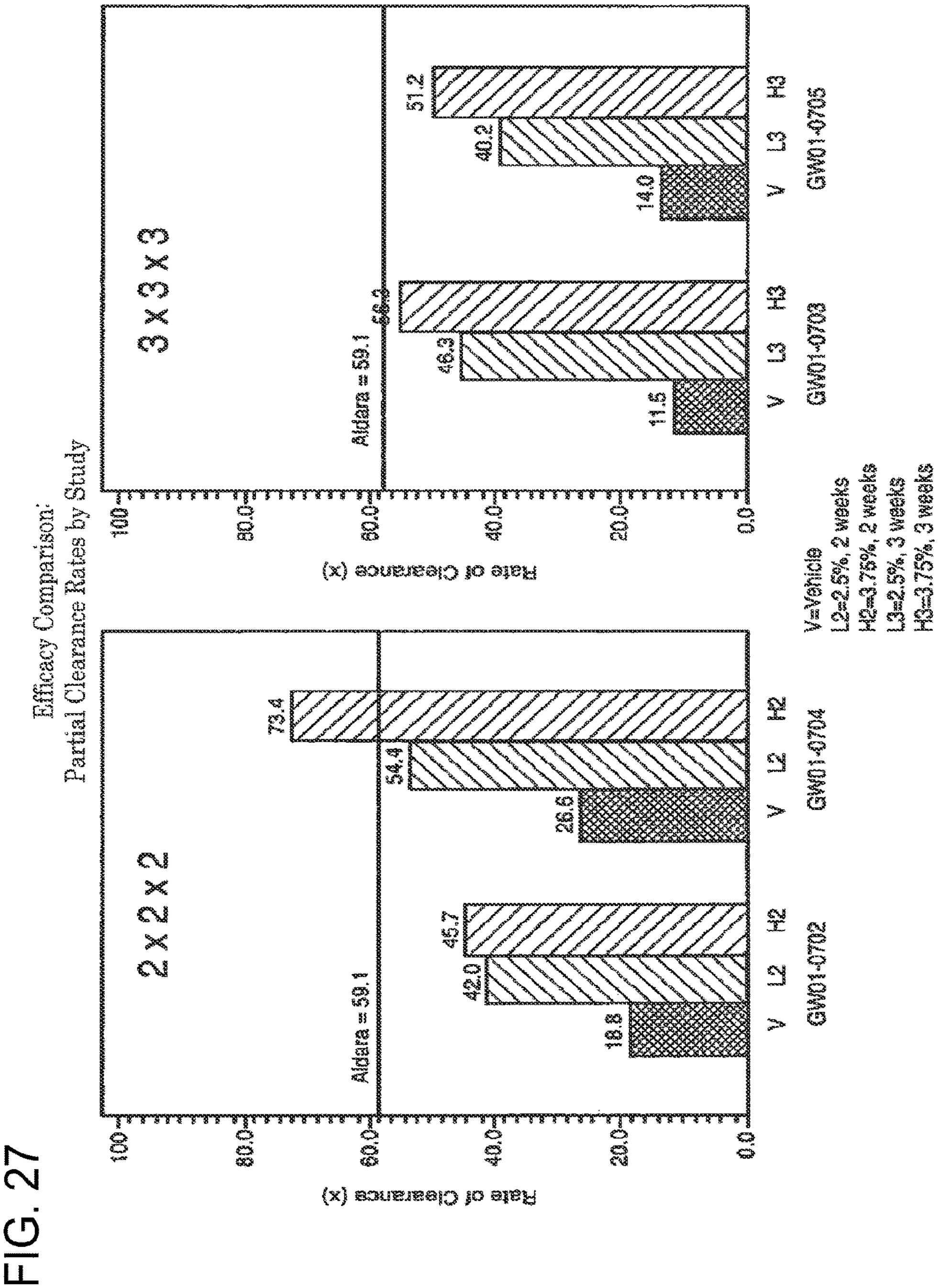
FIG. 27 shows efficacy comparison of partial clearance rates, by study, for studies GW01-0703, GW01-0702, GW01-0704 and GW01-0705. As used in this FIG. 27, "2×2×2" refers to a two week, 2-cycle therapy and "3×3×3" refers to a three week, 2-cycle therapy. See also FIG. 25A.

In FIG. 27, it shows the partial clearance rates for the 2.5% and 3.75% imiquimod formulations of Example 23, that are used in the short duration therapies, i.e., 2×2×2 weeks and 3×3×3 weeks, are about as equally effective as the Aldara® 5% imiquimod cream treatment even though Aldara® was applied twice a week for 16 weeks on treatment areas no greater than about 25 $cm^2$ and to no more than between about 4 and 8 AK lesions.

In FIGS. 28 and 28A-B, an adverse events comparison is shown between the 2.5% and 3.75% imiquimod formulations of Example 23 that are used in the short duration therapies, i.e., 2×2×2 and 3×3×3 weeks, and the Aldara® 5% imiquimod cream treatment that are used twice a week for 16 weeks on treatment areas no greater than about 25 $cm^2$ and no more than between about 4 and 8 AK lesions, to treat actinic keratosis. As depicted in FIGS. 28 and 28A-B, there is a higher percentage of application site reactions and upper respiratory infections with the Aldara® 5% imiquimod cream treatment than with the low dosage strength 2.5% and 3.75% imiquimod formulations that are used in the short duration therapies, i.e., 2×2×2 and 3×3×3 weeks, even though the 2.5% and 3.75% imiquimod formulations of Example 23 are applied daily on treatment areas much greater than 25 $cm^2$.

Figure 29:
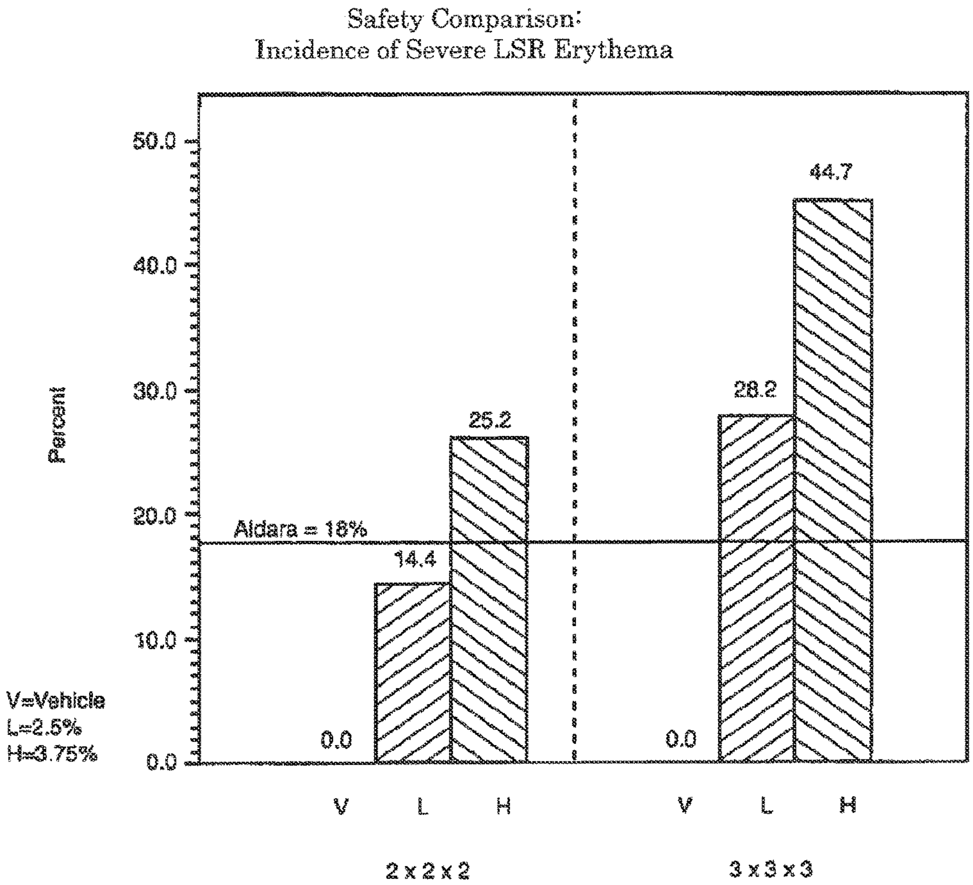
FIG. 29 shows a comparison of the incidence of severe erythema [(a local skin reaction (LSR)] for studies GW01-0703, GW01-0702, GW01-0704 and GW01-0705, as compared with Aldara® 5% imiquimod cream. As used in this FIG. 29, "H" refers to a 3.75% lower dosage strength imiquimod formulation of Examples 23-28, "L" refers to a 2.5% lower dosage strength imiquimod formulation of Examples 23-28 and "V" refers to vehicle, and "2×2×2" refers to a two week, 2-cycle treatment regimen and "3×3×3" refers to a three week, 2-cycle treatment regimen. See also FIG. 16A.

In FIG. 29, it shows the incidence of severe local skin reactions erythema for the 2.5% and 3.75% imiquimod formulations of Example 23 that are used in the 2×2×2 week short duration therapy are comparable to the Aldara® 5% imiquimod cream treatment, but higher for the 3×3×3 week therapy.

Figure 30:
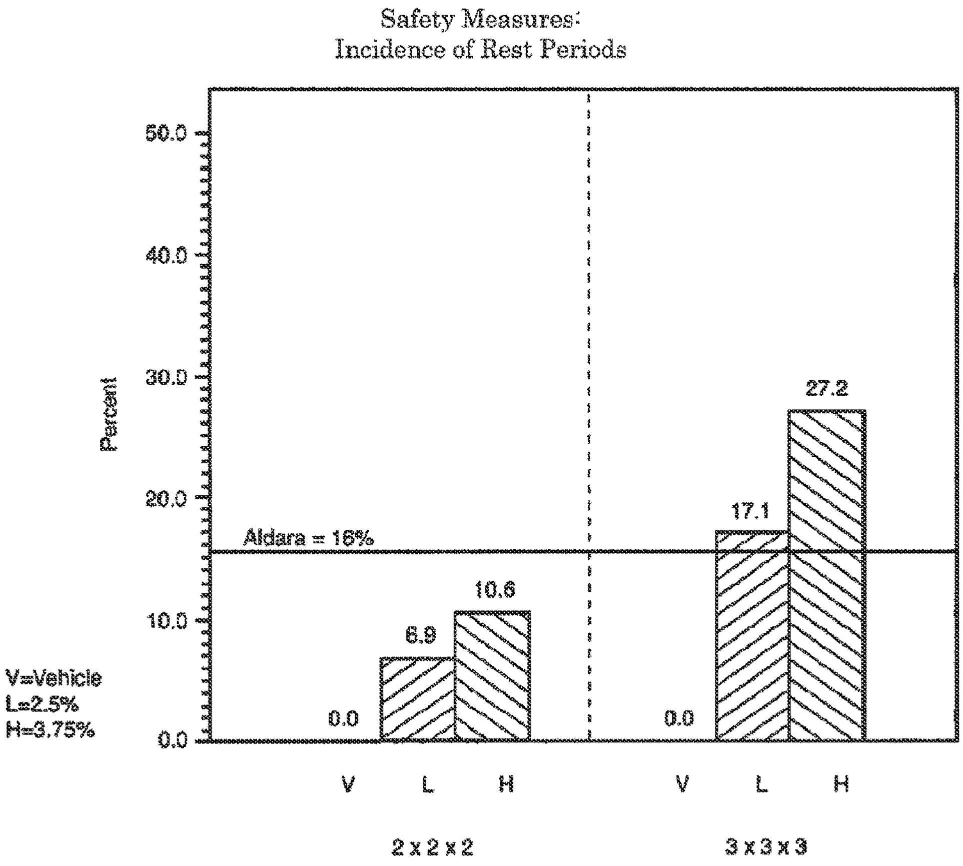
FIG. 30 shows safety measures of incidence of rest periods for studies GW01-0703, GW01-0702, GW01-0704 and GW01-0705, as compared with Aldara® 5% imiquimod cream. As used in this FIG. 30, "H" refers to a 3.75% lower dosage strength imiquimod formulation of Examples 23-28, "L" refers to a 2.5% lower dosage strength imiquimod formulation of Examples 23-28 and "V" refers to vehicle, and "2×2×2" refers to a two week, 2-cycle treatment regimen and "3×3×3" refers to a three week, 2-cycle treatment regimen. See also FIG. 21.
Figure 31:
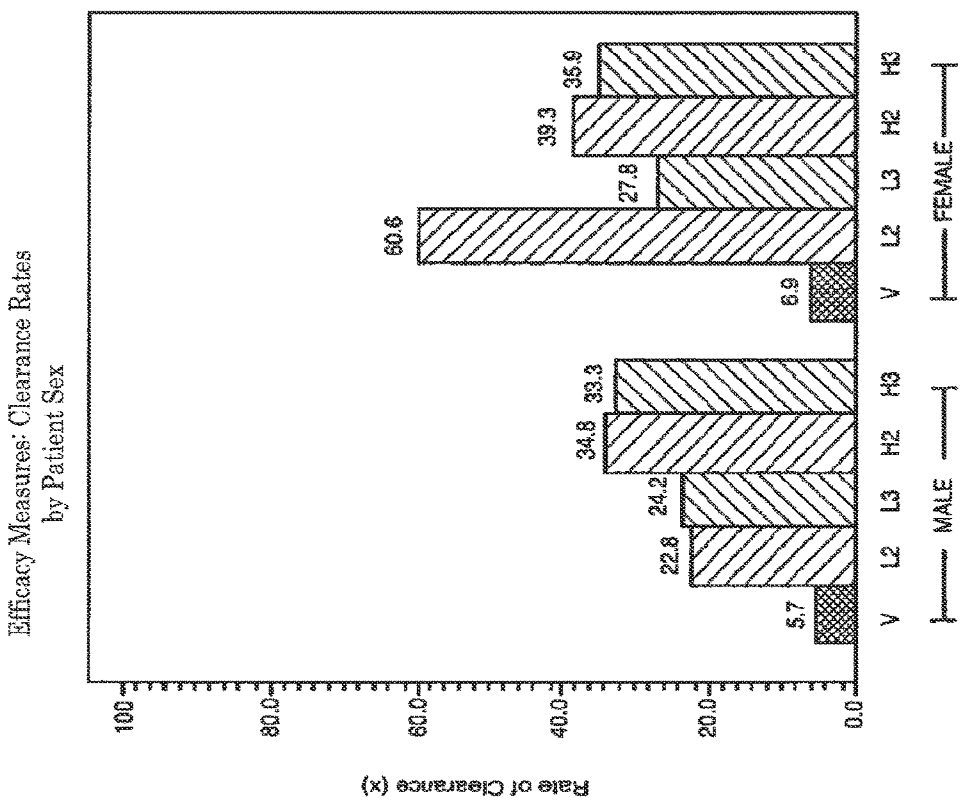
FIG. 31 shows efficacy measures of clearance rates, by subject sex, for studies GW01-0703, GW01-0702, GW01-0704 and GW01-0705. See also FIGS. 10A-10C.
Figure 32:
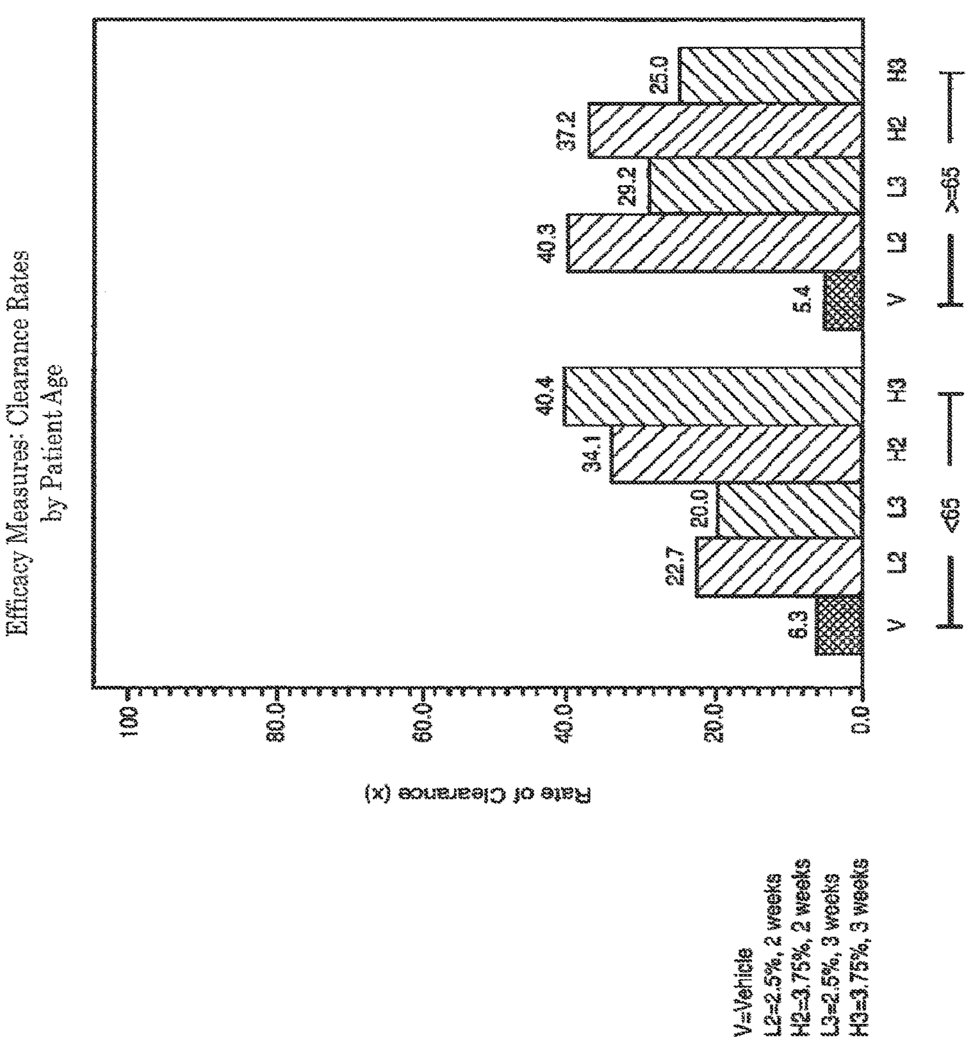
FIG. 32 shows efficacy measures of clearance rates, by subject age, for studies GW01-0703, GW01-0702, GW01-0704 and GW01-0705. See also FIGS. 10B-10C.
Figure 33:
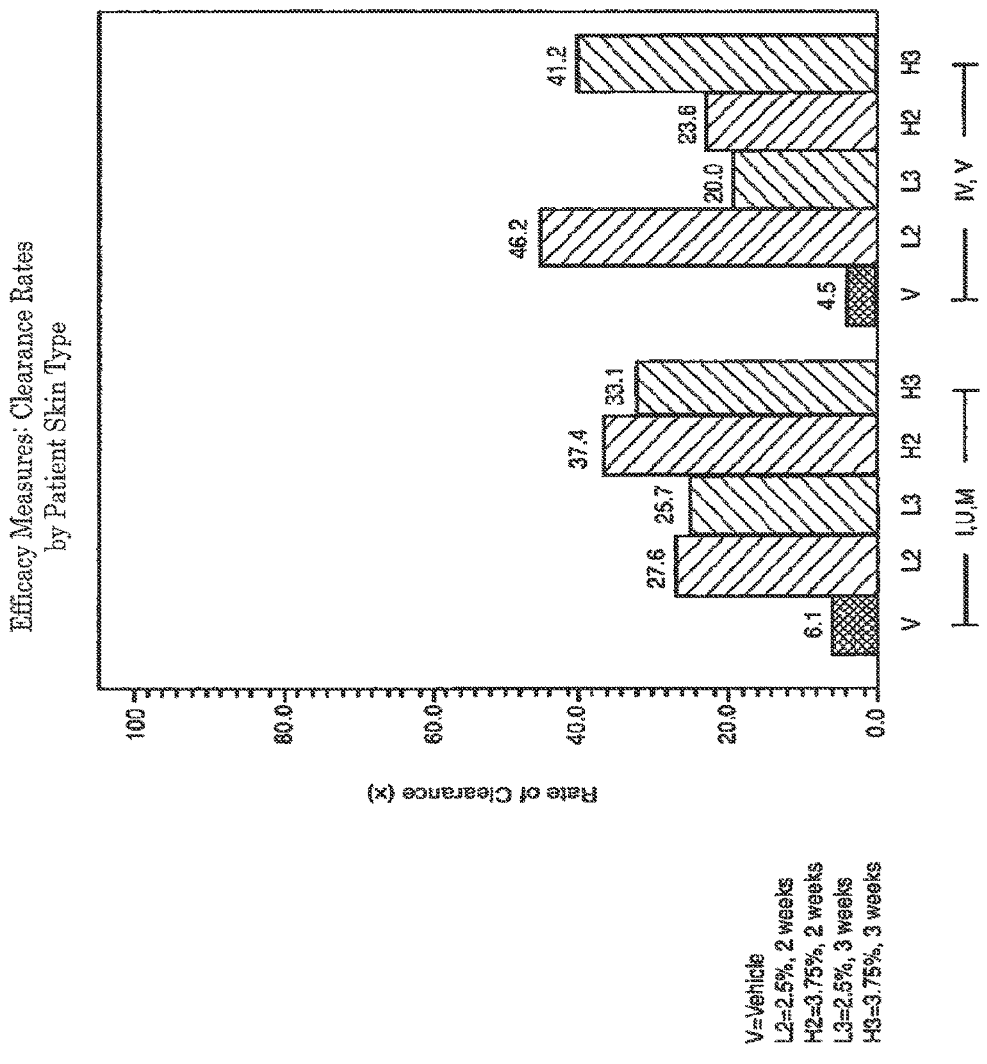
FIG. 33 shows efficacy measures of clearance rates, by subject skin type, for studies GW01-0703, GW01-0702, GW01-0704 and GW01-0705. See also FIGS. 10B-10C.
Figure 34:
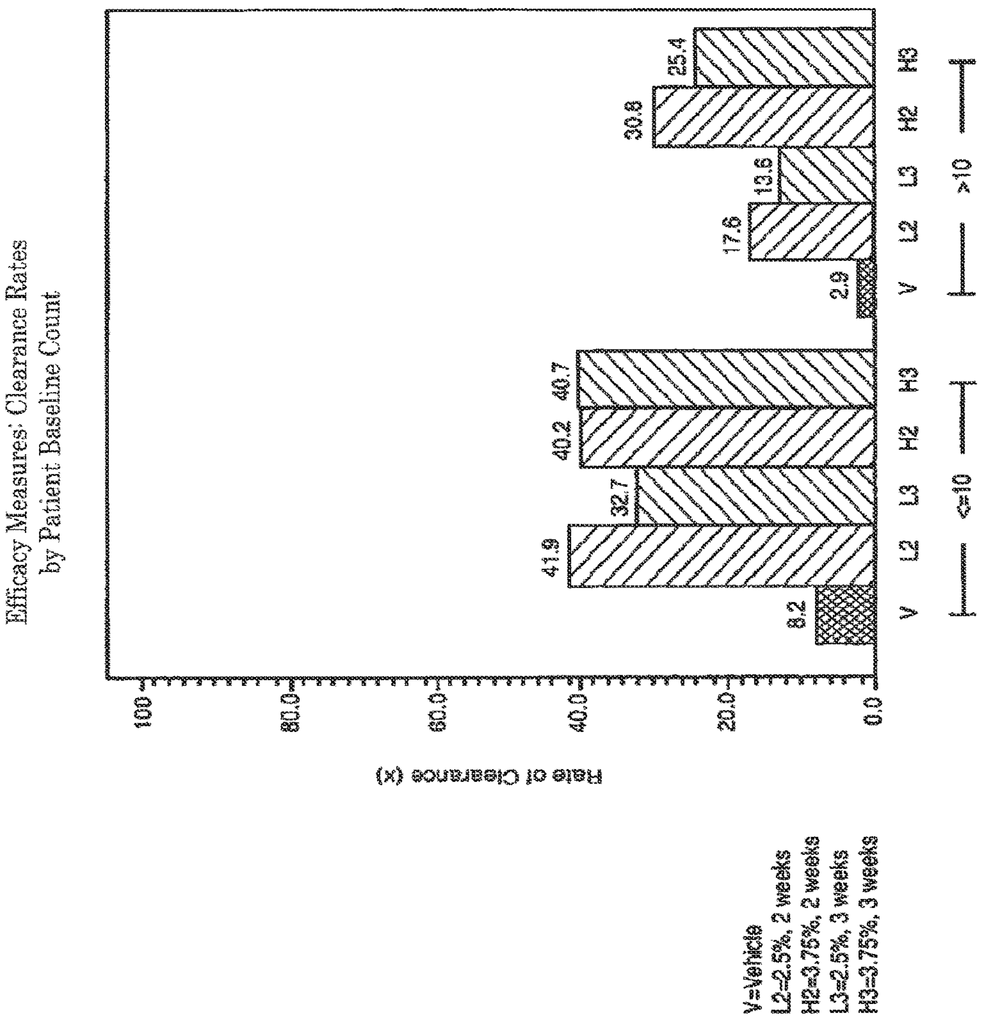
FIG. 34 shows efficacy measures of clearance rates, by subject Baseline count, for studies GW01-0703, GW01-0702, GW01-0704 and GW01-0705. See also FIGS. 10B-10C.
Figure 35:
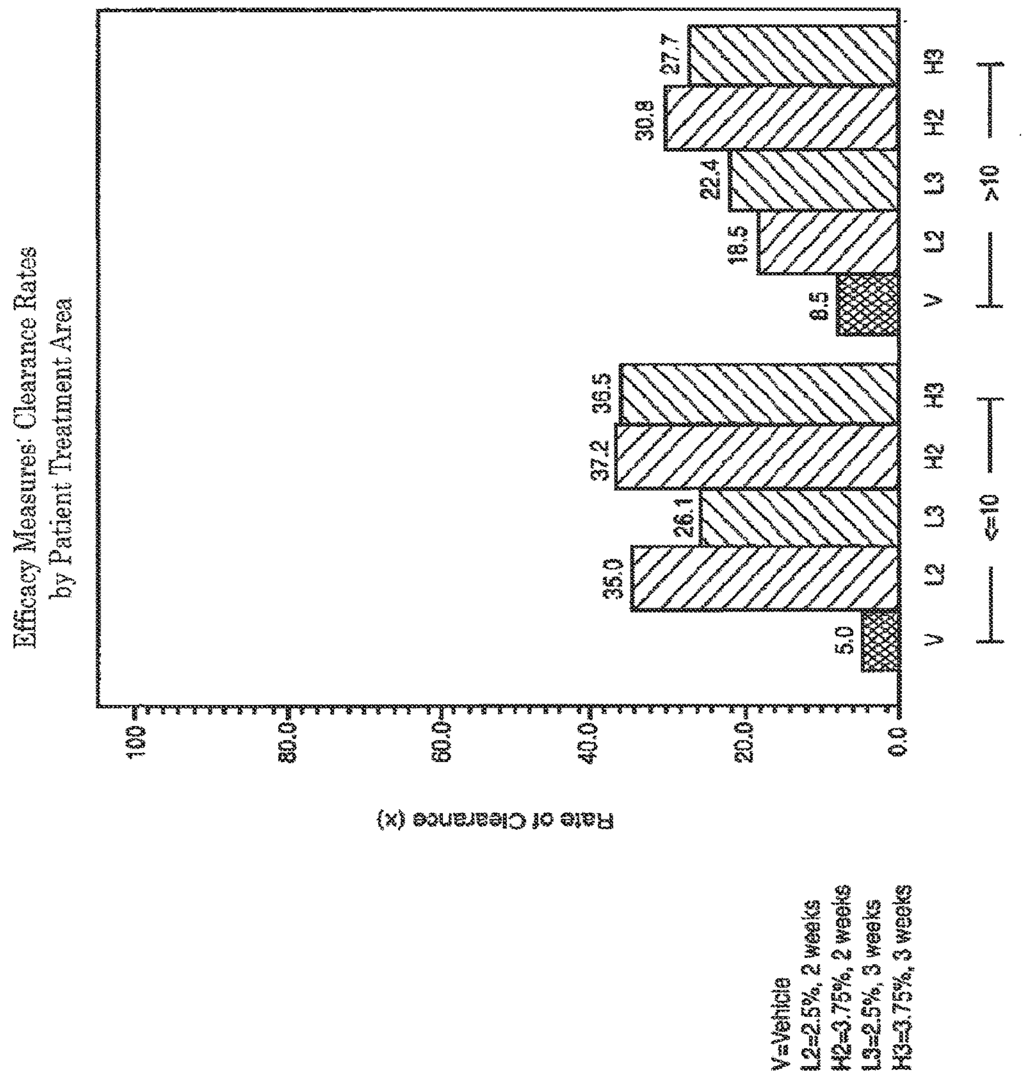
FIG. 35 shows efficacy measures of clearance rates, by subject treatment area, for studies GW01-0703, GW01-0702, GW01-0704 and GW01-0705. See also FIGS. 10B-10C.

In FIG. 30, it shows the incidence of rest periods for the 2.5% and 3.75% imiquimod formulations of Example 23 that are used in the 2×2×2 week short duration therapy are lower than the Aldara® 5% imiquimod cream treatment, but higher for the 3×3×3 week therapy.

Example 27

A Comparison Between the Four Clinical Studies Described in Example 24 and Aldara®

A comparative analysis is conducted across the four clinical studies described in Example 24 and Aldara®. See, e.g., FIGS. 28, 28A-B and 36-42. As previously indicated, treatment with Aldara® concerns much smaller size treatment areas and a smaller number of AK lesions per treatment than the clinical studies that are described in Example 24.

As to FIGS. 28 and 28A-B, see Example 27.

Turning now to FIGS. 36 and 36A, the pooled percent of complete clearance rates for the 2.5% and 3.75% imiquimod formulations of Example 23, that are used in the 2×2×2 weeks studies, and the 3×3×3 weeks studies of Example 24, are displayed. Results across treatment regimens (2 week or 3 week treatment cycles) are comparable. A dose response between 2.5% and 3.75% imiquimod formulations of Example 23 is evident irrespective of regimen (2 week or 3 week treatment cycles).

Turning now to FIGS. 37 and 37A, the pooled percent of partial complete clearance rates for the 2.5% and 3.75% imiquimod formulations of Example 23, that are used in the 2×2×2 weeks studies, and the 3×3×3 weeks studies of Example 24, are displayed. Results across treatment regimens (2 week or 3 week treatment cycles) are comparable. A dose response between 2.5% and 3.75% imiquimod formulations of Example 23 is evident irrespective of regimen (2 week or 3 week treatment cycles).

Turning now to FIGS. 38 and 38A, the pooled percent of AK lesion median % reduction for the 2.5% and 3.75% imiquimod formulations of Example 23, that are used in the 2×2×2 weeks studies, and the 3×3×3 weeks studies of Example 24, are displayed. Results across treatment regimens (2 week or 3 week treatment cycles) are comparable. A dose response between 2.5% and 3.75% imiquimod formulations of Example 23 is evident irrespective of regimen (2 week or 3 week treatment cycles).

Turning now to FIG. 39, they show that the percent of subjects who took at least one rest period during treatment for the 2.5% and 3.75% imiquimod formulations of Example 23, that are used in the 2×2×2 weeks studies of Example 24, are less than those taken with Aldara® 5% imiquimod cream.

Turning now to FIG. 39A, the selected safety parameters for the combined 2×2×2 or 3×3×3 studies show that the safety events are less favorable in the 3×3×3 studies than the 2×2×2 studies.

Turning now to FIG. 40, it shows the percent of local skin reactions (LSRs) of subjects with severe LSRs for the 2.5% and 3.75% imiquimod formulations of Example 23, that is used in the 2×2×2 week studies of Example 24. Overall, the incidence rates for severe LSRs are relatively low, and as for Aldara® 5% imiquimod cream, the most common severe LSR is erythema.

Turning now to FIG. 41, it shows the incidence of adverse events of subjects for the 2.5% and 3.75% imiquimod formulations of Example 23, that is used in the 2×2×2 week studies of Example 24. The most common adverse event is application site reactions which occurs at a lower rate than Aldara® 5% imiquimod cream.

Turning now to FIG. 41A, it shows the incidence of treatment-related adverse events of subjects for the combined 2×2×2 or 3×3×3 studies. This shows that the incidence of adverse events are less favorable in the 3×3×3 studies than the 2×2×2 studies.

Figure 42:
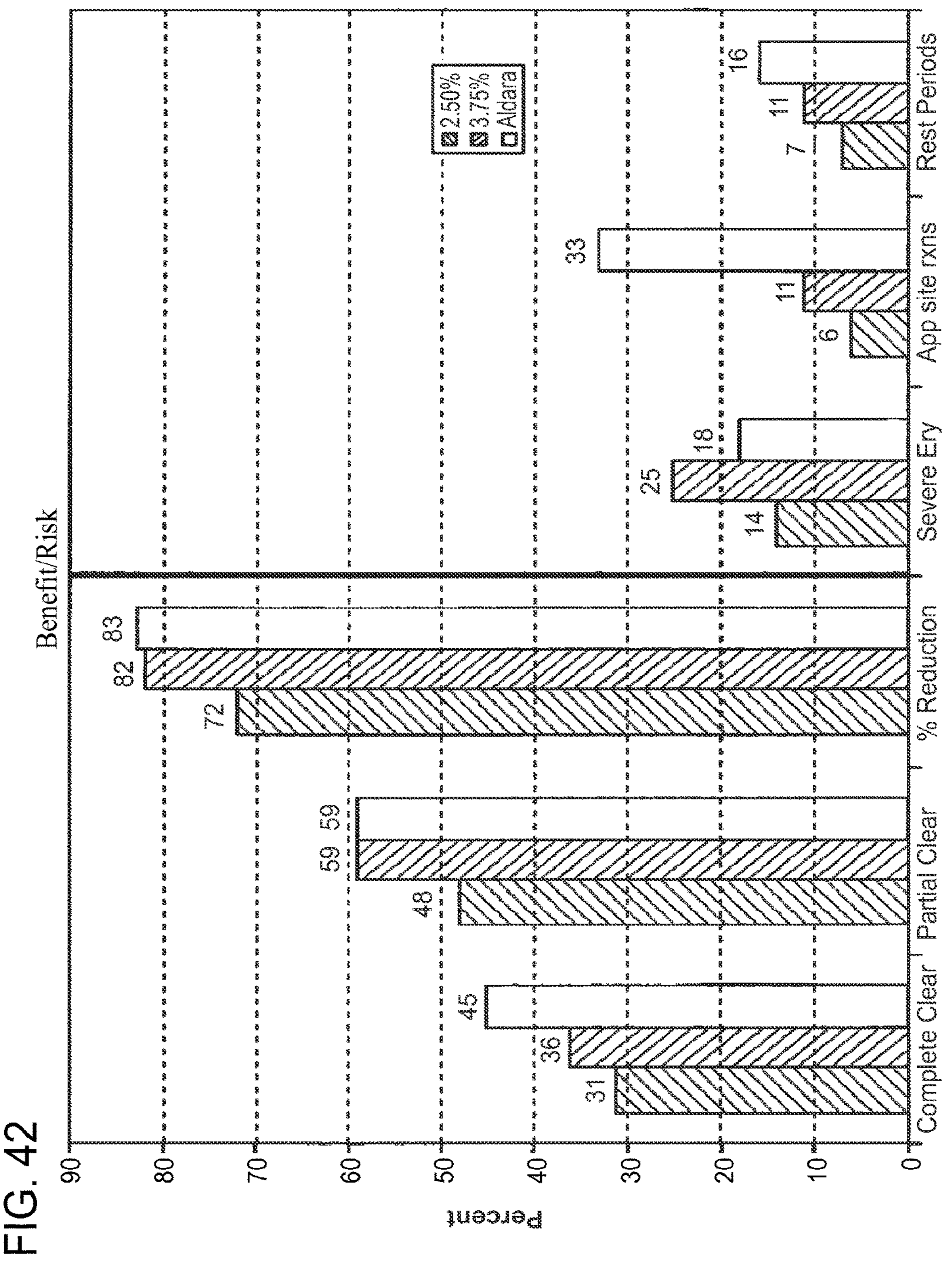
FIG. 42 shows benefit/risk for the 2-cycle, 2×2×2 (2 week) treatment regimen, as compared with Aldara® 5% imiquimod cream. In this FIG. 42, "Severe ery" refers to severe erythema, "App site rxns" refers to application site reactions, "Rest Periods" refers to the percent of patients who took rest periods during the study in addition to the two week rest period (no treatment period) sandwiched between the 2-cycles of two week treatments, "Complete Clear" refers to the rate of complete AK lesion clearance, "Partial Clear" refers to the rate of partial AK lesion clearance (defined as at least about 75% reduction in the number of AK lesions in the treatment area as compared with Baseline), "% Reduction" refers to median percent reduction in AK lesions, "2.5%" refers to a 2.5% imiquimod lower dosage strength formulation of Examples 23-28, "3.75%" refers to a 3.75% imiquimod lower dosage strength formulation of Examples 23-28, and "Aldara" refers to Aldara® 5% imiquimod cream.

Turning now to FIG. 42, it shows the benefit/risk analysis for both (1) the 2.5% and 3.75% imiquimod formulations of Example 23, that are used in the 2×2×2 week studies of Example 24, and (2) the Aldara® 5% imiquimod cream, to treat actinic keratosis. As is shown, the 3.75% imiquimod formulation provides incremental efficacy benefit to the 2.5% imiquimod formulation as defined by results for complete clearance, partial clearance and median percent reductions. The 3.75% imiquimod formulation provides comparable efficacy to Aldara® 5% imiquimod cream as defined by partial clearance and median percent reductions not withstanding the differences in treatment area size and baseline numbers of AK lesions in the studies of the 3.75% and 5% imiquimod formulations. As to risk, the incidences of severe erythema and the incidences of rest periods among the 2.5%, 3.75% and 5% (Aldara®) imiquimod formulations are generally similar (that is within approximately 10% of each other). As noted with the assessment of benefits, these results are not withstanding the differences in treatment area size and baseline numbers of AK lesions in the studies of the 2.5%, 3.75% and 5% imiquimod formulations. The third measure of risk, that is incidence of application site reactions, shows low incidence rates for both the 2.5% and 3.75% imiquimod formulations and a minimum 3-fold higher incidence rate with the Aldara® 5% imiquimod cream formulation.

Example 28

Eight Individual Clinical Cases—Four Individual Two Week, 2-Cycle Clinical Cases and Four Individual Three Week, 2-Cycle Clinical Cases This Example 28 is directed to eight clinical cases wherein subjects diagnosed with actinic keratosis are treated with either 2.5% or 3.75% low dosage strength imiquimod formulations of Example 23 in accordance with either a two-cycle, 2 week on×2 week off×2 week on treatment regimen or a two-cycle, 3 week on×3 week off×3 week on treatment regimen, as described herein. See, e.g., FIGS. 43-50 for a summary of results.

According to the clinical case summarized in FIG. 43, a 39 year old white male has an AK lesion count of 11 on his balding scalp at treatment initiation. Consistent with the present invention, the full balding scalp is treated daily with a single dose of a 2.5% imiquimod formulation of Example 23. The 2.5% imiquimod formulation is packaged in individual packets in an amount of 250 mg/packet. The number of average packets that are used by this 39 year old white male for each individual daily dose is 1.25 packets. During the two-cycle, 2×2×2 weeks, treatment period, this 39 year old white male neither misses a dose nor takes a rest period.

Referring now to FIG. 43, the 39 year old white male is treated as follows: during the first cycle of treatment, one dose (1.25 packets on average) of the 2.5% imiquimod formulation is applied to his full balding scalp once per day for 14 days; during the next 14 days, treatment is suspended; during the second cycle of treatment, treatment is carried out identical to the treatment that is used during the first cycle. At the end of the second cycle, the 39 year old white male is monitored for an additional 8 weeks. During the entire 14 weeks, the 39 year old white male is monitored for total or partial clearance, local skin reactions, including erythema, and adverse events at (a) baseline, (b) week 2, (c) week 6, (d) week 10, and (e) week 14.

In still referring to FIG. 43, at baseline before therapy, there is an AK lesion count of 11 and a local skin reaction (erythema) score of 0. At week 2, the AK lesion count is IND, but there is a local skin reaction erythema score of 2. At week 6, the AK lesion count remains IND, but the local skin reaction erythema score is reduced to 1. At week 14, the AK lesion count remains 0 (total clearance) and the local skin reaction erythema score returns to normal or baseline score. Lymphadenopathy is reported as a related adverse event.

Thus, this clinical case as summarized in FIG. 43, demonstrates efficacy without treatment limiting local skin reactions or adverse events and further demonstrates that total or complete clearance is achieved with a 2.5% imiquimod formulation of Example 23 when applied to the full balding scalp of a subject diagnosed with actinic keratosis following a 2 cycle, 2×2×2 weeks, treatment period. This Example 28, as described in FIG. 43, also demonstrates the unique bimodal or camelback pattern as to the local skin reaction score for erythema during the 2 cycle, 2×2×2 weeks, treatment regimen, which is generated when following the short durations of therapy in accordance with the present invention.

According to the clinical case summarized in FIG. 44, a 74 year old white male with Fitzpatrick skin type III has an AK lesion count of 8 on his balding scalp at treatment initiation. Consistent with the present invention, the entire balding scalp is treated daily with a single dose of a 2.5% imiquimod formulation of Example 23. The 2.5% imiquimod formulation is packaged in individual packets in an amount of 250 mg/packet. The number of average packets that are used by this 74 year old white male for each individual daily dose is 2.0 packets. During the two-cycle, 2×2×2 weeks, treatment period, this 74 year old white male neither misses a dose nor takes a rest period.

Referring now to FIG. 44, the 74 year old white male, is treated as follows: during the first cycle of treatment, one dose (2.0 packets on average) of the 2.5% imiquimod formulation is applied to his full balding scalp once per day for 14 days; during the next 14 days, treatment is suspended; during the second cycle of treatment, treatment is carried out identical to the treatment that is used during the first cycle. At the end of the second cycle, the 74 year old white male is monitored for an additional 8 weeks. During the entire 14 weeks, the 74 year old white male is monitored for total or partial clearance, local skin reactions, including erythema, and adverse events at (a) baseline, (b) week 2, (c) week 4, (d) week 6, (e) week 10, and (f) week 14.

In still referring to FIG. 44, at baseline before therapy, there is an AK lesion count of 8 and a local skin reaction (erythema) score of 0, a baseline score of 0. At week 2, the AK lesion count is 19, but there is a local skin reaction erythema score of 2. At week 4, the AK lesion count is reduced to 12, and the local skin reaction erythema score is reduced to 1. At week 6, the AK lesion count is increased to 33 and the local skin reaction erythema score is increased to 3. At week 10, the AK lesion count is reduced to 1 and the local skin reaction erythema score is now 0. At week 14, the AK lesion count is up to 2 (partial clearance) and the local skin reaction erythema score remains 0 or the same as the baseline score. No adverse events are reported.

Thus, this clinical case as summarized in FIG. 44, demonstrates efficacy without treatment limiting local skin reactions or adverse events and further demonstrates that a reduction in AK lesions (partial clearance) of about 75% from baseline is achieved with a 2.5% imiquimod formulation of Example 23 when applied to the full balding scalp of a subject diagnosed with actinic keratosis following a 2 cycle, 2×2×2 weeks, treatment period. This Example 28, as described in FIG. 44, is another example of the unique bimodal or camelback pattern as to the local skin reaction score for erythema during the 2 cycle, 2×2×2 week, treatment regimen, that is generated when following the short durations of therapy in accordance with the present invention.

According to the clinical case summarized in FIG. 45, a 66 year old white female with Fitzpatrick skin type II has an AK lesion count of 9 on her face at treatment initiation. Consistent with the present invention, the full face is treated daily with a single dose of a 3.75% imiquimod formulation of Example 23. The 3.75% imiquimod formulation is packaged in individual packets in an amount of 250 mg/packet. The number of average packets that are used by this 66 year old white female for each individual daily dose is 1.26 packets. During the two-cycle, 2×2×2 weeks, treatment period, this 66 year old white female neither missed a dose on day 29 and took rest periods on days 11, 12, 13 and 14.

Referring now to FIG. 45, the 66 year old white female is treated as follows: during the first cycle of treatment, one dose (1.26 packets on average) of the 3.75% imiquimod formulation is applied to her full face once per day for 14 days; during the next 14 days, treatment is suspended; during the second cycle of treatment, treatment is carried out identical to the treatment that is used during the first cycle. At the end of the second cycle, the 66 year old white female is monitored for an additional 8 weeks. During the entire 14 weeks, the 66 year old white female is monitored for total or partial clearance, local skin reactions, including erythema, and adverse events at (a) baseline, (b) week 2, (c) week 6 and (d) week 14.

In still referring to FIG. 45, at baseline before therapy, there is an AK lesion count of 9 and a local skin reaction (erythema) score of 0. At week 2, the AK lesion count is IND, but there is a local skin reaction erythema score of 2. At week 6, the AK lesion count remains IND, but the local skin reaction erythema score is reduced to 1. At week 14, the AK lesion count is 0 (total clearance) and the local skin reaction erythema score remains at 1. Dizziness, facial stinging, sunburn (mild) are reported as related adverse events.

Thus, this clinical case as summarized in FIG. 45, demonstrates efficacy without treatment limiting local skin reactions or adverse events and further demonstrates that total clearance is achieved with a 3.75% imiquimod formulation of Example 23 when applied to the full face of a subject diagnosed with actinic keratosis following a 2 cycle, 2×2×2 weeks, treatment period. This Example 28, as described in FIG. 45, also demonstrates the unique bimodal or camelback pattern as to the local skin reaction score for erythema during the 2 cycle, 2×2×2 weeks, treatment regimen, which is generated when following the short durations of therapy in accordance with the present invention.

According to the clinical case summarized in FIG. 46, a 73 year old white male with Fitzpatrick skin type H has an AK lesion count of 9 on his face at treatment initiation. Consistent with the present invention, the full face is treated daily with a single dose of a 3.75% imiquimod formulation of Example 23. The 3.75% imiquimod formulation is packaged in individual packets in an amount of 250 mg/packet. The number of average packets that are used by this 73 year old white male for each individual daily dose is 1.18 packets. During the two-cycle, 2×2×2 weeks, treatment period, this 73 year old white male neither misses a dose nor takes a rest period.

Referring now to FIG. 46, the 73 year old white male, is treated as follows: during the first cycle of treatment, one dose (1.18 packets on average) of the 3.75% imiquimod formulation is applied to his full face once per day for 14 days; during the next 14 days, treatment is suspended; during the second cycle of treatment, treatment is carried out identical to the treatment that is used during the first cycle. At the end of the second cycle, the 73 year old white male is monitored for an additional 8 weeks. During the entire 14 weeks, the 73 year old white male is monitored for total or partial clearance, local skin reactions, including erythema, and adverse events at (a) baseline, (b) week 2, (c) week 4, (d) week 6, (e) week 10, and (f) week 14.

In still referring to FIG. 46, at baseline before therapy, there is an AK lesion count of 9 and a local skin reaction (erythema) score of 0. At week 2, the AK lesion count is 22, but there is a local skin reaction erythema score of 3. At week 4, the AK lesion count is reduced to 3, and the local skin reaction erythema score is reduced to 0. At week 6, the AK lesion count is increased to 5 and the local skin reaction erythema score is increased to 2. At week 10, the AK lesion count is reduced to 2 and the local skin reaction erythema score is now 0. At week 14, the AK lesion count remains at 2 (partial clearance) and the local skin reaction erythema score remains at 0 or the same as the baseline score. No adverse events are reported.

Thus, this clinical case as summarized in FIG. 46, further demonstrates efficacy without treatment limiting local skin reactions or adverse events and further demonstrates that a reduction in AK lesions (partial clearance) of greater than about 75% from baseline is achieved with a 3.75% imiquimod formulation of Example 23 when applied to the full face of a subject diagnosed with actinic keratosis following a 2 cycle, 2×2×2 weeks, treatment regimen. This Example 28, as described in FIG. 46, is another example of the unique bimodal or camelback pattern as to the local skin reaction score for erythema during the 2 cycle, 2×2×2 weeks, treatment regimen, which is generated when following the short durations of therapy in accordance with the present invention.

According to the clinical case summarized in FIG. 47, a 70 year old white male has an AK lesion count of 10 on his face at treatment initiation. Consistent with the present invention, the full face is treated daily with a single dose of a 2.5% imiquimod formulation of Example 23. The 2.5% imiquimod formulation is packaged in individual packets in an amount of 250 mg/packet. The number of average packets that are used by this 70 year old white male for each individual daily dose is 2.0 packets. During the two-cycle, 3×3×3 weeks, treatment period, this 70 year old white male neither misses a dose nor takes a rest period.

Referring now to FIG. 47, the 70 year old white male is treated as follows: during the first cycle of treatment, one dose (2.0 packets on average) of the 2.5% imiquimod formulation is applied to his full face once per day for 21 days; during the next 21 days, treatment is suspended; during the second cycle of treatment, treatment is carried out identical to the treatment that is used during the first cycle. At the end of the second cycle, the 70 year old white male is monitored for an additional 8 weeks. During the entire 17 weeks, the 70 year old white male is monitored for total or partial clearance, local skin reactions, including erythema, and adverse events at (a) baseline, (b) week 3, (c) week 9, and (d) week 17.

In still referring to FIG. 47, at baseline before therapy, there is an AK lesion count of 10 and a local skin reaction (erythema) score of 1. At week 3, the AK lesion count is IND, but there is a local skin reaction erythema score of 3. At week 9, the AK lesion count increases to 13, but the local skin reaction erythema score remains at 3. At week 17, the AK lesion count is reduced to 5 (partial clearance) and the local skin reaction erythema score returns to 1, i.e., normal or baseline score. No adverse events are recorded.

Thus, this clinical case as summarized in FIG. 47, demonstrates efficacy without treatment limiting local skin reactions or adverse events and further demonstrates that partial clearance is achieved with a 2.5% imiquimod formulation of Example 23 when applied to the full face of a subject diagnosed with actinic keratosis following a 2 cycle, 3×3×3 week, treatment regimen. This Example 28, as described in FIG. 47, also demonstrates the unique bimodal or camelback pattern as to the local skin reaction score for erythema during the 2 cycle, 3×3×3 weeks, treatment regimen, which is generated when following the short durations of therapy in accordance with the present invention.

According to the clinical case summarized in FIG. 48, a 65 year old white female has an AK lesion count of 7 on her face at treatment initiation. Consistent with the present invention, the full face is treated daily with a single dose of a 2.5% imiquimod formulation of Example 23. The 2.5% imiquimod formulation is packaged in individual packets in an amount of 250 mg/packet. The number of average packets that are used by this 65 year old white female for each individual daily dose is 1.69 packets. During the two-cycle, 3×3×3 weeks, treatment period, this 65 year old white female neither misses a dose nor takes a rest period.

Referring now to FIG. 48, the 65 year old white female is treated as follows: during the first cycle of treatment, one dose (1.69 packets on average) of the 2.5% imiquimod formulation is applied to her full face once per day for 21 days; during the next 21 days, treatment is suspended; during the second cycle of treatment, treatment is carried out identical to the treatment that is used during the first cycle. At the end of the second cycle, the 65 year old white female is monitored for an additional 8 weeks. During the entire 17 weeks, the 65 year old white female is monitored for total or partial clearance, local skin reactions, including erythema, and adverse events at (a) baseline, (b) week 3, (c) week 9, and (d) week 17.

In still referring to FIG. 48, at baseline before therapy, there is an AK lesion count of 7 and a local skin reaction (erythema) score of 1. At week 3, the AK lesion count is 1, but the local skin reaction erythema score remains at 1. At week 9, both the AK lesion count and the local skin reaction erythema score are reduced to 0. At week 17, the AK lesion count remains at 0 (complete clearance) and the local skin reaction erythema score remains at 0, i.e., below normal or baseline score. All adverse events that are recorded are unrelated.

Thus, this clinical case as summarized in FIG. 48, demonstrates efficacy without treatment limiting local skin reactions or adverse events and further demonstrates that complete clearance is achieved with a 2.5% imiquimod formulation of Example 23 when applied to the full face of a subject diagnosed with actinic keratosis following a 2 cycle, 3×3×3 weeks, treatment regimen. This Example 28, as described in FIG. 48, also demonstrates the unique bimodal or camelback pattern as to the local skin reaction score for erythema during the 2 cycle, 3×3×3 week, treatment regimen, which is generated when following the short durations of therapy in accordance with the present invention.

According to the clinical case summarized in FIG. 49, a 79 year old white male has an AK lesion count of 14 on his face at treatment initiation. Consistent with the present invention, the full face is treated daily with a single dose of a 3.75% imiquimod formulation of Example 23. The 3.75% imiquimod formulation is packaged in individual packets in an amount of 250 mg/packet. The number of average packets that are used by this 79 year old white male for each individual daily dose is 1.14 packets. During the two-cycle, 3×3×3 week, treatment period, this 79 year old white male neither misses a dose nor takes a rest period.

Referring now to FIG. 49, the 79 year old white male is treated as follows: during the first cycle of treatment, one dose (1.14 packets on average) of the 3.75% imiquimod formulation is applied to his full face once per day for 21 days; during the next 21 days, treatment is suspended; during the second cycle of treatment, treatment is carried out identical to the treatment that is used during the first cycle. At the end of the second cycle, the 79 year old white male is monitored for an additional 8 weeks. During the entire 17 weeks, the 79 year old white male is monitored for total or partial clearance, local skin reactions, including erythema, and adverse events at (a) baseline, (b) week 3, (c) week 9 and (d) week 17.

In still referring to FIG. 49, at baseline before therapy, there is an AK lesion count of 14 and a local skin reaction (erythema) score of 1. At week 3, the AK lesion count is up to 16, and the local skin reaction erythema score is increased to 3. At week 9, however, the AK lesion count falls to 6 and local skin reaction erythema score is reduced to 2. At week 17, the AK lesion count is 0 (total or complete clearance) and the local skin reaction erythema score falls to 0, below normal or baseline. No adverse events are reported.

Thus, this clinical case as summarized in FIG. 49, demonstrates efficacy without treatment limiting local skin reactions or adverse events and further demonstrates that total or complete clearance is achieved with a 3.75% imiquimod formulation of Example 23 when applied to the full face of a subject diagnosed with actinic keratosis following a 2 cycle, 3×3×3 week, treatment regimen. This Example 28, as described in FIG. 49, also demonstrates the unique bimodal or camelback pattern as to the local skin reaction score for erythema during the 2 cycle, 3×3×3 weeks, treatment regimen, which is generated when following the short durations of therapy in accordance with the present invention.

According to the clinical case summarized in FIG. 50, a 78 year old white male has an AK lesion count of 8 on his balding scalp at treatment initiation. Consistent with the present invention, the entire balding scalp is treated daily with a single dose of a 3.75% imiquimod formulation of Example 23. The 3.75% imiquimod formulation is packaged in individual packets in an amount of 250 mg/packet. The number of average packets that are used by this 78 year old white male for each individual daily dose is 2.0 packets. During the two-cycle, 3×3×3 weeks, treatment period, this 78 year old white male neither misses a dose nor takes a rest period.

Referring now to FIG. 50, the 78 year old white male, is treated as follows: during the first cycle of treatment, one dose (2.0 packets on average) of the 3.75% imiquimod formulation is applied to his full balding scalp once per day for 21 days; during the next 21 days, treatment is suspended; during the second cycle of treatment, treatment is carried out identical to the treatment that is used during the first cycle. At the end of the second cycle, the 78 year old white male is monitored for an additional 8 weeks. During the entire 17 weeks, the 78 year old white male is monitored for total or partial clearance, local skin reactions, including erythema, and adverse events at (a) baseline, (b) week 3, (c) week 9, and (d) week 17.

In still referring to FIG. 50, at baseline before therapy, there is an AK lesion count of 8 and a local skin reaction (erythema) score of 1. At week 3, the AK lesion count is IND, but there is a local skin reaction erythema score of 3. At week 9, the AK lesion count is up to 2, but the local skin reaction erythema score is reduced to 1. At week 17, both the AK lesion count and the local skin reaction erythema score are at 0. All adverse events that incur are recorded as unrelated to treatment.

Thus, this clinical case as summarized in FIG. 50, further demonstrates efficacy without treatment limiting local skin reactions or adverse events and further demonstrates that complete clearance is achieved with a 3.75% imiquimod formulation of Example 23 when applied to the full balding scalp of a subject diagnosed with actinic keratosis following a 2 cycle, 3×3×3 weeks, treatment regimen. This Example 28, as described in FIG. 50, is another example of the unique bimodal or camelback pattern as to the local skin reaction score for erythema during the 2 cycle, 3×3×3, treatment regimen, which is generated when following the short durations of therapy in accordance with the present invention. In Example 23 herein above, formulations 126 and 182, wherein the fatty acid is isa, are the formulations that are used in Examples 24-28 and in FIGS. 1-54 discussed and described herein above. In addition, isa formulations 126 and 182 pass the PET tests when stored at about 40° C. for about 3 months.

The complete disclosures of the patents, patent documents, and publications cited herein are incorporated by reference in their entireties as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of treating actinic keratoses (AK) in an immunocompetent adult patient in need thereof in a six week treatment course, the method comprising:

(a) topically applying a 3.75% (w/w) imiquimod composition once daily to the full face or balding scalp of the immunocompetent adult patient over a first two-week treatment period; and (b) topically applying a 3.75% (w/w) imiquimod composition once daily to the full face or balding scalp of the immunocompetent adult patient over a second two-week treatment period; and wherein the first treatment period and the second treatment period are separated by one, two-week non-treatment period during which no imiquimod is applied to the immunocompetent adult patient;

wherein the 3.75% (w/w) imiquimod composition is a cream; and wherein the method of treating actinic keratoses involves only the topical application of the 3.75% (w/w) imiquimod composition; and is completed in six weeks.

2. The method of claim 1, wherein 250-500 mg of the imiquimod composition is applied.

3. The method of claim 1, wherein the imiquimod composition is not removed from the skin for about eight hours.

4. The method of claim 1, wherein 9.3 mg to 18.8 mg of imiquimod is applied daily.

5. The method of claim 1, wherein 65.6 mg to 131.3 mg of imiquimod is applied in one week of the two-week treatment period.

6. The method of claim 1, wherein 131.2 mg to 262.5 mg of imiquimod is applied in a two-week treatment period.

7. The method of claim 1, wherein 262.5 mg to 525 mg of imiquimod is applied in a 6-week treatment course.

8. The method of claim 1, wherein performance of the method results in complete clearance of the actinic keratoses in the immunocompetent adult patient.

9. The method of claim 8, wherein application of the method in a population of immunocompetent adult patients results in a statistically significant improvement in the percent of total clearance in actinic keratoses as compared to treatment with placebo.

10. The method of claim 9, wherein application of the method in the population of immunocompetent adult patients results in about 25% or greater complete clearance of actinic keratoses in the immunocompetent adult patients in the population.

11. The method of claim 1, wherein the AK is clinically typical, visible or palpable.

12. The method of claim 1, wherein applying the 3.75% imiquimod composition increases the number of AK lesions for some period of time.

13. The method of claim 1, wherein application of 3.75% imiquimod continues in a two-week treatment period even if no actinic keratoses are visible.

14. The method of claim 1, wherein the composition is applied to the full face.

15. The method of claim 1, wherein the composition is applied to the balding scalp.

16. The method of claim 1 or claim 12, wherein the full face is at least 200-250 $cm^2$.

17. The method of claim 3, wherein the eight hours is overnight.

18. The method of claim 1, wherein the method results in clearance of at least 75% of the baseline actinic keratoses.

19. The method of claim 1, wherein in performance of the method the imiquimod is the sole active pharmaceutical ingredient required to be applied to the full face or scalp of the immunocompetent adult patient.

20. A method of treating actinic keratoses (AK) in an immunocompetent adult patient in need thereof in a six week treatment course, the method comprising:

(a) topically applying a 2.5% (w/w) imiquimod composition once daily to the full face or balding scalp of the immunocompetent adult patient over a first two-week treatment period; and (b) topically applying a 2.5% (w/w) imiquimod composition once daily to the full face or balding scalp of the immunocompetent adult patient over a second two-week treatment period; and wherein the first treatment period and the second treatment period are separated by one, two-week non-treatment period during which no imiquimod is applied to the immunocompetent adult patient;

wherein the 2.5% (w/w) imiquimod composition is a cream; and wherein the method of treating actinic keratoses involves only the topical application of the 3.75% (w/w) imiquimod composition; and is completed in six weeks.

* * * * *

UNITED STATES PATENT AND TRADEMARK OFFICE
CERTIFICATE OF CORRECTION

PATENT NO. : 10,238,644 B2
APPLICATION NO. : 15/187751
DATED : March 26, 2019
INVENTOR(S) : Michael T. Nordsiek et al.

Page 1 of 1

It is certified that error appears in the above-identified patent and that said Letters Patent is hereby corrected as shown below:

In the Claims

Column 170, Line 57: Delete "3.75%" and insert in its place --2.5%--.

Signed and Sealed this
Seventh Day of May, 2019

Andrei Iancu
*Director of the United States Patent and Trademark Office*